(12) United States Patent
Heim et al.

(10) Patent No.: US 7,563,944 B2
(45) Date of Patent: Jul. 21, 2009

(54) EXPRESSION CASSETTE FOR NUCLEIC ACIDS IN PLANT TISSUE CONTAINING STARCH

(75) Inventors: Ute Heim, Gatersleben (DE); Karin Herbers, Quedlinburg (DE); Uwe Sonnewald, Quedlinburg (DE); Eric Glickmann, Ditfurt (DE)

(73) Assignee: SunGene GmbH & Co. KGaA (DE)

( * ) Notice: Subject to any disclaimer, the term of this patent is extended or adjusted under 35 U.S.C. 154(b) by 314 days.

(21) Appl. No.: 10/542,516

(22) PCT Filed: Jan. 15, 2004

(86) PCT No.: PCT/EP2004/000241

§ 371 (c)(1),
(2), (4) Date: Jul. 18, 2005

(87) PCT Pub. No.: WO2004/065537

PCT Pub. Date: Aug. 5, 2004

(65) Prior Publication Data

US 2006/0130182 A1 Jun. 15, 2006

(30) Foreign Application Priority Data

Jan. 20, 2003 (DE) ............................... 103 02 324

(51) Int. Cl.
 C12N 15/63 (2006.01)
 C12N 15/11 (2006.01)
 C12N 15/82 (2006.01)
 C12N 5/04 (2006.01)
 A01H 5/00 (2006.01)

(52) U.S. Cl. ...................... 800/287; 800/278; 800/295; 800/298; 435/320.1; 435/468; 435/410; 536/23.1; 536/24.1; 536/24.3

(58) Field of Classification Search .................. None
 See application file for complete search history.

(56) References Cited

U.S. PATENT DOCUMENTS

| 5,608,150 A | 3/1997 | Conner |
| 5,859,330 A | 1/1999 | Bestwick et al. |
| 6,127,179 A | 10/2000 | DellaPenna et al. |
| 6,730,825 B1 * | 5/2004 | Goldsbrough et al. ....... 800/284 |

FOREIGN PATENT DOCUMENTS

| EP | 0 375092 A1 | 12/1989 |
| EP | 0 779363 A3 | 5/1998 |
| WO | WO 91/19806 | 12/1991 |
| WO | WO 00/26388 | 5/2000 |
| WO | WO 00/66610 | 11/2000 |
| WO | WO-00/66745 | 11/2000 |
| WO | WO0066745 | * 11/2000 |

OTHER PUBLICATIONS

Kim et al 1994, Plant Molecular Biology 24:105-117.*
Donald et al 1990, EMBO J. 9:1717-1726.*
Dolferus et al 1994, Plant Physiology 105:1075-1087.*
Marshall, Jacqueline, et al., "Identification of the Major Starch Synthase in the Soluble Fraction of Potato Tubers", The Plant Cell, vol. 8, 1996, pp. 1121-1135.
Pear, Julie R., et al., "Isolation and Characterization of a Fruit-Specific cDNA and the Corresponding Genomic Clone from Tomato", Plant Molecular Biology, vol. 13, 1989, pp. 639-651.
Bevan, M., et al., "The Structure and Transcription Start Site of a Major Potato Tuber Protein Gene", Nucleic Acids Res., vol. 14, No. 11, 1986, pp. 4625-4638.
Müller-Röber, Bernd Thomas, et al., "One of Two Different ADP-Glucose Pyrophosphorylase Genes from Potato Responds Strongly to Elevated Levels of Sucrose", Mol Gen Genet, vol. 224, 1990, pp. 136-146.
Salanoubat, Marcel, et al., "The Steady-State Level of Potato Sucrose Synthase mRNA is Dependent on Wounding, Anaerobiosis and Sucrose Concentration", Gene, vol. 84, 1989, 181-185.
Jefferson, Richard, et al., "Transcriptional Regulation of a Patatin-1 Gene in Potato", Plant Molecular Biology, vol. 14., 1990, pp. 995-1006.
Li, Z., et al., "Cloning and Characterization of a Gene Encoding Wheat Starch Synthase I", Theor Appl. Genet, vol. 98, 1999, 1208-1216.
Baba, Tadashi et al., "Identification, cDNA Cloning, and Gene Expression of Soluble Starch Synthase in Rice (*Oryza sativa* L.) Immature Seeds", Plant Physiol, vol. 103, 1993, pp. 565-573.
Dry, Ian, et al., "Characterization of cDNAs Encoding Two Isoforms of Granule-Bound Starch Synthase which Show Differential Expression in Developing Storate Organs of Pea and Potato", The Plant Journal, vol. 2, No. 2, 1992, pp. 193-202.
Harn, Chee, et al., "Isolation and Characterization of the *zSSIIa* and *zSSIIb* Starch Synthase cDNA Clones from Maize Endosperm", Plant Molecular Biology, vol. 37, 1998, pp. 639-649.
Abel, Gernot, J.W., et al., "Cloning and Functional Analysis of a cDNA Encoding a Novel 139 kDA Starch Synthase from Potato (*Solanum tuberosum* L.)", The Plant Journal, vol. 10, No. 6, 1996, 981-991.

(Continued)

*Primary Examiner*—Russell Kallis
*Assistant Examiner*—Brent Page
(74) *Attorney, Agent, or Firm*—Connolly Bove Lodge & Hutz LLP

(57) ABSTRACT

The invention relates to methods for the transgenic expression of nucleic acid sequences predominantly in starch-comprising tissues of plants, preferably in fruits, roots, seeds or tubers, wherein the nucleic acid sequence is expressed under the control of a promoter of a starch synthase 3. Furthermore in accordance with the invention are transgenic expression cassettes and vectors comprising a promoter of a starch synthase 3, and the use thereof for the production of foodstuffs, feedstuffs, seed, pharmaceuticals or fine chemicals.

27 Claims, 12 Drawing Sheets

OTHER PUBLICATIONS

Gao, Ming, et al., "Characterization of *dull1*, a Maize Gene Coding for a Novel Starch Synthase", The Plant Cell, vol. 10, 1998, pp. 399-412.

Kossmann, Jens, et al., "Cloning and Functional Analysis of a cDNA Encoding a Starch Synthase from Potato (*Solanum tuberosum* L.) that is Predominantly Expressed in Leaf Tissue", Pianta, vol. 208, 1999, pp. 503-511.

Block, M., et al., "Triticum easticum Soluble Starch Synthase mRNA, Partial Cds", Jun. 12, 1996, Accession No. U48277.

Li, Zhongyi, et al., "The Structure and Expression of the Wheat Starch Synthase III Gene. Motifs in the Expressed Gene Define the Lineage of the Starch Synthase III Gene Family," Plant Physiology, vol. 123, 2000, pp. 613-624.

Deikman, Jim, et al., "Interaction of a DNA Binding Factor with 5'-Flanking Region of an Ethylene-Responsive Fruit Ripening Gene From Tomato", The Embo Journal, vol. 7, No. 11, 1988, pp. 3315-3320.

Herbers, Karin, et al., "Cloning and Characterization of a Cathepsin D Inhibitor Gene from *Solanum tuberosum* L.", Plant Molecular Biology, vol. 26, 1994, pp. 73-83.

Salanoubat, Marcel, et al., "Molecular Cloning and Sequencing of Sucrose Synthase cDNA from Potato (*Solanum tuberosum* L.): Preliminary Characterization of Sucrose Synthase mRNA Distribution", Gene, vol. 60, 1987, pp. 47-56.

Hannapel, David, "Differential Expression of Potato Tuber Protein Genes", Plant Physiol., vol. 94, 1990, pp. 919-925.

Rocha-Sosa, Mario, et al., "Both Developmental and Metabolic signals activate the promoter of a Class 1 Patatin Gene", The EMBO Journal, vol. 8, No. 1, 1989, pp. 23-29.

Mette, M. F. et al., "Production of Aberrant Promoter Transcripts Contributes To Methylation and Silencing of Unlinked Homologous Promoters in Trans", The EMBO Journal, vol. 18, No. 1, 1999, pp. 241-248.

Edwards, Anne, et al., "Biochemical And Molecular Characterization Of A Novel Starch Synthase From Potato Tubers", The Plant Journal, vol. 8, No. 2, 1995, pp. 283-294.

Marshall, Jacqueline, et al., "Identification of the Major Starch Synthase in the Soluble Fraction of Potato Tubers", The Plant Cell, vol. 8, 1996, pp. 1121-1135.

Lin, Ershen, et al., "Fruit Developmental Regulation Of The Kiwifruit Actinidin Promoter Is Conserved In Transgenic Petunia Plants", Plant Molecular Biology, vol. 23, 1993, pp. 489-499.

Li, Z., et al., "*Triticum aestivum* Starch Synthase III Mrna, Complete Cds", Jul. 29, 2000, Accession No. AF258608.

Abel, G.J.W., et al., "*Solanum tuberosum* mRNA For Soluble Starch Synthase", Jul. 22, 2003, Accession No. Y10416.

Walter, L., et al., "*Triticum aestivum* Starch Synthase mRNA, Partial Cds", Mar. 4, 2000, Accession No. U66377.

Marshall, J., et al., "*S. tuberosum* mRNA For Starch Synthase", Aug. 27, 1996, Accession No. X95759.

Abel, G., et al., "*S. tuberosum* mRNA For Soluble-starch-synthase", Apr. 16, 1997, Accession No. X94400.

Gao, M., et al., "*Zea mays* Starch Synthase Dull1 (dull1) mRNA, Complete Cds", Apr. 23, 1998, Accession No. AF023159.

Kossman, J., et al., "Sequence 1 From Patent WO9744472", Jan. 22, 2000, Accession No. A93359.

Baba, T., "*Oryza sativa* mRNA For Soluble Starch Synthase, Complete Cds", Mar. 1, 2003, Accession No. D16202.

Chibbar, R.N., "*Triticum aestivum* mRNA For Starch Synthase I-2 (wSsI-2 gene)", Dec. 6, 2001, Accession No. AJ292522.

Li, Z., et al., "*Aegilops tauschii* Starch Synthase III Gene, Complete Cds", Jul. 29, 2000, Accession No. AF258609.

Bhullar, S.S., "*Vigna unguiculata* Starch Synthase Isoform SS III", Apr. 1, 1999, Accession No. AJ225088.

Vysotskaia, V.S., et al., "*Arabidopsis thaliana* Chromosome 1 BAC F25C20 Sequence, Complete Sequence", May 17, 1999, Accession No. AC007296.

* cited by examiner

A

B

```
          1                                               50
STSSS3    (1)  --------------------------------------------------
AtSSS3    (1)  --------------------------------------------------
VUSSS3    (1)  --------------------------------------------------
ATaSSS3   (1)  MEMALRPRSPLCPRSSQPLVVVRPAGRGGGLAQPFLMNGRFTRSRTLRCM
TASSS3    (1)  MEMSLWPRSPLCPRSRQPLVVVRPAGRGG-LTQPFLMNGRFTRSRTLRCM
OS SSS3   (1)  -----------------------------MDSLALHSVTMGKV
ZM SSS3   (1)  MEMVLRSQSPLCLRSGPVLIFRPTVAGGGGGTQSLLRTTRFARRRVLRCV
Consensus (1)                                                L  M
          51                                              100
STSSS3    (1)  --------------------------------------------------
AtSSS3    (1)  --------------------------------------------------
VUSSS3    (1)  --------------------------------------------------
ATaSSS3   (51) VASSDPPNRKSRKMVSPQVKVISSRGYTTRLIVEPSTENIEHNNRDEETL
TASSS3    (50) VASSDPPNRKSRRMVPPQVKVISSRGYTTRLIVEPSNENTEHNNRDEETL
OS SSS3   (15) DAINAAGAEGDKFEVDLSALASNNS------MIEAVNVMDEAKAIEDTLE
ZM SSS3   (51) VASPGCPNRKSR-TASPNVKVAAYSNYAPRLLVESSSK------------
Consensus (51) A            R                  IVE
          101                                             150
STSSS3    (1)  --------------------------------------------------
AtSSS3    (1)  --------------------------------------------------
VUSSS3    (1)  --------------------------------------------------
ATaSSS3   (101) DTYNALLSTETAEWTDTREAETAKADSSQNALSSSIIGGVDVADEDILAA
TASSS3    (100) DTYNALLSTETAEWTDNREAETAKADSSQNALSSSIIGEVDVADEDILAA
OS SSS3   (59) VDLSGNATSSSTYGEVKFEVDSLGNTSSTVMYGPADGAYEPRSDEVTFKV
ZM SSS3   (88) ---KSEHHDSSRHREETIDTYNGLSGSDAAELTSNRDVEIEVDLQHISEE
Consensus (101)              S          E          S
          151                                             200
STSSS3    (1)  --------------------------------------------------
AtSSS3    (1)  --------------------------------------------------
VUSSS3    (1)  --------------------------------------------------
ATaSSS3   (151) DLTVNSLSSITKKEVDAVDKARVKEDVFELDLPATTLRSVIVDVMDHN--
TASSS3    (150) DLTVYSLSSVMKKEVDAADKARVKEDAFELDLPATTLRSVIVDVMDHNGT
OS SSS3   (109) DSSENASNNVMYGRADVVDESWADEGIFEVDFFTNASSGAEYGKVDVV--
ZM SSS3   (135) ELPGKVSINASLGEMETVDEAEVEEDKFEVDTSGIVLRNVAVREVDPK--
Consensus (151) D              D   D A     E    FELD          MD
          201                                             250
STSSS3    (1)  --------------------------------------------------
AtSSS3    (1)  --------------------------------------------------
VUSSS3    (1)  --------------------------------------------------
ATaSSS3   (199) ---------------GTVQETLRSVIVDVMDDAADKARVEEDVFELDLS
TASSS3    (200) VQETLRSVIVDVMDHNGTVQETLRSVIVDVMDDAADKARVEEDVFELDLS
OS SSS3   (157) --------------------------D-----EAKTDDFTSELDSL
ZM SSS3   (183) ------------------------------DEHNAKDVFVVDSS
Consensus (201)                                               LD
          251                                             300
STSSS3    (1)  --------------------------------------------------
AtSSS3    (1)  --------------------------------------------------
VUSSS3    (1)  --------------------------------------------------
ATaSSS3   (233) GNISSSATTVELDAVDEVGPVQDTFEANSSGNVSNSATVREVDTSAEAGN
TASSS3    (250) GNISSSATTVELDAVDEVGPVQDKFEATSSGNVSNSATVREVDASDEAGN
OS SSS3   (172) EKDSNNKMHGKAHMVDEAWDGEAIFEVDLFGNASSIPIYGEVNVLDEARA
ZM SSS3   (197) GTAPDN--AAVEEVVDEAEVEEDMVDVDILGLDLNNATIEETDLMEEALL
Consensus (251)              VDE         E    G         EV    EA
```

Fig. 7a

```
                 301                                              350
STSSS3     (1)   --------------------------------------------------
AtSSS3     (1)   --------------------------------------------------
VuSSS3     (1)   --------------------------------------------------
ATaSSS3  (283)   DQGIFRADLSGNVFSSSTTVEVGAVDEAGSIKDRFETDSSGNVSISATMW
TASSS3   (300)   DQGIFRADLSGNVFSSSTTVEVGAVDEAGSIKDRFETDSSGNVSISAPMW
OS SSS3  (222)   DDGKFEVDLLGNTSSNSTHEEVDVMDEAQTGEATFEVDLLGNALSSAIYK
ZM SSS3  (245)   EN--FDVDSPGNASSGRTYGGVDELGELPSTSVDCIAIN-GKRRSLKPKP
Consensus(301)   D    F   D  GN   S  T  V  VE S           G    S
                 351                                              400
STSSS3     (1)   --------------------------------------------------
AtSSS3     (1)   --------------------------------------------------
VuSSS3     (1)   --------------------------------------------------
ATaSSS3  (333)   DAIDETVADQDAVEADLSGNASSCATYREVDDVVDETRSEEEIFAMDLFA
TASSS3   (350)   DAIDETVADQDTFEADLSGNASSCATYREVDDVVDETRSEEEIFAMDLFA
OS SSS3  (272)   EVPVMGGAQDDEVDVDFSINASITETEKEAD-AVDEARVEDETFDMDLVG
ZM SSS3  (292)   LPIVRFQEQEQIVLSIVDEEGLIASSCEEGQPVVDYDKQEENSTAFDEQK
Consensus(351)                        A    T E    VD  R EE T    D
                 401                                              450
STSSS3     (1)   ------------------MDVPFPLHRPLSCTSVSNAITHLKIKPFLG
AtSSS3     (1)   --------------------------------------------------
VuSSS3     (1)   ----------------------------------------MEMSLQLNYKTP
ATaSSS3  (383)   SESGHE-----KHMAVDHVGEATDEEETYQQQYPVPSSFSMWDKAIAKTG
TASSS3   (400)   SESGHE-----KHMAVDYVGEATDEEETYQQQYPVPSSFSMWDKAIAKTG
OS SSS3  (321)   ----------KQISIDSMNDDVVEEGTKHHRYPMLSSAFIEVKTIHETP
ZM SSS3  (342)   QLTDDFPEEGISIVHFPEPNNDIVGSSKFLEQKQELDGSYKQDRSTTGLH
Consensus(401)                  M                         S     M K    T
                 451                                              500
STSSS3    (31)   FVSHGTTSLSVQSSSWRKDGMVTGVSFPFCANLSGRRRRKVSTTRSQGSS
AtSSS3     (1)   -----------------------------------MAASGPKSSG
VuSSS3    (13)   FCFKLTPFSVLTPSSWHKASIRVSCVNASADFSRKRQQKKSSIAKPKGSN
ATaSSS3  (428)   VSLNPELRLVRVEEQGK--VNFSDKKDLSIDDLPGQNQSIIGSYKQDKSI
TASSS3   (445)   VSLNPELRLVRVEEQGK--VNFSDKKDLSIDDLPGQNQSIIGSYKQDKSI
OS SSS3  (360)   VSLKPELMSVVMDQEQDKPISSVYQQEGSIFNLHAENQSTVDFHEREQMA
ZM SSS3  (392)   EQDQSVVSSHGQDKSIVGVPQQIQYNDQSIAGSHRQDQSIAGAPEQIQSV
Consensus(451)         L  V   D             D SI    L G NQS  IGA K    S
                 501                                              550
STSSS3    (81)   PKGFVPRKPSGMSIQRKVQKSNGDKESQSTSISKESE---ISNQKTVEAR
AtSSS3    (11)   PRGFG-RRITVGSAQKRTQKKNGEKDSNATSIATNEV---SGISKLPAAK
VuSSS3    (63)   PKGFVPKSSIGSSSKKNPRVSK-KGDSLAPVVSEVLE---DDNKQTLDVI
ATaSSS3  (476)   ADVAGPTQSIFGSSKQHRSIVAFPKQNQSIVSVTEQKQSIVGFRSQDLSA
TASSS3   (493)   ADVAGPTQSIFGSSKQHRSIVAFPKQNQSIVSVTEQKQSIVGFRSQDLSA
OS SSS3  (410)   ITFDKQKESVAKLSKEDQQTAGLPEQNMSFDGVHRKSQSIIGLPFHQSI
ZM SSS3  (442)   AGYIKPNQSIVGSCKQHELIIPEPKKIESIISYNEIDQSIVGSHKQDKSV
Consensus(501)           PK SI GSSK    I    PK QS VS  E QSIVG    Q  S
                 551                                              600
STSSS3   (128)   VETSDDDTKVVVRD--------------HKFIEDEDEINGSTKSISMSP
AtSSS3    (57)   VDVQKQSSVVIN--------------------ERNVLDRSD
VuSSS3   (109)   IDDDEDEFSVEENCGVDD-------KINKIAREFGESSIIDETFDVENIP
ATaSSS3  (526)   VSLPKQNVPIVGTSREGQ--------TKQVPVVDRQDAIYVNGLEAKEGD
TASSS3   (543)   VSLPKQNVPIVGTSREGQ--------TKQVPVVDRQDAIYVNGLEAKEGD
OS SSS3  (460)   VSSPEKYRSIVGFHGQNQSIISSHKQDKSIVGVPKKIQSIVGSTKHDDSI
ZM SSS3  (492)   VSVPEQIQSIVSHSKPNQSTVDSYRQAESIIGVPEKVQSITSYDKLDQSI
Consensus(551)   VSLPEQ   IV       Q             I  V    L     LD S
```

Fig. 7b

```
                    601                                                  650
STSSS3      (163)   VRVSSQFVESEETGGDDKDAVKLNKSKRSEESDFLID-------------
AtSSS3       (78)   IEDGSDRLDKKTTDDDDLLEQKLKLERE---------------------
VUSSS3      (152)   IIDDVQLYEEGNSYVGDDGNVKDSEGRR---------------------
ATaSSS3     (568)   HTSEKTDEDVLHVKFNVDNVLRKHQADRTQAVETITW------------
TASSS3      (585)   HTSEKTDEDALHVKFNVDNVLRKHQADRTQAVEKKTW------------
OS SSS3     (510)   VGFRKQDRSIVSVPEQKQSTVGFHKQDLSIVAVSEQN------------
ZM SSS3     (542)   VGSLKQDEPILSVPEKIQSIVHYTKPNQSIVGLPKQQQSIVHIVEPKQSI
Consensus   (601)   V   KQD D L V      IVK    RS
                    651                                                  700
STSSS3      (200)   --------SVIREQSGSQGETNASSKGSHAVGTKLYEILQVDVEPQQLKE
AtSSS3      (106)   --------------------------------------------------
VUSSS3      (180)   --------------------------------------------------
ATaSSS3     (605)   -------KKVDEEHLYMTEHQIGAAEGQMVVNEDELSITEIG--------
TASSS3      (622)   -------KKVDEEHLYMTEHQKRAAEGQMVVNEDELSITEIG--------
OS SSS3     (547)   -------LSIVAIPRESQSKQISIVRRHDPLHLKEVETKDRDGISK----
ZM SSS3     (592)   DGFPKQDLSIVGISNEFQTKLATVGTHDGLLMKGVEAKETSQKTEGDTL
Consensus   (651)           V         Q      V   L   E
                    701                                                  750
STSSS3      (242)   NNAGNVEY---------KG--P----------------------------
AtSSS3      (106)   --------------------------------------------------
VUSSS3      (180)   --------------------------------------------------
ATaSSS3     (640)   --------------------------------------------------
TASSS3      (657)   --------------------------------------------------
OS SSS3     (586)   --------------------------------------------------
ZM SSS3     (642)   QATFNVDNLSQKQEGLTKEADEITIIEKINDEDLVMIEEQKSIAMNEEQT
Consensus   (701)
                    751                                                  800
STSSS3      (253)   ---------VASKLLEITKASDVEHTESNEIDDLDTNSFFKSDLIEEDEP
AtSSS3      (106)   --------------------------------------------------
VUSSS3      (180)   -------------------LYYAEIDGNLRGTYTDTNGEIAGNIVEETSA
ATaSSS3     (640)   --------------MGRGDKIQHVLSEEELSWSEDEVQLIEDDGQYEVDE
TASSS3      (657)   --------------MGRGDKIQHVLSEEELSWSEDEVQLIEDDGQYEVDE
OS SSS3     (586)   --------------KSGGDDDLPHMLFEEELSQVEDEARAIAYKKQHEVDV
ZM SSS3     (692)   IVTEEDIPMAKVEIGIDKAKFLHILSEEESSWDENEVGIIEADEQYEVDE
Consensus   (751)                    HVLSEEE S  EDE   I D QYEVD
                    801                                                  850
STSSS3      (294)   LAAGTVETGDSSLNLRLEMEANLRRQAIERLAEENLLQGIRLFCFPEVVK
AtSSS3      (106)   -------------------NLRRKEIETLAAENLARGDRMFVYPVTVK
VUSSS3      (211)   AIDDVKINEEASRMLKLKLEENLRKQEIERIAEENFLRGAKLFVPPVVK
ATaSSS3     (676)   TSVSVNVEQDIQGSPQDVVDPQALKVMLQELAEKNYSMRNKLFVFPEVVK
TASSS3      (693)   TSVSVNVEQDIQGSPQDVVDPQALKVMLQELAEKNYSMRNKLFVFPEVVK
OS SSS3     (623)   ISITP---DIQE-SPQDNIDPQELRRMLQELADQNCSMGNKLFVFPEAVK
ZM SSS3     (742)   TSMST--EQDIQESPNDDIDPQALWSMLQELAEKNYSLGNKLFTYPDVLK
Consensus   (801)    SVS      D    SPQD LDPQ LK MLQELAE NYSMGNKLFVFPEVVK
                    851                                                  900
STSSS3      (344)   PDEDVEIFLNRGLSTLKNESDVLIMGAFNEWRYRSFTTRLTETHLNGDWW
AtSSS3      (135)   PDEDIEVFLNRNLSTLNNEPDVLIMGAFNEWRWKSFTRRLEKTWIHEDWL
VUSSS3      (261)   PDEDIEVFLNKNLSTLSDEPDILILGAFNDWEKSFTIRLNKTHLKDDWW
ATaSSS3     (726)   ADSVIDLYFNRDLTALANEPDVVIKGAFNGWKWRLFTERLHKSDLGGVWW
TASSS3      (743)   ADSVIDLYLNRDLTALANEPDVVIKGAFNGWKWRLFTERLHKSDLGGVWW
OS SSS3     (669)   ANSTIDVYLNRNLSALANEPDVHIKGAFNSWRWRPFTERLHKSELSGDWW
ZM SSS3     (790)   ADSTIDLYFNRDLSAVANEPDVLIKGAFNGWKWRFFTEKIHKSELAGDWW
Consensus   (851)   ADS IDLYLNR LSALANEPDVLIKGAFN WKWR FTERLHKSDL GDWW
```

Fig. 7c

```
                901                                                  950
STSSS3    (394) SCKIIVPKEAYRADFVFFNGQDVYDNNDGNDFSITVKGGMQIIDFENFLL
AtSSS3    (185) SGLLHIPKEAYKMDFVFFNGQSVYDNNDSKDFCVEIKGGMDKVDPENFLL
VUSSS3    (311) SCQLYVPREAYKIDFVFFNGQSVYDNNDQKDFCIPVVGGMDALVFEDFLL
ATaSSS3   (776) SCKLYIPKEAYRLDFVFFNGRTVYENNGNNDFCIGIEGTMNEDLFEDFLV
TASSS3    (793) SCKLYIPKEAYRLDFVFFNGRTVYENNGNNDFCIGIEGTMNEDLFEDFLV
OS SSS3   (719) SCKLHILKEAYRLDFVFFNGRLVYDNNDSNDFVFQVESTMDEDSLFFFLV
ZM SSS3   (840) CCKLYIPKQAYRMDFVFFNGHTVYFNNNNNDFVIQIESTMDENLFEDFLA
Consensus (901) SCKLYIPKEAYRLDFVFFNG TVYDNNDNNDFCI IEGTMDE LFEDFLL
                951                                                 1000
STSSS3    (444) EEKWREQEKLAKEQAFRERLAEFQRRIEAEKAEIEADRAQAKEFAAKKKK
AtSSS3    (235) EEKLREQEKLAKEEAERERQKEEKRRIEAQKAAIEADRAQAKAETQKRRE
VUSSS3    (361) EEKRKELEKLAKEQAERERQAEEQRRIDADKAVKGEDRLQARMEVEKMQD
ATaSSS3   (826) KEKQRELEKLARMEAERRTQTEEQRRKSKEARAADEAVRAQAKAEIEIKNK
TASSS3    (843) KEEQRELEKLAMEEAERRTQTEEQRRKEARAADEAVRAQAKAEIEIKKK
OS SSS3   (769) EEKKRELEKVATEEAERRRHAEEQQRMGEQRAAEQAAREQAKKEIELKKN
ZM SSS3   (890) EEKQRELENLANEEAERRRQTDLQRRMEEERAADKADEVQAKVIVETKKN
Consensus (951) EEK RELEKLA EEAERRRQ EEQRRIEE RAADEADRAQAK EIE KK
                1001                                                1050
STSSS3    (494) VEREIMVKATKTRDITWYIEPSEEKCEDKVRLYYNKSSGPLSHAKDLWIH
AtSSS3    (285) LLQPAIKKAVVSAENVWYIEPSDEKAEDTVKLYYNKRSGPITNSKELWIH
VUSSS3    (411) TLLQLMKNAVTSIDNVWYIEPSEENSNDSVRLYYNGNSGPLQHAKEVWYH
ATaSSS3   (876) KLQSMLSLARTCVDNLWYIEASTDTSGDTIRLYYNRNSRPLAHSTEIWMH
TASSS3    (893) KLQSMLSLARTCVDNLWYIEASTDTRGDTIRLYYNRNSRPLAHSTEIWMH
OS SSS3   (819) KLQNELSSARTIIVDNLWYIEPSTYRQGDTVRLYYNRNSRPLMHSTEIWMH
ZM SSS3   (940) KICNVLGLARAPVDNLWYIEPITTGQEATVRLYYNINGRPLVHSTEIWMH
Consensus (1001) KLQ LL  ART VDNLWYIEPSTF  DTVRLYYNRNSRPL HSTEIWMH
                1051                                                1100
STSSS3    (544) GGYNNWKDGLSIVKELVKSERIDGD-----WWYTEVVFPDQALFLDWVFA
AtSSS3    (335) GGNNWVDGLSIVVKLVNAELKDVDPKSGNWWFAEVVVPGGALVLDWVFA
VUSSS3    (461) GGHNNWKDGILIVERLVKSGLKGGA-----WWYADVVVFDQALVLDWVFA
ATaSSS3   (926) GGYNNWSDGLSIVESFVKCNDRDGD-----WWYADVIPPEKALVLDWVFA
TASSS3    (943) GGYNNWTDGLSIVESFVKCNDKDGD-----WWYADVIPPEKALVLDWVFA
OS SSS3   (869) GGCNSWTEGLSIVERLVECDDENGD-----WWYANVIPEKAFVLDWVFA
ZM SSS3   (990) GGYNWIEGLSFAERLVHHHDKDCD-----WWFADVVVPEKTYVLDWVFA
Consensus (1051) GGYNNW DGLSIVERLVK  DKDGD     WWYADVVVPEKALVLDWVFA
                1101                                                1150
STSSS3    (589) DGPPKHAIAYDNNHRQDFHAIVPN-HIPEELYVVEEEHQTFKTLQEERRL
AtSSS3    (385) DGPPKGAFLYDNNGYQDFHALVPQ-KLPEELYWIEEFNMFERKLQEDRRL
VUSSS3    (506) DGPPQNAVVYDNNRMQDFHAIVPM-ATPDAQYWVEEFQLIYRKLQEERKL
ATaSSS3   (971) DGPAGNARNYDNNARQDFHAILPNNNVTEEGFWVQEFQNIYTRLQERRE
TASSS3    (988) DGPAGNARNYDNNARQDFHAILPNNNVTEEGWAQEFQNIYTRLQERRE
OS SSS3   (914) DGPPGNARNYDNNGRQDFHAILPN-AMTNEEYWVEENCIYTRLHEIRE
ZM SSS3   (1035) DGPPGSARNYDNNGGHDFFATLPN-NMTEEEYWHEEQRIYTRLQQERRE
Consensus (1101) DGPPGNARNYDNNGRQDFHAILPN  MTEE YWVEEEQ IYTRLQ ERRE
                1151                                                1200
STSSS3    (638) REAAMRAKVEKTALIRTETKERTMKSPILSQKHVVYTEPLDIQAGSSVTV
AtSSS3    (434) KEEVMRAKMEKTARLKALTKERTLKRKFLLSQKDVVYTEPIEIQAGNPVIV
VUSSS3    (555) KEEVIRAKAEKTAQMKAFTKEKLLKRLLLSQKHIVYTEPLDIQAGSTVTV
ATaSSS3   (1021) KEETMKRKAFRSANTKAFMKAKTMRRFLLSQKHIVYTEPLEIRAGTTVDV
TASSS3    (1038) KEETMKRKAFRSANTKAFMKAKTMRFFLSQKHIVYTEPLEIRAGTTVDV
OS SSS3   (963) REEAIKIKVEKRAKMKAFMKEKMRMLLSQKHIVYTEPLEHAGTTVDV
ZM SSS3   (1084) REEAIKRKAERNAKMKAEMKEKMRMFVSQKHIVYTEPLEIHAGTTIDV
Consensus (1151) KEE MK KAEKTA MKAEMKEKTMRKFLLSQKHIVYTEPLEI AGTTVDV
```

Fig. 7d

```
                  1201                                             1250
STSSS3     (688)  YYNPANTVLNGKPETWFRCSFNRWTHRLGPLPPQ-KMSPAENGTHVRATV
AtSSS3     (484)  LYNPANTVLNGKPEVWFRGSFNRWTHRLGPLPPQKMEATDEESSHVKTTA
VUSSS3     (605)  FYNPSNTNLNGKPEVWFRGSFNRWSHRNGPLPPQ-RMLPAESGTHVKASV
ATaSSS3    (1071) LYNPSNTVLNGKPEVWFRCSFNLWMHPSGALPPQ-KMVKSGDGPLLKATV
TASSS3     (1088) LYNPSNTVLNGKSEGWTRCSFNLWMHSSGALPLQ-KMVKSGDGPLLKATV
OS SSS3    (1013) LYNPSNTVLNGKPEVWFRWSFNRWMHPSGVLPCK-KMVKTEDGCHLKATV
ZM SSS3    (1134) LYNPSNTVLTGKPEVWFRCSFNRWMYPGGVLPEQ-KMVQAENGSHLKATV
Consensus  (1201) LYNPSNTVLNGKPEVWFRCSFNRWMH G LPPQ KMV AEDGSHLKATV
                  1251                                             1300
STSSS3     (737)  KVPLDAYMMDFVFSEREDGGIFDNKSGMDYHIPVFGGVAKEPPMHIVHIA
AtSSS3     (534)  KVPLDAYMMDFVFSEKEDGGIFDNKNGLDYHLPVVGGISKEPPLHIVHIA
VUSSS3     (654)  KVPLDAYMMDFVFSESLNGGVFDNKFGMDYLIPVFGGIVKEPPMHIVHIA
ATaSSS3    (1120) NVPPDAYMMDFVFSEWEEDGIYDNRNGMDYHIPVSDSIETENYMRIIHIA
TASSS3     (1137) DVPPDAYMMDFVFSEWEEDGIYDNRNGMDYHIPVSDSIETENYMRIIHIA
OS SSS3    (1062) SVPSDAYMMDFVFSLSEEGGIYDNRNGTDYHIPVSGSNAKEPPLHIVHIA
ZM SSS3    (1183) YVPRDAYMMDFVFSLSLEGGIYDNRNGLDYHILVFGSIAKEPPMILVHIA
Consensus  (1251)   VP DAYMMDFVFSE EEGGIYDNRNGMDHIPV GSIAKEPPMHIVHIA
                  1301                                             1350
STSSS3     (787)  VEMAPIAKVGGLGDVVTSLSRAVQDLNHNVEIILPKYDCLKMNNVKDFRF
AtSSS3     (584)  VEMAPIAKVGGLGDVVTSLSRAVQELNHNVDIVFPKYDCTKHNFVKDLQF
VUSSS3     (704)  VEMAPIAKVGGLGDVVTSLSRAVQDLNHNVDIILPKYDCLNLSNVKDLQF
ATaSSS3    (1170) VEMAPVAKVGGLGDVVTSLSRAVQDLGHTVEVILPKYDCLNQSSVKDLHL
TASSS3     (1187) VEMAPVAKVGGLGDVVTSLSRAIQDLGHTVEVILPKYDCLNQSSVKDLHL
OS SSS3    (1112) VEMAPIAKVGGLADVVTSLSRAIQELGHVEVILPKYNFMNQSNVKNLHV
ZM SSS3    (1233) VEMAPIAKVGGLGDVVTSLSRAVQDLGHNVEVILPKYGCLNLSNVKNLQI
Consensus  (1301) VEMAPIAKVGGLGDVVTSLSRAVQDLGHNVEVILPKYDCLN SNVKDL L
                  1351                                             1400
STSSS3     (837)  HKNYFWGGTEIKVWFGKVEGLSVYFLEPQNGLPSKGCVYGCSNDGERFGF
AtSSS3     (634)  NRSYHWGGTEIKVWHGKVFGLSVYFLDPQNCLLQRGCVYGCADDAGRFGF
VUSSS3     (754)  HKSYFWSGTEIKVWHGKVEGLSVYFLEPQNGLLWVGCVYGRANDAERFGF
ATaSSS3    (1220) YQSFSWGGTEIKVWVGRVEDLTVYFLEPQNCMFGVGCVYG-RNDDRRFGF
TASSS3     (1237) YQSFSWGGTEIKVWVGRVEDLTVYFLEPQNCMFGVGCVYG-RNDDRRFGF
OS SSS3    (1162) RQSFSLGGTEIKVWFGLVEDLSVYFLEPQNGMFGGCVYG-GNDAGRFGL
ZM SSS3    (1283) HQSFSWGGSEINVWRGLVEGLCVYFLEPQNGMFGVGYVYG-RDDDRRFGF
Consensus  (1351) HQSFSWGGTEIKVW GKVEGLSVYFLEPQNCMFGVGCVYG NDA RFGF
                  1401                                             1450
STSSS3     (887)  FCHAALEFLLQGGFSPDIIHCHDWSSAPVAWLFKEQYTHYGLSKSRLVFI
AtSSS3     (684)  FCHAALEFLLQGGFHDDIIHCHDWSSAPVSWLFKDHYVFQYGLIKTRVFI
VUSSS3     (804)  FCHAALEFLLQNGSHFDIIHCHDWSSAPVAWLFKEQYTHYGLSKARVVFI
ATaSSS3    (1269) FCHSALEFLLQNEFSFHIIHCHDWSSAPVAWLYKEHYSQSRMASTRVVFI
TASSS3     (1286) FCHSALEFLLQNEFSFHIIHCHDWSSAPVAWLYKEHYSQSRMASTRVVFI
OS SSS3    (1211) FFQSALEFLLGSGSSPHIIHCHDWSSAPVAWLYKEHYAESRLATARILFI
ZM SSS3    (1332) FCRSALEFLLGSGSSFNIIHCHDWSSAPVAWLHKENYAKSSLANARVVFI
Consensus  (1401) FCHSALEFLLQ GFSP IIHCHDWSSAPVAWLFKEHYT S LA TRVVFT
                  1451                                             1500
STSSS3     (937)  IHNLEFGADLIGRAMTNADKATVSPTYSQEVSGNPVIAPLHKFHGTVN
AtSSS3     (734)  IHNLEFGANAIGKAMTFADKATTVSPTYAKEVAGNSVISALYKFHGIIN
VUSSS3     (854)  IHNLEFGANLIGKAMAYADKATTVSPTYSRETAGNHAVATLHKFHGIIN
ATaSSS3    (1319) IHNLEFGAHYIGKAMTYCDKATTVSPTYSRDVAGHGAIAPHREKFYGILN
TASSS3     (1336) IHNLEFGAHYIGKAMTYCDKATTVSPTYSRDVAGHGAIAPHREKFYGILN
OS SSS3    (1261) IHNLEFGAHFIGKAMTYCDKATTVSHTYSKEVAGHGAIAPHRGNFYGILN
ZM SSS3    (1382) IHNLEFGAHHIGKAMRYCDKATTVSNTYSKEVSGHGAIVPHLGKFYGILN
Consensus  (1451) IHNLEFGAH IGKAMTYCDKATTVSPTYSKEVAGHGAIAPHL KFYGILN
```

Fig. 7e

```
                    1501                                              1550
STSSS3    (987)  GIDPDIWDPLNDKFIPIPYTSENVVEGKTAAKEALQRKLGLKQADLPLVG
AtSSS3    (784)  GIDPDIWDPYNDNFIPVPYTSENVVEGKRAAKEELQNRLGLKSADFPVVG
VUSSS3    (904)  GIDPDIWDPFNDNSIPVPYTAENVVEGKRASKEALQQKLGLKKADLPLVG
ATaSSS3  (1369)  GIDPDIWDPYTDNFIPVPYTCENVVEGKRAAKRALQQKFGLQQTDVPIVG
TASSS3   (1386)  GIDPDIWDPYTDNFIPVPYTCENVVEGKRAAKRALQQKFGLQQTDVIIVG
OS SSS3  (1311)  GIDPDIWDEYTDNFIPMHYTSENVVEGKNAAKRALQQRFGLQQTDVPIVG
ZM SSS3  (1432)  GIDPDIWDFYNDNFIPVHYTCENVVEGKRAAKRALQQKFGLQQIDVPVVG
Consensus(1501)  GIDPDIWDPYNDNFIPVPYTSENVVEGKRAAKRALQQKFGLQQ DVPIVG
                    1551                                              1600
STSSS3   (1037)  IITRLTHQKGIHLIKHAIWRTLERNGQVVLLGSAPDPRVQNDFVNLANQL
AtSSS3    (834)  IITRLTHQKGIHLIKHAIWRTLERNGQVVLLGSAPDPRIQNDFVNLANQL
VUSSS3    (954)  VITRLTHQKGIHLIKHAIWRTLERGGQVVLLGSAPDHRIQNDFVNLANQL
ATaSSS3  (1419)  IITRLTAQKGIHLIKHAIHRTLESNGQVVLLGSAPDHRIQGDFCRIADAL
TASSS3   (1436)  IITRLTAQKGIHLIKHAIHRTLESNGHVVLLGSAPDHRIQGDFCRIADAL
OS SSS3  (1361)  IITRLTAQKGIHLIKHAIHRTLERNGQVVLLGSAPDPRIQSDFCRIADSL
ZM SSS3  (1482)  IVTRLTAQKGIHLIKHAIHRTLERNGQVVLLGSAPDSRIQADFVNLANTL
Consensus(1551)  IITRLTAQKGIHLIKHAIHRTLERNGQVVLLGSAPD RIQ DFVNLAN L
                    1601                                              1650
STSSS3   (1087)  HSKYNDRARECLTYDEPLSHLIYAGADFILVPSIFEPCGLTQLTAMRYGS
AtSSS3    (884)  HSSHGDRAREVLTYDEPLSHLIYAGADFILVPSIFEPCGLTQLTAMRYGA
VUSSS3   (1004)  HSSHNDRARECLAYDEPLSHMIYAGADFILVPSIFEPCGLTQLTAMRYGS
ATaSSS3  (1469)  HGVYHGRVKLVLTYDEPLSHLIYAGSDFILVPSIFEPCGLTQLVAMRYGS
TASSS3   (1486)  HGVYHGRVKLVLTYDEPLSHLIYAGSDFILVPSIFEPCGLTQLVAMRYGS
OS SSS3  (1411)  HGENHGRVRLCLTYDEPLSHLIYAGSDFILVPSIFEPCGLTQLVAMRYGS
ZM SSS3  (1532)  HGVNHGQVRLSLTYDEPLSHLIYAGSDFILVPSIFEPCGLTQLVAMRYGI
Consensus(1601)  HG YHGRVRL LTYDEPLSHLIYAGSDFILVPSIFEPCGLTQLVAMRYGS
                    1651                                              1700
STSSS3   (1137)  IPVVRKTGGLYDTVFDVDHDKERAQQCGLEPNGFSFDGADAGGVDYALNR
AtSSS3    (934)  VPVVRKTGGLFDTVFDVDHDKERAQAQVLEPNGFSFDGADAPGVDYALNR
VUSSS3   (1054)  IPIVRKTGGLYDTVFDVNDKDRAQVQGLEPNGFSFDGADAGGVDYALNR
ATaSSS3  (1519)  IPIVKKTGGLYDTVFDVNDKDKARSLGLEPNGFSFDGADSNGVDYALNR
TASSS3   (1536)  IPIVRKTGGLHDTVFDVNDKDRARSLGLEPNGFSFDGADSNGVDYALNR
OS SSS3  (1461)  IPIVRKTGGLYDTVFDVDHDKDRARVLCLEPNGFSFDGADCNGVDYALNR
ZM SSS3  (1582)  IPIVRKTGGLFDTVFDVDNDKERARDRGLEPNGFSFDGADSNGVDYALNR
Consensus(1651)  IPIVRKTGGLYDTVFDVDNDKDRAR   GLEPNGFSFDGADANGVDYALNR
                    1701                                       1744
STSSS3   (1187)  AISAWYDGRDWFNSLCRQVMEQDWSWNRPALDYLELYHAARKLE
AtSSS3    (984)  AISAWYDGREWFNSLCKTVMEQDWSWNRPALEYLELYHSARK---
VUSSS3   (1104)  AISAWYDGREWFNTLCKTVMEQDWSWNRPALDYLELYHAACKLE
ATaSSS3  (1569)  AIGAWFDARDWFHSLCKRVMEQDWSWNRPALDYIELYHAARKF-
TASSS3   (1586)  AIGAWFDARDWFHSLCKRVMEQDWSWNRPALDYIELYHAARKF-
OS SSS3  (1511)  AISSWFEARGWFHSLCKRVMEQDWSWNRPALDYIELYHSAHKF-
ZM SSS3  (1632)  AISAWFDARSWFHSLCKRVMEQDWSWNRPALDYIELYRSASKL-
Consensus(1701)  AISAWFDARDWFHSLCKRVMEQDWSWNRPALDYIELYHAARK
```

Fig. 7f

EXPRESSION CASSETTE FOR NUCLEIC ACIDS IN PLANT TISSUE CONTAINING STARCH

RELATED APPLICATIONS

This application is a national stage application (under 35 U.S.C. 371) of PCT/EP2004/000241 filed Jan. 15, 2004 which claims benefit to German application 103 02 324.0 filed Jan. 20, 2003.

SEQUENCE LISTING SUBMISSION

The Sequence Listing associated with this application is filed in electronic format via EPS-Web and hereby incorporated by reference into the specification in its entirety. The name of the text file containing the Sequence Listing is SequenceListing_13173_00015. The size of the text file is 219 KB, and the text file was created on Apr. 25, 2008.

The invention relates to methods for the transgenic expression of nucleic acid sequences predominantly in starch-comprising tissues of plants, preferably in fruits, roots, seeds or tubers, wherein the nucleic acid sequence is expressed under the control of a promoter of a starch synthase 3. Furthermore in accordance with the invention are transgenic expression cassettes and vectors comprising a promoter of a starch synthase 3, and the use thereof for the production of foodstuffs, feedstuffs, seed, pharmaceuticals or fine chemicals.

The aim of plant biotechnology work is the generation of plants with improved properties, for example for increasing agricultural productivity. Transcriptional regulatory sequences or promoters which regulate the expression of genes in plants are essential elements of plant biotechnology. Various promoters which have been used successfully for the expression of heterologous genes in plants are available; they comprise not only plant promoters (such as, for example, cauliflower heat shock protein hsp80 promoters; U.S. Pat. No. 5,612,472), but also promoters from other nonplant sources such as, for example, promoters of plant viruses (for example the cauliflower mosaic virus 35S promoter) or of plant-infecting bacteria (for example the promoter of the agrobacterial octopine synthase; Leisner and Gelvin (1988) Proc Natl Acad Sci USA 85(8):2553-2557).

Frequently, what are known as constitutive promoters, which regulate, in the plant, the expression of a gene product largely at any time and in any tissue are employed for the expression of heterologous nucleic acid sequences in transgenic plants. A directed expression of genes in specific plant parts or at specific points in time of development is not possible using these promoters. Thus, the protein to be expressed transgenically is expressed at locations and at times where it is not required, which, for example, unnecessarily consumes energy, causes metabolic modifications and can thus have an adverse effect on plant growth. For reasons of product licensing and product acceptance too, it is desirable to express a transgenic protein only where it is required owing to its intended effect.

Tissue- and development-specific promoters are of great interest for this purpose. Various such promoters are known. Thus, the promoter of the *Vicia faba* "sucrose-binding-protein-like gene" (SBP) mediates strong and specific expression in seeds of oilseed rape and other plants (WO 00/26388).

Fruits, seeds, beets/swollen tap roots or tubers, being important storage organs of plant organisms, are of great agronomical relevance. They serve for the storage of proteins, oils and carbohydrates (in particular starch). As a rule, such tissues are photosynthetically inactive and are also referred to as sink tissues or sink organs. They rely on the import of photoassimilates from the photosynthetically active plant parts (source organs or source tissues). Both traditional breeding and biotechnological methods have been used for improving specific aspects of fruit and tuber quality. High-quality, mature fruits are the result of a number of coordinated biochemical and metabolic modifications which can occur not only during maturation, but also during fruit development. These modifications determine the final quality and the quantity of the fruits. Examples of modified properties, for example in the case of tomato fruits, are increased sucrose import, conversion of starch, accumulation of various organic acids, modifications of pigments and modifications in fungicidal and insecticidal compounds. Such results can be achieved by means of the overexpression of genes/proteins or by inhibition by means of double-stranded RNA, antisense RNA or cosuppression. Since sink tissues act as storage site of the most important plant raw materials, promoters which make possible a selective expression in these tissues are of particular interest in plant biotechnology since they permit a directed modification of these tissues and of their constituents.

The skilled worker is familiar with a variety of promoters which can be used for the expression of nucleic acid sequences in fruits, seeds or tubers. The promoter of the tomato genomic clone 2A11 must be mentioned (Pear et al. (1989) Plant Mol Biol 13:639-651; WO 91/19806). However, the 2A11 promoter governs expression during the very early stages and is relatively weak. The tomato ethylene-inducible E4 and E8 promoters (U.S. Pat. No. 5,859,330; Deickmann et al. (1988) EMBO J. 7:3315-3320) and the polygalacturonase promoter (U.S. Pat. No. 6,127,179) have likewise been described as being fruit-specific. The abovementioned promoters, however, show expression only during the late phases of fruit development, and their use is therefore only limited. The promoters TFM7 and TFM9 (U.S. Pat. No. 5,608,150) are active during fruit development in green and yellow stages. The fruit-specific regulation of the kiwi fruit actinidin promoter has been detected for expression in petunia (Lin et al. (1993) Plant Mol Biol 23:489-499). Thi-1, MADS2 and a promoter fusion between Thi-1 and the melon actin promoter regulate the expression of heterologous genes specifically in apples (WO 00/66610).

Further promoters are, for example, promoters with specificity for tubers, storage roots or other roots such as, for example, the tuber-specific patatin class I promoter (Bevan et al. (1986) Nucl Acids Res 14:4625-4638), the potato cathepsin D inhibitor promoter (Herbers et al. (1994) Plant Mol. Biol. 26: 73-83), the starch synthase (GBSS1) promoter or the sporamin promoter. Other genes with specific high activity in tubers are, for example, the promoter of the ADP-glucose pyrophosphorylase gene (Müller-Röber et al. (1990) Mol Gen Genet 224:136-146), of sucrose synthase (Salanoubat and Belliard (1987) Gene 60:47-56; Salanoubat and Belliard (1989) Gene 84:181-185), the promoters of the 22 kD protein complex and of the proteinase inhibitor (Hannapel (1990) Plant Physiol 94:919-925) and the other class I patatins (B33) (EP-A1 0 375 092; Rocha-Sosa et al. (1989) EMBO J. 8:23-29). A disadvantage of the patatin 1 promoter is that it is induced by high sucrose concentrations, also in tissues other than the tuber (Jefferson R et al. (1990) Plant Mol Biol 14:995-1006).

The promoters described in the prior art have one or more of the following disadvantages:

1) The promoters do not show the desired expression level and/or are active in a few plant species only.

2) The promoters are only active very early or very late during fruit or tuber development.
3) The expression pattern does not agree with what has been expected, i.e. for example undesired expression activities in other tissues are found.
4) The expression of many of the abovementioned promoters is ethylene-dependent.

Moreover, the number of existing promoters is greatly limited. This may become a limiting factor, in particular in approaches which require the expression of more than one heterologous nucleic acid sequence. The expression, under the same promoter, of different heterologous sequences, in one plant organism, can result in "switching off" ("epigenic silencing") of the transgenic expression cassettes in question (Mette et al. (1999) EMBO J 18:241-248).

A multiplicity of biosynthetic enzymes such as, for example, the starch synthases (EC 2.4.1.21) are involved in the synthesis of starch, which takes place in the plastids of higher plants. Starch synthases serve for extending the chain of α-1,4-glucans by means of transferring glucosyl units from ADP-glucose to the non-reducing ends of existing α-1,4-glucans. In addition to the granule-bound starch synthase (GBSS), three further classes of starch synthases in plants are described: SS1 (wheat: Li et al. (1999) Theor Appl Genet 98:1208-1216; GenBank Acc. No.: U48227; rice: Baba et al. (1993) Plant Physiol 103:565-573; potato: Genbank Acc. No.: Y10416), SS2 (pea: Dry et al. (1992) Plant J 2:193-202; potato: Edwards et al. (1995) Plant J 8:283-294; maize: Harn et al. (1998) Plant Mol Biol 37:639-649; GenBank Acc. No. U66377) and SS3 (potato: Abel et al. (1996) Plant J 10:981-91, Marshall et al. (1996) Plant Cell 8:1121-1135; maize: Gao et al. (1998) Plant Cell 10:399-412).

Various publications describe the isolation and characterization of soluble starch synthases from the potato tuber, of which three isoforms in the soluble fraction of potato tuber extracts are known. For example, known are the isoform 3 (Marshall et al. (1996) Plant J 10:981-991; GenBank Acc. No.: X95759; EP 0779363-A3), the SS1 isoform (GenBank Acc. No.: Y10416; Kossmann et al. (1999) Planta 208:503-11), which is expressed predominantly in leaves and only a little in tubers. Furthermore, there are described the soluble starch synthase 3 from potato (GenBank Acc. No.: X94400; Abel et al. (1996) Plant J 10:981-91), maize (GenBank Acc. No.: AF023159, A93359), rice (GenBank Acc. No.:D16202), wheat (GenBank Acc. No.: AJ292522 *Triticum aestivum*; AF258609 *Aegilops tauschii*), from the asparagus bean (*Vigna unguiculata*; GenBank Acc. No.: AJ225088), and *Arabidopsis* (GenBank Acc. No.: AC007296). Abel et al. teach that the potato SSS3 is predominantly expressed in the tubers, but also in the sink-and-source leaves. Promoters of the SSS3 genes or transgenic expression constructs comprising them are not described.

It was therefore an object to provide novel promoters and transgenic expression cassettes derived therefrom, which ensure a transgenic expression of nucleic acid sequences during the entire development time of the tubers from the youngest stages to the storage of the tubers and which have a high specificity for starch-comprising tissues. This object is achieved by the present invention.

A first subject of the invention relates to methods for the directed, transgenic expression of nucleic acid sequences in at least one starch-comprising tissue of a plant, which comprises the following steps 1. introducing, into plant cells, a transgenic expression cassette, where the transgenic expression cassette comprises at least the following elements a) at least one promoter sequence of a gene encoding a starch synthase 3, and b) at least one further nucleic acid sequence, where at least one of said promoter sequences and a further nucleic acid sequence are functionally linked with one another and said further nucleic acid sequence is heterologous with regard to the promoter sequence, and 2. selection of transgenic cells which comprise said expression cassette stably integrated into the genome, and 3. regeneration of intact plants from said transgenic cells, where at least one of the further nucleic acid sequence is expressed in a starch-comprising tissue in a directed manner.

A further subject of the invention therefore relates to an isolated nucleic acid sequence comprising the promoter of the starch synthase 3 from potato. Preferably, said isolated nucleic acid sequence comprises a nucleic acid sequence selected from 1. the sequences as shown in SEQ ID NO: 1 or 44 or the sequences which are complementary thereto, 2. fragments of at least 25 contiguous nucleotides, preferably at least 50 contiguous nucleotides, especially preferably at least 100 contiguous nucleotides, of the sequence as shown in SEQ ID NO: 1 or 44 or the sequences which are complementary thereto, 3. sequences which have at least 50%, preferably 70%, by preference at least 80%, especially preferably at least 90%, very especially preferably at least 95%, most preferably 99%, homology with the sequence as shown in SEQ ID NO: 1 or 44 or the sequences which are complementary thereto, where the homology extends over a length of at least 100 base pairs, preferably at least 200 base pairs, especially preferably at least 300 base pairs, very especially preferably at least 400 base pairs, most preferably over the entire length of the sequence as shown in SEQ ID NO: 1 or 44.

In the context of the present invention, homology between two nucleic acids is understood as meaning the identity of the nucleic acid sequence over the sequence length indicated in each case, which is calculated by comparison with the aid of the GAP program algorithm (Wisconsin Package Version 10.0, University of Wisconsin, Genetics Computer Group (GCG), Madison, USA), setting the following parameters:

| Gap Weight: 12 | Length Weight: 4 |
|---|---|
| Average Match: 2.912 | Average Mismatch: −2.003 |

For example, a sequence which has at least 50% homology with the sequence SEQ ID NO: 1 on nucleic acid basis over the entire length of the sequence as shown in SEQ ID NO:1 is understood as meaning a sequence which, upon comparison with the sequence SEQ ID NO: 1 by the above program algorithm with the above set of parameters has at least 50% homology.

A further subject relates to transgenic expression cassettes as they can be employed for example in the method according to the invention. Preferably, the transgenic expression cassettes for the directed, transgenic expression of nucleic acid sequences in at least one starch-comprising tissue of a plant comprise a) at least one promoter sequence of a gene coding for a starch synthase 3, and b) at least one further nucleic acid sequence, where at least one promoter sequence and one further nucleic acid sequence are functionally linked with one another and the further nucleic acid sequence is heterologous with regard to the promoter sequence.

The expression cassettes according to the invention may comprise further genetic control sequences and/or additional functional elements. Preferably, the transgenic expression cassettes can make possible, owing to the nucleic acid sequence to be expressed transgenically, the expression of a protein encoded by said nucleic acid sequence and/or the expression of a sense RNA, antisense RNA or double-stranded RNA encoded by said nucleic acid sequence.

A further subject of the invention relates to transgenic expression vectors which comprise one of the expression cassettes according to the invention.

A further subject of the invention relates to transgenic organisms which comprise one of the expression cassettes or expression vectors according to the invention. The organism can be selected from the group consisting of bacteria, yeasts, fungi, nonhuman animal and plant organisms or cells, cell cultures, parts, tissues, organs or propagation material derived therefrom; preferably, the organism is selected from the group of the agricultural useful plants. In said plants, the expression of the nucleic acid sequence to be expressed transgenically is preferably higher in at least one starch-comprising tissue, (for example the potato tuber, beet/swollen tap root or other root, the seed or the tomato fruit) than in another tissue.

A further subject relates to the use of the isolated nucleic acid sequences, transgenic expression vectors or transgenic organisms according to the invention for the transgenic expression of nucleic acids and/or proteins. Especially preferred is the use of said transgenic organisms or of cells, cell cultures, parts, tissues, organs or propagation material derived therefrom for the production of foodstuffs, feedstuffs, seed, pharmaceuticals or fine chemicals, the fine chemicals preferably being enzymes, vitamins, amino acids, sugars, saturated or unsaturated fatty acids, natural or synthetic flavorings, aroma substances or colorings. Furthermore comprised by the invention are methods for the production of said foodstuffs, feedstuffs, seed, pharmaceuticals or fine chemicals using the transgenic organisms according to the invention or cells, cell cultures, parts, tissues, organs or propagation material derived therefrom.

A particular advantage of the starch synthase 3 promoters according to the invention is their activity in starch-comprising tissues, preferably during the entire development and storage of potato tubers, and its high activity in green tomato fruits.

The expression of the natural starch synthase 3 from potato (i.e. the expression activity of the nontransgenic, homologous combination of the starch synthase 3 promoter and the coding region of the starch synthase 3 gene) also shows significant expression in the leaves (Abel et al. (1996) Plant J 10:981-91). In contrast, the heterologous transgenic expression cassettes provided within the scope of the present invention show no relevant expression in leaves, which is of great importance for a number of biotechnological applications.

The starch synthase 3 (SSS3) promoters provided within the scope of the present invention, in particular the potato SSS3 promoter, mediate not only high expression during all of the tuber development right into the late storage phase, but also high tissue specificity, which underlines the significant value for the exploitation in transgenic plants. An analysis in tomato has revealed that the SSS3 promoter likewise brings about strong expression in the fruits, predominantly in the green fruits. Weak secondary activities were only found in pollen and seed. Of particular interest is a pronounced activity post-harvest and during the storage of the transgenic plants (in particular tubers). This makes the promoters according to the invention suitable for what are known as post-harvest applications.

Owing to its high expression activity and specificity, the SSS3 promoter according to the invention is of particular value for plant biotechnology. Owing to the function of the soluble starch synthase 3 in the starch metabolism and the expression pattern which has been found, it can be expected that the promoter is active in all starch-comprising tissues, preferably in fruits, seeds, beets/swollen tap roots and tubers, of other plants. Very specially advantageous in this context is the use in approaches which serve for the modification of the carbohydrate and/or starch metabolism. Owing to their fruit or tuber specificity, the promoters according to the invention can be employed in particular for improving the quality of the developing fruit or tuber or for influencing the maturation process. In this context, it is preferred to transgenically express, under the control of the promoters according to the invention, nucleic acid sequences which influence a modulation of the sugar or starch metabolism, a modification of constituents, an improvement of nutritional values, a modification of the sink-source relations, flavor components, pathogen resistance, tissue consistency and the like. In the tomato fruits, for example, an SSS3 promoter can be employed for the modification of flavanoids and carotenoids. Specific use forms are listed hereinbelow. The genes which are regulated by the promoter according to the invention can be plant genes, fruit- and tuber-specific genes or heterologous genes whose expression in the fruits or tubers is desired.

"Promoter of a starch synthase 3 gene" or "starch synthase 3 promoter" (hereinbelow also SSS3 promoter) generally refers to the natural regulatory region of a gene coding for a starch synthase 3. The starch synthase 3 is also known as soluble starch synthase or soluble starch synthase 3. Analogous names are to be understood synonymously. Preferred promoters are those which comprise a sequence region of at least 250 base pairs, preferably at least 500 base pairs, especially preferably 1000 base pairs, most preferably at least 2000 base pairs in 5' direction upstream of the ATG start codon of said genomic sequences coding for a starch synthase 3.

For the purposes of the present invention, "starch synthase" means any enzymatically active peptide, polypeptide, oligopeptide, protein or enzyme molecule which is at least capable of transferring one glucosyl unit from ADP-glucose to an α-1,4-glucan molecule, and fragments of said enzymatically active molecules.

"Starch synthase 3", "soluble starch synthase 3" or "SSS3" means a starch synthase as defined above which furthermore has one or more of the following characteristics:

1. it is encoded by a nucleotide sequence comprising at least 20 nucleotides of a sequence as shown in SEQ ID NO: 5, 7, 9, 11, 13, 15 or 17;
2. it is encoded by a nucleotide sequence comprising a sequence which has at least 85% or more homology with a sequence as shown in SEQ ID NO: 5, 7, 9, 11, 13, 15 or 17;
3. it comprises an amino acid sequence with at least 85% homology with one of the sequences as shown in SEQ ID NO: 6, 8, 10, 12, 14, 16 or 18;
4. it comprises a sequence of at least 10 contiguous amino acids, preferably at least 20 contiguous amino acids, especially preferably at least 50 contiguous amino acids, of a sequence as shown in SEQ ID NO: 6, 8, 10, 12, 14, 16 or 18;

and wherein the amino acid sequence encoding for the starch synthase comprises at least one sequence motif selected from the group consisting of:

| | |
|---|---|
| (a) NE(P/S)DVXI(K/M)GAFN, | (SEQ ID NO: 19) |
| (b) PK(E/Q)AY(R/K)XDFVFFNG, | (SEQ ID NO: 20) |
| (c) DWVFADGP, | (SEQ ID NO: 21) |
| (d) FL(V/L)SQK(H/D)(V/I)VYTEPL, | (SEQ ID NO: 22) |
| (e) YNP(A/S)NT(V/N)L(N/T)GKPE(V/I)WFRXSFN, | (SEQ ID NO: 23) |
| (f) DAYMMDFVFSE, | (SEQ ID NO: 24) |
| (g) KVGGL(G/A)DVVTS, | (SEQ ID NO: 25) |
| preferably AKVGGL(G/A)DVVTSLSRA, | (SEQ ID NO: 26) |
| (h) HCHDWSSAPV(A/S)WL, | (SEQ ID NO: 27) |
| (i) FTIHNLEFGA, | (SEQ ID NO: 28) |
| (j) NGIDPDIWDP, | (SEQ ID NO: 29) |
| preferably GI(L/V/I)NGIDPDIWDP(Y/L)(T/N)D(N/K)FIP, | (SEQ ID NO: 30) |
| (k) VG(I/V)ITRLT(A/H)QKG, | (SEQ ID NO: 31) |
| preferably VG(I/V)ITRLT(A/H)QKGIHLIKHA, | (SEQ ID NO: 32) |
| (l) NGQVVLLGSA, | (SEQ ID NO: 33) |
| preferably TLERNGQVVLLGSAPD, | (SEQ ID NO: 34) |
| (m) LTYDEPLSHLIY, | (SEQ ID NO: 35) |
| (n) DFI(L/I)VPSIFEPCGLTQL, | (SEQ ID NO: 36) |
| preferably AG(S/A)DFI(L/I)VPSIFEPCGLTQL(V/I)AMRYG, | (SEQ ID NO: 37) |
| (h) DTVFDVD(H/N)DK, and | (SEQ ID NO: 38) |
| (i) VMEQDWSWNRP | (SEQ ID NO: 39) |

Further motifs which are characteristic of SSS3 proteins can be deduced readily from a comparison with known SSS3 protein or nucleic acid sequences (cf. FIG. 7).

Homology between two polypeptides is understood as meaning the identity of the amino acid sequence over the sequence length in each case, which is calculated by comparison with the aid of the GAP program algorithm (Wisconsin Package Version 10.0, University of Wisconsin, Genetics Computer Group (GCG), Madison, USA), setting the following parameters:

| | |
|---|---|
| Gap Weight: 8 | Length Weight: 2 |
| Average Match: 2.912 | Average Mismatch: −2.003 |

For example, a sequence which has at least 85% homology with the sequence SEQ ID NO: 6 on protein basis over the entire length is understood as meaning a sequence which, upon comparison with the sequence SEQ ID NO: 6 by the above program algorithm with the above set of parameters has at least 85% homology.

In particular, SSS3 promoter means nucleotide sequences which comprise a nucleic acid sequence selected from among 1. the sequences SEQ ID NO: 1, 2, 3, 4 or 44, or the sequences which are complementary thereto,
2. fragments of at least 25 contiguous nucleotides, preferably at least 50 contiguous nucleotides, especially preferably at least 100 contiguous nucleotides, of a sequence as shown in SEQ ID NO: 1, 2, 3, 4 or 44 or the sequences which are complementary thereto,
3. sequences which have at least 50%, preferably 70%, by preference at least 80%, especially preferably at least 90%, very especially preferably at least 95%, most preferably 99%, homology with one of the sequences as shown in SEQ ID NO: 1, 2, 3, 4 or 44 or the sequences which are complementary thereto, where the homology extends over a length of at least 100 base pairs, preferably at least 200 base pairs, especially preferably at least 300 base pairs, very especially preferably at least 400 base pairs, most preferably at least 500 base pairs.

Most preferably, an SSS3 promoter comprises the promoter of the potato SSS3 as shown in SEQ ID NO: 1 or 44 or fragments thereof with a length of at least 50 nucleotides, preferably 100 nucleotides.

Especially preferably, an SSS3 promoter has essentially the same promoter activity as one of the promoters as shown in SEQ ID NO: 1, 2, 3, 4 or 44, preferably as the promoter as shown in SEQ ID NO: 1 or 44. In this context, the expression level can deviate down or else up in comparison with a comparative value. Preferred in this context are those sequences whose expression level, measured with reference to the transcribed mRNA or the subsequently translated protein, differs quantitatively under otherwise unaltered conditions by not more than 50%, preferably 25%, especially preferably 10%, from a comparative value obtained with the promoters described by SEQ ID NO: 1 or 44. Especially preferred are those sequences whose expression level, measured with reference to the transcribed mRNA or the subsequently translated protein, exceeds quantitatively under otherwise unaltered conditions by more than 50%, preferably 100%, especially preferably 500%, very especially preferably 1000% a comparative value obtained with the promoter described by SEQ ID NO: 1 or 44.

A promoter activity is referred to as "essentially the same" with regard to an SSS3 promoter when the transcription of a certain nucleic acid sequence to be expressed transgenically under the control of said functionally equivalent promoter under otherwise unaltered conditions shows a directed expression in at least one starch-comprising tissue.

"Starch-comprising tissue" means tissues which, at least at one point in time of their development have a starch content which can be detected by means of a starch test. Preferred as starch test is staining with Lugol's solution (Lugol's solution: for example: dissolve 2 g of KI in 5 ml of water, therein dissolve 1 g of iodine, and add 300 ml of water). The staining procedure is carried out until a blue coloration is visible (approximately 15 min at RT) and can be stopped by washing with water. The starch content may also be determined photometrically by means of the method described by Hajirezaei et al. (1994, Planta 192: 16-30).

Especially preferably, "starch-comprising tissue" means storage tissue of a plant tuber, beet/swollen tap root or fruit such as, for example, the potato tuber, beetroot or tomato fruit. "Starch-comprising tissue" also comprises "sink tissues" of starch-producing plants. "Sink-tissue" means tissues which are net importers of photosynthetically fixed carbon dioxide and, as a rule, are not photosynthetically active. Examples of sink tissues which may be mentioned are: fruits, beets/swollen tap roots and other roots, tubers and seed kernels.

The expression under the control of one of the promoters according to the invention in a carbohydrate-storing, -synthesizing or -metabolizing sink tissue or a starch sink tissue amounts to preferably at least twice, very especially preferably at least five times, most preferably at least ten times that in another tissue, for example a source tissue.

"Directed" with regard to the expression in a starch-comprising tissue preferably means that the expression under the control of one of the promoters according to the invention in a first tissue amounts to preferably at least ten times, very especially preferably at least fifty times, most preferably at least hundred times that of a second tissue, the starch content in the first tissue (for example as determined by staining with Lugol's solution) amounting to at least twice, preferably at least five times, especially preferably at least ten times, most preferably at least fifty times, the starch content in the second tissue. For example "directed" means that the expression under the control of one of the promoters according to the invention in a starch-comprising "sink" tissue such as the tubers amounts to preferably at least ten times, especially preferably at least fifty times, most preferably at least hundred times that in a "source tissue", such as the leaves.

"Otherwise unaltered conditions" means that the expression which is initiated by one of the transgenic expression cassettes to be compared is not modified by combination with additional genetic control sequences, for example enhancer sequences. Unaltered conditions furthermore means that all external conditions such as, for example, plant species, developmental stage of the plants, culture conditions, assay conditions (such as buffer, temperature, substrates and the like) are kept identical between the expressions to be compared.

Preferably, the expression within at least one particular starch-comprising tissue is essentially constant over all developmental stages. "Essentially constant" means in this context preferably that the standard deviation of the expression between the individual point in time of the development of the tissue in question is less than 50%, preferably 20%, especially preferably 10%, very especially preferably 5%, based on the statistic mean of the expression over all the points in time of the developments.

Nucleic acid sequences which are preferably employed in the context of the determination of the expression level are nucleic acid sequences in functional linkage with the promoter to be tested which code for readily quantifiable proteins. Very especially preferred in this context are reporter proteins (Schenborn E, Groskreutz D (1999) Mol Biotechnol 13(1): 29-44) such as "green fluorescence protein" (GFP) (Chui W L et al. (1996) Curr Biol 6:325-330; Leffel S M et al. (1997) Biotechniques 23(5):912-8), chloramphenicol transferase, luciferase (Millar et al. (1992) Plant Mol Biol Rep 10:324-414), β-glucuronidase or β-galactosidase. β-Glucuronidase (Jefferson et al. (1987) EMBO J. 6:3901-3907) is very especially preferred.

The invention furthermore relates to the use of at least one nucleic acid sequence or a part thereof in methods for the identification and/or isolation of promoters of genes which code for said nucleic acid sequence, where said nucleic acid sequence codes for an amino acid sequence which comprises at least one sequence motif as shown in SEQ ID NO: 19, 20, 21, 22, 23, 24, 25, 26, 27, 28, 29, 30, 31, 32, 33, 34, 35, 36, 37, 38 or 39 or a variation stated for these sequences. Preferably, said nucleic acid sequence codes for an amino acid sequence comprising a sequence as shown in SEQ ID NO: 6, 8, 10, 12, 14, 16 or 18. Especially preferably, said nucleic acid sequence comprises a sequence as shown in SEQ ID NO: 5, 7, 9, 11, 13, 15 or 17. "Part" with regard to the nucleic acid sequence preferably means a sequence of at least 15 bases, preferably 25 bases, especially preferably 50 bases, most preferably 100 bases.

Also encompassed by the invention are methods for the identification and/or isolation of promoters of SSS3 genes, wherein at least one nucleic acid sequence or part thereof is employed in the identification and/or isolation, where said nucleic acid sequence codes for an amino acid sequence which comprises at least one sequence as shown in SEQ ID NO: 19, 20, 21, 22, 23, 24, 25, 26, 27, 28, 29, 30, 31, 32, 33, 34, 35, 36, 37, 38 or 39 or a variation stated for these sequences. Preferably, said nucleic acid sequence codes for an amino acid sequence comprising a sequence as shown in SEQ ID NO: 6, 8, 10, 12, 14, 16 or 18. Especially preferably, said nucleic acid sequence comprises a sequence as shown in SEQ ID NO: 5, 7, 9, 11, 13, 15 or 17. "Part" with regard to the nucleic acid sequence preferably means a sequence of at least 15 bases, preferably 25 bases, especially preferably 50 bases, most preferably 100 bases. In a preferred embodiment, the method according to the invention is based on the polymerase chain reaction, where said nucleic acid sequence or part thereof is employed as primer.

The skilled worker is familiar with various methods in order to identify and isolate the promoter of the gene in question, starting from a nucleic acid sequence (for example a gene transcript such as, for example, a cDNA). In principle, for example all methods for the amplification of flanking chromosomal sequences are available for this purpose. The two methods which are most frequently used are inverse PCR ("iPCR") and thermal asymmetric interlaced PCR ("TAIL PCR").

For "iPCR", genomic DNA of the organism from which the functionally equivalent promoter is to be isolated is digested completely with a given restriction enzyme, and the individual fragments are subsequently religated, i.e. linked with themselves to give a circular molecule, in a dilute mixture. Among the multiplicity of resulting circular DNA molecules are also those which comprise the known sequence (for example the sequence coding for the homologous protein). Starting therefrom, it is possible to amplify the circular molecule by means of PCR by using a primer pair where both primers are capable of annealing with the known sequence segment.

The "TAIL PCR" is based on the use of, firstly, a set of successively truncated highly specific primers which anneal with the known genomic sequence (for example the sequence coding for the homologous protein) and, secondly, a set of shorter random primers with a low melting point, so that a less sequence-specific annealing with genomic DNA which flanks the known genomic sequence takes place. Using such a primer combination, the annealing reaction of the primers onto the DNA to be amplified can be designed in such a way that a specific amplification of the desired target sequence is made possible.

A further possibility of amplifying unknown sequence segments is offered by what is known as the genome walking technology (Clontech). Here, what are known as uncloned, adaptor-ligated libraries of genomic DNA fragments are generated. Using gene-specific and adaptor-specific primers, the desired PCR products which comprise unknown DNA sequences are then amplified in a plurality of PCR steps.

Examples of the promoter sequences employed in the transgenic expression cassettes or transgenic expression vectors according to the invention can be found readily, for example in a variety of organisms whose genomic sequence is known, such as, for example, *Arabidopsis thaliana, Brassica napus, Nicotiana tabacum, Solanum tuberosum, Helianthium*

*annuus, Linum sativum* by homology comparisons in databases. To this end, it is preferred to be able to start from the coding regions of the genes whose promoters are described by SEQ ID NO: 1, 2, 3, 4 or 44. Starting from, for example, the cDNA sequences of these genes described by SEQ ID NO: 5, 7, 9 or 11 or the protein sequences derived therefrom, described by SEQ ID NO: 6, 8, 10 or 12, the corresponding homologous genes in other plant species can be identified readily in the manner with which the skilled worker is familiar by screening databases or genetic libraries (using suitable gene probes).

The invention furthermore relates to methods for the generation of a transgenic expression cassette, with specificity for starch-comprising tissues, comprising the following steps:

I. isolation of a promoter with specificity for starch-comprising tissues, wherein at least one nucleic acid sequence or part thereof is employed in the isolation, where said nucleic acid sequence codes for an amino acid sequence which comprises at least one sequence as shown in SEQ ID NO: 19, 20, 21, 22, 23, 24, 25, 26, 27, 28, 29, 30, 31, 32, 33, 34, 35, 36, 37, 38 or 39 or a variation stated for these sequences.

II. functional linkage of said promoter with a further nucleic acid sequence, where said nucleic acid sequence is heterologous with regard to the promoter.

Said nucleic acid sequence preferably codes for an amino acid sequence comprising a sequence as shown in SEQ ID NO: 6, 8, 10, 12, 14, 16 or 18. Said nucleic acid sequence especially preferably comprises a sequence as shown in SEQ ID NO: 5, 7, 9, 11, 13, 15 or 17. "Part" with regard to the nucleic acid sequence preferably means a sequence of at least 15 bases, preferably 25 bases, especially preferably 50 bases, most preferably 100 bases. In a preferred embodiment, the method according to the invention is based on the polymerase chain reaction, where said nucleic acid sequence or part thereof is employed as primer. For the purposes of functional linkage, methods with which the skilled worker is familiar, such as, for example, ligation and the like, may be employed (see hereinbelow).

Suitable SSS3 promoters also comprise natural or artificial mutations of the promoter sequences described under SEQ ID NO: 1, 2, 3, 4 or 44. "Mutation" means substitution, addition, deletion, inversion or insertion of one or more nucleotide residues. Thus, for example, the present invention also encompasses those nucleotide sequences which are obtained by modifying an SSS3 promoter as shown in SEQ ID NO: 1, 2, 3, 4 or 44. The purpose of such a modification may be the further delimitation of the sequence which is present therein, or else, for example, the introduction or removal of restriction endonuclease cleavage sites, the removal of excess DNA or the addition of further sequences, for example further regulatory sequences. Where insertions, deletions or substitutions, such as, for example, transitions and transversions, are suitable, techniques known per se such as in vitro mutagenesis, primer repair, restriction or ligation may be used. Transition means a base pair substitution of a purine/pyrimidine pair by another purine/pyrimidine pair (for example A-T by G-C). Transversion means a base pair substitution of a purine/pyrimidine pair by a pyrimidine/purine pair (for example A-T by T-A). Deletion means the removal of one or more base pairs. Insertion means the introduction of one or more base pairs. Complementary ends of the fragments may be made available for ligation by manipulations such as, for example, restriction, chewing-back or filling in overhangs for blunt ends. Analogous results may also be obtained by using the polymerase chain reaction (PCR) using specific oligonucleotide primers.

The skilled worker is familiar with methods for inducing mutations in nucleic acid sequences; by way of example, they include the use of oligonucleotides with one or more mutations in comparison with the region to be mutated (for example in what is known as "site-specific mutagenesis"). Typically, primers with approximately 15 to approximately 75 nucleotides or more are employed, where preferably approximately 10 to approximately 25 or more nucleotide residues are located on both sides of the sequence to be modified. Details and procedure of said mutagenic methods are known to the skilled worker (Kunkel et al. (1987) Methods Enzymol 154:367-382; Tomic et al. (1990) Nucl Acids Res 12:1656; Upender et al. (1995) Biotechniques 18(1):29-30; U.S. Pat. No. 4,237,224). A mutagenesis can also be performed by treatment of, for example, transgenic expression vectors which comprise one of the nucleic acid sequences according to the invention with mutation-inducing agents such as hydroxylamine.

As an alternative, it is possible to delete nonessential sequences of a promoter according to the invention, without this having a significant adverse effect on the abovementioned essential characteristics. Such deletion variants constitute fragments with functional equivalence to the promoters described by SEQ ID NO: 1, 2, 3, 4 or 44. The delimitation of the promoter sequence to certain essential regulatory regions can be effected for example with the aid of search routines for the search of promoter elements. Frequently, certain promoter elements occur in greater quantities in the regions which are relevant for the promoter activity. This analysis can be carried out for example with computer programs such as the program PLACE ("Plant Cis-acting Regulatory DNA Elements"; Higo K et al. (1999) Nucl Acids Res 27(1): 297-300), the BIOBASE database "Transfac" (Biologische Datenbanken GmbH, Brunswick; Wingender E et al. (2001) Nucleic Acids Res 29(1):281-3) or database PlantCARE (Lescot M et al. (2002) Nucleic Acids Res 30(1):325-7). Furthermore, individual fragments of said promoters can be used for example to generate or, advantageously, to optimize, synthetic promoters in combination with other regulatory elements.

Said fragments according to the invention preferably comprise at least 25 contiguous nucleotides, preferably at least 50 contiguous nucleotides, especially preferably at least 100 contiguous nucleotides, of one of the sequences as shown in SEQ ID NO: 1, 2, 3, 4 or 44.

Functionally equivalent fragments of one of the promoters according to the invention—for example the promoters described by SEQ ID NO: 1, 2, 3, 4 or 44—comprise at least 200 base pairs, very especially preferably at least 500 base pairs, most preferably at least 1000 base pairs of the 3' terminus of the respective promoter according to the invention— for example of the promoters described by SEQ ID NO: 1, 2, 3, 4 or 44—, the length being calculated upstream from the transcription start ("ATG" codon) in 5' direction.

Suitable SSS3 promoters furthermore comprise DNA sequences which hybridize under standard conditions with one of the nucleic acid sequences as shown in SEQ ID NO: 1, 2, 3, 4 or 44 or the nucleic acid sequences which are complementary thereto and which have essentially the same promoter characteristics.

The term standard hybridization conditions is to be understood broadly and means both stringent and less stringent hybridization conditions. Such hybridization conditions are described inter alia in Sambrook J, Fritsch E F, Maniatis T et al., in Molecular Cloning—A Laboratory Manual, 2$^{nd}$ edition, Cold Spring Harbor Laboratory Press, 1989, pages 9.31-9.57 or in Current Protocols in Molecular Biology, John Wiley & Sons, N.Y. (1989), 6.3.1-6.3.6. For example, the conditions during the washing step can be selected from the range of conditions limited by those of low stringency (with approximately 2×SSC at 50° C.) and of high stringency (with approximately 0.2×SSC at 50° C., preferably at 65° C.) (20× SSC: 0.3 M sodium citrate, 3 M NaCl, pH 7.0). In addition, the temperature during the washing step can be raised from low-stringency conditions at room temperature, approximately 22° C., to more stringent conditions at approximately 65° C. Both parameters, the salt concentration and the temperature, can be varied simultaneously, and it is also possible for one of the two parameters to be kept constant and only the other to be varied. It is also possible to employ denaturing agents such as, for example, formamide or SDS during the hybridization. Hybridization in the presence of 50% formamide is preferably carried out at 42° C. Some exemplary conditions for hybridization and washing steps are given below:

(1) Hybridization Conditions with for Example
　a) 4×SSC at 65° C., or
　b) 6×SSC, 0.5% SDS, 100 μg/ml denatured fragmented salmon sperm DNA at 65° C., or
　c) 4×SSC, 50% formamide at 42° C., or
　d) 2× or 4×SSC at 50° C. (low-stringency condition), or
　e) 2× or 4×SSC, 30 to 40% formamide at 42° C. (low-stringency condition), or
　f) 6×SSC at 45° C., or,
　g) 0.05 M sodium phosphate buffer pH 7.0, 2 mM EDTA, 1% BSA and 7% SDS.

(2) Washing Steps with for Example
　a) 0.1×SSC at 65° C., or
　b) 0.1×SSC, 0.5% SDS at 68° C., or
　c) 0.1×SSC, 0.5% SDS, 50% formamide at 42° C., or
　d) 0.2×SSC, 0.1% SDS at 42° C., or
　e) 2×SSC at 65° C. (low-stringency condition), or
　f) 40 mM sodium phosphate buffer pH 7.0, 1% SDS, 2 mM EDTA.

Methods for preparing functional equivalents of the invention preferably comprise the introduction of mutations into one of the promoters as shown in SEQ ID NO: 1, 2, 3, 4 or 44. Mutagenesis may be random, in which case the mutagenized sequences are subsequently screened for their properties by a trial-and-error procedure. Particularly advantageous selection criteria comprise for example the level of the resulting expression of the introduced nucleic acid sequence in a starch-comprising tissue.

"Expression" means the transcription of the nucleic acid sequence to be expressed transgenically, but can—in the case of an open reading frame in sense orientation—also include the translation of the transcribed RNA, of the nucleic acid sequence to be expressed transgenically, into a corresponding polypeptide.

"Transgenic" means—for example regarding a transgenic expression cassette, a transgenic expression vector, a transgenic organism or method for the transgenic expression of nucleic acids all —those constructs which are the result of transgenic methods, or all methods using them, in which either
a) an SSS3 promoter (for example a promoter as shown in SEQ ID NO: 1, 2, 3, 4 or 44), or
b) the nucleic acid sequence to be expressed transgenically, in functional linkage with the SSS3 promoter of a), or
c) (a) and (b)

are not located in their natural genetic environment or have been modified by transgenic methods, where the modification can be for example a substitution, addition, deletion, inversion or insertion of one or more nucleotide residues. Preferably, the SSS3 promoter sequence according to the invention which is present in the expression cassettes (for example as shown in SEQ ID NO: 1, 2, 3, 4 or 44) is heterologous with regard to the further nucleic acid sequence which is linked functionally with it and which is to be expressed transgenically. In this context, "heterologous" means that the further nucleic acid sequence does not encode the gene which is naturally under the control of said promoter.

"Natural genetic environment" means the natural chromosomal locus in the organism of origin or the presence in a genomic library. In the case of a genomic library, the natural genetic environment of the nucleic acid sequence is preferably retained at least in part. The environment flanks the nucleic acid sequence at least at one side and has a sequence length of at least 50 bp, preferably at least 500 bp, especially preferably at least 1000 bp, very especially preferably at least 5000 bp. A naturally occurring expression construct—for example the naturally occurring combination of the potato SSS3 promoter of SEQ ID NO: 1 or 44 and the coding sequence of the potato SSS3 gene becomes a transgenic expression construct when this combination is modified by nonnatural, synthetic ("artificial") methods such as, for example, an in-vitro mutagenesis. Such methods have been described (U.S. Pat. No. 5,565,350; WO 00/15815; see also hereinabove).

"Transgenic" with regard to an expression ("transgenic expression") preferably means all those expressions which have been carried out using a transgenic expression cassette, transgenic expression vector or transgenic organism, as defined hereinabove.

In transgenic expression cassettes according to the invention, at least one of the promoters according to the invention (for example described by SEQ ID NO: 1, 2, 3, 4 or 44) is in functional linkage with at least one nucleic acid sequence to be expressed transgenically.

A functional linkage means, for example, the sequential arrangement of one of the promoters according to the invention (for example described by SEQ ID NO: 1, 2, 3, 4 or 44) with a nucleic acid sequence to be expressed transgenically and, if appropriate, further genetic control sequences such as, for example, a terminator or a polyadenylation sequence in such a way that the promoter can fulfill its function under suitable conditions in the transgenic expression of the nucleic acid sequence and that expression of the nucleic acid sequence (i.e. transcription and, if appropriate, translation) takes place. "Suitable conditions" in this context preferably means the presence of the expression cassette in a plant cell, preferably a plant cell comprised by a starch-comprising tissue of a plant.

Preferred arrangements are those in which the nucleic acid sequence to be expressed transgenically is positioned behind one of the promoters according to the invention (e.g. described by SEQ ID NO: 1, 2, 3, 4 or 44) so that both sequences are linked covalently with one another. Preferably, the distance between the promoter sequence and the nucleic acid sequence to be expressed transgenically is less than 200 base pairs, especially preferably less than 100 base pairs, very especially preferably less than 50 base pairs.

A functional linkage or a transgenic expression construct can be produced by means of conventional recombination and cloning techniques as are described, for example, in Maniatis T, Fritsch E F and Sambrook J (1989) Molecular Cloning: A Laboratory Manual, Cold Spring Harbor Laboratory, Cold Spring Harbor, N.Y. and in Silhavy T J, Berman M L and Enquist L W (1984) Experiments with Gene Fusions, Cold Spring Harbor Laboratory, Cold Spring Harbor, N.Y. and in Ausubel F M et al. (1987) Current Protocols in Molecular Biology, Greene Publishing Assoc. and Wiley Interscience. A method which is suitable for this purpose is, for example, the GATEWAY™ cloning technology (Invitrogen Inc.), which is based on recombination.

However, it is possible, between promoter and nucleic acid sequence to be expressed transgenically, to position further sequences which have, for example, the function of a linker with certain restriction enzyme cleavage sites, or of a signal peptide. Also, the insertion of sequences may lead to the expression of fusion proteins.

A transgenic expression cassette according to the invention is prepared for example by fusing one of the promoters according to the invention as shown in SEQ ID NO: 1, 2, 3, 4 or 44 with a nucleotide sequence to be expressed transgenically, if appropriate with a sequence encoding a transit peptide, preferably a chloroplast-specific transit peptide, which is preferably arranged between the promoter and the nucleotide sequence in question, and optionally with a terminator or polyadenylation signal. Preferably, the transgenic expression construct, consisting of a linkage of promoter and nucleic acid sequence to be expressed, may be integrated in a vector and inserted into a plant genome by, for example, transformation.

However, an expression cassette also means those constructs in which one of the promoters of the invention (for example described by SEQ ID NO: 1, 2, 3, 4 or 44) is, without necessarily having been functionally linked beforehand to a nucleic acid sequence to be expressed, introduced into a host genome, for example by directed homologous recombination or random insertion, where it undertakes regulatory control over endogenous nucleic acid sequences then functionally linked thereto, and governs the transgenic expression thereof. Insertion of the promoter—for example by a homologous recombination—in front of a nucleic acid encoding for a particular polypeptide results in an expression cassette of the invention which governs the expression of the particular polypeptide selectively in a starch-comprising tissue. Also, for example, the natural promoter of an endogenous gene can be exchanged for one of the promoters according to the invention (for example described by SEQ ID NO: 1, 2, 3, 4 or 44) and the expression behavior of the endogenous gene can be modified thus.

Furthermore, the insertion of the promoter may also take place in such a way that antisense RNA to the nucleic acid coding for a particular polypeptide is expressed. This selectively downregulates or switches off the expression of the particular polypeptide in the starch-comprising tissue.

Analogously, it is also possible to place a nucleic acid sequence to be expressed transgenically—for example by homologous recombination—behind the sequence coding for one of the promoters according to the invention (for example described by SEQ ID NO: 1, 2, 3, 4 or 44), which is located in its natural chromosomal context so that an expression cassette according to the invention is obtained which controls the expression, in the starch-comprising tissue, of the nucleic acid sequence to be expressed transgenically.

The transgenic expression cassettes according to the invention may comprise further genetic control sequences. The concept of the genetic control sequences is to be understood broadly and means all those sequences which have an effect on the origin or the function of a transgenic expression cassette according to the invention. Genetic control sequences modify, for example, the transcription and translation in prokaryotic or eukaryotic organisms. Preferably, the transgenic expression cassettes according to the invention comprise a terminator sequence 3'-downstream from the particular nucleic acid sequence to be expressed transgenically as additional genetic control sequence, and, if appropriate, further customary regulatory elements, in each case functionally linked with the nucleic acid sequence to be expressed transgenically.

Genetic control sequences also comprise further promoters, promoter elements or minimal promoters which are capable of modifying expression-controlling properties. It is thus possible, by means of genetic control sequences, that for example tissue-specific expression takes place in addition in dependence on certain stress factors. Suitable elements are described, for example, for water stress, abscisic acid (Lam E and Chua N H (1991) J Biol Chem 266(26):17131-17135) and heat stress (Schoffl F et al. (1989) Mol Gen Genetics 217(2-3):246-53).

It is furthermore possible that further promoters which make possible transgenic expression in further plant tissues or in other organisms such as, for example, *E. coli* bacteria, are linked functionally with the nucleic acid sequence to be expressed. Suitable promoters are, in principle, all plant-specific promoters. Plant-specific promoters means in principle any promoter which is capable of controlling the expression of genes, in particular foreign genes, in plants or plant parts, plant cells, plant tissue or plant cultures. In this context, the expression can be for example constitutive, inducible or development-dependent. Preferred are constitutive promoters, tissue-specific promoters, development-dependent promoters, chemically-inducible, stress-inducible or pathogen-inducible promoters. Such promoters are generally known to the skilled worker.

Further advantageous control sequences can be found for example in the promoters of gram-positive bacteria, such as amy and SPO2, or in the yeast or fungal promoters ADC1, MFa, AC, P-60, CYC1, GAPDH, TEF, rp28, ADH.

It is possible in principle for all natural promoters with their regulatory sequences like those mentioned above to be used for the method of the invention. It is additionally possible also for synthetic promoters to be used advantageously.

Genetic control sequences further comprise also the 5'-untranslated regions, introns or noncoding 3' regions of genes such as, for example, the actin-1 intron, or the Adh1-S introns 1, 2 and 6 (generally: The Maize Handbook, Chapter 116, Freeling and Walbot, Eds., Springer, N.Y. (1994)), preferably of the *Arabidopsis thaliana* genes with the gene locus At2g46720, At3g01980 and At1g63140. It can be shown that these regions may play a significant function in the regulation of gene expression. It has thus been shown that 5'-untranslated sequences are able to enhance transient expression of heterologous genes. An example of a translation enhancer which may be mentioned is the 5' leader sequence from tobacco mosaic virus (Gallie et al. (1987) Nucl Acids Res 15:8693-8711) and the like. They may in addition promote tissue specificity (Rouster J et al. (1998) Plant J 15:435-440). Conversely, the 5'-untranslated region of the opaque-2 gene suppresses expression. A deletion of the region in question leads to an increase in the gene activity (Lohmer S et al. (1993) Plant Cell 5:65-73).

In transgenic rice cells, the use of the Act1 intron in combination with the 35S promoter resulted in a ten-fold increased expression rate in comparison with the isolated 35S promoter (McElroy et al. (1991) Mol Gen Genet 231(1):150-160). An optimization of the sequence environment of the translation initiation site of the GUS reporter gene resulted in a four-fold increase in the GUS expression in transformed rice cells. A combination of the optimized translation initiation site and the Act1 intron resulted in a 40-fold increase in the GUS expression by the CaMV35S promoter in transformed rice cells; similar results were obtained using transformed maize cells. In total, the conclusion of the above-described studies was that the expression vectors based on the Act1 promoter are suitable for controlling a sufficiently strong and constitutive expression of foreign DNA in transformed cells of monocotyledonous plants.

The promoter sequences shown in SEQ ID NO: 2, 3 and 4 comprise the segment of the respective SSS3 genes which represents the promoter and the 5'-untranslated region up to before the ATG start codon of the SSS3 protein. The promoter sequences shown in SEQ ID: 1 and 44 comprise the promoter including 75 bp of the 5'-untranslated region of the cDNA.

The transgenic expression construct may advantageously comprise one or more so-called enhancer sequences, which make increased transgenic expression of the nucleic acid sequence possible, functionally linked to the promoter. Additional advantageous sequences such as further regulatory elements or terminators can also be inserted at the 3' end of the nucleic acid sequences to be expressed transgenically. The nucleic acid sequences to be expressed transgenically may be present in one or more copies in the gene construct.

Polyadenylation signals suitable as control sequences are plant polyadenylation signals, preferably those which correspond essentially to T-DNA polyadenylation signals from *Agrobacterium tumefaciens*. In an especially preferred embodiment, the transgenic expression cassette comprises a terminator sequence which is functional in plants. The term terminator sequences which are functional in plants generally means those sequences which are capable of bringing about, in plants, the termination of the transcription of a DNA sequence. Examples of suitable terminator sequences are the OCS (octopine synthase) terminator and the NOS (nopalin synthase) terminator. However, plant terminator sequences are especially preferred. The term plant terminator sequences generally means those sequences which are part of a natural plant gene. Especially preferred in this context are the terminator of the potato cathepsin D inhibitor gene (GenBank Acc. No.: X74985) or the terminator of the storage protein gene VfLE1B3 (GenBank Acc. No.: Z26489) from the field bean. These terminators are at least equivalent to the viral terminators or T-DNA terminators described in the prior art.

Control sequences additionally mean those which make homologous recombination or insertion into the genome of a host organism possible or allow deletion from the genome. In homologous recombination for example the natural promoter of a particular gene can be replaced by one of the promoters according to the invention. One of the promoters according to the invention—as described Above—can be placed, by homologous recombination, upstream of an endogenous target gene to be expressed transgenically by linking the promoter with DNA sequences which are homologous for example to endogenous sequences which precede the reading frame of the target gene. Such sequences are to be understood as genetic control sequences. Methods such as cre/lox technology allow tissue-specific, and in some circumstances inducible, deletion of the transgenic expression cassette from the genome of the host organism (Sauer B (1998) Methods (Duluth) 14(4):381-92). In this case, particular flanking sequences are attached to the target gene (lox sequences) and make later deletion by means of cre recombinase possible. To select cells which have successfully undergone homologous recombination or else transformation, it is, as a rule, necessary additionally to introduce a selectable marker (see hereinbelow). Homologous recombination is a relatively rare event in higher eukaryotes, especially in plants. Random integrations into the host genome predominate. One possibility of removing the randomly integrated sequences, and thus to accumulate cell clones with a correct homologous recombination, consists in the use of a sequence-specific recombination system as described in U.S. Pat. No. 6,110,736.

The transgenic expression, of the proteins encoded by the nucleic acid sequences, under the control of an SSS3 promoter is possible in any desired cell compartment such as, for example, the endomembrane system, the vacuole and the chloroplasts. Utilizing the secretory pathway, desired glycosylation reactions, specific folding patterns and the like are possible. The signal peptide sequences required as genetic control sequences for this purpose can either be provided in individual transgenic expression cassettes or else be introduced into the transgenic expression cassette by using a suitable cloning strategy together with the nucleic acid sequence to be expressed transgenically. Signal or transit peptide sequences which can be utilized are both homologous or heterologous sequences. Additional heterologous sequences which are preferred for functional linkage, but not restricted thereto, are further targeting sequences for ensuring the subcellular localization in the apoplast, in the vacuole, in plastids, in mitochondria, in the endoplasmic reticulum (ER), in the nucleus, in oil bodies or in other compartments; and also translation enhancers such as the tobacco mosaic virus 5' leader sequence (Gallie et al. (1987) Nucl Acids Res 15:8693-8711) and the like. The method for the directed transport into plastids of proteins which per se are not localized in the plastids is described (Klosgen R B and Weil J H (1991) Mol Gen Genet 225(2):297-304; Van Breusegem F et al. (1998) Plant Mol Biol 38(3):491-496). Preferred sequences are:

a) the transit peptide of the SSS3 protein,
b) the transit peptide of the small subunit (SSU) of the ribulose-bisphosphate carboxylase (Rubisco ssu) from, for example, pea, maize or sunflower,
c) transit peptides derived from genes of plant fatty acid biosynthesis, such as the transit peptide of the plastidic "acyl carrier protein" (ACP), the stearyl-ACP desaturase, the β-ketoacyl-ACP synthase or the acyl-ACP thioesterase,
d) the transit peptide of the GBSSI ("granule-bound starch synthase I")
e) the transit peptide of the LHCP II genes
f) the transketolase transit peptide (EP-A1 0 723 017).

The target sequences can be linked with other targeting sequences which differ from sequences coding for the transit peptide in order to ensure a subcellular localization in the apoplast, in the vacuole, in plastids, in mitochondria, in the endoplasmic reticulum (ER), in the nucleus, in oil bodies or other compartments.

The transgenic expression cassettes according to the invention and the transgenic expression vectors derived from them may comprise further functional elements. The term functional element is to be understood broadly and means all those elements which have an effect on the generation, multiplication or function of the transgenic expression cassettes according to the invention or on transgenic expression vectors or organisms derived from them. The following may be mentioned by way of example, but not by limitation:

1) Selection Markers

The term "selection marker" comprises not only positive selection markers, which confer a resistance to an antibiotic, herbicide or other biocide, but also negative selection markers, which confer a sensitivity to precisely the abovementioned, and also markers which confer a growth advantage to the transformed organism (for example by expression of key genes of cytokine biosynthesis; Ebinuma H et al. (2000) Proc Natl Acad Sci USA 94:2117-2121). In the case of positive selection, only those organisms which express the selection marker in question thrive, while precisely these organisms die in the case of negative selection. The use of a positive selection marker is preferred in the generation of transgenic plants. Furthermore preferred is the use of selection markers which confer growth advantages. Negative selection markers can be used advantageously when the task at hand consists in eliminating certain genes or genome segments from an organism (for example for the purposes of a hybridization process).

i) Positive Selection Markers:

The selectable marker introduced with the transgenic expression cassette confers resistance to a biocide, for example a herbicide (such as phosphinothricin, glyphosate or bromoxynil), a metabolism inhibitor (such as 2-deoxyglucose-6-phosphate; WO 98/45456) or an antibiotic (such as, for example, tetracyclins, ampicillin, kanamycin, G 418, neomycin, bleomycin or hygromycin) to the successfully transformed cells. The selection marker permits the selection of the transformed cells from untransformed cells (McCormick et al. (1986) Plant Cell Reports 5:81-84). Especially preferred selection markers are those which confer resistance to herbicides. Selection markers which may be mentioned by way of example are:

DNA sequences which encode phosphinothricin acetyltransferases (PAT) (also referred to as Bialophos® resistance gene (bar)), which acetylate the free amino group of the glutamine synthase inhibitor phosphinothricin (PPT) and thus detoxify the PPT (de Block et al. (1987) EMBO J. 6:2513-2518; Vickers J E et al. (1996) Plant Mol Biol Reporter 14:363-368; Thompson C J et al. (1987) EMBO J. 6:2519-2523). The bar/PAT gene can be isolated for example from *Streptomyces hygroscopicus* or *S. viridochromogenes*. Such sequences are known to the skilled worker (*Streptomyces hygroscopicus* GenBank Acc. No.: X17220 and X05822; *Streptomyces viridochromogenes* GenBank Acc. No.: M22827 and X65195; U.S. Pat. No. 5,489,520). Synthetic genes are further described for expression in plastids (GenBank Acc. No.: AJ028212).

5-Enolpyruvylshikimate-3-phosphate synthase genes (EPSP synthase genes), which confer resistance to Glyphosat® (N-(phosphonomethyl)glycine). The nonselective herbicide glyphosate has 5-enolpyruvyl-3-phosphoshikimate synthase (EPSPS) as molecular target. This enzyme has a key function in the biosynthesis of aromatic amino acids in plants (Steinrucken H C et al. (1980) Biochem Biophys Res Commun 94:1207-1212; Levin J G and Sprinson D B (1964) J Biol Chem 239: 1142-1150; Cole D J (1985) Mode of action of glyphosate; A literature analysis, pp. 48-74. In: Grossbard E and Atkinson D (eds.). The herbicide glyphosate. Buttersworths, Boston). Glyphosate-tolerant EPSPS variants are preferably used as selection markers (Padgette S R et al. (1996). New weed control opportunities: development of soybeans with a Roundup Ready gene. In: Herbicide Resistant Crops (Duke S O, ed.), pp. 53-84. CRC Press, Boca Raton, Fla.; Saroha M K and Malik V S (1998) J Plant Biochemistry and Biotechnology 7:65-72). The EPSPS gene of Agrobacterium sp. strain CP4 has a natural tolerance to glyphosate which can be transferred to corresponding transgenic plants. The CP4 EPSPS gene has been cloned from *Agrobacterium* sp. strain CP4 (Padgette S R et al. (1995) Crop Science 35(5):1451-1461). 5-Enolpyruvylshikimate-3-phosphate synthases which are glyphosate-tolerant, such as, for example, those described in U.S. Pat. No. 5,510,471; U.S. Pat. No. 5,776,760; U.S. Pat. No. 5,864,425; U.S. Pat. No. 5,633,435; U.S. Pat. No. 5,627,061; U.S. Pat. No. 5,463,175; EP 0 218 571, are preferred, the sequences described in the patents in each case also being deposited in GenBank. Further sequences are described under GenBank Accession X63374. The aroA gene (GenBank Acc. No.: M10947) is furthermore preferred.

the gox gene (glyphosate oxidoreductase), which encodes the Glyphosat®-degrading enzymes. GOX (for example the glyphosate oxidoreductase from *Achromobacter* sp.) catalyzes the cleavage of a C—N bond in glyphosate, which is thus converted into aminomethylphosphonic acid (AMPA) and glyoxylate. GOX can thereby confer resistance to glyphosate (Padgette S R et al. (1996) J Nutr 126(3):702-16; Shah D et al. (1986) Science 233: 478-481).

the deh gene (encoding a dehalogenase which inactivates Dalapon®; WO 99/27116; GenBank Acc. No.: AX022822, AX022820)

bxn genes, which encode Bromoxynil®-degrading nitrilase enzymes, for example the Klebsiella ozanenae nitrilase. Sequences can be found in GenBank for example under the Acc. Nos: E01313 and J03196.

Neomycin phosphotransferases (npt) confer resistance to antibiotics (aminoglycosides) such as neomycin, G418, hygromycin, paromomycin or kanamycin, by reducing their inhibitory action by means of a phosphorylation reaction. Especially preferred is the nptII gene (GenBank Acc. No.: AF080390; AF080389). Moreover, the gene is already a component in a large number of expression vectors and can be isolated from them using methods with which the skilled worker is familiar (such as, for example, polymerase chain reaction) (GenBank Acc. No.: AF234316 pCAMBIA-2301; AF234315 pCAMBIA-2300, AF234314 pCAMBIA-2201). The NPTII gene encodes an aminoglycoside 3'-O-phosphotransferase from *E. coli*, Tn5 (GenBank Acc. No.: U000004 position 1401-2300; Beck et al. (1982) Gene 19 327-336).

the DOG$^R$1 gene was isolated from the yeast *Saccharomyces cerevisiae* (EP 0 807 836) and it encodes a 2-deoxyglucose-6-phosphate phosphatase, which confers resistance to 2-DOG (Randez-Gil et al. (1995) Yeast 11:1233-1240; Sanz et al. (1994) Yeast 10:1195-1202; GenBank Acc. No.: NC001140 position 194799-194056).

Sulfonylurea- and imidazolinone-inactivating acetolactate synthases, which confer resistance to imidazolinone/sulfonylurea herbicides. Examples which may be mentioned of imidazolinone herbicides are the active substances imazamethabenzmethyl, imazzamox, imazapyr, imazaquin and imazethapyr. Examples of sulfonylurea herbicides which may be mentioned are amidosulforon, azimsulfuron, chlorimuronethyl, chlorsulfuron, cinosulfuron, imazosulforon, oxasulforon, prosulforon, rimsulforon, sulfosulforon. The skilled worker is familiar with a large number of further active substances from the abovementioned classes. The sequence for the *Arabidopsis thaliana* Csr 1.2 gene (EC 4.1.3.18), which has been deposited under the GenBank Acc. No.: X51514, is suitable for example (Sathasivan K et al. (1990) Nucleic Acids Res. 18(8):2188). Acetolactate synthases, which confer resistance to imidazolinone herbicides, are furthermore described under the GenBank Acc. Nos:

AB049823, AF094326, X07645, X07644, A19547, A19546, A19545, 105376 (EP 0 257 993), 105373 (EP 0 257 993), AL133315.

Hygromycin phosphotransferases (e.g. GenBank Acc. No.: X74325) which confer resistance to the antibiotic hygromycin. The gene is a component of a large number of expression vectors and can be isolated from them using methods with which the skilled worker is familiar (such as, for example, polymerase chain reaction) (GenBank Acc. No.: AF294981 pINDEX4; AF234301 pCAMBIA-1380; AF234300 pCAMBIA-1304; AF234299 pCAMBIA-1303; AF234298 pCAMBIA-1302; AF354046 pCAMBIA-1305; AF354045 pCAMBIA-1305.1)

genes for resistance to
a) chloramphenicol (chloramphenicol acetyltransferase),
b) Tetracyclin; various resistance genes have been described, for example with GenBank Acc. Nos: X65876, X51366. In addition, the gene is already a component of a large number of expression vectors and can be isolated from these using methods known to the skilled worker (such as, for example, polymerase chain reaction)
c) Streptomycin; various resistance genes have been described, for example with the GenBank Acc. No.: AJ278607.
d) Zeocin; the corresponding resistance gene is a component of a large number of cloning vectors (for example GenBank Acc. No.: L36849 cloning vector pZEO) and can be isolated from these using methods known to the skilled worker (such as, for example, polymerase chain reaction).
e) Ampicillin (β-lactamase gene; Datta N, Richmond M H. (1966) Biochem J 98(1):204-9; Heffron F et al. (1975) J. Bacteriol 122:250-256; the Amp gene was first cloned for generating the *E. coli* vector pBR322; Bolivar F et al. (1977) Gene 2:95-114). The sequence is a component of a large number of cloning vectors and can be isolated from them using methods known to the skilled worker (such as, for example, polymerase chain reaction).

Genes such as the isopentenyl transferase from *Agrobacterium tumefaciens* (strain:PO22) (GenBank Acc. No.: AB025109). The ipt gene is a key enzyme of cytokine biosynthesis. Its overexpression facilitates the regeneration of plants (for example selection on cytokine-free medium). The method for utilizing the ipt gene has been described (Ebinuma H et al. (2000) Proc Natl Acad Sci USA 94:2117-2121; Ebinuma H et al. (2000) Selection of marker-free transgenic plants using the oncogenes (ipt, rol A, B, C) of *Agrobacterium* as selectable markers, In Molecular Biology of Woody Plants. Kluwer Academic Publishers).

Various other positive selection markers which confer a growth advantage to the transformed plants over non-transformed plants, and methods for their use, have been described, inter alia, in EP-A 0 601 092. Examples which may be mentioned are β-glucuronidase (in conjunction with, for example, cytokinin glucuronide), mannose-6-phosphate isomerase (in conjunction with mannose), UDP-galactose 4-epimerase (in conjunction with, for example, galactose), with mannose-6-phosphate isomerase in conjunction with mannose being especially preferred.

ii) Negative Selection Markers

Negative selection markers make possible for example the selection of organisms with successfully deleted sequences which comprise the marker gene (Koprek T et al. (1999) The Plant Journal 19(6):719-726). When carrying out a negative selection, a compound which otherwise has no disadvantageous effect on the plant is converted into a compound which is disadvantageous, for example owing to the negative selection marker introduced into the plant. Genes which have a disadvantageous effect per se are furthermore suitable. Negative selection markers which may be mentioned by way of example, but not by limitation, are TK thymidine kinase (TK), diphtheria toxin A fragment (DT-A), the coda gene product encoding a cytosine deaminase (Gleave A P et al. (1999) Plant Mol Biol 40(2):223-35; Perera R J et al. (1993) Plant Mol Biol 23(4): 793-799; Stougaard J (1993) Plant J 3:755-761), the cytochrome P450 gene (Koprek et al. (1999) Plant J 16:719-726), genes encoding a haloalkane dehalogenase (Naested H (1999) Plant J 18:571-576), the iaaH gene (Sundaresan V et al. (1995) Genes & Development 9:1797-1810) or the tms2 gene (Fedoroff N V & Smith D L (1993) Plant J 3:273-289).

2) Reporter Genes

Reporter genes encode readily quantifiable proteins which, via their color or enzyme activity, allow an assessment of the transformation efficiency, the site or time of expression (see also Schenborn E, Groskreutz D. Mol Biotechnol. 1999; 13(1):29-44). Examples which may be mentioned are:

"green fluorescent protein" (GFP) (Chui W L et al. (1996), Curr Biol 6:325-330; Leffel S M et al. (1997) Biotechniques 23(5):912-8; Sheen et al. (1995) Plant J 8(5):777-784; Haseloff et al. (1997) Proc Natl Acad Sci USA 94(6):2122-2127; Reichel et al. (1996) Proc Natl Acad Sci USA 93(12):5888-5893; Tian et al. (1997) Plant Cell Rep 16:267-271; WO 97/41228).

Chloramphenicol transferase (Fromm et al. (1985) Proc Natl Acad Sci USA 82:5824-5828), Luciferase (Millar et al. (1992) Plant Mol Biol Rep 10:324-414; Ow et al. (1986) Science 234:856-859); allows detection via bioluminescence.

β-Galactosidase, encodes an enzyme for which a variety of chromogenic substrates are available.

β-Glucuronidase (GUS) (Jefferson et al. (1987) EMBO J. 6:3901-3907) or the uida gene, which encodes an enzyme for a variety of chromogenic substrates.

R-Locus gene product: protein which regulates the production of anthocyanine pigments (red coloration) in plant tissue and thus makes possible the direct analysis of the promoter activity without addition of further auxiliary substances or chromogenic substrates (Dellaporta et al. (1988) In: Chromosome Structure and Function: Impact of New Concepts, $18^{th}$ Stadler Genetics Symposium, 11:263-282).

Tyrosinase (Katz et al. (1983) J Gen Microbiol 129:2703-2714), an enzyme which oxidizes tyrosine to DOPA and dopaquinone, which subsequently form melanin, which can be detected readily.

Aequorin (Prasher et al. (1985) Biochem Biophys Res Commun 126(3):1259-1268), can be used in the calcium-sensitive bioluminescence detection.

3) Replication Origins

Replication origins ensure the multiplication of the transgenic expression cassettes or transgenic expression vectors according to the invention in, for example, *E. coli* or agrobacteria. Examples which may be mentioned are ORI (origin of DNA replication), the pBR322 ori or the P15A ori (Sambrook et al.: Molecular Cloning. A Laboratory Manual, 2$^{nd}$ ed. Cold Spring Harbor Laboratory Press, Cold Spring Harbor, N.Y., 1989). Examples of replication origins which are functional in *Agrobacterium* which may be mentioned are pRK2, pRi, PVS1 or pSA.

4) Border Sequences

"Border sequences" (such as, for example, the right or left border of the T-DNA) make possible an agrobacteria-mediated transfer into plant cells for the transfer and integration into the plant genome.

5) Multiple Cloning Regions (MCS) Permit and Facilitate the Insertion of One or More Nucleic Acid Sequences Also according to the invention are transgenic expression vectors which comprise the above-described transgenic expression cassettes. Vectors generally means structures which are capable of replication and which are preferably host-specific, and which make possible the uptake of nucleic acid sequences and their transfer into other cells. Examples of vectors can be plasmids, cosmids, phages, viruses or else agrobacteria. Vectors which are particularly suitable for the purposes of plant biotechnology are described hereinbelow. The transgenic expression cassettes can be inserted into the vector (preferably a plasmid vector) via a suitable restriction cleavage site. The resulting vector can first be introduced into *E. coli* and then amplified. Correctly transformed *E. coli* are selected, grown, and the recombinant vector is obtained by methods with which the skilled worker is familiar. Restriction analysis and sequencing can serve for verifying the cloning step. Preferred vectors are those which make possible a stable integration of the expression cassette into the host genome. In the present context, host genome means all of the hereditary information of the host and comprises by way of example not only the chromosomal DNA of the nucleus, but also the DNA of the plastids and mitochondria. However, insertion into the chromosomal DNA of the nucleus is preferred.

In an advantageous embodiment, the introduction of the transgenic expression cassette into a cell or an organism is effected by means of plasmid vectors.

In the context of the invention, "introducing" comprises all methods which are suitable for introducing a nucleic acid sequence (for example an expression cassette according to the invention) directly or indirectly into an organism (for example a plant) or a cell, compartment, tissue, organ or propagation material (for example seed or fruits) of the same or generating it therein. Comprised are direct and indirect methods. The introduction may lead to a transient or else stable presence of said nucleic acid sequence. Introducing comprises for example methods such as transfection, transduction or transformation. Depending on the host organism, the organisms used in the methods are cultured or grown in the manner with which the skilled worker is familiar.

The generation of a transformed organism (or of a transformed cell or tissue) requires that the DNA in question (for example the expression vector) or the RNA in question is inserted or introduced into the host cell in question. A multiplicity of methods is available for this procedure, which is referred to as transformation (or transduction or transfection); (Keown et al. (1990) Methods in Enzymology 185:527-537). Thus, for example, the DNA or RNA can be introduced directly by microinjection or by bombardment with DNA-coated microparticles. Also, the cell can be permeabilized chemi0cally, for example with polyethylene glycol, so that the DNA can enter the cell by diffusion. The DNA can also be introduced by protoplast fusion with other DNA-comprising units such as minicells, cells, lysosomes or liposomes. A further suitable method for introducing DNA is electroporation, where the cells are reversibly permeabilized by means of an electrical pulse. Suitable methods are described (for example by Bilang et al. (1991) Gene 100:247-250; Scheid et al. (1991) Mol Gen Genet 228:104-112; Guerche et al. (1987) Plant Science 52:111-116; Neuhause et al. (1987) Theor Appl Genet 75:30-36; Klein et al. (1987) Nature 327:70-73; Howell et al. (1980) Science 208:1265; Horsch et al. (1985) Science 227:1229-1231; DeBlock et al. (1989) Plant Physiology 91:694-701; Methods for Plant Molecular Biology (Weissbach and Weissbach, eds.) Academic Press Inc. (1988); and Methods in Plant Molecular Biology (Schuler and Zielinski, eds.) Academic Press Inc. (1989)).

Preferred vectors for *E. coli* are pQE70, pQE60 and pQE-9 (QIAGEN, Inc.); pBluescript vectors, Phagescript vectors, pNH8A, pNH16a, pNH18A, pNH46A (Stratagene Cloning Systems, Inc.); ptrc99a, pKK223-3, pKK233-3, pDR540, pRIT5 (Pharmacia Biotech, Inc.). A large number of vectors for the transformation of mammals and other eukaryotic and prokaryotic organisms are known to the skilled worker. In principle, methods like those for the "direct" transformation of plant cells (see hereinbelow) are to be applied for the transformation of eukaryotic or prokaryotic cells. Especially preferred are methods such as the calcium-phosphate- or liposome-mediated transformation, or else electroporation.

Various methods and vectors for inserting genes into the genome of plants and for the regeneration of plants from plant tissues or plant cells are known (Plant Molecular Biology and Biotechnology (CRC Press, Boca Raton, Fla.), chapter 6/7, pp. 71-119 (1993); White F F (1993) Vectors for Gene Transfer in Higher Plants; in: Transgenic Plants, vol. 1, Engineering and Utilization, ed.: Kung and Wu R, Academic Press, 15-38; Jenes B et al. (1993) Techniques for Gene Transfer, in: Transgenic Plants, vol. 1, Engineering and Utilization, ed.: Kung and R. Wu, Academic Press, pp. 128-143; Potrykus (1991) Annu Rev Plant Physiol Plant Molec Biol 42:205-225; Halford N G, Shewry P R (2000) Br Med Bull 56(1):62-73). These include for example those mentioned above. In plants, the described methods for the transformation and regeneration of plants from plant tissues or plant cells for transient or stable transformation are used here. Suitable methods are mainly the transformation of protoplasts by polyethyleneglycol-induced DNA uptake, calcium-phosphate-mediated transformation, DEAE-dextran-mediated transformation, liposome-mediated transformation (Freeman et al. (1984) Plant Cell Physiol. 29:1353ff; U.S. Pat. No. 4,536,475), biolistic methods with the gene gun (particle bombardment method; U.S. Pat. No. 5,100,792; EP-A 0 444 882; EP-A 0 434 616; Fromm M E et al. (1990) Bio/Technology 8(9):833-9; Gordon-Kamm et al. (1990) Plant Cell 2:603), electroporation, the incubation of dry embryos in DNA-comprising solution, electroporation (EP-A 290 395, WO 87/06614), microinjection (WO 92/09696, WO 94/00583, EP-A 0 331 083, EP-A 0 175 966) or other methods for the direct introduction of DNA (DE 4 005 152, WO 90/12096, U.S. Pat. No. 4,684,611). Physical methods of introducing DNA into plant cells are reviewed by Oard (1991) Biotech Adv 9:1-11.

In the case of these "direct" transformation methods, the plasmid used does not need to meet any particular requirements. Simple plasmids such as those of the pUC series, pBR322, M13mp series, pACYC184 etc. can be used. If intact plants are to be regenerated from transformed cells, the plasmid must bear an additional selectable marker gene.

In addition to these "direct" transformation techniques, a transformation can also be carried out by bacterial infection by means of *Agrobacterium* (for example EP 0 116 718), viral infection by means of viral vectors (EP 0 067 553; U.S. Pat.

No. 4,407,956; WO 95/34668; WO 93/03161) or by means of pollen (EP 0 270 356; WO 85/01856; U.S. Pat. No. 4,684,611).

The strains *Agrobacterium tumefaciens* or *Agrobacterium rhizo*-genes, which are most frequently used for the agrobacterium transformation, comprise a plasmid (Ti or R1 plasmid) which is transferred to the plant after infection with *Agrobacterium*. A part of this plasmid, referred to as T-DNA (transferred DNA), is integrated into the genome of the plant cell. The transformation is preferably carried out by means of agrobacteria which comprise disarmed Ti plasmid vectors, exploiting their natural ability of transferring genes to plants (EP-A 0 270 355; EP-A 0 116 718). As an alternative, it is also possible to transfer binary vectors (mini Ti plasmids) to plants by means of *Agrobacterium* and to integrate them into their genome. Various binary vectors are known and in some cases commercially available such as, for example, pBIN19 (Bevan et al. (1984) Nucl Acids Res 12:8711f.; Clontech Laboratories, Inc. USA) or pSUN derivatives (SunGene GmbH & Co.KGaA; WO 02/00900). The expression cassette according to the invention can be inserted into these binary vectors and—as described hereinbelow—integrated into the plant genome.

The use of T-DNA for transformation of plant cells has been intensely studied and described (Horsch R B et al. (1985) Science 225:1229ff.; Fraley et al. (1983) Proc Natl Acad Sci USA 80: 4803-4807; Bevans et al. (1983) Nature 304:184-187; Jenes B et al. (1993) Techniques for Gene Transfer, in: Transgenic Plants, Vol. 1, Engineering and Utilization, Kung S D and Wu R Ed., Academic Press, pp. 128-143; Potrykus (1991) Annu Rev Plant Physiol Plant Molec Biol 42:205-225; EP 120 516; Hoekema, In: The Binary Plant Vector System, Offsetdrukkerij Kanters B. V., Alblasserdam, Chapter V; and An et al. (1985) EMBO J. 4:277-287).

The DNA is transferred into the plant cell by coculturing plant explants with *Agrobacterium tumefaciens* or *Agrobacterium rhizo*-genes. Starting from infected plant material (e.g. leaf, root or stem parts, but also protoplasts or plant cell suspensions), it is possible to regenerate whole plants by using a suitable medium which may comprise, for example, antibiotics or biocides for selection of transformed cells. The plants obtained may then be screened for the presence of the introduced DNA, in this case the transgenic expression cassette of the invention. As soon as the DNA has integrated into the host genome, the corresponding genotype is normally stable and the corresponding insertion is also found again in subsequent generations. Normally, the integrated transgenic expression cassette comprises a selection marker which imparts to the transformed plant a resistance to a biocide (for example a herbicide), a metabolism inhibitor such as 2-DOG or an antibiotic such as kanamycin, G 418, bleomycin, hygromycin or phosphinothricin etc. The selection marker allows the selection of transformed cells from untransformed cells (McCormick et al. (1986) Plant Cell Reports 5:81-84). The plants obtained may be cultivated and crossed in the common manner. Two or more generations should be cultured in order to ensure that the genomic integration is stable and hereditary.

*Agrobacterium* transformation is widely used for the transformation of dicots, but also increasingly applied to monocots (Toriyama et al. (1988) Bio/Technology 6: 1072-1074; Zhang et al. (1988) Plant Cell Rep 7:379-384; Zhang et al. (1988) Theor Appl Genet 76:835-840; Shimamoto et al. (1989) Nature 338:274-276; Datta et al. (1990) Bio/Technology 8: 736-740; Christou et al. (1991) Bio/Technology 9:957-962; Peng et al. (1991) International Rice Research Institute, Manila, Philippines 563-574; Cao et al. (1992) Plant Cell Rep 11:585-591; Li et al. (1993) Plant Cell Rep 12:250-255; Rathore et al. (1993) Plant Mol Biol 21:871-884; Fromm et al. (1990) Bio/Technology 8:833-839; Gordon-Kamm et al. (1990) Plant Cell 2:603-618; D'Halluin et al. (1992) Plant Cell 4:1495-1505; Walters et al. (1992) Plant Mol Biol 18:189-200; Koziel et al. (1993) Biotechnology 11:194-200; Vasil I K (1994) Plant Mol Biol 25:925-937; Weeks et al. (1993) Plant Physiol 102:1077-1084; Somers et al. (1992) Bio/Technology 10:1589-1594; WO 92/14828; Hiei et al. (1994) Plant J 6:271-282).

Many strains of *Agrobacterium tumefaciens* are capable of transferring genetic material—for example the expression cassettes according to the invention—such as, for example, the strains EHA101[pEHA101], EHA105[pEHA105], LBA4404[pAL4404], C58C1[pMP90] and C58C1 [pGV2260] (Hood et al. (1993) Transgenic Res 2:208-218; Hoekema et al. (1983) Nature 303:179-181; Koncz and Schell (1986) Gen Genet 204:383-396; Deblaere et al. (1985) Nucl Acids Res 13: 4777-4788).

If agrobacteria are used, the expression cassette is to be integrated into specific plasmids, either into a shuttle, or intermediate, vector, or into a binary vector. It is preferred to use binary vectors, which are capable of replication both in *E. coli* and in *Agrobacterium*. As a rule, they comprise a selection marker gene and a linker or polylinker flanked by the right and left T-DNA border sequence. They can be transformed directly into *Agrobacterium* (Holsters et al. (1978) Mol Gen Genet 163:181-187). The *Agrobacterium* which acts as host organism in this case should already comprise a plasmid with the vir region. The latter is required for transferring the T-DNA to the plant cell. An *Agrobacterium* transformed thus can be used for the transformation of plant cells. The use of T-DNA for the transformation of plant cells has been studied and described intensively (EP-A 0 120 516; Hoekema, In: The Binary Plant Vector System, Offsetdrukkerij Kanters B. V., Alblasserdam, Chapter V; An et al. (1985) EMBO J. 4:277-287). A variety of binary vectors are known and in some cases commercially available such as, for example, pBI101.2 or pBIN19 (Clontech Laboratories, Inc. USA; Bevan et al. (1984) Nucl Acids Res 12:8711), pBinAR, pPZP200 or pPTV.

Then, the agrobacteria which have been transformed with such a vector can be used in the known manner for the transformation of plants, in particular crop plants, such as, for example, oilseed rape, for example by bathing scarified leaves or leaf segments in an agrobacterial solution and subsequently culturing them in suitable media. The transformation of plants by agrobacteria is described (White F F (1993) Vectors for Gene Transfer in Higher Plants; in Transgenic Plants, Vol. 1, Engineering and Utilization, edited by S D Kung and R Wu, Academic Press, pp. 15-38; Jenes B et al. (1993) Techniques for Gene Transfer, in: Transgenic Plants, Vol. 1, Engineering and Utilization, edited by S. D. Kung and R. Wu, Academic Press, pp. 128-143; Potrykus (1991) Annu Rev Plant Physiol. Plant Molec Biol 42:205-225). The transformed cells of the scarified leaves or leaf segments can then be used for regenerating transgenic plants in the known manner, and these transgenic plants have integrated the above-described expression systems according to the invention.

Stably transformed cells (i.e. those which comprise the introduced DNA integrated into the DNA of the host cell) can be selected from untransformed cells when a selectable marker is component of the DNA which has been introduced. By way of example, any gene which is capable of conferring a resistance to a biocide (for example an antibiotic or herbicide (see hereinabove) can be used as marker (see hereinabove). Transformed cells which express such a marker gene are capable of surviving in the presence of concentrations of a suitable biocide which kill an untransformed wild type. The selection marker permits the selection of transformed cells from untransformed cells (McCormick et al. (1986) Plant Cell Reports 5:81-84). The resulting plants can be bred and hybridized in the customary manner. Two or more generations should be cultured in order to ensure that the genomic integration is stable and hereditary.

As soon as a transformed plant cell has been generated, an intact plant can be obtained using methods with which the skilled worker is familiar. The starting materials here are, for example, callus cultures, single cells (for example protoplasts) or leaf disks (Vasil et al. (1984) Cell Culture and Somatic Cel Genetics of Plants, Vol I, II and III, Laboratory Procedures and Their Applications, Academic Press; Weissbach and Weissbach (1989) Methods for Plant Molecular Biology, Academic Press). The formation of shoot and root can be induced in the known manner from this as yet undifferentiated callus cell biomass. The resulting plantlets can be planted out and grown. Relevant methods are described (Fennell et al. (1992) Plant Cell Rep. 11: 567-570; Stoeger et al. (1995) Plant Cell Rep. 14:273-278; Jahne et al. (1994) Theor Appl Genet 89:525-533).

The expression efficacy of the transgenically expressed nucleic acids can be determined for example in vitro by shoot meristem propagation using one of the above-described selection methods. Moreover, the expression, of a target gene, which has been modified in terms of type and level and the effect on the phenotype of the plant can be tested in greenhouse experiments, using test plants.

Another subject of the invention relates to transgenic organisms, transformed with at least one transgenic expression cassette according to the invention or one transgenic expression vector according to the invention, and to cells, cell cultures, tissues, parts—such as, for example in the case of plant organisms, leaves, roots and the like—or propagation material derived from such organisms.

Organism, starting organisms or host organisms are understood as meaning prokaryotic or eukaryotic organisms such as, for example, microorganisms or plant organisms. Preferred microorganisms are bacteria, yeasts, algae or fungi.

Preferred bacteria are bacteria of the genus *Escherichia, Erwinia, Agrobacterium, Flavobacterium, Alcaligenes* or cyanobacteria, for example of the genus *Synechocystis*.

Especially preferred are microorganisms which are capable of infecting plants and thus of transferring the cassettes according to the invention. Preferred microorganisms are those from the genus *Agrobacterium* and in particular the species *Agrobacterium tumefaciens*.

Preferred yeasts are *Candida, Saccharomyces, Hansenula* or *Pichia*.

Preferred fungi are *Aspergillus, Trichoderma, Ashbya, Neurospora, Fusarium, Beauveria* or further fungi described in Indian Chem Engr. Section B. Vol 37, No 1,2 (1995) on page 15, Table 6.

Host or starting organisms which are preferred as transgenic organisms are, above all, plant organisms. "Plant organism" or cells derived therefrom generally comprises any cell, tissue, parts or propagation material (such as seeds or fruits) of an organism which is capable of photosynthesis. Included as plant organisms in the context of the invention are all genera and species of the higher and lower plants of the plant kingdom. Annual, perennial, monocotyledonous and dicotyledonous plants are preferred.

In the context of the present invention, "plants" means all genera and species of the higher and lower plants of the Plant Kingdom. The term includes the mature plants, seed, shoots and seedlings, and parts, propagation material (for example tubers, seeds or fruits) derived therefrom, plant organs, tissues, protoplasts, callus cultures and other cultures, for example cell or callus cultures, and any other types of groups of plant cells which give functional or structural units. Mature plants means plants of any developmental stage beyond the seedling. Seedling means a young immature plant in an early developmental stage.

Plant organisms for the purposes of the invention are furthermore other photosynthetically active organisms such as, for example, algae, cyanobacteria and mosses. Preferred algae are green algae such as, for example, algae of the genus *Haematococcus, Phaedactylum tricornatum, Volvox* or *Dunaliella*. Especially preferred are *Synechocystis, Chlamydomonas* and *Scenedesmus*.

Included as plant organisms within the scope of the invention are all genera and species of the higher and lower plants of the plant kingdom. The mature plants, seed, tubers, beets/swollen tap roots, fruits, shoots and seedlings and also parts, propagation material and cultures, for example cell cultures, derived therefrom are also included. Mature plants means plants at any developmental stage beyond the seedling. Seedling means a young immature plant in an early developmental stage.

Annual, perennial, monocotyledonous and dicotyledonous plants are preferred host organisms for preparing transgenic plants. The expression of genes is furthermore advantageous in all ornamental plants, useful or ornamental trees, flowers, cut flowers, shrubs or lawns. Plants which may be mentioned by way of example but not by limitation are angiosperms, bryophytes such as, for example, *Hepaticae* (liverworts) and *Musci* (mosses); pteridophytes such as ferns, horsetail and club mosses; gymnosperms such as conifers, cycades, ginkgo and Gnetalae; algae such as *Chlorophyceae, Phaeophpyceae, Rhodophyceae, Myxophyceae, Xanthophyceae, Bacillariophyceae*(diatoms) and *Euglenophyceae*.

Preference is given to plants of the following plant families: Amaranthaceae, Asteraceae, Brassicaceae, Carophyllaceae, Chenopodiaceae, Compositae, Cruciferae, Cucurbitaceae, Labiatae, Leguminosae, Papilionoideae, Liliaceae, Linaceae, Malvaceae, rosacea, Rubiaceae, Saxifragaceae, Scrophulariaceae, Solanacea, Sterculiaceae, Tetragoniacea, Theaceae, Umbelliferae.

Preferred monocotyledonous plants are in particular selected from the monocotyledonous crop plants, for example of the *Gramineae* family, such as rice, corn, wheat, or other cereal species such as barley, malt, rye, triticale or oats, and also sugar cane and all grass species.

Preferred dicotyledonous plants are in particular selected from the dicotyledonous crop plants, for example

*Asteraceae* such as sunflower, *Tagetes* or *Calendula* and others,

*Compositae*, particularly the genus *Lactuca*, very particularly the species *sativa* (lettuce), and others,

*Cruciferae*, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli), and further cabbage species; and the genus *Arabidopsis*, very particularly the species *thaliana*, and also cress or canola, and others,

*Cucurbitaceae* such as melon, pumpkin or zucchini, and others,

*Leguminosae*, particularly the genus *Glycine*, very particularly the species max (soybean), soya and also alfalfa, pea, bean plants or peanut, and others,

*Rubiaceae*, preferably of the subclass *Lamiidae*, such as, for example, *Coffea arabica* or *Coffea liberica* (coffee bush), and others,

*Solanaceae*, in particular the genus *Lycopersicon*, very particularly the species *esculentum* (tomato), and the genus *Solanum*, very particularly the species *tuberosum* (potato) and *melongena* (aubergine) and the genus *Capsicum*, very especially the species *annum* (pepper), and also tobacco, and others,

*Sterculiaceae*, preferably of the subclass *Dilleniidae*, such as, for example, *Theobroma cacao* (cacao bush) and others,

*Theaceae*, preferably of the subclass *Dilleniidae*, such as, for example, *Camellia sinensis* or *Thea sinensis* (tea bush) and others,

*Umbelliferae*, particulary the genus *Daucus*, very particularly the species *carota* (carrot), and *Apium*, very particularly the species *graveolens dulce* (celery), and others;

*Chenopodiaceae*, preferably the genus *Beta vulgaris*, in particular the species *Beta vulgaris* ssp. vulgaris var. *altissima L.* (sugar beet) and others;

and also linseed, cotton, hemp, flax, cucumber, spinach and the various tree, nut and vine species, in particular banana and kiwi fruit.

Most preferred are plants of the family Solanaceae, especially the genus *Lycopersicon*, very especially the species *esculentum* (tomato), the genus *Solanum*, very especially the species *tuberosum* (potato) and *melongena* (aubergine), of the family Chenopodiaceae, in particular the genus *Beta vulgaris*, in particular the species *Beta vulgaris* ssp. *vulgaris* var. *altissima* L. (sugar beet) and others, of the family Leguminosae, especially the genus *Glycine*, very especially the species max (soybean) and alfalfa, pea, bean plants, especially the genus *Vicia* or peanut and others, and other plants with starch-containing seeds, tubers, beets/swollen tap roots, fruits or tissues. Preferred among these, in turn, are tomato, potato, aubergine, soybean, alfalfa, pea, field bean, fodder beet, sugar beet and peanut.

Furthermore in accordance with the invention are cells, cell cultures, parts—such as, for example, in the case of transgenic plant organisms, roots, leaves and the like—which are derived from the above-described transgenic organisms, and transgenic propagation material such as seeds, tubers, beets/swollen tap roots or fruits. Genetically modified plants according to the invention which can be consumed by humans and animals can also be used as foodstuffs or feedstuffs, for example either directly or after processing known per se.

The skilled worker is familiar with a multiplicity of nucleic acids or proteins whose expression, controlled by the transgenic expression cassettes according to the invention, is advantageous. Furthermore, the skilled worker is familiar with a multiplicity of genes which, when repressed or switched off by means of transgenic expression, for example by means of a suitable double-stranded RNA or an antisense RNA, likewise allow advantageous effects to be achieved. Especially suitable target genes for the scope of the present invention are those which play a role in the sugar or starch metabolism, in sink/source relations, in the balance of organic acids, as flavor components, in the resistance to biotic stress factors (pathogens such as, for example, viruses, insects or fungi), in the resistance to abiotic stress factors (heat, cold, drought, increased moisture, environmental toxins, UV radiation), in the consistency of the tissues, or in water/pH conditions, in the improvement of nutritional or feed properties, the improvement of the germination and/or storage characteristics, and in the improvement of the growth rate or the yield.

Increasing the starch content is of particular interest in particular for tomato and potato. A normal tomato consists of approximately 80 to 95% of water, while starch—as the actually relevant component for the production of, for example, tomato paste, ketchup—is degraded during maturation and only amounts to a small percentage. Even a minor increase in the starch content (and thus the content of solubles) would be of considerable economic importance. The starch content of tomatoes is markedly higher during the early maturation stages, amounting to 20%, but then drops during the development as the result of starch mobilization and conversion into sugars. In the case of potatoes, an increased starch content has in particular an advantageous effect on the deep-frying characteristics.

The high activity of the SSS3 promoter during the early stages of tuber development (starch synthesis) is outstandingly suitable for influencing starch quality. Processing (chips, fries, dry products) is a promising field of application for practical potato breeding. Since criticism of germination inhibitors is on the increase, the method of choice would be storage at 4° C., during which, however, the undesired reduced sugars are formed (cold sweetening). Depending on the variety and the storage time, heating then results in undesirable brown, bitter-tasting Maillard products (probably also acrylamide from asparagin and reducing sugars). This is why the breeding aim "suppressing the formation of reducing sugars" is of great interest. The SSS3 promoters according to the invention could be used for example to suppress invertase activities, which are probably involved in the manifestation of the trait cold sweetening, as described by Menendez et al. (2002) Genetics 162:1423-14349. These gene activities can be suppressed for example by means of double-stranded RNA, cosuppression, antisense RNA or by expressing an invertase inhibitor.

Nucleic acid sequences whose expression under the control of one of the promoters according to the invention has advantageous effects may be mentioned below by way of example, but not by limitation:

1. Improved protection of the plant from abiotic stress factors such as drought, heat or chill, for example by overexpressing antifreeze polypeptides from Myoxocephalus Scorpius (WO 00/00512), Myoxocephalus octodecemspinosus, the *Arabidopsis thaliana* transcription activator CBF1, glutamate dehydrogenases (WO 97/12983, WO 98/11240), calcium-dependent protein kinase genes (WO 98/26045), calcineurins (WO 99/05902), casein kinase from yeast (WO 02/052012), farnesyltransferases (WO 99/06580; Pei Z M et al. (1998) Science 282:287-290), ferritin (Deak M et al. (1999) Nature Biotechnology 17:192-196), oxalate oxidase (WO 99/04013; Dunwell J M (1998) Biotechn Genet Eng Rev 15:1-32), DREB1A factor ("dehydration response element B 1A"; Kasuga M et al. (1999) Nature Biotech 17:276-286), genes of mannitol or trehalose synthesis such as trehalose-phosphate synthase or trehalose-phosphate phosphatase (WO 97/42326) or by inhibiting genes such as trehalase (WO 97/50561).

2. Expression of metabolic enzymes for use in the food-and-feed sector, for example of phytases and cellulases. Especially preferred are nucleic acids such as the artificial cDNA which encodes a microbial phytase (GenBank Acc. No.: A19451) or functional equivalents thereof.

3. Achieving a resistance, for example to fungi, insects, nematodes and diseases, by targeted secretion or accumulation of certain metabolites or proteins. Examples which may be mentioned are antibodies to pathogen proteins, sucrose isomerase, glucosinolates (defense against herbivores), chitinases or glucanases and other enzymes which destroy the cell wall of parasites, ribosome-inactivating proteins (RIPs) and other proteins of the plant resistance and stress reaction as are induced when plants are wounded or attacked by microbes, or chemically, by, for example, salicylic acid, jasmonic acid or ethylene, or lysozymes from nonplant sources such as, for example, T4-lysozyme or lysozyme from a variety of mammals, insecticidal proteins such as *Bacillus thuringiensis* endotoxin, α-amylase inhibitor or protease inhibitors (cowpea trypsin inhibitor), lectins such as wheatgerm agglutinin, RNAses or ribozymes. Further examples are nucleic acids which encode the *Trichoderma harzianum* chit42 endochitinase (GenBank Acc. No.: S78423) or the N-hydroxylating, multifunctional cytochrome P-450 (CYP79) protein from *Sorghum bicolor* (GenBank Acc. No.: U3.2624), or functional equivalents of these.

The accumulation of glucosinolates in food as protection from pests (Rask L et al. (2000) Plant Mol Biol 42:93-113; Menard R et al. (1999) Phytochemistry 52:29-35), the expression of *Bacillus thuringiensis* endotoxins (Vaeck et al. (1987) Nature 328:33-37) or the protection against attack by fungi, by expression of chitinases, for example from beans (Broglie et al. (1991) Science 254:1194-1197), is advantageous.

The expression of synthetic cryIA(b) and cryIA(c) genes, which encode lepidoptera-specific *Bacillus thuringiensis* Δ-endotoxins can bring about a resistance to insect pests in various plants (Goyal R K et al. (2000) Crop Protection 19(5): 307-312).

Further target genes which are suitable for pathogen defense comprise "polygalacturonase-inhibiting protein" (PGIP), thaumatine, invertase and antimicrobial peptides such as lactoferrin (Lee T J et al. (2002) J Amer Soc Horticult Sci 127(2):158-164).

4. Expression of genes which bring about an accumulation of fine chemicals such as of tocopherols, tocotrienols, vitamin C or carotenoids. An example which may be mentioned is phytoene desaturase. Preferred are nucleic acids which encode the *Narcissus pseudonarcissus* phytoene desaturase (GenBank Acc. No.: X78815) or functional equivalents thereof. For example, the production of vitamin C can be modified and increased via the expression of GDP-mannose 3',5'-epimerase (WO 02/103001). The carotenoid content in plants, for example potatoes, can be increased by expressing a protein which has the enzymatic activity of a zeaxanthin epoxidase (WO 02/103021).

5. Production of nutraceuticals such as, for example, polyunsaturated fatty acids (for example arachidonic acid, eicosapentaenoic acid or docosahexaenoic acid) by expression of fatty acid elongases and/or desaturases, or production of proteins with improved nutritional value such as, for example, with a high content of essential amino acids (for example the high-methionine 2S albumin gene of the Brazil nut). Preferred are nucleic acids which encode the *Bertholletia excelsa* high-methionine 2S albumin (GenBank Acc. No.: AB044391), the *Physcomitrella patens* Δ6-acyl-lipid desaturase (GenBank Acc. No.: AJ222980; Girke et al. (1998) Plant J 15:39-48), the *Mortierella alpina* Δ6-desaturase (Sakuradani et al. 1999 Gene 238:445-453), the *Caenorhabditis elegans* Δ5-desaturase (Michaelson et al. 1998, FEBS Letters 439:215-218), the Caenorhabditis elegans Δ5-fatty acid desaturase (des-5) (GenBank Acc. No.: AF078796), the *Mortierella alpina* Δ5-desaturase (Michaelson et al. JBC 273:19055-19059), the *Caenorhabditis elegans* Δ6-elongase (Beaudoin et al. 2000, PNAS 97:6421-6426), the *Physcomitrella patens* Δ6-elongase (Zank et al. 2000, Biochemical Society Transactions 28:654-657), or functional equivalents of these.

The overexpression of glutamate dehydrogenase (GDH), for example, results in an accumulation of free amino acids and an improved yield in transgenic potatoes (WO 03/000041). A production of polyfructans (levans) in plants can be achieved by overexpressing a bacterial sucrase in transgenic plants (U.S. Pat. No. 6,501,005). The content in, and the structure of, sterol glycosides has been modified by expressing a sterol glucosyltransferase (U.S. Pat. No. 6,498, 239).

6. Production of high-quality proteins and enzymes for industrial purposes (for example enzymes, such as lipases) or as pharmaceuticals (such as, for example, antibodies, blood clotting factors, interferons, lymphokins, colony stimulation factor, plasminogen activators, hormones or vaccines, as described by Hood E E, Jilka J M (1999) Curr Opin Biotechnol 10(4):382-6; Ma J K, Vine N D (1999) Curr Top Microbiol Immunol 236:275-92). For example, it has been possible to produce recombinant avidin from chicken albumen and bacterial β-glucuronidase (GUS) on a large scale in transgenic maize plants (Hood et al. (1999) Adv Exp Med Biol 464:127-47). The expression of monoclonal antibodies against cariogenic organisms in edible fruits of plants is described in the patent WO 02/102975.

8. Obtaining an increased storability in cells which normally comprise fewer storage proteins or storage lipids, with the purpose of increasing the yield of these substances, for example by expression of an acetyl-CoA carboxylase. The expression of an acetyl-CoA carboxylase leads to a modification of the quality and quantity with regard to the oil and fatty acid production in plants (WO 94/17188). Preferred nucleic acids are those which encode the *Medicago sativa* acetyl-CoA carboxylase (accase) (GenBank Acc. No.: L25042), or functional equivalents thereof. Further examples are described in Herbers & Sonnewald (1999) Curr Opinion Biotechnol 10 163-168; Biesgen & Herbers (2000) J Plant Biotechnol 2:1-12; Biesgen et al. (2002) Phytochemistry Reviews 1:79-85.

9. Modification of the carbohydrate metabolism:
The SSS3 promoter can be used for example for expressing a starch synthase from wheat in order to modify the content in, or composition of, plant starch, which can be used for the optimization of foodstuffs, the development of coatings, adhesives or packaging materials, and applications in the construction industry (WO 00/66745). Further possible applications are described in DE06483010 and WO 02/086112. The SSS3 promoter is particularly suitable for reducing the accumulation of sugars as the result of the expression of a phosphofructose kinase. This can be exploited in particular during the storage of potatoes at low temperatures to suppress what is known as cold sweetening (U.S. Pat. No. 6,489,539). As the result of the expression or repression of plant sugar transporters, the carbohydrate metabolism is modulated (WO 02/0199217). Further advantageous examples are invertase inhibitor (Börnke et al. (1999) Nature Biotech 17:708-711), sucrose isomerase (Börnke et al. (2002) Planta 214:356-364, starch-related R1 protein (Lorberth et al. (1998) Nature Biotechnology 16(5):473-7, Ritte et al. (2000) Plant Journal 21(4):387-91).

10. The SSS3 promoter can also be used for expressing proteins in starch-comprising tissues, such as, for example, potato tubers, to increase the nutritional value (Chakraborty et al. (2000) Proc Natl Acad Sci USA 97:3724-3729). As the result of the expression of an endo-1,4-β-D-galactanase, pectin can be modified (Sørensen et al. (2000) Proc Natl Acad Sci USA 97: 7639-7644). For example, the content of storage substances, such as lipids, fatty acids, starch or seed proteins, can be modulated as the result of the expression of lipid metabolism proteins (LMPS) (WO 02/099076). The starch content and the yield can be increased as the result of overexpression of the plastidic adenylate kinase in transgenic potato plants (Regierer et al. (2002) Nature Biotechnology 20:1256).

11. The SSS3 promoter can be used for expressing xylanase to control the growth, dying down and fruit maturation of plants (U.S. Pat. No. 6,495,743).

Further examples of advantageous genes are mentioned for example in Dunwell J M, Transgenic approaches to crop improvement, J Exp Bot. 2000; 51 Spec No; pages 487-96.

Furthermore, it is possible to express functional analogs of the abovementioned nucleic acids or proteins. In this context, functional analogs means all those sequences which have essentially the same function, i.e. which are capable of exerting the function (for example a substrate conversion or a signal transduction), as the protein mentioned by way of example. In this context, the functional analog may indeed differ with regard to other features. For example, it may have a higher or lower activity or else have further functionalities. Functional analogs furthermore means sequences which encode fusion proteins consisting of one of the preferred proteins and other proteins, for example a further preferred protein, or else a signal peptide sequence.

Furthermore, the skilled worker knows that the above-described genes need not be expressed directly using the nucleic acid sequences encoding these genes or repress these above-described genes, for example by antisense. It is also possible to use for example artificial transcription factors of the zinc finger protein type (Beerli R R et al. (2000) Proc Natl Acad Sci USA 97(4):1495-500). These factors attach in the regulatory regions of the endogenous genes to be expressed or to be repressed and, depending on the design of the factor, bring about an expression or repression of the endogenous gene. Thus, the desired effects can also be achieved by expressing a suitable zinc finger transcription factor under the control of one of the promoters according to the invention. By expressing certain Myb transcription factors, flavonoid biosynthesis can be modulated, for example (Moyano et al. (1996) Plant Cell 8:1519-32). Further examples of the regulation of the secondary metabolism are described (Memelink (2001) Advances in Biochemical Engineering-Biotechnology 72:103-25).

Likewise, the transgenic expression cassettes according to the invention can be employed for the reduction (suppression) of transcription and/or translation of target genes by "gene silencing". Thus, the transgenic expression cassettes according to the invention can express nucleic acids which bring about PTGS (post-transcriptional gene silencing) or TGS (transcriptional silencing) effects and thus a reduction of the expression of endogenous genes. Said reduction can be achieved for example by expression of an antisense RNA (EP-A1 0 458 367; EP-A1 0 140 308; van der Krol A R et al. (1988) BioTechniques 6(10):658-676; de Lange P et al. (1995) Curr Top Microbiol Immunol 197:57-75, inter alia) or of a double-stranded RNA, each of which has homology with the endogenous target gene to be reduced. Also, the expression of a suitable sense RNA can bring about a reduction of the expression of endogenous genes, by means of what is known as cosuppression (EP-A1 0 465 572). Especially preferred is the expression of a double-stranded RNA for reducing the gene expression of a target gene. WO 99/32619 and WO 99/53050 describe methods for inhibiting individual target genes using an RNA with double-stranded structure, where the target gene and the region of the RNA duplex have at least partial identity (see also: Montgomery M K et al. (1998) Proc Natl Acad Sci USA 95:15502-15507; Sharp P A (1999) Genes & Development 13(2):139-141; Fire A et al. (1998) Nature 391:806-11). The method is currently also referred to as RNA interference (RNAi).

Preferred applications where the reduction (suppression) of gene expression brings about an advantageous phenotype comprise by way of example, but not by limitation:

1. Modification of the Carbohydrate Composition

A modification of the carbohydrate composition can be achieved for example by reducing the gene expression of genes of the carbohydrate metabolism or of carbohydrate biosynthesis, for example the biosynthesis of amylose, pectins, cellulose or cell-wall carbohydrates. A multiplicity of cellular processes (maturation, starch composition, starch content and the like) can thus be influenced in an advantageous manner. Target genes which may be mentioned by way of example, but not by limitation, are phosphorylases, starch synthetases, branching enzymes, lipoxygenases (Griffiths A. et al. (1999) Postharvest Biology & Technology 17(3):163-173), debranching enzymes, and various amylases. The genes in question are described (Dunwell J M (2000) J Exp Botany 51 Spec No: 487-96; Brar D S et al. (1996) Biotech Genet Eng Rev 13:167-79; Kishore G M and Somerville C R (1993) Curr Opin Biotech 4(2):152-8). Advantageous genes for influencing the carbohydrate metabolism—in particular starch biosynthesis—are described in WO 92/11375, WO 92/11376, U.S. Pat. No. 5,365,016 and WO 95/07355 and WO 02/097101. The fusion of an SSS3 promoter with a sequence, in antisense orientation, of one or both subunits of the ADP-glucose pyrophosphorylase is capable of inhibiting the activity of the latter during the early development of fruits and tubers and of increasing the ratio between soluble sugars and starch.

In a further advantageous embodiment, a shift of the amylose/amylopectin ratio in starch can be brought about by suppression of the two isoforms of the branching enzyme which are responsible for the α-1,6-glycosidic linkage. Such procedures are described (for example by Schwall G P et al. (2000) Nat Biotechnol 18(5):551-554). Nucleic acid sequences such as that of the potato starch branching enzyme II (GenBank Acc. No.: AR123356; U.S. Pat. No. 6,169,226) or its homologs from other genera and species are preferably used for this purpose. A further application is the suppression of endogenous activities (enzymes, signal transduction, phytohormone and the like) by immunomodulation.

Especially advantageous is the reduction of starch mobilization and conversion into sugars at low temperatures (cold sweetening) by means of reducing the expression of glucan phosphorylase (systematic name: 1,4-α-D-glucan:phosphate α-D-glucosyltransferase; U.S. Pat. No. 5,998,710).

2. Delayed Fruit Maturation

Delayed fruit maturation or a modified maturation phenotype (prolonged maturation, later senescence) can be achieved for example by reducing the gene expression of genes selected from the group consisting of polygalacturonases, pectin esterases, β-(1,4)glucanases (cellulases), β-galactanases (β-galactosidases), or genes of ethylene biosynthesis, such as 1-aminocyclopropane-1-carboxylate synthase, adenosylmethionine hydrolase (SAMase), aminocyclopropane-1-carboxylate deaminase, aminocyclopropane-1-carboxylate oxidase, genes of carotenoid biosynthesis such as, for example, genes of pre-phytoene biosynthesis or phytoene biosynthesis, for example phytoene desaturases, and O-methyltransferases, acyl carrier protein (ACP), elongation factor, auxin-induced gene, cysteine(thiol) proteinases, starch phosphorylases, pyruvate decarboxylases, chalcone reductases, protein kinases, auxin-related gene, sucrose transporters, meristem pattern gene. Further advantageous genes are described for example in WO 91/16440, WO 91/05865, WO 91/16426, WO 92/17596, WO 93/07275 or wo 92/04456. Especially preferred is the reduction of the expression of polygalacturonase for the prevention of cell degradation and mushiness of plants and fruits, for example tomatoes. Nucleic acid sequences such as that of the tomato polygalacturonase gene (GenBank Acc. No.: X14074) or its homologs are preferably used for this purpose.

3. Improved protection against abiotic stress factors (heat, chill, drought, elevated moisture, pollutants, UV radiation). It is preferred to reduce the expression of genes which are implicated in stress reactions.

4. Reduction of the Storage Protein Content

The reduction of the gene expression of genes encoding storage proteins (hereinbelow SPs) has numerous advantages, such as, for example, the reduction of the allergenic potential or modification regarding the composition or quantity of other metabolites, such as, for example, oil or starch content.

5. Obtaining a Resistance to Plant Pathogens

Resistance to plant pathogens such as arachnids, fungi, insects, nematodes, protozoans, viruses, bacteria and diseases can be achieved by reducing the gene expression of genes which are essential for the growth, survival, certain developmental stages (for example pupation) or the multiplication of a specific pathogen. Such a reduction can bring about a complete inhibition of the abovementioned steps, or else a delay of same. They can take the form of plant genes which for example make possible the penetration of the pathogen, but may also be homologous pathogen genes. The transgenically expressed nucleic acid sequence (for example the double-stranded RNA) is preferably directed against genes of the pathogen. The antipathogenic agent which acts may be, in this context, the transgenically expressed nucleic acid sequence itself (for example the double-stranded RNA), but also the transgenic expression cassettes or transgenic organisms. The plants themselves, in the form of a transgenic organism, may contain the agents and pass them on to the pathogens, for example in the form of a stomach poison. Various essential genes of a variety of pathogens are known to the skilled worker (for example for nematode resistance WO 93/10251, WO 94/17194). Virus resistance can be achieved for example by reducing the expression of a viral coat protein, a viral replicase, a viral protease and the like. A large number of plant viruses and suitable target genes are known to the skilled worker.

8. Reduction of undesired, allergenic or toxic plant constituents such as, for example, glucosinolates. Suitable target genes are described (in WO 97/16559, inter alia). The target genes which are preferred for reduction of 14-16 kDa allergenic proteins are described for example by Tada Y et al. (1996) FEBS Lett 391(3):341-345 or Nakamura R (1996) Biosci Biotechnol Biochem 60(8):1215-1221.

9. Delayed signs of senescence. Suitable target genes are, inter alia, cinnamoyl-CoA:NADPH reductases or cinnamoyl-alcohol dehydrogenases. Further target genes are described (in WO 95/07993, inter alia).

10. Reduction of the susceptibility to bruising of, for example potatoes by reducing for example polyphenol oxidase (WO 94/03607) and the like.

11. Increase of the methionine content by reducing threonine biosynthesis, for example by reducing the expression of threonine synthase (Zeh M et al. (2001) Plant Physiol 127(3):792-802).

Antisense nucleic acid firstly means a nucleic acid sequence which is fully or in part complementary to at least part of the sense strand of said target protein. The skilled worker knows that an alternative is the use of the cDNA or the corresponding gene as starting template for suitable antisense constructs. Preferably, the antisense nucleic acid is complementary to the coding region of the target protein or part of same. However, the antisense nucleic acid may also be complementary to the noncoding region or part of same. Starting from the sequence information of a target protein, an antisense nucleic acid can be of designed in the manner with which the skilled worker is familiar, taking into consideration the Watson-Crick base pair rules. An antisense nucleic acid can be complementary to all or part of the nucleic acid sequence of a target protein. In a preferred embodiment, the antisense nucleic acid is an oligonucleotide with a length of, for example, 25, 30, 35, 40, 45 or 50 nucleotides.

The antisense strategy can advantageously be combined with a ribozyme method. Ribozymes are catalytically active RNA sequences which, when linked with the antisense sequences, catalytically cleave the target sequences (Tanner N K (1999) FEMS Microbiol Rev 23(3):257-75). The efficiency of an antisense strategy may thereby be increased. The expression of ribozymes for reducing certain proteins is known to the skilled worker and described for example in EP-A1 0 291 533, EP-A1 0 321 201 and EP A1 0 360 257. Suitable target sequences and ribozymes can be identified for example as described by Steinecke (Ribozymes, Methods in Cell Biology 50, Galbraith et al. eds Academic Press, Inc. (1995), 449-460) by calculating the secondary structures of ribozyme and target RNA and also by their interaction (Bayley C C et al. (1992) Plant Mol Biol 18(2):353-361; Lloyd A M and Davis R W et al. (1994) Mol Gen Genet 242(6):653-657). Examples which may be mentioned are hammerhead ribozymes (Haselhoff and Gerlach (1988) Nature 334:585-591). Preferred ribozymes are based on derivatives of the Tetrahymena L-19 IVS RNA (U.S. Pat. Nos. 4,987,071; 5,116,742). Further ribozymes with selectivity for an L119 mRNA can be selected (Bartel D and Szostak J W (1993) Science 261:1411-1418).

Also comprised is the use of the above-described sequences in sense orientation which, as the skilled worker will know, can lead to cosuppression. The expression of sense RNA to an endogenous gene can reduce or eliminate expression thereof, in a similar manner to what has been described for antisense approaches (Goring et al. (1991) Proc Natl Acad Sci USA, 88:1770-1774; Smith et al. (1990) Mol Gen Genet 224:447-481; Napoli et al. (1990) Plant Cell 2:279-289; Van der Krol et al. (1990) Plant Cell 2:291-299). In this context, the construct introduced may represent the gene to be reduced either fully or only in part. No possibility of translation is necessary.

Also very especially preferred is the use of methods such as gene regulation by means of double-stranded RNA (double-stranded RNA interference). Such methods are known to the skilled worker and described in detail (for example Matzke M A et al. (2000) Plant Mol Biol 43:401-415; Fire A. et al. (1998) Nature 391:806-811; WO 99/32619; WO 99/53050; WO 00/68374; WO 00/44914; WO 00/44895; WO 00/49035; WO 00/63364). The methods and processes described in the references cited are expressly referred to. Here, a highly efficient suppression of native genes is brought about by the simultaneous introduction of strand and counterstrand.

A further subject of the invention relates to the use of the above-described transgenic organisms according to the invention and of the cells, cell cultures, parts—such as, for example, roots, leaves and the like in the case of transgenic plant organisms—and transgenic propagation material, such as seeds or fruits, derived from these transgenic organisms for the production of foodstuffs or feedstuffs, pharmaceuticals or fine chemicals.

Preference is further given to a method for the recombinant production of pharmaceuticals or fine chemicals in host organisms, in which a host organism is transformed with one of the above-described expression cassettes and said expression cassette contains one or more structural genes which code for the fine chemical of interest or catalyze the biosynthesis of the fine chemical of interest, and the transformed host organism is cultivated and the fine chemical of interest is isolated from the cultivation medium. This method is broadly applicable for fine chemicals such as enzymes, vitamins, amino acids, sugars, fatty acids, natural and synthetic flavorings, aromatizing substances and colorants. Particular preference is given to the production of tocopherols and tocotrienols and also carotenoids such as astaxanthin. Cultivation of the transformed host organisms and isolation from said host organisms or from the cultivation medium are carried out by means of the methods known to the skilled worker. The production of pharmaceuticals such as, for example, antibodies or vaccines is described in Hood E E & Jilka J M (1999) Curr Opin Biotechnol 10(4):382-6; Ma J K & Vine N D (1999) Curr Top Microbiol Immunol 236:275-92.

SEQUENCES

1. SEQ ID NO: 1 Promoter of the SSS3 gene from potato (*Solanum tuberosum*)
2. SEQ ID NO: 2 Promoter of the SSS3 gene from *Arabidopsis thaliana*
3. SEQ ID NO: 3 Promoter of the SSS3 gene from rice (*Oryza sativa*)
4. SEQ ID NO: 4 Promoter of the SSS3 gene from wheat (*Triticum aestivum*)
5. SEQ ID NO: 5 Nucleic acid sequence coding for starch synthase 3 (SSS3) from potato (*Solanum tuberosum*)
6. SEQ ID NO: 6 Amino acid sequence coding for starch synthase 3 (SSS3) from potato (*Solanum tuberosum*)
7. SEQ ID NO: 7 Nucleic acid sequence coding for starch synthase 3 (SSS3) from *Arabidopsis thaliana*
8. SEQ ID NO: 8 Amino acid sequence coding for starch synthase 3 (SSS3) from *Arabidopsis thaliana*
9. SEQ ID NO: 9 Nucleic acid sequence coding for starch synthase 3 (SSS3) from rice (*Oryza sativa*)
10. SEQ ID NO: 10 Amino acid sequence coding for starch synthase 3 (SSS3) from rice (*Oryza sativa*)
11. SEQ ID NO: 11 Nucleic acid sequence coding for starch synthase 3 (SSS3) from wheat (*Triticum aestivum*)
12. SEQ ID NO: 12 Amino acid sequence coding for starch synthase 3 (SSS3) from wheat (*Triticum aestivum*)
13. SEQ ID NO: 13 Nucleic acid sequence coding for starch synthase 3 (SSS3) from wheat (*Aegilops tauschii*)
14. SEQ ID NO: 14 Amino acid sequence coding for starch synthase 3 (SSS3) from wheat (*Aegilops tauschii*)
15. SEQ ID NO: 15 Nucleic acid sequence coding for starch synthase 3 (SSS3) from asparagus bean (*Vigna unguiculata*)
16. SEQ ID NO: 16 Amino acid sequence coding for starch synthase 3 (SSS3) from asparagus bean (*Vigna unguiculata*)
17. SEQ ID NO: 17 Nucleic acid sequence coding for starch synthase 3 (SSS3) from maize (*Zea mays*)
18. SEQ ID NO: 18 Amino acid sequence coding for starch synthase 3 (SSS3) from maize (*Zea mays*)
19-39. SEQ ID NO: 19 to 39: Sequence motifs for starch synthase 3 proteins
40. SEQ ID NO: 40 Oligonucleotide primer R-DSS3-263 (27-mer)

5'-TGCATTGGAGACACTTGTGCAACTCAA-3'

41. SEQ ID NO: 41 Oligonucleotide primer R-DSS3-317 (27-mer)

5'-TGTGGTTCCATGAGAGACAAACCCAAG-3'

42. SEQ ID NO: 42 Oligonucleotide primer L-DS3 (44-mer)

5'-GTCGACTCTAGAGGAAGAAATCTTCTCTGTCTAAAAAATTGACG-3'

43. SEQ ID NO: 43 Oligonucleotide primer R-DS3: (38-mer)

5'-CCCGGGATCCTCTCTCCCTCTCTGTATCTGTGCTGCAA-3'

44. SEQ ID NO: 44 Promoter of the SSS3 gene from potato (*Solanum tuberosum*; polymorphous to SEQ ID NO: 1)
45. SEQ ID NO: 45 Oligonucleotide primer 5'actin AC1 (23-mer)

5'-ATGGCAGACGGTGAGGATATTCA-3'

46. SEQ ID NO: 46 Oligonucleotide primer 3'actin AC2 (23-mer)

5'-GCCTTTGCAATCCACATCTGTTG-3'

47. SEQ ID NO: 47 Oligonucleotide primer L-SSS3-G50 (24-mer)

5'-GCAGCACAGATACAGAGAGGGAGA-3'

48. SEQ ID NO: 48 Oligonucleotide primer R-GUS-G809 (22-mer)

5'-TGGCTGTGACGCACAGTTCATA-3'

B: Detection of the correlation of the glucuronidase activity expressed under the control of the potato SSS3 promoter and the starch production (X-Gluc staining: section on the left; starch staining: section on the right) of potato tubers of line 13.

Figure 2:
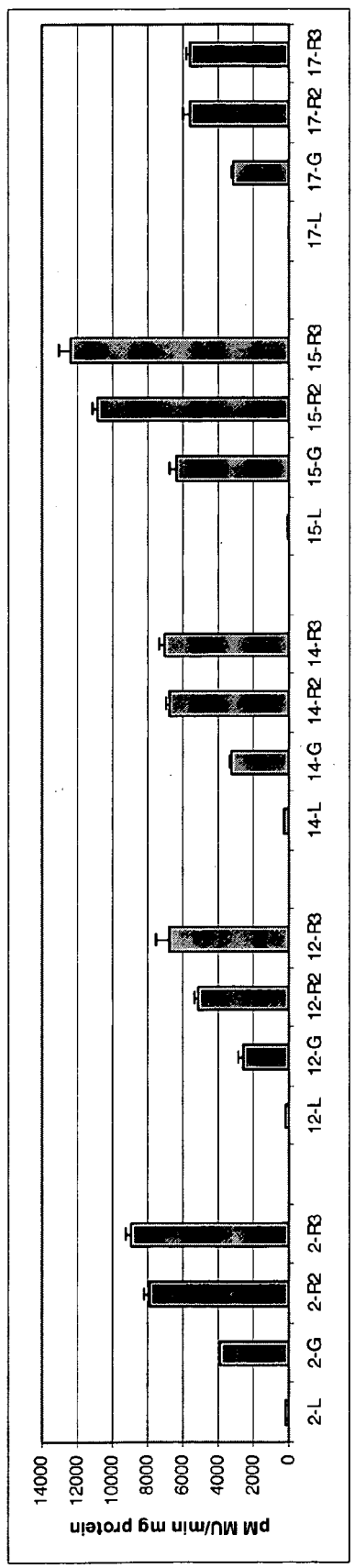

2. FIG. 2: GUS activity in tubers of 5 potato lines (2, 12, 14, 15 and 17) transformed with SSS3 promoter: GUS construct. L: leaves; G: developing tubers; R2: 45 days storage at room temperature; R3: 90 days storage at room temperature.

Figure 3:
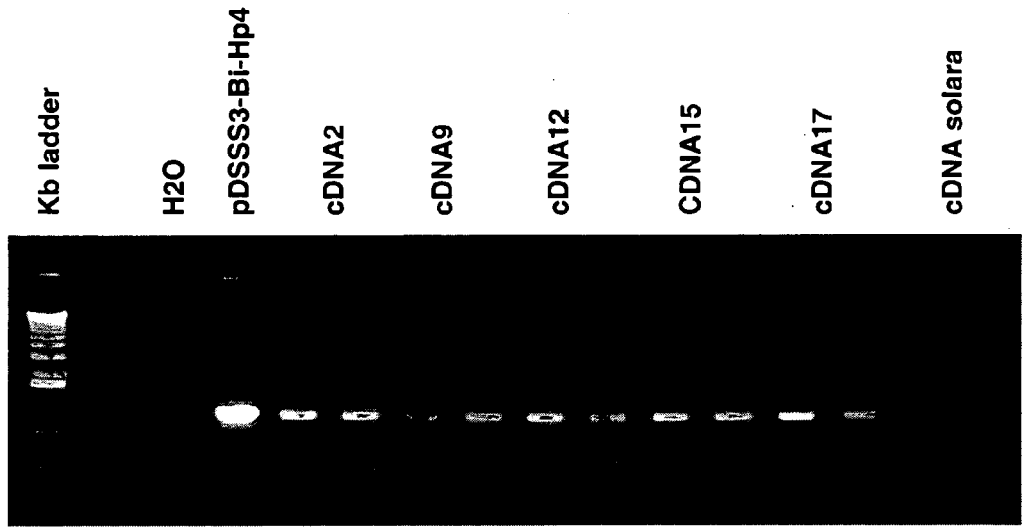
Figure 4:
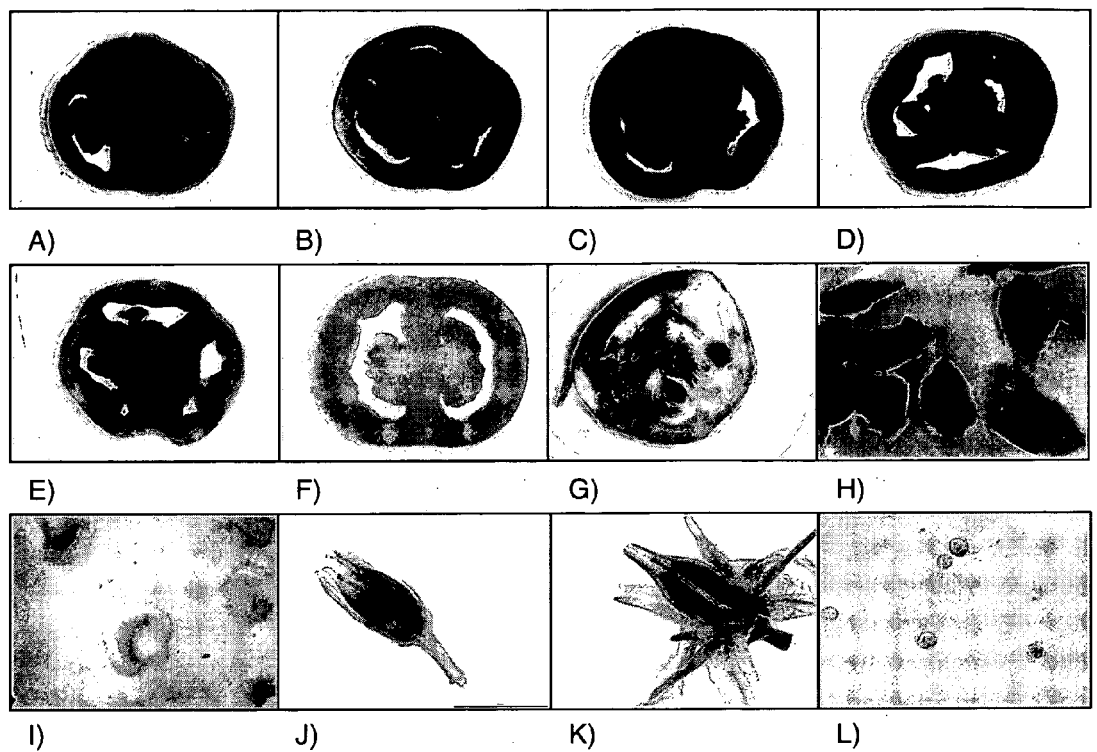

3. FIG. 3: PCR amplification of the cDNA (primer in the 5'-untranslated region of the SSS3 promoter and in the GUS gene) H2O: Negative control; pDSSS-Bi-Hp4: plasmid DNA as positive control, cDNA after 45 days' (left) and after 90 days' (right) storage of the tubers of lines 2, 9, 12, 15 and 17; cDNA solara: wild-type control 4. FIG. 4: Green fruits of lines 1 (A), 2 (B), 6 (C), 21 (D), 30 (E), WT (F), orange fruit of line 23 (G), blue-stained seeds (H), unstained sections across petioles (I), bud with stained anthers (J) and flower (K) and stained pollen (L) of tomato plants transformed with pSun0301_SSS3

Figure 5:
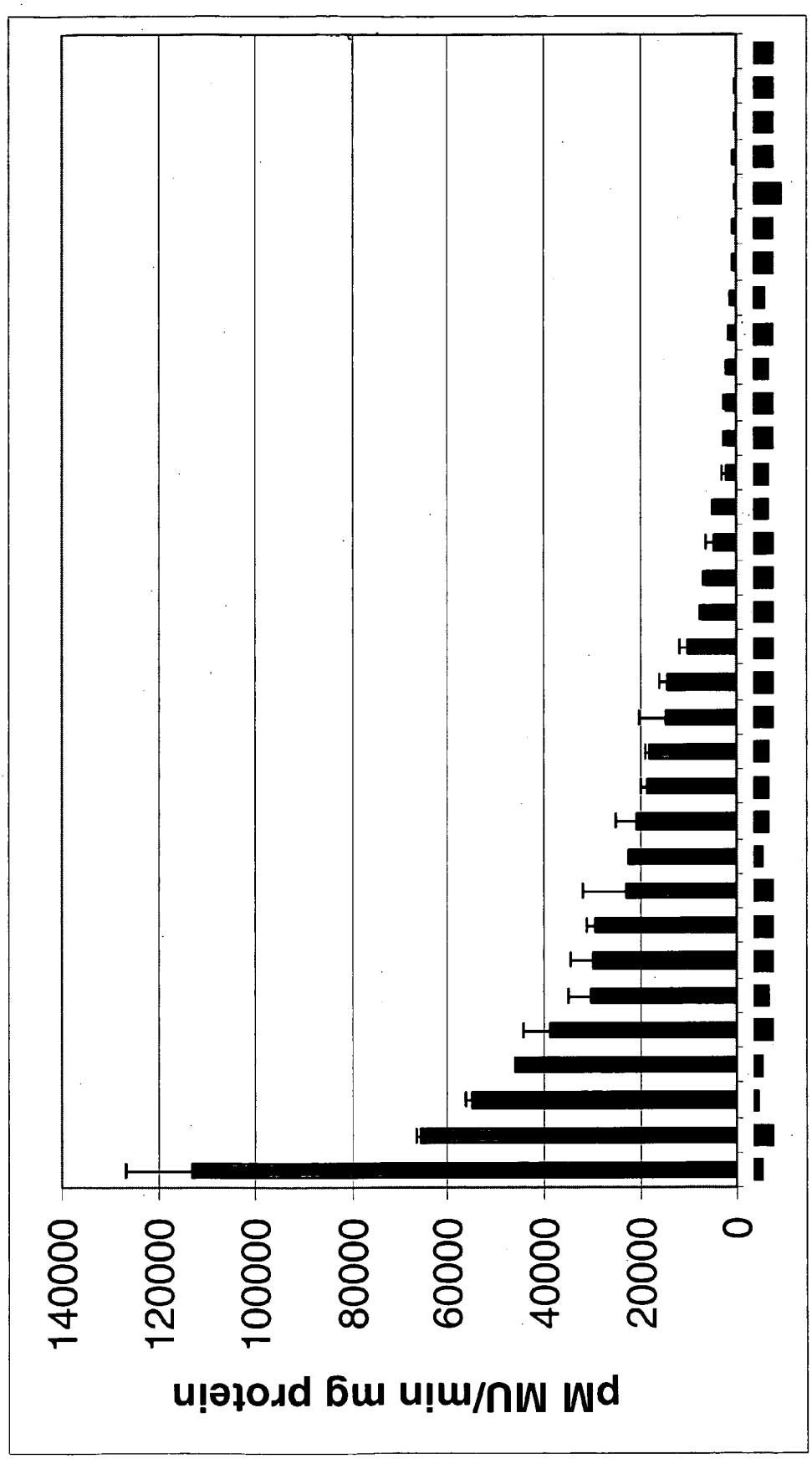
Figure 6:
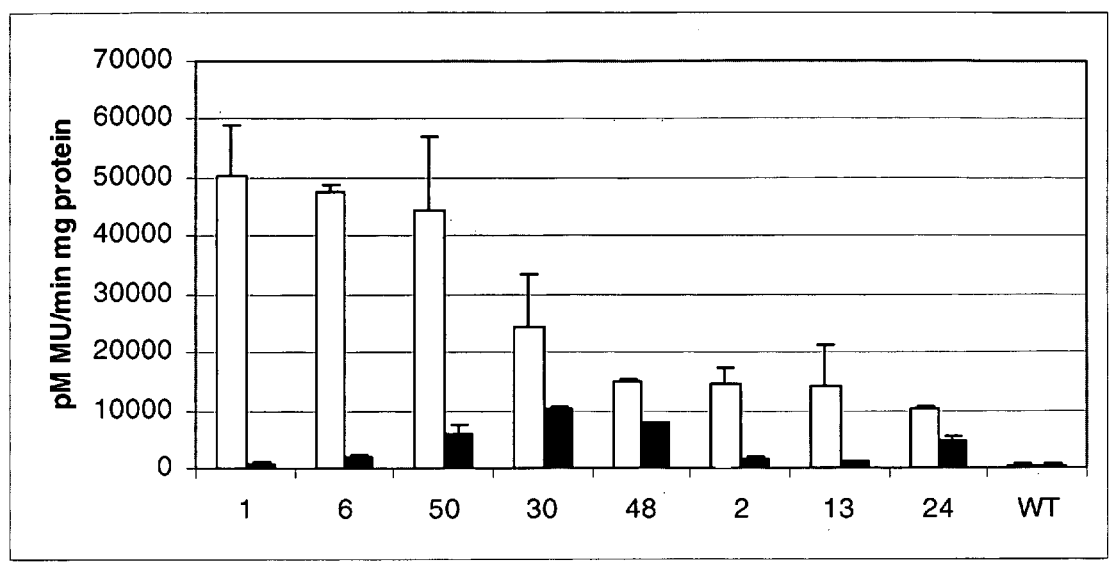

5. FIG. 5: GUS activity in the green fruits of tomato lines, transformed with pSun0301_SSS3. Error bars show in each case the standard error 6. FIG. 6: Comparison of the GUS activity in selected lines of transgenic tomato plants (white bars: green fruits, black bars: red fruits; error bars show in each case the standard error).

7. FIG. 7a-g: Alignment of SSS3 protein sequences from potato (STSSS3; SEQ ID NO: 6), *Arabidopsis thaliana* (AtSSS3; SEQ ID NO: 8), asparagus bean (*Vigna unguiculata*; VUSSS3; SEQ ID NO: 16), *Aegilops tauschii* (AtaSSS3; SEQ ID NO: 14), wheat (*Triticum aestivum*; TASSS3; SEQ ID NO: 12), rice (OS SSS3; SEQ ID NO: 49), maize (ZM SSS3; SEQ ID NO: 18). Identical amino acids are shown against a gray background and emphasized by the additionally shown consensus sequence.

EXAMPLES

General Methods

Recombinant DNA techniques were carried out as described by Maniatis et al., Molecular Cloning—A Laboratory Manual (Cold Spring Harbor Lab., Cold Spring Harbor, N.Y., 1982). The enzymes employed were used as specified. The cloning vectors used were pCR2.1 and pCR-BLUNT (Invitrogen). The vectors pBI101 (Jefferson et al. (1987) EMBO J. 6:3901-3907) and pSUN3 (SunGene GmbH & Co KgaA, WO 02/00900) were employed for the transformation of plants. Strain DH5α (Hanahan D (1983) J Mol Biol 166: 557-580) was used for the transformation into *E. coli*. The agrobacteria LBA4404 and C58C1 [pGV2260] strains were transformed directly by means of the freeze-thaw method as described by An G (1987) Mol Gen Genet 207:210-216.

Example 1

Transformation of Potato and Tomato 1.1 Potato 20 small leaves of a sterile potato culture which had been scarified using a surgical blade were placed into 10 ml of MS medium supplemented with 2% sucrose and comprising 50 µl of an *Agrobacterium tumefaciens* overnight culture grown under selection. After the Petri dishes had been shaken gently for 5 minutes, they were incubated at 25° C. in the dark. After two days, the leaves were plated onto MS medium supplemented with 1.6% glucose, 2 mg/l zeatin ribose, 0.02 mg/l gibberellic acid, 500 mg/l Claforan, 50 mg/l kanamycin and 0.8% Bacto agar. After incubation for one week at 25° C. and 3000 lux, the Claforan concentration in the medium was halved. Cultivation was continued for a further week under known conditions (Rocha-Sosa et al. (1989) EMBO J. 8:23-29).

1.2 Tomato

The starting explant for the transformation are cotyledons of seven- to ten-day-old seedlings of the line Microtom. The culture medium as described by Murashige and Skoog (Murashige and Skoog, 1962, Physiol. Plant. 15, 473-497) supplemented with 2% sucrose, pH 6.1, is used for the germination. Germination takes place at 21° C. under low-light conditions (20-100 µE). After seven to ten days, the cotyledons are divided transversely and placed on the medium MSBN (MS, pH 6.1, 3% sucrose+1 mg/l BAP, 0.1 mg/l NAA) which had been charged with suspension-cultured tobacco cells on the previous day. The tobacco cells are covered with sterile filter paper so that air bubbles are excluded. The explants are precultured on the above-described medium for three to five days. Thereafter the explants are infected with the *Agrobacterium tumefaciens* strain LBA4404, which harbors the binary plasmid with the gene to be transformed, as follows: the strain which had been cultured overnight at 28° C. in YEB medium with the antibiotic for the binary plasmid is centrifuged. The bacterial pellet is resuspended in liquid MS medium (3% sucrose, pH 6.1) and adjusted to an optical density of 0.3 (at 600 nm). The precultured explants are transferred into the suspension and incubated for 30 minutes at room temperature with gentle shaking. Thereafter, the explants are dried with sterile filter paper and returned to their preculture medium for three days of cocluturing (21° C.).

After cocluturing, the explants are transferred to MSZ2 medium (MS pH 6.1 supplemented with 3% sucrose, 2 mg/l zeatin, 100 mg/l kanamycin, 160 mg/l Timentin) and retained for the selective regeneration at 21° C. under low-light conditions (20-100 µE, photoperiod 16 h/8 h). The explants are transferred every two to three weeks until shoots form. Small shoots can be excised from the explant and rooted on MS (pH 6.1+3% sucrose) 160 mg/l Timentin, 30 mg/l kanamycin, 0.1 mg/l IAA. Rooted plants are transferred into the greenhouse.

Example 2

Isolation of Genomic DNA

The genomic DNA of transgenic potato and tomato plants was isolated with the aid of the DNA isolation kit from Macherey & Nagel. In a first step, the transgenic lines were identified via PCR, using gene-specific primers. The integration of the foreign DNA was analyzed by means of Southern blot analyses of 20 Mg of DNA after a suitable restriction cleavage.

The following method was applied for obtaining genomic potato DNA for isolating the SSS3 promoter: mortar and pestle were cooled with liquid nitrogen, and 5 g of young leaf material was homogenized to give a fine powder. This powder was transferred into a 50 ml centrifuge tube. The material was shaken vigorously with 15 ml of freshly prepared extraction buffer. After 1 ml of 20% SDS pH 7.2 had been added, the mixture was incubated for 10 minutes at 65° C. Thereafter, 5 ml of 5M potassium acetate was added, the mixture was incubated on ice for a further 30 minutes and subsequently centrifuged at 12 000 rpm. The supernatant was filtered through a Miracloth membrane, transferred into a fresh centrifuge tube and again centrifuged as described above. Then, 10 ml of isopropanol were added to the supernatant and the mixture was mixed, incubated for 30 minutes at −20° C. and again centrifuged at 8000 rpm. The supernatant was decanted off and the pellet was dried for 10 minutes in the tube which had been turned upside down. The pellet was then dissolved in 700 µl of 50× TE buffer and transferred into an Eppendorf tube, 5 µl RNase (10 mg/ml) were added, and the mixture was digested for 30 minutes at 37° C.

After addition of 75 µl of 3 M sodium acetate and mixing, the mixture was centrifuged for 15 minutes at 13 000 rpm, the supernatant was transferred into a fresh tube, 500 µl of isopropanol were added, and the mixture was mixed, precipitated for 5 minutes at room temperature and centrifuged for 15 minutes at 13 000 rpm. The pellet is dried for a few minutes at room temperature. The DNA is dissolved overnight at 4° C. in 400 µl of TE buffer.

Solutions:

Extraction Buffer:
100 mM Tris-HCl pH 8.0
500 mM NaCl
10 mM β-mercaptoethanol
50 mM EDTA pH 8.0

50×TE
50 mM Tris-HCl pH 8.0
10 mM EDTA pH 8.0

TE buffer
10 mM Tris-HCl pH 8.0
1 mM EDTA pH 8.0

Example 3

Isolation of the Promoter of the Soluble Starch Synthase 3 from Potato

Starting from the cDNA sequence of the soluble starch synthase isoform 3 of *Solanum tuberosum* cultivar Désirée, Acc. No. X94400, which has been published by Abel et al. (Plant Journal 10:981-91) 1996, primers were derived in order to isolate the desired SSS3 promoter in what is known as a genome walking experiment. The Universal Genome Walker Kit from Clontech Laboratories, (catalog No. K1807-1) was used for this experiment. This kit can be used for isolating an unknown sequence which is next to a known sequence. The first step consisted in the generation of uncloned, adaptor-ligated genomic DNA fragments, what are known as genome walker libraries, for which the genomic DNA of *Solanum tuberosum* cultivar Desireé was used. As described in the protocol, the enzyme HpaI was used as restriction enzyme for this purpose ("library DNA").

The following primers were derived for the amplification of the promoter fragment:

(SEQ ID NO: 40)
Primer R-DSS3-263 (27-mer):
5' TGC ATT GGA GAC ACT TGT GCA ACT CAA 3'

(SEQ ID NO: 41)
Primer R-DSS3-317 (27-mer):
5' TGT GGT TCC ATG AGA GAC AAA CCC AAG 3' and the PCR was carried out under the following conditions:

| PCR 1: Mix: | |
|---|---|
| Library DNA | 1.4 µl |
| Sterile water | 18.0 µl |
| 10X PCR reaction buffer | 2.5 µl |
| dNTP (10 mM of each) | 0.5 µl |
| Mg(OAc)₂ | 1.1 µl |
| Tth polymerase mix | 0.5 µl |
| Primer AP1 from the kit | 0.5 µl |
| Primer R-DSS3-263 (10 pmol) | 0.5 µl |

The PCR reaction was carried out using a Perkin Elmer GeneAmp PCR System 2400 Thermal Cycler.

PCR Conditions:
7 cycles: 94° C. for 2 sec; 68° C. for 4 min
38 cycles: 94° C. for 2 sec; 63° C. for 4 min
1 cycle: 63° C. for 6 min; 4° C. until further use PCR 2:
3 µl of the PCR reaction 1 were diluted with 97 µl of water and used for the PCR reaction 2.

| Mix: | |
|---|---|
| Dilute DNA from PCR 1 | 2.0 µl |
| Sterile water | 36.8 µl |
| 10X PCR reaction buffer | 5.0 µl |
| dNTP (10 mM of each) | 1.0 µl |
| Mg(OAc)₂ | 2.2 µl |
| Tth polymerase mix | 1.0 µl |
| Primer AP2 from the kit | 1 µl |
| Primer R-DSS3-263 (10 pmol) | 1 µl |

PCR Conditions:
7 cycles: 94° C. for 2 sec; 68° C. for 4 min
25 cycles 94° C. for 2 sec; 63° C. for 4 min
1 cycle 63° C. for 6 min; 4° C. until further processing After separation on a 1% agarose (1× TAE) gel for 4 hours at 70V, a 1.2 kb fragment was obtained. This band was isolated with the "Quiagel Purification Kit" from Quiagen and cloned into the vector pCR2.1 by means of the TA cloning kit from Invitrogen. The resulting plasmid was named pDSSS3-Hp263-1. This plasmid was sequenced and verified on the basis of the agreement with the known portion of the sequence.

Example 4

Cloning the SSS3 Promoter into the Plasmid pCR-BLUNT

Primers were derived from the sequence of the amplified product, and another PCR starting from genomic DNA was carried out to ensure that it is indeed the genomic promoter region of the SSS3 gene. Using the high fidelity PfuTurbo DNA Polymerase (Stratagene) a 1.1 kb fragment was amplified under the following conditions.

The primers (derived and ordered on Mar. 8, 2000) comprise the restriction sites SalI, XbaI, SmaI and BamHI for the subsequent cloning step.

L-DS3: (5' primer for the promoter amplification, 44-mer)
5' GTC GAC TCT AGA GGA AGA AAT CTT CTC TGT CTA AAA AAT TGA CG 3' (SEQ ID NO: 42; the primer starts with SalI and XbaI restriction sites; printed in bold)

R-DS3: (3' primer for the promoter amplification, 38-mer)
5' CCC GGG ATC CTC TCT CCC TCT CTG TAT CTG TGC TGC AA 3' (SEQ ID NO: 43; the primer starts with SmaI and BamHI sites; printed in bold).

The 3' end of the isolated SSS3 promoter ends at position 75 of the cDNA sequence of the SSS3 gene (Acc. No. X94400), which is 131 bp upstream of the start codon ATG. The sequence without the added cleavage sites is shown by SEQ ID NO: 1 and 44.

| PCR Mix: | |
|---|---|
| Genomic potato DNA (~100 ng) | 1.0 μl |
| Sterile water | 37.8 μl |
| 10X PCR Pfu polymerase mix | 5.0 μl |
| dNTP (10 mM of each) | 1.0 μl |
| MgCl$_2$ (25 mM) | 2.2 μl |
| Pfu polymerase mix | 1.0 μl (2.5 U) |
| Primer R-DS3 (10 pmol) | 1.0 μl |
| Primer L-DS3 (10 pmol) | 1.0 μl |

PCR Conditions for the Amplification of Genomic Potato (Désirée) DNA:

1 cycle: 94° C. for 1 min
10 cycles: 94° C. for 30 sec; 70° C. for 4 min
40 cycles: 94° C. for 30 sec; 66° C. for 4 min
1 cycle: 66° C. for 4 min; 4° C. until further processing The PCR reaction was separated on a 1% strength agarose gel, and the 1.1 kb PCR fragment was isolated as described above. This fragment was cloned into the vector pCR-Blunt (Invitrogen, Zero blunt PCR Cloning Kit, #K2700-20). The sequence data showed that two promoters which differ slightly from one another were isolated. The corresponding plasmids were named pDSSS-Hp4 (Seq ID NO: 1) and pDSSS-Hp6 (SEQ ID NO: 44). In addition to some base pair substitutions and minor deletions, they differ from each other by an additional XbaI site (SEQ ID NO: 44) in the plasmid pDSSS-Hp6.

Example 5

Cloning the Promoters into the Binary Vector pBI101

The binary vector pBI101 (Jefferson et al. (1987) EMBO J. 6:3901-3907) was used for the transformation into potato, and the promoters were cloned before the GUS gene.

The plasmid pDSSS-Hp4 was cut with XbaI and BamHI. The 1.1 kb promoter fragment was isolated and ligated into pBI101, which had been cut with the same enzymes. The resulting plasmid was named pDSSS3-Bi-Hp4 and transformed into the agrobacterial strain C58C1[pGV2260].

The plasmid pDSSS-Hp6 was cut with restriction enzymes SalI and BamHI. The 1.1 kb promoter fragment was isolated and ligated into pBI101, which had been cut with the same enzymes. The resulting plasmid was named pDSSS3-Bi-Hp6 and transformed into the agrobacterial strain C58C1 [pGV2260]. The agrobacterial colonies were selected on Km50/Amp50/Rif25 (μg/ml). These strains were used for the transformation into potato.

Example 6

Detection of the Tissue-Specific Expression

To determine the characteristics of the promoter, it is necessary to place the promoter before what is known as a reporter gene, which makes possible a determination of the expression activity. An example which may be mentioned is the bacterial β-glucuronidase (Jefferson et al. (1987) EMBO J. 6:3901-3907). The β-glucuronidase activity can be determined in planta by means of a chromogenic substrate such as 5-bromo-4-chloro-3-indolyl-β-D-glucuronic acid (X-Gluc) in connection with an activity staining. To examine the tissue specificity, the plant tissue is prepared, treated with the X-Gluc reaction solution and stained at 37° C.

A second assay permits a quantitative determination of the GUS activity in the test tissue. β-Glucuronidase MUG (4-methylumbelliferyl-β-D-glucuronide) is used as substrate for the quantitative activity determination; the former is cleaved into MU (methylumbelliferone) and glucuronic acid.

Example 7

Figure 1:
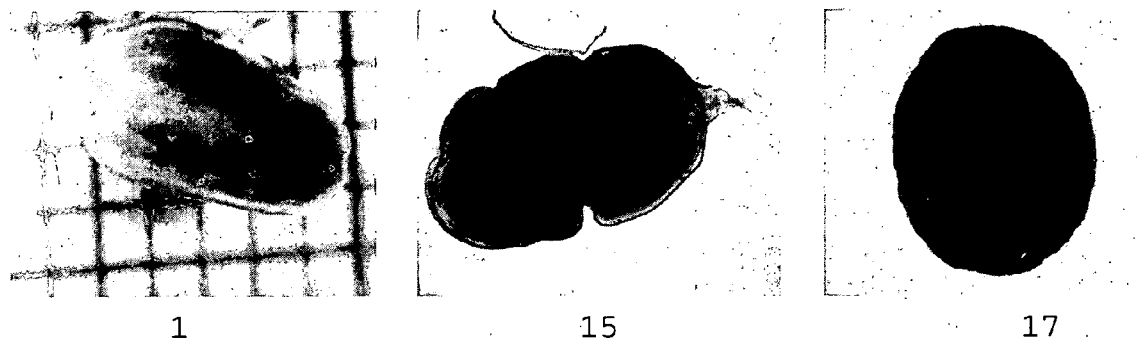
FIG. 1:
A: Detection by means of Xgluc staining of the glucuronidase activity expressed under the control of the potato SSS3 promoter in tubers of lines 1, 15 and 17. This correlates with the presence of starch in this tissue (FIG. 1B).
Figure 1:
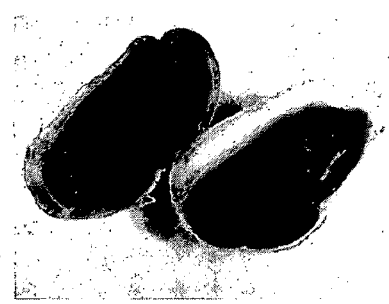

Results of the GUS Analysis for the Tissue Specificity of the Transgenic Potato Plants High-level expression of glucuronidase in the tubers was detected in all transgenic potato plants which had been transformed with the plasmid pDSSS3-Bi-Hp4. The tubers of the best lines showed a blue staining after as little as 30 minutes after the beginning of the enzyme detection (X-Gluc) at room temperature. Surprisingly, the staining was visible even during the very early stages of tuber development. Glucuronidase activity was detected in tubers only 5 mm in length (FIG. 1A). This correlates with the occurrence of starch in this tissue (FIG. 1B). No staining was observed in the potato skin.

A detailed analysis of the GUS expression of the SSS3-Hp4 promoter in the potato plant was carried out by means of the above-described histochemical method, using X-Gluc. To this end, the different tissue types were incubated with the X-Gluc solution, and the blue staining was recorded. The analyses showed that the promoter mediates expression exclusively in starch-comprising tissues. A moderate activity was observed in sections across the internodes, limited to the region below the leaf bud. A weak activity was also shown by the ovaries and the pollen of the flowers of individual lines. Staining was never observed in roots, shoot axis or petioles. In some lines, weak (6 of 18) to moderate (2 of 18) GUS staining was also found in the leaves. Quantitative analyses showed that the activities in the leaves are only very low in comparison with the highly pronounced activities in the tubers.

The analyzed transgenic plants which had been transformed with the plasmid pDSSS3-Bi-Hp6 showed an activity exclusively in the tubers.

Example 8

Quantitative Determination of the Strength of the SSS3-Hp4 Promoter

The quantitative analysis of the activity of the SSS3-Hp4 promoter of these lines was carried out by means of the fluorimetric GUS assay. The data of 10 lines are shown in Table 1.

TABLE 1

GUS activity in developing tubers and mature leaves of selected SSSIII::GUS lines. The lines were obtained by transformation with pDSSS-BiHp4. The means of in each case 4 measurements are shown. The data are shown in picomol MU/mg protein/min; line 10 is a negative control.

| SSSIII::GUS line | GUS activity in developing tubers | GUS activity in mature leaves | Ratio tuber/leaf |
|---|---|---|---|
| 1 | 1033 ± 180 | 55 ± 2 | 19 |
| 2 | 3884 ± 33 | 162 ± 19 | 24 |
| 9 | 3089 ± 165 | 56 ± 6 | 55 |
| 10 | 6 ± 9 | 7 ± 4 | — |
| 11 | 2175 ± 53 | 46 ± 5 | 47 |
| 12 | 2550 ± 280 | 217 ± 11 | 12 |

TABLE 1-continued

GUS activity in developing tubers and mature leaves of
selected SSSIII::GUS lines. The lines were obtained by transformation
with pDSSS-BiHp4. The means of in each case 4 measurements
are shown. The data are shown in picomol MU/mg protein/min;
line 10 is a negative control.

| SSSIII::GUS line | GUS activity in developing tubers | GUS activity in mature leaves | Ratio tuber/leaf |
|---|---|---|---|
| 13 | 1316 ± 73 | 63 ± 1 | 21 |
| 14 | 3252 ± 86 | 272 ± 38 | 12 |
| 15 | 6339 ± 437 | 88 ± 8 | 72 |
| 16 | 862 ± 32 | 23 ± 11 | 37 |
| 17 | 3166 ± 117 | −58 ± 53 | — |

Growing tubers 10 g in weight and leaf material (source leaves from a point in time where the amount of starch should have reached a maximum) were used for the analysis. The data agree with histochemical data. In mature leaves, the activity varies greatly, if measurable in the first place, but, if so, is approximately 50 times lower than in the tubers.

Example 9

Analysis of the Activity of the SSS3 Promoter During Tuber Storage

The activity of the SSS3 promoter during tuber storage was determined mined by means of the above-described fluorimetric GUS assay. To do so, samples were taken from developing tubers and 45 and 90 days after putting the tubers into storage. The results of the best 5 lines are shown in FIG. 2. For comparison reasons, the data for the adult leaves are also shown. In most lines, the GUS activity in the tubers which had been stored for 45 days was approximately twice as high as in the developing tubers. During further storage, the GUS activity in the tubers continued to rise slightly.

The line with the highest activity is line 15. During tuber growth, a GUS activity of 6339±437 pM MU/min mg protein was measured. After storage for 45 days at room temperature, the GUS activity was 10843±329 and after 90 days 12344±681. Thus, this activity was twice as high as in growing tubers and 140× higher than in leaves.

Example 10

Nalysis of the Expression of the SSS3 Promoter by RT-PCR

To rule out that the high GUS activity in the tubers is caused by the storage and the high stability of glucuronidase, the glucuronidase mRNA was detected via RT-PCR.

The cDNA of the potato tubers was isolated via the method of Bauer et al. (Plant Physiol. 105: 585-592, 1994). The actin gene, which was amplified by means of the primers stated hereinbelow, acted as the positive control.

```
                                          (SEQ ID NO: 45)
5'actin AC1 (23-mer)
5' ATG GCA GAC GGT GAG GAT ATT CA 3'

(SEQ ID NO: 46)
3'actin AC2 (23-mer)
5' GCC TTT GCA ATC CAC ATC TGT TG 3'
```

| Mix: | |
|---|---|
| H$_2$O | 37 µl |
| cDNA | 1 µl |
| 10x PCR buffer | 5 µl |
| dNTP (2.5 mM of each) | 4 µl |
| Primer AC1 (10 pmol) | 1.25 µl |
| Primer AC2 (10 pmol) | 1.25 µl |
| Takara Taq polymerase | 0.5 µl (2.5 U) |

PCR Conditions:
1 cycle: 95° C. for 5 min
35 cycles: 95° C. for 5 sec; 52° C. for 40 sec; 72° C. for 70 sec
1 cycle. 72° C. for 3 min; 4° C. until further processing The mRNA as negative control to verify the amplification of genomic DNA and the cDNA of the tubers, isolated from lines 2, 9, 12, 15 and 17, in each case after 45 and 90 days, are shown. The amplificates (1.1 kb) show that the method works and that the expression of the actin gene is comparably high in all of the transgenic lines and that no genomic DNA is present.

Primers were deduced in order to detect the expression of the GUS gene mediated by the SSS3 promoter. The 5' primer L-SSS3-G50 corresponds with the 5'-untranslated region of the SSS3 gene, which is also present in the binary plasmid pDSSS3-Bi-Hp4. The 3' primer R-GUS-G809 was derived from the GUS gene. The PCR mix and the PCR conditions were as described for the amplification of the actin gene, with the exception that the PCR reaction was carried out in 25 µl with 0.125 µl TaKaRa Taq polymerase and 1 µl of primer.

```
                                          (SEQ ID NO: 47)
Primer L-SSS3-G50 (24-mer):
5' GCA GCA CAG ATA CAG AGA GGG AGA 3'

(SEQ ID NO: 48)
Primer R-GUS-G809 (22-mer):
5' TGG CTG TGA CGC ACA GTT CAT A 3'
```

To detect the glucuronidase mRNA, 0.1 µg of the cDNA of the tubers of lines 2, 9, 12, 15 and 17 and, as negative control, of the wild type were used. To rule out contamination of the mRNA with genomic DNA, 0.2 µg of DNase-treated mRNA were also used as template. cDNA was isolated from tubers of each line after 45 days and after 90 days. The left side shows the result of the amplification of the mRNA or cDNA after 45 days and the right after 90 days. The expected 0.5 kb PCR product became apparent after separation on a 1% strength agarose gel. The result showed that the amount of the cDNA was similar for each preparation and that no contamination with genomic DNA was discernible (FIG. 4).

Example 11

Cloning the SSS3 Promoter into the Binary Vector pSUN0301 for Analyzing the Expression Pattern in Tomato The plasmid pDSSS-Hp4 was cut with the restriction enzymes BamHI and EcoRI, and the resulting 1 kb fragment was cloned into the binary plasmid pSUN0301 (derivative of pSUN; SunGene GmbH & Co KgaA, WO 0200900) before the GUS gene which was present therein. The resulting plasmid was named pSUN0301_SSS3 and verified via a sequence analysis. After transformation into the agrobacterial strain LBA4404, a tomato transformation was carried out by means of the above-described protocol.

Example 12

Tissue-Specific Analysis of the Transgenic Lines

Using X-Gluc staining, a staining exclusively in the anthers, pollen and seeds and a very pronounced staining in the green tomato fruits was observed in the transgenic tomato plants. The staining is weaker in mature fruits than in the green fruits (FIG. 5). GUS staining was never observed in leaves, roots, petals and calyces, in petioles and shoot axes.

Example 13

Quantitative Determination of the Strength of the SSS3 Promoter in Green Fruits of Transgenic Tomato Plants FIG. 6 shows the evaluation of the quantitative analysis of the GUS activity in the green fruits of tomato lines which had been transformed with the construct pSUN0301_SSS3. The diagram shows the high expression level of the SSS3 promoter, which is also suitable for expressing other genes at a high level, specifically in the green fruits.

Example 14

Comparison of the Gus Expression in Green Immature and Red Mature Fruits of Transgenic Tomato Plants As can be seen from FIG. 7, the GUS activity in the immature green fruits of the tomatoes, transformed with the construct pSun0301_SSS3 is markedly higher than in the mature red fruits.

We claim:

1. A method for directing transgenic expression of a nucleic acid sequence in at least one starch-comprising tissue of a plant, which comprises
  I. introducing, into plant cells, a transgenic expression cassette, wherein the transgenic expression cassette comprises at least the following elements:
     a) the promoter sequence of the gene encoding SEQ ID NO: 6, or a fragment thereof having the same promoter activity, and
     b) at least one further nucleic acid sequence,
  wherein said promoter sequence or the fragment thereof and the at least one further nucleic acid sequence are functionally linked with one another, and the further nucleic acid sequence is heterologous with regard to the promoter sequence,
  II. selecting transgenic cells which comprise said expression cassette stably integrated into the genome, and
  III. regenerating intact plants from said transgenic cells, wherein the at least one further nucleic acid sequence is expressed in a starch-comprising tissue in a directed manner.

2. The method as claimed in claim 1, wherein the promoter sequence comprises a nucleic acid sequence selected from the group consisting of i) the sequence as shown in SEQ ID NO: 1 or 44,
ii) a fragment of the sequence as shown in SEQ ID NO: 1 or 44 which directs transgenic expression of a nucleic acid sequence in at least one starch-comprising tissue of a plant; and
iii) a promoter sequence comprising a nucleic acid sequence having at least 95% identity with the sequence of SEQ ID NO: 1 or 44 which directs transgenic expression of a nucleic acid sequence in at least one starch-comprising tissue of a plant.

3. An isolated nucleic acid sequence comprising
i) the nucleic acid sequence of SEQ ID NO: 1 or 44,
ii) a fragment of the nucleic acid sequence of SEQ ID NO: 1 or 44 which directs transgenic expression of a nucleic acid sequence in at least one starch-comprising tissue of a plant, or
iii) a nucleic acid sequence having at least 95% identity with the sequence as shown in SEQ ID NO: 1 or 44 which directs transgenic expression of a nucleic acid sequence in at least one starch-comprising tissue of a plant.

4. A method for the generation of a transgenic expression cassette having specificity for at least one-starch-comprising tissue of a plant, comprising:
  I. isolating a promoter with specificity for at least one starch-comprising tissue of a plant, wherein at least one nucleic acid sequence or part thereof is employed in the isolation and wherein said nucleic acid sequence comprises the sequence as shown in SEQ ID NO: 5 or codes for an amino acid sequence comprising the sequence as shown in SEQ ID NO: 6 or a part thereof and wherein the promoter comprises at least one nucleic acid sequence of claim 3; and
  II. functionally linking said promoter with a further nucleic acid sequence, where said nucleic acid sequence is heterologous with regard to the promoter.

5. The method according to claim 4, wherein the method is carried out using the polymerase chain reaction and said nucleic acid sequence or a part thereof is employed as primer.

6. A transgenic expression cassette for directing transgenic expression of a nucleic acid sequence in at least one starch-comprising tissue of a plant, comprising
  a) the promoter sequence of the gene encoding SEQ ID NO: 6, or a fragment thereof having the same promoter activity, and
  b) at least one further nucleic acid sequence,
  wherein said promoter sequence or the fragment thereof and the at least one further nucleic acid sequence are functionally linked with one another, and the further nucleic acid sequence is heterologous with regard to the promoter sequence.

7. A transgenic expression cassette comprising the isolated nucleic acid sequence according to claim 5.

8. The transgenic expression cassette according to claim 7, wherein
  a) the nucleic acid sequence to be expressed is linked functionally with further genetic control sequences, or
  b) the expression cassette comprises additional functional elements, or
  c) a) and b) apply.

9. The transgenic expression cassette according to claim 7, wherein the nucleic acid sequence to be expressed transgenically makes possible
  a) the expression of a protein encoded by said nucleic acid sequence, or
  b) the expression of a sense RNA, antisense RNA or double-stranded RNA encoded by said nucleic acid sequence.

10. A transgenic expression vector comprising the expression cassette according to claim 7.

11. A transgenic cell or organism transformed with the expression cassette according to claim 7 or with an expression vector comprising said expression cassette.

12. The transgenic cell or organism according to claim 11, selected from the group consisting of bacteria, yeasts, fungi, nonhuman animal and plant organisms, or transgenic cells, cell cultures, parts, tissues, organs or propagation material derived therefrom.

13. The transgenic cell or organism according to claim 11, wherein the cell is from or the organism is an agricultural crop plant.

14. A method for the production of foodstuffs, feedstuffs, seed, pharmaceuticals or fine chemicals comprising growing or culturing the transgenic cell or organism according to claim 11 or transgenic cells, cell cultures, parts, tissues, organs or propagation material derived therefrom.

15. A method for the production of pharmaceuticals or fine chemicals in the transgenic cell or organism according to claim 11 or in transgenic cells, cell cultures, parts, tissues, organs or propagation material derived therefrom, comprising growing or culturing the transgenic cell or organism of claim 11 or transgenic cells, cell cultures, parts, tissues, organs or propagation material derived therefrom and isolating the desired pharmaceutical or fine chemical.

16. A method for producing a transgenic plant cell, comprising transforming a plant cell with the nucleic acid of claim 5, an expression cassette comprising the nucleic acid, or a vector comprising the expression cassette.

17. A method for identifying and/or isolating a promoter sequence which directs transgenic expression of a nucleic acid sequence in at least one starch-comprising tissue of a plant, comprising
  a) providing the nucleic acid sequence of SEQ ID NO: 1 or 44;
  b) obtaining variants of the nucleic acid sequence of SEQ ID NO: 1 or 44;
  c) testing the variants obtained for directing expression of a nucleic acid sequence in at least one starch-comprising tissue of a plant; and
  d) identifying and/or isolating a variant which directs transgenic expression of a nucleic acid sequence in at least one starch-comprising tissue of a plant and wherein the variant has the tissue specificity of the promoter sequence described by SEQ ID NO: 1 or 44.

18. The isolated nucleic acid of claim 5, wherein the isolated nucleic acid sequence comprises a nucleic acid sequence having at least 99% identity with the sequence as shown in SEQ ID NO: 1 or 44 which directs transgenic expression of a nucleic acid sequence in at least one starch-comprising tissue of a plant.

19. A method for directing transgenic expression of a nucleic acid sequence in at least one starch-comprising tissue of a plant, which comprises
  I. introducing, into plant cells, a transgenic expression cassette, wherein the transgenic expression cassette comprises at least the following elements:
    a) a promoter sequence comprising a nucleic acid sequence having at least 95% identity with the sequence of SEQ ID NO: 1 or 44 which direct transgenic expression of a nucleic acid sequence in at least one starch-comprising tissue of a plant, and
    b) at least one further nucleic acid sequence, wherein said promoter sequence and the at least one further nucleic acid sequence are functionally linked with one another, and the further nucleic acid sequence is heterologous with regard to the promoter sequence, II. selecting transgenic cells which comprise said expression cassette stably integrated into the genome, and III. regenerating intact plants from said transgenic cells, wherein the at least one further nucleic acid sequence is expressed in a starch-comprising tissue in a directed manner.

20. The transgenic expression cassette according to claim 6, wherein the promoter sequence comprises a nucleic acid sequence selected from the group consisting of
   i) the sequence as shown in SEQ ID NO: 1 or 44;
   ii) a fragment of the sequence as shown in SEQ ID NO: 1 or 44 which directs transgenic expression of a nucleic acid sequence in at least one starch-comprising tissue of a plant; and
   iii) a promoter sequence comprising a nucleic acid sequence having at least 95% identity with the sequence of SEQ ID NO: 1 or 44 which directs transgenic expression of a nucleic acid sequence in at least one starch-comprising tissue of a plant.

21. A method for identifying and/or isolating a promoter sequence which directs transgenic expression of a nucleic acid sequence in at least one starch-comprising tissue of a plant, comprising
   a) preparing fragments of the nucleic acid sequence of SEQ ID NO: 1 or 44,
   b) testing the fragments obtained for directing expression of a nucleic acid sequence in at least one starch-comprising tissue of a plant, and
   c) identifying and/or isolating a fragment which directs transgenic expression of a nucleic acid sequence in at least one starch-comprising tissue of a plant.

22. An expression cassette for directing transgenic expression of a nucleic acid sequence in at least one starch-comprising tissue of a plant, comprising at least one promoter sequence, wherein the promoter sequence directs transgenic expression of a nucleic acid sequence in at least one starch-comprising tissue of a plant and comprises a fragment obtained by the method of claim 21.

23. The expression cassette of claim 7, further comprising at least one further nucleic acid sequence which is functionally linked to the promoter sequence and is heterologous with regard to the promoter sequence.

24. The method of claim 2, wherein the isolated nucleic acid sequence comprises a nucleic acid sequence having at least 99% identity with the sequence as shown in SEQ ID NO: 1 or 44 which directs trans genie expression of a nucleic acid sequence in at least one starch-comprising tissue of a plant.

25. The method of claim 19, wherein the isolated nucleic acid sequence comprises a nucleic acid sequence having at least 99% identity with the sequence as shown in SEQ ID NO: 1 or 44 which directs transgenic expression of a nucleic acid sequence in at least one starch-comprising tissue of a plant.

26. The transgenic expression cassette of claim 20, wherein the promoter sequence comprises a nucleic acid sequence having at least 99% identity with the sequence of SEQ ID NO: 1 or 44 which directs transgenic expression of a nucleic acid sequence in at least one starch-comprising tissue of a plant.

27. A method for identifying and/or isolating a promoter sequence which directs transgenic expression of a nucleic acid sequence in at least one starch-comprising tissue of a plant, comprising
   a) providing a nucleic acid sequence encoding the amino acid sequence of SEQ ID NO: 6;
   b) using the nucleic acid of a) as a gene probe to obtain a homologue of the nucleic acid;
   c) obtaining the promoter sequence of the homologue;
   d) testing the promoter sequence of c) for directing expression of a nucleic acid sequence in at least one starch-comprising tissue of a plant; and
   e) identifying and/or isolating a promoter, or fragment thereof having the same promoter activity, which directs transgenic expression of a nucleic acid sequence in at least one starch-comprising tissue of a plant and which has the tissue specificity of the promoter sequence described by SEQ ID NO: 1 or 44.

* * * * *

UNITED STATES PATENT AND TRADEMARK OFFICE
CERTIFICATE OF CORRECTION

PATENT NO. : 7,563,944 B2
APPLICATION NO. : 10/542516
DATED : July 21, 2009
INVENTOR(S) : Ute Heim It is certified that error appears in the above-identified patent and that said Letters Patent is hereby corrected as shown below:

On Page 2:

Other Publications, column 1, line 16, "Deikman, Jim, et al., "Interaction of a DNA Binding Factor with 5'-" should read -- Deikman, Jill, et al., "Interaction of a DNA Binding Factor with 5'- --.

In the Claims:

In Claim 4, in column 171, on line 23, "cassette having specificity for at least one-starch-comprising" should read -- cassette having specificity for at least one starch-comprising --.

In Claim 7, in column 171, on line 54, "nucleic acid sequence according to claim 5." should read -- nucleic acid sequence according to claim 3. --.

In Claim 16, in column 172, on line 32, "5, an expression cassette comprising the nucleic acid, or a" should read -- 3, an expression cassette comprising the nucleic acid, or a --.

In Claim 18, in column 172, on line 50, "18. The isolated nucleic acid of claim 5, wherein the iso-" should read -- 18. The isolated nucleic acid of claim 3, wherein the iso- --.

In Claim 24, in column 174, on lines 7 and 8, "24. The method of claim 2, wherein the isolated nucleic acid sequence comprises a nucleic acid sequence having at" should read -- 24. The method of claim 2, wherein the promoter sequence comprises a nucleic acid sequence having at --.

In Claim 24, in column 174, on line 10, "1 or 44 which directs trans genie expression of a nucleic acid" should read -- 1 or 44 which directs transgenic expression of a nucleic acid --.

In Claim 25, in column 174, on lines 12 and 13, "25. The method of claim 19, wherein the isolated nucleic acid sequence comprises a nucleic acid sequence having at" should read -- 25. The method of claim 19, wherein the promoter sequence comprises a nucleic acid sequence having at --.

Signed and Sealed this

Twenty-sixth Day of January, 2010

David J. Kappos
*Director of the United States Patent and Trademark Office*

SEQUENCE LISTING

```
<160> NUMBER OF SEQ ID NOS: 48

<210> SEQ ID NO 1
<211> LENGTH: 1015
<212> TYPE: DNA
<213> ORGANISM: Solanum tuberosum
<220> FEATURE:
<221> NAME/KEY: promoter
<222> LOCATION: (1)..(1015)
<223> OTHER INFORMATION: promoter of the SSS3 gene

<400> SEQUENCE: 1
ggaagaaatc ttctctgtct aaaaaattga cggttgatgt tataagagtt ttttttttt       60 ttttttttcc tttacaaat tgaagtgaca aaagagtgaa tcacagtgga tcgtgataac      120
aaagaatgtt ctgagagtat tgctattgtg aattttattt tatatgacgt aaatggtcaa     180
atttgcttaa ttttgtgaaa tagaacaaat ttatcctcta gttggagaca aatatactct     240
tgaactatac aaaatagaat aaatttttg ttatttttaa atttatcgcc caatgatatt     300
aaagatagtt tttttttttt ttaaatgaat tgaaactttc gcatagttca attttttttt     360
cttgcacaat atataggaaa atttaatcct tctttctagt tttgaatttt agaaatcttt     420
tcttcctcct ttctctctct accacccatt accccttttt ttctccttct tccttgaaca     480
acgccataca attttttatt tcttttttcc cctcattttt tttttaattc caatcaaatt     540
gtataatcca agtatagtta attttgataa catataaatt ataaagtaat gtgtaaataa     600
tagtactata gtataataag ttaaataaat caaactcaaa taaatttaga ccgctgctgt     660
cactctctag gctctccata gccaaatttt gtcgcaacct tttttgctca tttccaagaa     720
aaaaaagaag cctactgtaa tttaaaaaat tccacgtgtc aatatctaaa ttaccaccgt     780
catatcgaac caaacaattt caaccgtcag atttacaggt acaacgtaag caaaatagag     840
agcattacac agaaacaaca cacttcaggc tgaaatttgt aggactcctc caatttgtta     900
tcgcagttcg tagaatctga agaaagagta ttattcttga ttttttaata gattttaaa     960 accccattaa agcaaatacg tatataattg cagcacagat acagagaggg agaga          1015
```

```
<210> SEQ ID NO 2
<211> LENGTH: 921
<212> TYPE: DNA
<213> ORGANISM: Arabidopsis thaliana
<220> FEATURE:
<221> NAME/KEY: promoter
<222> LOCATION: (1)..(921)
<223> OTHER INFORMATION: promoter region of the SSS3 gene

<400> SEQUENCE: 2
ggcagctatg gaagtgtgtt ggcagataca gagaccagcg agtctcagac cgggttttca      60
ggaaaagggt cgggtcaaga tcaatacttt ttctgttggg ttttttcctc gctccattc     120
tagtgtaaat ctcttttgtt tcttctcgtc tcaattttt tcgctgatat gtttgtatat     180
ctctttagat tctacttatc gggaatttaa gtgtaaagtg ttctactttt tcatagtgag     240
atcgcctttt cgattagtat atctttaatt gaatcaatgt actatttta aataagattc     300
aactctggta gggtctctgg attgggattc tcatgttaga acctcgtttg aaattggtaa     360
gagtatagga attgacttaa tttctctagg aaatgttcaa tttcttctgg tcaaaatcgt     420
cacctcattg agaataccaa ctcgagggga gagaaatgat tttggggact atgagctaga     480
agtaagagtc agctgaagat tcacagtaga atgaaaatgt ctcatctttt atagtttgat     540
tttaatatcc accttgtttt acttatagtg tgattagttt aggtgttctt ggagatgaaa     600
atgtctcatt caatatggtt tgatttata atggctaat attcttctg tttattgctg     660
gtgtggctag tttatgtatt tgttagagct tgtgaaccag gtgactgaac agttttataa     720
tcgatttcta accatcagac atgtttggct ttcagattgc ttcattggaa agtcaataca     780
aatcaaatgg gtttctgcat cagatcacgg caagtgcagg ttaagaatct gtgataacct     840
ttcattgtga ttactgattc agtccttttg atgatttctt attttcttaa ccaagacttt     900
tcaaggaaga agcaaggaag a                                               921

<210> SEQ ID NO 3
<211> LENGTH: 1464
<212> TYPE: DNA
<213> ORGANISM: Oryza sativa
<220> FEATURE:
<221> NAME/KEY: promoter
<222> LOCATION: (1)..(1464)
<223> OTHER INFORMATION: promoter region of the SSS3 gene

<400> SEQUENCE: 3
tgattccggc tgctcttgct tttcttgatt tgcttgatcc accaagtgtt cgtccttctg      60
aaggggcatg caagattatt tactcagtta catgatctca atattaata ttttggttgt     120
gtttcctgtg gttttgattc atttcatctt gggaacatac tctggtgatg aaggggaaat     180
tcatgttatg gggagttctt tcctggactt tcttacggtt gttgatagat ttgattgaaa     240
tattttggga aatatttctg tggtcaatga tcttaattct caaattaga ttaggttaaa     300
acaacgggac tgaaagttcc tttctggaga tcgaaggta gttaattcta ctccatttgt     360
taaaatttcc ccccaagtac ttgtatattt aggtctgcat aatcattgaa agatttcctc     420
atctgggcta attctgttca gttttgaagt gaagcctaaa agaccttgtc ctcttgtttt     480
gatttgttgg gttcttgttt tgtaaggaaa aataccgctc attatgcacc cccttttta     540
tctacagttg aacattatgc atttacatta atgtgagagg gtatcatcca ttctaaaccg     600
acatgctaag aaatatggtt tcggagtgca attcagtata atttttaaa tattttctg     660
acaggaattc tttcaataat tttatattga ggatctgaga ggcatagatt ttttatagta     720
```

```
aaataaccta catatttcaa aacagcaata ttgattcaaa taattcaata ctccctccgt    780 cccctttataa ttgtcgtttg ggagttgtgc ccccctcaca agcacagatt cctagcgact   840
aataaaaggg gacagaggga gtaagttctt tttattgaaa catctcgagc tacaatattt    900
actttctttt cttttttccag tatttcttaa tgaccaggag atatactgga agcagaattg   960
ttcgatgcat ggtttcaagt tcaggtttgt gtaggatagc ttcgtaaaag ctttattaat   1020
tttcttattt gctatgctaa ggtcatgttt gttaaaatta tatcatgcag actgtcctaa  1080
taggaaagca aagaggacga tttcccttca tacggaagtc gcttcttcta ggggatatgc  1140
tccgagaatt gctgctgaat caagtattca ggagcgagaa catattaata gtgatgaaga  1200
aacatttgat acgtacaaca gattactacg taatgagtca acagagtgga aaaagttaga  1260
tactactgaa gtggatttgt cacaagatgt ttcaagcagt tcaatgagga agtggatgc   1320 gacggatgaa gctaagctag atatacttga ggatgatttg cccagaaatt tgttgaacgg  1380
tgtaacaatg ggggaagtag atatgttgga tgaagctggg gcagaagatg atgtatttga  1440
ggtggacttg tcagccttgc ataa                                          1464

<210> SEQ ID NO 4
<211> LENGTH: 973
<212> TYPE: DNA
<213> ORGANISM: Triticum aestivum
<220> FEATURE:
<221> NAME/KEY: promoter
<222> LOCATION: (1)..(973)
<223> OTHER INFORMATION: promoter region of the SSS3 gene

<400> SEQUENCE: 4
taatccgttt gtctaatgaa atatatgtga tgggagagga tttggagcat tggggtgctc     60
cacccccccc ctatatgagt attaaattca aaaacaaac cgaggatatt caaaaagtct    120
acaattttgg gatactaaac ctggatgctc agtctactcc catgtgaagt ttcatgaaaa   180
aaatatcagg aaacgtattc tcagtaaaaa cagacaaaaa attcttatgc acagaaaaaa   240
ctgtttgggt ggatcatagg tcagactata ttttcttcca tggatacatg tcatggtatt   300
ttttcacaaa acttcacatg agagtagatt tgggcatcca agtttgatat ccccatattc   360
caagttcttt cgaattttcc tagtatttt tgaaattaat attcgtatag ggtggagca    420 tccaggagct ctggtgtatt tttcaatata tgtatggtta tttaaaaaaa aactcgtaca   480
acaatctcag aaaaaactgg acggtttatt ctagctgatt ttgtgtgcag tttcccataa  540
tcagaagtgg ccctcagccc ctcactcttc ttcctcctac cttctgctct gtcttccgct  600
tcctgcacga acattcgcgt tgaagttttt tcaaaagaaa acaatatact tgctggaaaa  660
agaaagcaag tacaaaaaac accagccatc caccaccgtc cgttactggt ccacctgcat  720
ttccatgtgt gcgcacacgg agaagcagct cgaacaaaaa aaccaaacga aaataaagga  780
tcgaagctgc tctcggacaa aatggttgaa ggacgaagga gccttttttgg tgcgcagatc  840 tccacgccag agcgttgtat tccaatttta gttctttccc cgtgaggagg ggaggctagg  900
cgggcgaggc agaggggata gggcagtcgc cgctgcgtgg tggactgact ggtgtggtgg  960
gtggtgggtt ttg                                                      973

<210> SEQ ID NO 5
<211> LENGTH: 3693
<212> TYPE: DNA
<213> ORGANISM: Solanum tuberosum
<220> FEATURE:
<221> NAME/KEY: CDS
```

<222> LOCATION: (1)..(3690)
<223> OTHER INFORMATION: coding for SSS3

<400> SEQUENCE: 5

| | | | | | | | | | | | | | | | | |
|---|---|---|---|---|---|---|---|---|---|---|---|---|---|---|---|---|
| atg | gat | gtt | cca | ttt | cca | ctg | cat | aga | cca | ttg | agt | tgc | aca | agt | gtc | 48 |
| Met | Asp | Val | Pro | Phe | Pro | Leu | His | Arg | Pro | Leu | Ser | Cys | Thr | Ser | Val | |
| 1 | | | | 5 | | | | | 10 | | | | | 15 | | |

| tcc | aat | gca | ata | acc | cac | ctc | aag | atc | aaa | cct | ttt | ctt | ggg | ttt | gtc | 96 |
|---|---|---|---|---|---|---|---|---|---|---|---|---|---|---|---|---|
| Ser | Asn | Ala | Ile | Thr | His | Leu | Lys | Ile | Lys | Pro | Phe | Leu | Gly | Phe | Val | |
| | | | 20 | | | | | 25 | | | | | 30 | | | |

| tct | cat | gga | acc | aca | agt | cta | tca | gta | caa | tct | tct | tca | tgg | agg | aag | 144 |
|---|---|---|---|---|---|---|---|---|---|---|---|---|---|---|---|---|
| Ser | His | Gly | Thr | Thr | Ser | Leu | Ser | Val | Gln | Ser | Ser | Ser | Trp | Arg | Lys | |
| | | 35 | | | | | 40 | | | | | 45 | | | | |

| gat | gga | atg | gtt | act | ggg | gtt | tca | ttt | cca | ttt | tgt | gca | aat | ctc | tcg | 192 |
|---|---|---|---|---|---|---|---|---|---|---|---|---|---|---|---|---|
| Asp | Gly | Met | Val | Thr | Gly | Val | Ser | Phe | Pro | Phe | Cys | Ala | Asn | Leu | Ser | |
| | 50 | | | | | 55 | | | | | 60 | | | | | |

| gga | aga | aga | cgg | aga | aaa | gtt | tca | act | act | agg | agt | caa | gga | tct | tca | 240 |
|---|---|---|---|---|---|---|---|---|---|---|---|---|---|---|---|---|
| Gly | Arg | Arg | Arg | Arg | Lys | Val | Ser | Thr | Thr | Arg | Ser | Gln | Gly | Ser | Ser | |
| 65 | | | | | 70 | | | | | 75 | | | | | 80 | |

| cct | aag | ggg | ttt | gtg | cca | agg | aag | ccc | tca | ggg | atg | agc | acg | caa | aga | 288 |
|---|---|---|---|---|---|---|---|---|---|---|---|---|---|---|---|---|
| Pro | Lys | Gly | Phe | Val | Pro | Arg | Lys | Pro | Ser | Gly | Met | Ser | Thr | Gln | Arg | |
| | | | | 85 | | | | | 90 | | | | | 95 | | |

| aag | gtt | cag | aag | agc | aat | ggt | gat | aaa | gaa | agt | caa | agt | act | tca | aca | 336 |
|---|---|---|---|---|---|---|---|---|---|---|---|---|---|---|---|---|
| Lys | Val | Gln | Lys | Ser | Asn | Gly | Asp | Lys | Glu | Ser | Gln | Ser | Thr | Ser | Thr | |
| | | | 100 | | | | | 105 | | | | | 110 | | | |

| tct | aaa | gaa | tct | gaa | att | tcc | aac | cag | aag | acg | gtt | gaa | gca | aga | gtt | 384 |
|---|---|---|---|---|---|---|---|---|---|---|---|---|---|---|---|---|
| Ser | Lys | Glu | Ser | Glu | Ile | Ser | Asn | Gln | Lys | Thr | Val | Glu | Ala | Arg | Val | |
| | | 115 | | | | | 120 | | | | | 125 | | | | |

| gaa | act | agt | gac | gat | gac | act | aaa | gta | gtg | gtg | agg | gac | cac | aag | ttt | 432 |
|---|---|---|---|---|---|---|---|---|---|---|---|---|---|---|---|---|
| Glu | Thr | Ser | Asp | Asp | Asp | Thr | Lys | Val | Val | Val | Arg | Asp | His | Lys | Phe | |
| | 130 | | | | | 135 | | | | | 140 | | | | | |

| ctg | gag | gat | gag | gat | gaa | atc | aat | ggt | tct | act | aaa | tca | ata | agt | atg | 480 |
|---|---|---|---|---|---|---|---|---|---|---|---|---|---|---|---|---|
| Leu | Glu | Asp | Glu | Asp | Glu | Ile | Asn | Gly | Ser | Thr | Lys | Ser | Ile | Ser | Met | |
| 145 | | | | | 150 | | | | | 155 | | | | | 160 | |

| tca | cct | gtt | cgt | gta | tca | tct | caa | ttt | gtt | gaa | agt | gaa | gaa | act | ggt | 528 |
|---|---|---|---|---|---|---|---|---|---|---|---|---|---|---|---|---|
| Ser | Pro | Val | Arg | Val | Ser | Ser | Gln | Phe | Val | Glu | Ser | Glu | Glu | Thr | Gly | |
| | | | | 165 | | | | | 170 | | | | | 175 | | |

| ggt | gat | gac | aag | gat | gct | gta | aag | tta | aac | aaa | tca | aag | aga | tcg | gaa | 576 |
|---|---|---|---|---|---|---|---|---|---|---|---|---|---|---|---|---|
| Gly | Asp | Asp | Lys | Asp | Ala | Val | Lys | Leu | Asn | Lys | Ser | Lys | Arg | Ser | Glu | |
| | | | 180 | | | | | 185 | | | | | 190 | | | |

| gag | agt | gat | ttt | cta | att | gat | tct | gta | ata | aga | gaa | caa | agt | gga | tct | 624 |
|---|---|---|---|---|---|---|---|---|---|---|---|---|---|---|---|---|
| Glu | Ser | Asp | Phe | Leu | Ile | Asp | Ser | Val | Ile | Arg | Glu | Gln | Ser | Gly | Ser | |
| | | 195 | | | | | 200 | | | | | 205 | | | | |

| cag | ggg | gaa | act | aat | gcc | agt | agc | aag | gga | agc | cat | gct | gtg | ggt | aca | 672 |
|---|---|---|---|---|---|---|---|---|---|---|---|---|---|---|---|---|
| Gln | Gly | Glu | Thr | Asn | Ala | Ser | Ser | Lys | Gly | Ser | His | Ala | Val | Gly | Thr | |
| | 210 | | | | | 215 | | | | | 220 | | | | | |

| aaa | ctt | tat | gag | ata | ttg | cag | gtg | gat | gtt | gag | cca | caa | caa | ttg | aaa | 720 |
|---|---|---|---|---|---|---|---|---|---|---|---|---|---|---|---|---|
| Lys | Leu | Tyr | Glu | Ile | Leu | Gln | Val | Asp | Val | Glu | Pro | Gln | Gln | Leu | Lys | |
| 225 | | | | | 230 | | | | | 235 | | | | | 240 | |

| gaa | aat | aat | gct | ggg | aat | gtt | gaa | tac | aaa | gga | cct | gta | gca | agt | aag | 768 |
|---|---|---|---|---|---|---|---|---|---|---|---|---|---|---|---|---|
| Glu | Asn | Asn | Ala | Gly | Asn | Val | Glu | Tyr | Lys | Gly | Pro | Val | Ala | Ser | Lys | |
| | | | | 245 | | | | | 250 | | | | | 255 | | |

| cta | ttg | gaa | att | act | aag | gct | agt | gat | gtg | gaa | cac | act | gaa | agc | aat | 816 |
|---|---|---|---|---|---|---|---|---|---|---|---|---|---|---|---|---|
| Leu | Leu | Glu | Ile | Thr | Lys | Ala | Ser | Asp | Val | Glu | His | Thr | Glu | Ser | Asn | |
| | | | 260 | | | | | 265 | | | | | 270 | | | |

| gag | att | gat | gac | tta | gac | act | aat | agt | ttc | ttt | aaa | tca | gat | tta | att | 864 |
|---|---|---|---|---|---|---|---|---|---|---|---|---|---|---|---|---|
| Glu | Ile | Asp | Asp | Leu | Asp | Thr | Asn | Ser | Phe | Phe | Lys | Ser | Asp | Leu | Ile | |
| | | 275 | | | | | 280 | | | | | 285 | | | | |

| gaa | gag | gat | gag | cca | tta | gct | gca | gga | aca | gtg | gag | act | gga | gat | tct | 912 |
|---|---|---|---|---|---|---|---|---|---|---|---|---|---|---|---|---|
| Glu | Glu | Asp | Glu | Pro | Leu | Ala | Ala | Gly | Thr | Val | Glu | Thr | Gly | Asp | Ser | |

-continued

```
              290                 295                 300
tct cta aac tta aga ttg gag atg gaa gca aat cta cgt agg cag gct        960
Ser Leu Asn Leu Arg Leu Glu Met Glu Ala Asn Leu Arg Arg Gln Ala
305                 310                 315                 320 ata gaa agg ctt gcc gag gaa aat tta ttg caa ggg atc aga tta ttt       1008
Ile Glu Arg Leu Ala Glu Glu Asn Leu Leu Gln Gly Ile Arg Leu Phe
                325                 330                 335 tgt ttt cca gag gtt gta aaa cct gat gaa gat gtc gag ata ttt ctt       1056
Cys Phe Pro Glu Val Val Lys Pro Asp Glu Asp Val Glu Ile Phe Leu
                340                 345                 350 aac aga ggt ctt tcc act ttg aag aat gag tct gat gtc ttg att atg       1104
Asn Arg Gly Leu Ser Thr Leu Lys Asn Glu Ser Asp Val Leu Ile Met
                355                 360                 365 gga gct ttt aat gag tgg cgc tat agg tct ttt act aca agg cta act       1152
Gly Ala Phe Asn Glu Trp Arg Tyr Arg Ser Phe Thr Thr Arg Leu Thr
370                 375                 380 gag act cat ctc aat gga gat tgg tgg tct tgc aag atc cat gtt ccc       1200
Glu Thr His Leu Asn Gly Asp Trp Trp Ser Cys Lys Ile His Val Pro
385                 390                 395                 400 aag gaa gca tac agg gct gat ttt gtg ttt ttt aat gga caa gat gtc       1248
Lys Glu Ala Tyr Arg Ala Asp Phe Val Phe Phe Asn Gly Gln Asp Val
                405                 410                 415 tat gac aac aat gat gga aat gac ttc agt ata act gtg aaa ggt ggt       1296
Tyr Asp Asn Asn Asp Gly Asn Asp Phe Ser Ile Thr Val Lys Gly Gly
                420                 425                 430 atg caa atc att gac ttt gaa aat ttc ttg ctt gag gag aaa tgg aga       1344
Met Gln Ile Ile Asp Phe Glu Asn Phe Leu Leu Glu Glu Lys Trp Arg
                435                 440                 445 gaa cag gag aaa ctt gct aaa gaa caa gct gaa aga gaa aga cta gcg       1392
Glu Gln Glu Lys Leu Ala Lys Glu Gln Ala Glu Arg Glu Arg Leu Ala
                450                 455                 460 gaa gaa caa aga cga ata gaa gca gag aaa gct gaa att gaa gct gac       1440
Glu Glu Gln Arg Arg Ile Glu Ala Glu Lys Ala Glu Ile Glu Ala Asp
465                 470                 475                 480 aga gca caa gca aag gaa gag gct gca aag aaa aag aaa gta ttg cga       1488
Arg Ala Gln Ala Lys Glu Glu Ala Ala Lys Lys Lys Lys Val Leu Arg
                485                 490                 495 gaa ttg atg gta aaa gcc acg aag act cgt gat atc acg tgg tac ata       1536
Glu Leu Met Val Lys Ala Thr Lys Thr Arg Asp Ile Thr Trp Tyr Ile
                500                 505                 510 gag cca agt gaa ttt aaa tgc gag gac aag gtc agg tta tac tat aac       1584
Glu Pro Ser Glu Phe Lys Cys Glu Asp Lys Val Arg Leu Tyr Tyr Asn
                515                 520                 525 aaa agt tca ggt cct ctc tcc cat gct aag gac ttg tgg atc cac gga       1632
Lys Ser Ser Gly Pro Leu Ser His Ala Lys Asp Leu Trp Ile His Gly
                530                 535                 540 gga tat aat aat tgg aag gat ggt ttg tct att gtc aaa aag ctt gtt       1680
Gly Tyr Asn Asn Trp Lys Asp Gly Leu Ser Ile Val Lys Lys Leu Val
545                 550                 555                 560 aaa tct gag aga ata gat ggt gat tgg tgg tat aca gag gtt gtt att       1728
Lys Ser Glu Arg Ile Asp Gly Asp Trp Trp Tyr Thr Glu Val Val Ile
                565                 570                 575 cct gat cag gca ctt ttc ttg gat tgg gtt ttt gct gat ggt cca ccc       1776
Pro Asp Gln Ala Leu Phe Leu Asp Trp Val Phe Ala Asp Gly Pro Pro
                580                 585                 590 aag cat gcc att gct tat gat aac aat cac cgc caa gac ttc cat gcc       1824
Lys His Ala Ile Ala Tyr Asp Asn Asn His Arg Gln Asp Phe His Ala
                595                 600                 605 att gtc ccc aac cac att ccg gag gaa tta tat tgg gtt gag gaa gaa       1872
```

```
Ile Val Pro Asn His Ile Pro Glu Glu Leu Tyr Trp Val Glu Glu Glu
    610                 615                 620 cat cag atc ttt aag aca ctt cag gag gag aga agg ctt aga gaa gcg    1920
His Gln Ile Phe Lys Thr Leu Gln Glu Glu Arg Arg Leu Arg Glu Ala
625                 630                 635                 640 gct atg cgt gct aag gtt gaa aaa aca gca ctt ctg aaa act gaa aca    1968
Ala Met Arg Ala Lys Val Glu Lys Thr Ala Leu Leu Lys Thr Glu Thr
                645                 650                 655 aag gaa aga act atg aaa tca ttt tta ctg tct cag aag cat gta gta    2016
Lys Glu Arg Thr Met Lys Ser Phe Leu Leu Ser Gln Lys His Val Val
            660                 665                 670 tat act gag cct ctt gat atc caa gct gga agc agc gtc aca gtt tac    2064
Tyr Thr Glu Pro Leu Asp Ile Gln Ala Gly Ser Ser Val Thr Val Tyr
        675                 680                 685 tat aat ccc gcc aat aca gta ctt aat ggt aaa cct gaa att tgg ttc    2112
Tyr Asn Pro Ala Asn Thr Val Leu Asn Gly Lys Pro Glu Ile Trp Phe
    690                 695                 700 aga tgt tca ttt aat cgc tgg act cac cgc ctg ggt cca ttg cca cct    2160
Arg Cys Ser Phe Asn Arg Trp Thr His Arg Leu Gly Pro Leu Pro Pro
705                 710                 715                 720 cag aaa atg tcg cct gct gaa aat ggc acc cat gtc aga gca act gtg    2208
Gln Lys Met Ser Pro Ala Glu Asn Gly Thr His Val Arg Ala Thr Val
                725                 730                 735 aag gtt cca ttg gat gca tat atg atg gat ttt gta ttt tcc gag aga    2256
Lys Val Pro Leu Asp Ala Tyr Met Met Asp Phe Val Phe Ser Glu Arg
            740                 745                 750 gaa gat ggt ggg att ttt gac aat aag agc gga atg gac tat cac ata    2304
Glu Asp Gly Gly Ile Phe Asp Asn Lys Ser Gly Met Asp Tyr His Ile
        755                 760                 765 cct gtg ttt gga gga gtc gct aaa gaa cct cca atg cat att gtc cat    2352
Pro Val Phe Gly Gly Val Ala Lys Glu Pro Pro Met His Ile Val His
    770                 775                 780 att gct gtc gaa atg gca cca att gca aag gtg gga ggc ctt ggt gat    2400
Ile Ala Val Glu Met Ala Pro Ile Ala Lys Val Gly Gly Leu Gly Asp
785                 790                 795                 800 gtt gtt act agt ctt tcc cgt gct gtt caa gat tta aac cat aat gtg    2448
Val Val Thr Ser Leu Ser Arg Ala Val Gln Asp Leu Asn His Asn Val
                805                 810                 815 gat att atc tta cct aag tat gac tgt ttg aag atg aat aat gtg aag    2496
Asp Ile Ile Leu Pro Lys Tyr Asp Cys Leu Lys Met Asn Asn Val Lys
            820                 825                 830 gac ttt cgg ttt cac aaa aac tac ttt tgg ggt ggg act gaa ata aaa    2544
Asp Phe Arg Phe His Lys Asn Tyr Phe Trp Gly Gly Thr Glu Ile Lys
        835                 840                 845 gta tgg ttt gga aag gtg gaa ggt ctc tcg gtc tat ttt ttg gag cct    2592
Val Trp Phe Gly Lys Val Glu Gly Leu Ser Val Tyr Phe Leu Glu Pro
    850                 855                 860 caa aac ggg tta ttt tcg aaa ggg tgc gtc tat ggt tgt agc aat gat    2640
Gln Asn Gly Leu Phe Ser Lys Gly Cys Val Tyr Gly Cys Ser Asn Asp
865                 870                 875                 880 ggt gaa cga ttt ggt ttc ttc tgt cac gcg gct ttg gag ttt ctt ctg    2688
Gly Glu Arg Phe Gly Phe Phe Cys His Ala Ala Leu Glu Phe Leu Leu
                885                 890                 895 caa ggt gga ttt agt ccg gat atc att cat tgc cat gat tgg tct agt    2736
Gln Gly Gly Phe Ser Pro Asp Ile Ile His Cys His Asp Trp Ser Ser
            900                 905                 910 gct cct gtt gct tgg ctc ttt aag gaa caa tat aca cac tat ggt cta    2784
Ala Pro Val Ala Trp Leu Phe Lys Glu Gln Tyr Thr His Tyr Gly Leu
        915                 920                 925
```

```
agc aaa tct cgt ata gtc ttc acg ata cat aat ctt gaa ttt ggg gca      2832
Ser Lys Ser Arg Ile Val Phe Thr Ile His Asn Leu Glu Phe Gly Ala
    930                 935                 940 gat ctc att ggg aga gca atg act aac gca gac aaa gct aca aca gtt      2880
Asp Leu Ile Gly Arg Ala Met Thr Asn Ala Asp Lys Ala Thr Thr Val
945                 950                 955                 960 tca cca act tac tca cag gag gtg tct gga aac cct gta att gcg cct      2928
Ser Pro Thr Tyr Ser Gln Glu Val Ser Gly Asn Pro Val Ile Ala Pro
                965                 970                 975 cac ctt cac aag ttc cat ggt ata gtg aat ggg att gac cca gat att      2976
His Leu His Lys Phe His Gly Ile Val Asn Gly Ile Asp Pro Asp Ile
            980                 985                 990 tgg gat cct tta aac gat aag ttc att ccg att ccg tac acc tca gaa      3024
Trp Asp Pro Leu Asn Asp Lys Phe Ile Pro Ile Pro Tyr Thr Ser Glu
        995                 1000                1005 aac gtt gtt gaa ggc aaa aca gca gcc aag gaa gct ttg cag cga aaa      3072
Asn Val Val Glu Gly Lys Thr Ala Ala Lys Glu Ala Leu Gln Arg Lys
    1010                1015                1020 ctt gga ctg aaa cag gct gac ctt cct ttg gta gga att atc acc cgc      3120
Leu Gly Leu Lys Gln Ala Asp Leu Pro Leu Val Gly Ile Ile Thr Arg
1025                1030                1035                1040 tta act cac cag aaa gga atc cac ctc att aaa cat gct att tgg cgc      3168
Leu Thr His Gln Lys Gly Ile His Leu Ile Lys His Ala Ile Trp Arg
                1045                1050                1055 acc ttg gaa cgg aac gga cag gta gtc ttg ctt ggt tct gct cct gat      3216
Thr Leu Glu Arg Asn Gly Gln Val Val Leu Leu Gly Ser Ala Pro Asp
            1060                1065                1070 cct agg gta caa aac gat ttt gtt aat ttg gca aat caa ttg cac tcc      3264
Pro Arg Val Gln Asn Asp Phe Val Asn Leu Ala Asn Gln Leu His Ser
        1075                1080                1085 aaa tat aat gac cgc gca cga ctc tgt cta aca tat gac gag cca ctt      3312
Lys Tyr Asn Asp Arg Ala Arg Leu Cys Leu Thr Tyr Asp Glu Pro Leu
    1090                1095                1100 tct cac ctg ata tat gct ggt gct gat ttt att cta gtt cct tca ata      3360
Ser His Leu Ile Tyr Ala Gly Ala Asp Phe Ile Leu Val Pro Ser Ile
1105                1110                1115                1120 ttt gag cca tgt gga cta aca caa ctt acc gct atg aga tat ggt tca      3408
Phe Glu Pro Cys Gly Leu Thr Gln Leu Thr Ala Met Arg Tyr Gly Ser
                1125                1130                1135 att cca gtc gtg cgt aaa act gga gga ctt tat gat act gta ttt gat      3456
Ile Pro Val Val Arg Lys Thr Gly Gly Leu Tyr Asp Thr Val Phe Asp
            1140                1145                1150 gtt gac cat gac aaa gag aga gca caa cag tgt ggt ctt gaa cca aat      3504
Val Asp His Asp Lys Glu Arg Ala Gln Gln Cys Gly Leu Glu Pro Asn
        1155                1160                1165 gga ttc agc ttt gat gga gca gat gct ggc gga gtt gat tat gct ctg      3552
Gly Phe Ser Phe Asp Gly Ala Asp Ala Gly Gly Val Asp Tyr Ala Leu
    1170                1175                1180 aat aga gct ctc tct gct tgg tac gat ggt cgg gat tgg ttc aac tct      3600
Asn Arg Ala Leu Ser Ala Trp Tyr Asp Gly Arg Asp Trp Phe Asn Ser
1185                1190                1195                1200 tta tgc aag cag gtc atg gaa caa gat tgg tct tgg aac cga cct gct      3648
Leu Cys Lys Gln Val Met Glu Gln Asp Trp Ser Trp Asn Arg Pro Ala
                1205                1210                1215 ctt gat tat ttg gag ctt tac cat gct gct aga aag tta gaa tag          3693
Leu Asp Tyr Leu Glu Leu Tyr His Ala Ala Arg Lys Leu Glu
            1220                1225                1230

<210> SEQ ID NO 6
<211> LENGTH: 1230
```

```
<212> TYPE: PRT
<213> ORGANISM: Solanum tuberosum

<400> SEQUENCE: 6
```

Met Asp Val Pro Phe Pro Leu His Arg Pro Leu Ser Cys Thr Ser Val
1               5                   10                  15

Ser Asn Ala Ile Thr His Leu Lys Ile Lys Pro Phe Leu Gly Phe Val
            20                  25                  30

Ser His Gly Thr Thr Ser Leu Ser Val Gln Ser Ser Trp Arg Lys
        35                  40                  45

Asp Gly Met Val Thr Gly Val Ser Phe Pro Phe Cys Ala Asn Leu Ser
    50                  55                  60

Gly Arg Arg Arg Lys Val Ser Thr Thr Arg Ser Gln Gly Ser Ser
65              70                  75                  80

Pro Lys Gly Phe Val Pro Arg Lys Pro Ser Gly Met Ser Thr Gln Arg
            85                  90                  95

Lys Val Gln Lys Ser Asn Gly Asp Lys Glu Ser Gln Ser Thr Ser Thr
            100                 105                 110

Ser Lys Glu Ser Glu Ile Ser Asn Gln Lys Thr Val Glu Ala Arg Val
            115                 120                 125

Glu Thr Ser Asp Asp Asp Thr Lys Val Val Arg Asp His Lys Phe
130                 135                 140

Leu Glu Asp Glu Asp Glu Ile Asn Gly Ser Thr Lys Ser Ile Ser Met
145                 150                 155                 160

Ser Pro Val Arg Val Ser Ser Gln Phe Val Glu Ser Glu Glu Thr Gly
                165                 170                 175

Gly Asp Asp Lys Asp Ala Val Lys Leu Asn Lys Ser Lys Arg Ser Glu
            180                 185                 190

Glu Ser Asp Phe Leu Ile Asp Ser Val Ile Arg Glu Gln Ser Gly Ser
        195                 200                 205

Gln Gly Glu Thr Asn Ala Ser Ser Lys Gly Ser His Ala Val Gly Thr
    210                 215                 220

Lys Leu Tyr Glu Ile Leu Gln Val Asp Val Glu Pro Gln Gln Leu Lys
225                 230                 235                 240

Glu Asn Asn Ala Gly Asn Val Glu Tyr Lys Gly Pro Val Ala Ser Lys
                245                 250                 255

Leu Leu Glu Ile Thr Lys Ala Ser Asp Val Glu His Thr Glu Ser Asn
            260                 265                 270

Glu Ile Asp Asp Leu Asp Thr Asn Ser Phe Phe Lys Ser Asp Leu Ile
        275                 280                 285

Glu Glu Asp Glu Pro Leu Ala Ala Gly Thr Val Glu Thr Gly Asp Ser
    290                 295                 300

Ser Leu Asn Leu Arg Leu Glu Met Glu Ala Asn Leu Arg Arg Gln Ala
305                 310                 315                 320

Ile Glu Arg Leu Ala Glu Glu Asn Leu Leu Gln Gly Ile Arg Leu Phe
                325                 330                 335

Cys Phe Pro Glu Val Val Lys Pro Asp Glu Asp Val Glu Ile Phe Leu
            340                 345                 350

Asn Arg Gly Leu Ser Thr Leu Lys Asn Glu Ser Asp Val Leu Ile Met
        355                 360                 365

Gly Ala Phe Asn Glu Trp Arg Tyr Arg Ser Phe Thr Thr Arg Leu Thr
    370                 375                 380

Glu Thr His Leu Asn Gly Asp Trp Trp Ser Cys Lys Ile His Val Pro
385                 390                 395                 400

-continued

```
Lys Glu Ala Tyr Arg Ala Asp Phe Val Phe Asn Gly Gln Asp Val
                405                 410                 415

Tyr Asp Asn Asn Asp Gly Asn Asp Phe Ser Ile Thr Val Lys Gly Gly
            420                 425                 430

Met Gln Ile Ile Asp Phe Glu Asn Phe Leu Leu Glu Glu Lys Trp Arg
        435                 440                 445

Glu Gln Glu Lys Leu Ala Lys Glu Gln Ala Arg Glu Arg Leu Ala
    450                 455                 460

Glu Glu Gln Arg Arg Ile Glu Ala Glu Lys Ala Glu Ile Glu Ala Asp
465                 470                 475                 480

Arg Ala Gln Ala Lys Glu Ala Ala Lys Lys Lys Val Leu Arg
                485                 490                 495

Glu Leu Met Val Lys Ala Thr Lys Thr Arg Asp Ile Thr Trp Tyr Ile
            500                 505                 510

Glu Pro Ser Glu Phe Lys Cys Glu Asp Lys Val Arg Leu Tyr Tyr Asn
        515                 520                 525

Lys Ser Ser Gly Pro Leu Ser His Ala Lys Asp Leu Trp Ile His Gly
    530                 535                 540

Gly Tyr Asn Asn Trp Lys Asp Gly Leu Ser Ile Val Lys Lys Leu Val
545                 550                 555                 560

Lys Ser Glu Arg Ile Asp Gly Asp Trp Trp Tyr Thr Glu Val Val Ile
                565                 570                 575

Pro Asp Gln Ala Leu Phe Leu Asp Trp Val Phe Ala Asp Gly Pro Pro
            580                 585                 590

Lys His Ala Ile Ala Tyr Asp Asn Asn His Arg Gln Asp Phe His Ala
        595                 600                 605

Ile Val Pro Asn His Ile Pro Glu Glu Leu Tyr Trp Val Glu Glu Glu
    610                 615                 620

His Gln Ile Phe Lys Thr Leu Gln Glu Glu Arg Arg Leu Arg Glu Ala
625                 630                 635                 640

Ala Met Arg Ala Lys Val Glu Lys Thr Ala Leu Leu Lys Thr Glu Thr
                645                 650                 655

Lys Glu Arg Thr Met Lys Ser Phe Leu Leu Ser Gln Lys His Val Val
            660                 665                 670

Tyr Thr Glu Pro Leu Asp Ile Gln Ala Gly Ser Ser Val Thr Val Tyr
        675                 680                 685

Tyr Asn Pro Ala Asn Thr Val Leu Asn Gly Lys Pro Glu Ile Trp Phe
    690                 695                 700

Arg Cys Ser Phe Asn Arg Trp Thr His Arg Leu Gly Pro Leu Pro Pro
705                 710                 715                 720

Gln Lys Met Ser Pro Ala Glu Asn Gly Thr His Val Arg Ala Thr Val
                725                 730                 735

Lys Val Pro Leu Asp Ala Tyr Met Met Asp Phe Val Phe Ser Glu Arg
            740                 745                 750

Glu Asp Gly Gly Ile Phe Asp Asn Lys Ser Gly Met Asp Tyr His Ile
        755                 760                 765

Pro Val Phe Gly Gly Val Ala Lys Glu Pro Pro Met His Ile Val His
    770                 775                 780

Ile Ala Val Glu Met Ala Pro Ile Ala Lys Val Gly Gly Leu Gly Asp
785                 790                 795                 800

Val Val Thr Ser Leu Ser Arg Ala Val Gln Asp Leu Asn His Asn Val
                805                 810                 815
```

-continued

```
Asp Ile Ile Leu Pro Lys Tyr Asp Cys Leu Lys Met Asn Asn Val Lys
            820                 825                 830

Asp Phe Arg Phe His Lys Asn Tyr Phe Trp Gly Gly Thr Glu Ile Lys
        835                 840                 845

Val Trp Phe Gly Lys Val Glu Gly Leu Ser Val Tyr Phe Leu Glu Pro
    850                 855                 860

Gln Asn Gly Leu Phe Ser Lys Gly Cys Val Tyr Gly Cys Ser Asn Asp
865                 870                 875                 880

Gly Glu Arg Phe Gly Phe Phe Cys His Ala Ala Leu Glu Phe Leu Leu
                885                 890                 895

Gln Gly Gly Phe Ser Pro Asp Ile Ile His Cys His Asp Trp Ser Ser
            900                 905                 910

Ala Pro Val Ala Trp Leu Phe Lys Glu Gln Tyr Thr His Tyr Gly Leu
        915                 920                 925

Ser Lys Ser Arg Ile Val Phe Thr Ile His Asn Leu Glu Phe Gly Ala
    930                 935                 940

Asp Leu Ile Gly Arg Ala Met Thr Asn Ala Asp Lys Ala Thr Thr Val
945                 950                 955                 960

Ser Pro Thr Tyr Ser Gln Glu Val Ser Gly Asn Pro Val Ile Ala Pro
                965                 970                 975

His Leu His Lys Phe His Gly Ile Val Asn Gly Ile Asp Pro Asp Ile
            980                 985                 990

Trp Asp Pro Leu Asn Asp Lys Phe Ile Pro Ile Pro Tyr Thr Ser Glu
        995                 1000                1005

Asn Val Val Glu Gly Lys Thr Ala Ala Lys Glu Ala Leu Gln Arg Lys
    1010                1015                1020

Leu Gly Leu Lys Gln Ala Asp Leu Pro Leu Val Gly Ile Ile Thr Arg
1025                1030                1035                1040

Leu Thr His Gln Lys Gly Ile His Leu Ile Lys His Ala Ile Trp Arg
                1045                1050                1055

Thr Leu Glu Arg Asn Gly Gln Val Val Leu Leu Gly Ser Ala Pro Asp
            1060                1065                1070

Pro Arg Val Gln Asn Asp Phe Val Asn Leu Ala Asn Gln Leu His Ser
        1075                1080                1085

Lys Tyr Asn Asp Arg Ala Arg Leu Cys Leu Thr Tyr Asp Glu Pro Leu
    1090                1095                1100

Ser His Leu Ile Tyr Ala Gly Ala Asp Phe Ile Leu Val Pro Ser Ile
1105                1110                1115                1120

Phe Glu Pro Cys Gly Leu Thr Gln Leu Thr Ala Met Arg Tyr Gly Ser
                1125                1130                1135

Ile Pro Val Val Arg Lys Thr Gly Gly Leu Tyr Asp Thr Val Phe Asp
            1140                1145                1150

Val Asp His Asp Lys Glu Arg Ala Gln Gln Cys Gly Leu Glu Pro Asn
        1155                1160                1165

Gly Phe Ser Phe Asp Gly Ala Asp Ala Gly Val Asp Tyr Ala Leu
    1170                1175                1180

Asn Arg Ala Leu Ser Ala Trp Tyr Asp Gly Arg Asp Trp Phe Asn Ser
1185                1190                1195                1200

Leu Cys Lys Gln Val Met Glu Gln Asp Trp Ser Trp Asn Arg Pro Ala
                1205                1210                1215

Leu Asp Tyr Leu Glu Leu Tyr His Ala Ala Arg Lys Leu Glu
            1220                1225                1230
```

<210> SEQ ID NO 7
<211> LENGTH: 3078
<212> TYPE: DNA
<213> ORGANISM: Arabidopsis thaliana
<220> FEATURE:
<221> NAME/KEY: CDS
<222> LOCATION: (1)..(3075)
<223> OTHER INFORMATION: coding for SSS3

<400> SEQUENCE: 7

```
atg gct gct tca gga cca aaa agc tca ggt ccc aga ggt ttt ggg cga      48
Met Ala Ala Ser Gly Pro Lys Ser Ser Gly Pro Arg Gly Phe Gly Arg
 1               5                  10                  15 cga aca aca gta gga agt gct cag aaa aga act cag aag aag aat ggt      96
Arg Thr Thr Val Gly Ser Ala Gln Lys Arg Thr Gln Lys Lys Asn Gly
                20                  25                  30 gaa aaa gat agt aat gcc act tct aca gca aca aac gag gtt tca ggg     144
Glu Lys Asp Ser Asn Ala Thr Ser Thr Ala Thr Asn Glu Val Ser Gly
            35                  40                  45 att agt aag ttg ccc gca gct aaa gtg gat gta cag aag caa agc tct     192
Ile Ser Lys Leu Pro Ala Ala Lys Val Asp Val Gln Lys Gln Ser Ser
        50                  55                  60 gtt gtt ttg aat gag aga aat gtg tta gat agg tcg gat att gag gat     240
Val Val Leu Asn Glu Arg Asn Val Leu Asp Arg Ser Asp Ile Glu Asp
 65                  70                  75                  80 gga agt gat cgt ttg gac aag aaa aca acc gat gat gat gat ttg tta     288
Gly Ser Asp Arg Leu Asp Lys Lys Thr Thr Asp Asp Asp Asp Leu Leu
                85                  90                  95 gaa caa aag tta aaa ctt gaa aga gag aat ctt cgt agg aag gaa ata     336
Glu Gln Lys Leu Lys Leu Glu Arg Glu Asn Leu Arg Arg Lys Glu Ile
               100                 105                 110 gaa acg ctt gca gcg gaa aat ttg gcg aga ggt gat aga atg ttt gtg     384
Glu Thr Leu Ala Ala Glu Asn Leu Ala Arg Gly Asp Arg Met Phe Val
           115                 120                 125 tat ccc gtt att gtg aaa cct gat gaa gac ata gaa gtg ttt ctc aac     432
Tyr Pro Val Ile Val Lys Pro Asp Glu Asp Ile Glu Val Phe Leu Asn
       130                 135                 140 agg aat ctg tcg act ctg aat aac gaa ccc gat gtt ttg atc atg ggg     480
Arg Asn Leu Ser Thr Leu Asn Asn Glu Pro Asp Val Leu Ile Met Gly
145                 150                 155                 160 gcg ttt aac gaa tgg aga tgg aag tct ttc aca agg aga ttg gaa aag     528
Ala Phe Asn Glu Trp Arg Trp Lys Ser Phe Thr Arg Arg Leu Glu Lys
               165                 170                 175 acc tgg atc cat gaa gat tgg ttg tca tgt ctc ctt cat atc ccc aaa     576
Thr Trp Ile His Glu Asp Trp Leu Ser Cys Leu Leu His Ile Pro Lys
           180                 185                 190 gaa gcg tat aag atg gac ttc gtg ttt ttc aat ggg caa agt gta tat     624
Glu Ala Tyr Lys Met Asp Phe Val Phe Phe Asn Gly Gln Ser Val Tyr
       195                 200                 205 gac aac aat gac tca aaa gat ttt tgt gta gag ata aaa ggt ggg atg     672
Asp Asn Asn Asp Ser Lys Asp Phe Cys Val Glu Ile Lys Gly Gly Met
       210                 215                 220 gat aaa gtt gac ttt gag aat ttt ctt cta gaa gag aaa ctg cga gag     720
Asp Lys Val Asp Phe Glu Asn Phe Leu Leu Glu Glu Lys Leu Arg Glu
225                 230                 235                 240 caa gag aag tta gcc aag gaa gaa gct gag agg gag agg caa aaa gaa     768
Gln Glu Lys Leu Ala Lys Glu Glu Ala Glu Arg Glu Arg Gln Lys Glu
               245                 250                 255 gag aag aga aga atc gaa gct caa aag gct gca att gaa gct gat aga     816
Glu Lys Arg Arg Ile Glu Ala Gln Lys Ala Ala Ile Glu Ala Asp Arg
           260                 265                 270
```

```
gca caa gca aag gcg gag act cag aag aga cgt gaa ttg ctt caa ccg    864
Ala Gln Ala Lys Ala Glu Thr Gln Lys Arg Arg Glu Leu Leu Gln Pro
        275                 280                 285 gct att aag aaa gct gta gtc tcg gct gag aat gtt tgg tac att gag    912
Ala Ile Lys Lys Ala Val Val Ser Ala Glu Asn Val Trp Tyr Ile Glu
290                 295                 300 ccg agt gat ttc aag gct gaa gat aca gtg aag cta tat tac aat aaa    960
Pro Ser Asp Phe Lys Ala Glu Asp Thr Val Lys Leu Tyr Tyr Asn Lys
305                 310                 315                 320 agg tca ggt cct ctg act aat tcc aaa gaa ctg tgg tta cat gga ggg   1008
Arg Ser Gly Pro Leu Thr Asn Ser Lys Glu Leu Trp Leu His Gly Gly
            325                 330                 335 ttt aat aat tgg gtt gat gga tta tct atc gtt gta aag ctt gtt aat   1056
Phe Asn Asn Trp Val Asp Gly Leu Ser Ile Val Val Lys Leu Val Asn
                340                 345                 350 gct gag tta aag gat gtt gat cca aag agc gga aat tgg tgg ttc gct   1104
Ala Glu Leu Lys Asp Val Asp Pro Lys Ser Gly Asn Trp Trp Phe Ala
            355                 360                 365 gaa gtt gta gtg cct ggc ggt gca cta gtc att gac tgg gtc ttt gct   1152
Glu Val Val Val Pro Gly Gly Ala Leu Val Ile Asp Trp Val Phe Ala
370                 375                 380 gat gga cca cct aaa gga gcg ttt ctg tat gac aat aat ggt tac caa   1200
Asp Gly Pro Pro Lys Gly Ala Phe Leu Tyr Asp Asn Asn Gly Tyr Gln
385                 390                 395                 400 gac ttc cac gca ctt gtt cct caa aaa ctt cct gaa gaa ctt tac tgg   1248
Asp Phe His Ala Leu Val Pro Gln Lys Leu Pro Glu Glu Leu Tyr Trp
            405                 410                 415 tta gag gaa gaa aat atg att ttt aga aaa ctt cag gag gat agg cgg   1296
Leu Glu Glu Glu Asn Met Ile Phe Arg Lys Leu Gln Glu Asp Arg Arg
                420                 425                 430 tta aaa gag gaa gtt atg cgt gcc aag atg gaa aaa aca gct cgc ttg   1344
Leu Lys Glu Glu Val Met Arg Ala Lys Met Glu Lys Thr Ala Arg Leu
            435                 440                 445 aaa gct gaa act aag gaa aga aca ctg aaa aag ttt ctg cta tcc cag   1392
Lys Ala Glu Thr Lys Glu Arg Thr Leu Lys Lys Phe Leu Leu Ser Gln
450                 455                 460 aaa gac gtg gtt tac acc gag cct cta gag att caa gca gga aac cct   1440
Lys Asp Val Val Tyr Thr Glu Pro Leu Glu Ile Gln Ala Gly Asn Pro
465                 470                 475                 480 gtg act gta ttg tac aat cct gca aac acg gtt ttg aat gga aaa cct   1488
Val Thr Val Leu Tyr Asn Pro Ala Asn Thr Val Leu Asn Gly Lys Pro
            485                 490                 495 gaa gtt tgg ttt aga ggc tct ttt aat cgt tgg act cac cgc ttg ggc   1536
Glu Val Trp Phe Arg Gly Ser Phe Asn Arg Trp Thr His Arg Leu Gly
                500                 505                 510 cct ttg cca cct cag aaa atg gaa gca aca gat gat gaa agc tca cat   1584
Pro Leu Pro Pro Gln Lys Met Glu Ala Thr Asp Asp Glu Ser Ser His
            515                 520                 525 gtg aag act acg gct aag gtc cca ttg gat gct tac atg atg gac ttt   1632
Val Lys Thr Thr Ala Lys Val Pro Leu Asp Ala Tyr Met Met Asp Phe
530                 535                 540 gtg ttc tct gag aaa gag gat ggc gga ata ttt gat aac aaa aat ggt   1680
Val Phe Ser Glu Lys Glu Asp Gly Gly Ile Phe Asp Asn Lys Asn Gly
545                 550                 555                 560 ctg gat tac cat tta cca gtc gtg gga ggt att tca aag gaa cca cca   1728
Leu Asp Tyr His Leu Pro Val Val Gly Gly Ile Ser Lys Glu Pro Pro
            565                 570                 575 ttg cac att gtt cat att gct gtt gaa atg gca ccc atc gca aag gtt   1776
Leu His Ile Val His Ile Ala Val Glu Met Ala Pro Ile Ala Lys Val
                580                 585                 590
```

-continued

| | |
|---|---|
| ggt ggc cta ggt gat gtt gtc act agt cta tct cgc gct gtt caa gaa<br>Gly Gly Leu Gly Asp Val Val Thr Ser Leu Ser Arg Ala Val Gln Glu<br>595                   600                605 | 1824 |
| tta aac cat aat gtg gat ata gtt ttt cca aag tat gat tgc ata aag<br>Leu Asn His Asn Val Asp Ile Val Phe Pro Lys Tyr Asp Cys Ile Lys<br>610                  615                620 | 1872 |
| cac aat ttt gtg aag gac ttg caa ttt aac aga agc tat cac tgg gga<br>His Asn Phe Val Lys Asp Leu Gln Phe Asn Arg Ser Tyr His Trp Gly<br>625                    630                635                640 | 1920 |
| gga act gaa ata aaa gtt tgg cat gga aaa gta gaa ggc ctt tcg gtt<br>Gly Thr Glu Ile Lys Val Trp His Gly Lys Val Glu Gly Leu Ser Val<br>645                  650                655 | 1968 |
| tac ttc tta gat cca caa aat gga ttg ttt cag cga gga tgt gtt tac<br>Tyr Phe Leu Asp Pro Gln Asn Gly Leu Phe Gln Arg Gly Cys Val Tyr<br>660                  665                670 | 2016 |
| ggt tgt gca gat gat gca gga aga ttc ggt ttc ttc tgt cat gcg gct<br>Gly Cys Ala Asp Asp Ala Gly Arg Phe Gly Phe Phe Cys His Ala Ala<br>675                    680                685 | 2064 |
| ctt gaa ttt ctt ctc caa gga ggt ttc cat cca gac att ctt cac tgt<br>Leu Glu Phe Leu Leu Gln Gly Gly Phe His Pro Asp Ile Leu His Cys<br>690                    695                700 | 2112 |
| cat gac tgg tct agt gct ccg gtt tca tgg tta ttc aag gat cat tac<br>His Asp Trp Ser Ser Ala Pro Val Ser Trp Leu Phe Lys Asp His Tyr<br>705                    710                715                720 | 2160 |
| aca cag tac ggt tta att aaa acc cgt att gtc ttc aca att cat aat<br>Thr Gln Tyr Gly Leu Ile Lys Thr Arg Ile Val Phe Thr Ile His Asn<br>725                    730                735 | 2208 |
| ttg gaa ttt gga gcg aat gcc att ggt aaa gca atg aca ttt gca gac<br>Leu Glu Phe Gly Ala Asn Ala Ile Gly Lys Ala Met Thr Phe Ala Asp<br>740                    745                750 | 2256 |
| aaa gcc aca acg gtt tca cca act tat gct aag gaa gtt gct gga aac<br>Lys Ala Thr Thr Val Ser Pro Thr Tyr Ala Lys Glu Val Ala Gly Asn<br>755                    760                765 | 2304 |
| tct gta atc tct gca cat tta tac aaa ttt cac gga att ata aac ggg<br>Ser Val Ile Ser Ala His Leu Tyr Lys Phe His Gly Ile Ile Asn Gly<br>770                    775                780 | 2352 |
| att gac cca gat ata tgg gat cca tat aac gat aac ttt att ccc gta<br>Ile Asp Pro Asp Ile Trp Asp Pro Tyr Asn Asp Asn Phe Ile Pro Val<br>785                    790                795                800 | 2400 |
| cct tat act tca gag aac gtt gta gaa ggc aaa aga gca gcc aag gaa<br>Pro Tyr Thr Ser Glu Asn Val Val Glu Gly Lys Arg Ala Ala Lys Glu<br>805                    810                815 | 2448 |
| gaa ttg caa aac agg ctt gga cta aag agt gcc gat ttt cca gta gta<br>Glu Leu Gln Asn Arg Leu Gly Leu Lys Ser Ala Asp Phe Pro Val Val<br>820                    825                830 | 2496 |
| gga att att acg cgc tta aca cac cag aag gga ata cat ttg atc aag<br>Gly Ile Ile Thr Arg Leu Thr His Gln Lys Gly Ile His Leu Ile Lys<br>835                    840                845 | 2544 |
| cac gct att tgg cgt acc ttg gaa cgg aat gga cag gtt gtc tta tta<br>His Ala Ile Trp Arg Thr Leu Glu Arg Asn Gly Gln Val Val Leu Leu<br>850                    855                860 | 2592 |
| ggt tca gct cca gat cct cgg atc caa aat gat ttt gta aac ttg gca<br>Gly Ser Ala Pro Asp Pro Arg Ile Gln Asn Asp Phe Val Asn Leu Ala<br>865                    870                875                880 | 2640 |
| aac caa tta cat tct tct cat ggt gac cgg gct cgg ctt gtt cta acc<br>Asn Gln Leu His Ser Ser His Gly Asp Arg Ala Arg Leu Val Leu Thr<br>885                    890                895 | 2688 |
| tac gat gaa cct ctt tcc cat ttg att tat gct ggg gct gac ttt att<br>Tyr Asp Glu Pro Leu Ser His Leu Ile Tyr Ala Gly Ala Asp Phe Ile | 2736 |

```
                900             905             910
ctt gta ccg tcg ata ttt gag cca tgt gga ctg aca cag ctc ata gcc      2784
Leu Val Pro Ser Ile Phe Glu Pro Cys Gly Leu Thr Gln Leu Ile Ala
            915                 920                 925 atg aga tac ggc gct gtt cct gtt gtt aga aaa act gga gga ctc ttt      2832
Met Arg Tyr Gly Ala Val Pro Val Val Arg Lys Thr Gly Gly Leu Phe
930                 935                 940 gat acg gtt ttt gat gtt gac cac gat aaa gaa agg gca caa gct caa      2880
Asp Thr Val Phe Asp Val Asp His Asp Lys Glu Arg Ala Gln Ala Gln
945                 950                 955                 960 gtt cta gaa cct aat ggt ttc agc ttc gac gga gct gat gct cct ggt      2928
Val Leu Glu Pro Asn Gly Phe Ser Phe Asp Gly Ala Asp Ala Pro Gly
                965                 970                 975 gtt gat tat gct ctc aat agg gcg ata tcg gcg tgg tac gat ggt aga      2976
Val Asp Tyr Ala Leu Asn Arg Ala Ile Ser Ala Trp Tyr Asp Gly Arg
            980                 985                 990 gag tgg ttt aac tcg ctg tgc aag acg gtg atg gag caa gac tgg tca      3024
Glu Trp Phe Asn Ser Leu Cys Lys Thr Val Met Glu Gln Asp Trp Ser
        995                 1000                1005 tgg aac cgt cct gca ctt gag tat ctt gag ctc tat cac tct gca cgc      3072
Trp Asn Arg Pro Ala Leu Glu Tyr Leu Glu Leu Tyr His Ser Ala Arg
    1010                1015                1020 aag taa                                                               3078
Lys
1025

<210> SEQ ID NO 8
<211> LENGTH: 1025
<212> TYPE: PRT
<213> ORGANISM: Arabidopsis thaliana

<400> SEQUENCE: 8

Met Ala Ala Ser Gly Pro Lys Ser Ser Pro Arg Gly Phe Gly Arg
 1               5                  10                  15

Arg Thr Thr Val Gly Ser Ala Gln Lys Arg Thr Gln Lys Lys Asn Gly
            20                  25                  30

Glu Lys Asp Ser Asn Ala Thr Ser Thr Ala Thr Asn Glu Val Ser Gly
        35                  40                  45

Ile Ser Lys Leu Pro Ala Ala Lys Val Asp Val Gln Lys Gln Ser Ser
    50                  55                  60

Val Val Leu Asn Glu Arg Asn Val Leu Asp Arg Ser Asp Ile Glu Asp
65                  70                  75                  80

Gly Ser Asp Arg Leu Asp Lys Lys Thr Thr Asp Asp Asp Leu Leu
                85                  90                  95

Glu Gln Lys Leu Lys Leu Glu Arg Glu Asn Leu Arg Arg Lys Glu Ile
            100                 105                 110

Glu Thr Leu Ala Ala Glu Asn Leu Ala Arg Gly Asp Arg Met Phe Val
        115                 120                 125

Tyr Pro Val Ile Val Lys Pro Asp Glu Asp Ile Glu Val Phe Leu Asn
    130                 135                 140

Arg Asn Leu Ser Thr Leu Asn Asn Glu Pro Asp Val Leu Ile Met Gly
145                 150                 155                 160

Ala Phe Asn Glu Trp Arg Trp Lys Ser Phe Thr Arg Arg Leu Glu Lys
                165                 170                 175

Thr Trp Ile His Glu Asp Trp Leu Ser Cys Leu Leu His Ile Pro Lys
            180                 185                 190

Glu Ala Tyr Lys Met Asp Phe Val Phe Phe Asn Gly Gln Ser Val Tyr
```

-continued

```
            195                 200                 205
Asp Asn Asn Asp Ser Lys Asp Phe Cys Val Glu Ile Lys Gly Gly Met
    210                 215                 220
Asp Lys Val Asp Phe Glu Asn Phe Leu Leu Glu Glu Lys Leu Arg Glu
225                 230                 235                 240
Gln Glu Lys Leu Ala Lys Glu Ala Glu Arg Glu Arg Gln Lys Glu
            245                 250                 255
Glu Lys Arg Arg Ile Glu Ala Gln Lys Ala Ala Ile Glu Ala Asp Arg
            260                 265                 270
Ala Gln Ala Lys Ala Glu Thr Gln Lys Arg Arg Glu Leu Leu Gln Pro
            275                 280                 285
Ala Ile Lys Lys Ala Val Val Ser Ala Glu Asn Val Trp Tyr Ile Glu
            290                 295                 300
Pro Ser Asp Phe Lys Ala Glu Asp Thr Val Lys Leu Tyr Tyr Asn Lys
305                 310                 315                 320
Arg Ser Gly Pro Leu Thr Asn Ser Lys Glu Leu Trp Leu His Gly Gly
                325                 330                 335
Phe Asn Asn Trp Val Asp Gly Leu Ser Ile Val Val Lys Leu Val Asn
            340                 345                 350
Ala Glu Leu Lys Asp Val Asp Pro Lys Ser Gly Asn Trp Trp Phe Ala
            355                 360                 365
Glu Val Val Pro Gly Gly Ala Leu Val Ile Asp Trp Val Phe Ala
            370                 375                 380
Asp Gly Pro Pro Lys Gly Ala Phe Leu Tyr Asp Asn Asn Gly Tyr Gln
385                 390                 395                 400
Asp Phe His Ala Leu Val Pro Gln Lys Leu Pro Glu Glu Leu Tyr Trp
                405                 410                 415
Leu Glu Glu Glu Asn Met Ile Phe Arg Lys Leu Gln Glu Asp Arg Arg
                420                 425                 430
Leu Lys Glu Glu Val Met Arg Ala Lys Met Glu Lys Thr Ala Arg Leu
            435                 440                 445
Lys Ala Glu Thr Lys Glu Arg Thr Leu Lys Lys Phe Leu Leu Ser Gln
450                 455                 460
Lys Asp Val Val Tyr Thr Glu Pro Leu Glu Ile Gln Ala Gly Asn Pro
465                 470                 475                 480
Val Thr Val Leu Tyr Asn Pro Ala Asn Thr Val Leu Asn Gly Lys Pro
                485                 490                 495
Glu Val Trp Phe Arg Gly Ser Phe Asn Arg Trp Thr His Arg Leu Gly
                500                 505                 510
Pro Leu Pro Pro Gln Lys Met Glu Ala Thr Asp Asp Glu Ser Ser His
            515                 520                 525
Val Lys Thr Thr Ala Lys Val Pro Leu Asp Ala Tyr Met Met Asp Phe
530                 535                 540
Val Phe Ser Glu Lys Glu Asp Gly Gly Ile Phe Asp Asn Lys Asn Gly
545                 550                 555                 560
Leu Asp Tyr His Leu Pro Val Gly Gly Ile Ser Lys Glu Pro Pro
                565                 570                 575
Leu His Ile Val His Ile Ala Val Glu Met Ala Pro Ile Ala Lys Val
            580                 585                 590
Gly Gly Leu Gly Asp Val Val Thr Ser Leu Ser Arg Ala Val Gln Glu
            595                 600                 605
Leu Asn His Asn Val Asp Ile Val Phe Pro Lys Tyr Asp Cys Ile Lys
610                 615                 620
```

```
His Asn Phe Val Lys Asp Leu Gln Phe Asn Arg Ser Tyr His Trp Gly
625                 630                 635                 640

Gly Thr Glu Ile Lys Val Trp His Gly Lys Val Gly Leu Ser Val
            645                 650                 655

Tyr Phe Leu Asp Pro Gln Asn Gly Leu Phe Gln Arg Gly Cys Val Tyr
                660                 665                 670

Gly Cys Ala Asp Ala Gly Arg Phe Gly Phe Phe Cys His Ala Ala
            675                 680                 685

Leu Glu Phe Leu Leu Gln Gly Gly Phe His Pro Asp Ile Leu His Cys
690                 695                 700

His Asp Trp Ser Ser Ala Pro Val Ser Trp Leu Phe Lys Asp His Tyr
705                 710                 715                 720

Thr Gln Tyr Gly Leu Ile Lys Thr Arg Ile Val Phe Thr Ile His Asn
                725                 730                 735

Leu Glu Phe Gly Ala Asn Ala Ile Gly Lys Ala Met Thr Phe Ala Asp
                740                 745                 750

Lys Ala Thr Thr Val Ser Pro Thr Tyr Ala Lys Glu Val Ala Gly Asn
            755                 760                 765

Ser Val Ile Ser Ala His Leu Tyr Lys Phe His Gly Ile Ile Asn Gly
770                 775                 780

Ile Asp Pro Asp Ile Trp Asp Pro Tyr Asn Asp Asn Phe Ile Pro Val
785                 790                 795                 800

Pro Tyr Thr Ser Glu Asn Val Val Glu Gly Lys Arg Ala Ala Lys Glu
                805                 810                 815

Glu Leu Gln Asn Arg Leu Gly Leu Lys Ser Ala Asp Phe Pro Val Val
            820                 825                 830

Gly Ile Ile Thr Arg Leu Thr His Gln Lys Gly Ile His Leu Ile Lys
            835                 840                 845

His Ala Ile Trp Arg Thr Leu Glu Arg Asn Gly Gln Val Val Leu Leu
850                 855                 860

Gly Ser Ala Pro Asp Pro Arg Ile Gln Asn Asp Phe Val Asn Leu Ala
865                 870                 875                 880

Asn Gln Leu His Ser Ser His Gly Asp Arg Ala Arg Leu Val Leu Thr
                885                 890                 895

Tyr Asp Glu Pro Leu Ser His Leu Ile Tyr Ala Gly Ala Asp Phe Ile
                900                 905                 910

Leu Val Pro Ser Ile Phe Glu Pro Cys Gly Leu Thr Gln Leu Ile Ala
            915                 920                 925

Met Arg Tyr Gly Ala Val Pro Val Val Arg Lys Thr Gly Gly Leu Phe
930                 935                 940

Asp Thr Val Phe Asp Val Asp His Asp Lys Glu Arg Ala Gln Ala Gln
945                 950                 955                 960

Val Leu Glu Pro Asn Gly Phe Ser Phe Asp Gly Ala Asp Ala Pro Gly
                965                 970                 975

Val Asp Tyr Ala Leu Asn Arg Ala Ile Ser Ala Trp Tyr Asp Gly Arg
            980                 985                 990

Glu Trp Phe Asn Ser Leu Cys Lys Thr Val Met Glu Gln Asp Trp Ser
            995                 1000                1005

Trp Asn Arg Pro Ala Leu Glu Tyr Leu Glu Leu Tyr His Ser Ala Arg
    1010                1015                1020

Lys
1025
```

<210> SEQ ID NO 9
<211> LENGTH: 1881
<212> TYPE: DNA
<213> ORGANISM: Oryza sativa
<220> FEATURE:
<221> NAME/KEY: CDS
<222> LOCATION: (1)..(1878)
<223> OTHER INFORMATION: coding for SSS3

<400> SEQUENCE: 9

```
atg gcg acg gcg gcg ggg atg ggg atc ggg gcg gcg tgc ctg gtg gcg        48
Met Ala Thr Ala Ala Gly Met Gly Ile Gly Ala Ala Cys Leu Val Ala
 1               5                  10                  15 ccg cag gtg agg ccg ggg agg agg ttg cgg ctc cag cgg gtg cgg agg        96
Pro Gln Val Arg Pro Gly Arg Arg Leu Arg Leu Gln Arg Val Arg Arg
             20                  25                  30 cgg tgc gtg gcg gag ctg agc agg gac ggt ggg tcg gcg cac ggc ccg       144
Arg Cys Val Ala Glu Leu Ser Arg Asp Gly Gly Ser Ala His Gly Pro
         35                  40                  45 ctg gca ccg gcg ccg ctg gtg aag cag ccg gtc ctg ccg acc ttc ctc       192
Leu Ala Pro Ala Pro Leu Val Lys Gln Pro Val Leu Pro Thr Phe Leu
     50                  55                  60 gtg ccg acg tcg acg cca ccc gcg ccc acg cag tcg ccg gcg ccg gcg       240
Val Pro Thr Ser Thr Pro Pro Ala Pro Thr Gln Ser Pro Ala Pro Ala
 65                  70                  75                  80 ccg acc ccg ccg ccg ttg ccg gac tcc ggc gtg ggg gag atc gag ccc       288
Pro Thr Pro Pro Pro Leu Pro Asp Ser Gly Val Gly Glu Ile Glu Pro
                 85                  90                  95 gat cta gaa ggt ctc aca gaa gat tcc atc gac aaa aca att ttt gtg       336
Asp Leu Glu Gly Leu Thr Glu Asp Ser Ile Asp Lys Thr Ile Phe Val
            100                 105                 110 gct agt gag cag gag tct gag atc atg gat gtg aag gag caa gct caa       384
Ala Ser Glu Gln Glu Ser Glu Ile Met Asp Val Lys Glu Gln Ala Gln
        115                 120                 125 gct aaa gta aca cgc agc gtt gtc ttt gta acc ggt gaa gct tct cct       432
Ala Lys Val Thr Arg Ser Val Val Phe Val Thr Gly Glu Ala Ser Pro
    130                 135                 140 tat gca aag tca ggt gga cta gga gat gtt tgt ggt tca ctg cca att       480
Tyr Ala Lys Ser Gly Gly Leu Gly Asp Val Cys Gly Ser Leu Pro Ile
145                 150                 155                 160 gct ctt gct ctt cgt ggt cat cgt gtg atg gtt gta atg ccg aga tac       528
Ala Leu Ala Leu Arg Gly His Arg Val Met Val Val Met Pro Arg Tyr
                165                 170                 175 atg aac ggg gcc ttg aac aaa aat ttt gca aac gca ttt tac act gag       576
Met Asn Gly Ala Leu Asn Lys Asn Phe Ala Asn Ala Phe Tyr Thr Glu
            180                 185                 190 aag cac att aag att cca tgc ttt ggc gga gaa cat gaa gtt act ttt       624
Lys His Ile Lys Ile Pro Cys Phe Gly Gly Glu His Glu Val Thr Phe
        195                 200                 205 ttt cac gag tat agg gat tct gtt gat tgg gtg ttt gtt gat cat ccc       672
Phe His Glu Tyr Arg Asp Ser Val Asp Trp Val Phe Val Asp His Pro
    210                 215                 220 tca tat cat aga cct gga aat ttg tat gga gat aat ttt ggt gct ttt       720
Ser Tyr His Arg Pro Gly Asn Leu Tyr Gly Asp Asn Phe Gly Ala Phe
225                 230                 235                 240 ggc gat aat cag ttc aga tac aca ctc ctg tgc tat gcg gcg tgt gaa       768
Gly Asp Asn Gln Phe Arg Tyr Thr Leu Leu Cys Tyr Ala Ala Cys Glu
                245                 250                 255 gcc cca tta att ctt gaa ctg gga gga tat atc tat gga cag aaa tgc       816
Ala Pro Leu Ile Leu Glu Leu Gly Gly Tyr Ile Tyr Gly Gln Lys Cys
            260                 265                 270
```

-continued

| | |
|---|---|
| atg ttt gtt gtg aat gat tgg cat gcc agt ctt gtg cca gtc ctt ctt<br>Met Phe Val Val Asn Asp Trp His Ala Ser Leu Val Pro Val Leu Leu<br>275                 280                 285 | 864 |
| gct gca aaa tat aga cca tat ggt gtt tac agg gat gcc cgc agt gtt<br>Ala Ala Lys Tyr Arg Pro Tyr Gly Val Tyr Arg Asp Ala Arg Ser Val<br>290                 295                 300 | 912 |
| ctt gtc ata cat aat cta gca cat cag ggt gtg gag cct gcc agt aca<br>Leu Val Ile His Asn Leu Ala His Gln Gly Val Glu Pro Ala Ser Thr<br>305                 310                 315                 320 | 960 |
| tat cct gac ctg gga ttg cca cct gaa tgg tat gga gca tta gaa tgg<br>Tyr Pro Asp Leu Gly Leu Pro Pro Glu Trp Tyr Gly Ala Leu Glu Trp<br>               325                 330                 335 | 1008 |
| gtg ttt cca gag tgg gca agg cgg cat gcc ctt gac aag ggt gag gca<br>Val Phe Pro Glu Trp Ala Arg Arg His Ala Leu Asp Lys Gly Glu Ala<br>               340                 345                 350 | 1056 |
| gtc aat ttt tta aaa ggc gca gtt gtg aca gca gat cga att gtg act<br>Val Asn Phe Leu Lys Gly Ala Val Val Thr Ala Asp Arg Ile Val Thr<br>               355                 360                 365 | 1104 |
| gtc agc cag ggg tat tca tgg gag gtc aca act gct gaa ggt ggg caa<br>Val Ser Gln Gly Tyr Ser Trp Glu Val Thr Thr Ala Glu Gly Gly Gln<br>370                 375                 380 | 1152 |
| ggc ctc aat gag ctc tta agc tcc cgg aag agt gta ttg aat gga att<br>Gly Leu Asn Glu Leu Leu Ser Ser Arg Lys Ser Val Leu Asn Gly Ile<br>385                 390                 395                 400 | 1200 |
| gta aat gga att gac att aat gat tgg aac cca tcc aca gac aag ttt<br>Val Asn Gly Ile Asp Ile Asn Asp Trp Asn Pro Ser Thr Asp Lys Phe<br>               405                 410                 415 | 1248 |
| ctc cct tat cat tat tct gtt gat gac ctg tcc gga aag gcc aag tgt<br>Leu Pro Tyr His Tyr Ser Val Asp Asp Leu Ser Gly Lys Ala Lys Cys<br>               420                 425                 430 | 1296 |
| aaa gct gaa ttg cag aag gag ctg ggt tta cct ata agg ccc gat gtg<br>Lys Ala Glu Leu Gln Lys Glu Leu Gly Leu Pro Ile Arg Pro Asp Val<br>               435                 440                 445 | 1344 |
| cct ctg att ggc ttt att gga aga ttg gac tat caa aaa ggc att gat<br>Pro Leu Ile Gly Phe Ile Gly Arg Leu Asp Tyr Gln Lys Gly Ile Asp<br>450                 455                 460 | 1392 |
| cta att aaa ctt gcc att cca gat ctc atg cgg gac aat att caa ttc<br>Leu Ile Lys Leu Ala Ile Pro Asp Leu Met Arg Asp Asn Ile Gln Phe<br>465                 470                 475                 480 | 1440 |
| gtc atg ctt gga tct ggt gac cca ggt ttt gaa gga tgg atg aga tcc<br>Val Met Leu Gly Ser Gly Asp Pro Gly Phe Glu Gly Trp Met Arg Ser<br>               485                 490                 495 | 1488 |
| aca gaa tca ggg tac agg gat aaa ttt cgt gga tgg gtt gga ttt agt<br>Thr Glu Ser Gly Tyr Arg Asp Lys Phe Arg Gly Trp Val Gly Phe Ser<br>               500                 505                 510 | 1536 |
| gtt cca gtt tcc cac cga ata act gca ggt tgc gat ata ttg ttg atg<br>Val Pro Val Ser His Arg Ile Thr Ala Gly Cys Asp Ile Leu Leu Met<br>               515                 520                 525 | 1584 |
| cca tcc aga ttc gaa cct tgt ggc ctc aat cag cta tat gct atg caa<br>Pro Ser Arg Phe Glu Pro Cys Gly Leu Asn Gln Leu Tyr Ala Met Gln<br>530                 535                 540 | 1632 |
| tat ggt aca gtg cct gtt gtt cat gga act gga ggc ctc aga gat aca<br>Tyr Gly Thr Val Pro Val Val His Gly Thr Gly Gly Leu Arg Asp Thr<br>545                 550                 555                 560 | 1680 |
| gtg gag aat ttt aac ccg ttt gct gag aaa gga gag cag ggt aca ggg<br>Val Glu Asn Phe Asn Pro Phe Ala Glu Lys Gly Glu Gln Gly Thr Gly<br>               565                 570                 575 | 1728 |
| tgg gca ttc tcg cca cta acc att gaa aaa aat gct gtg ggc att gcg<br>Trp Ala Phe Ser Pro Leu Thr Ile Glu Lys Asn Ala Val Gly Ile Ala | 1776 |

```
                         580                 585                 590
gat ggc aat ttc gac ata cag gga aca caa gtc ctc ttg gga ggg tct      1824
Asp Gly Asn Phe Asp Ile Gln Gly Thr Gln Val Leu Leu Gly Gly Ser
        595                 600                 605 aat gaa gcg agg cat gtc aag cga ctt tac atg gga cca tgc cgc ctc      1872
Asn Glu Ala Arg His Val Lys Arg Leu Tyr Met Gly Pro Cys Arg Leu
    610                 615                 620 aca gta tga                                                          1881
Thr Val
625

<210> SEQ ID NO 10
<211> LENGTH: 626
<212> TYPE: PRT
<213> ORGANISM: Oryza sativa

<400> SEQUENCE: 10

Met Ala Thr Ala Ala Gly Met Gly Ile Gly Ala Ala Cys Leu Val Ala
  1               5                  10                  15

Pro Gln Val Arg Pro Gly Arg Arg Leu Arg Leu Gln Arg Val Arg Arg
             20                  25                  30

Arg Cys Val Ala Glu Leu Ser Arg Asp Gly Gly Ser Ala His Gly Pro
         35                  40                  45

Leu Ala Pro Ala Pro Leu Val Lys Gln Pro Val Leu Pro Thr Phe Leu
     50                  55                  60

Val Pro Thr Ser Thr Pro Pro Ala Pro Thr Gln Ser Pro Ala Pro Ala
 65                  70                  75                  80

Pro Thr Pro Pro Pro Leu Pro Asp Ser Gly Val Gly Glu Ile Glu Pro
                 85                  90                  95

Asp Leu Glu Gly Leu Thr Glu Asp Ser Ile Asp Lys Thr Ile Phe Val
            100                 105                 110

Ala Ser Glu Gln Glu Ser Glu Ile Met Asp Val Lys Glu Gln Ala Gln
        115                 120                 125

Ala Lys Val Thr Arg Ser Val Val Phe Val Thr Gly Glu Ala Ser Pro
    130                 135                 140

Tyr Ala Lys Ser Gly Gly Leu Gly Asp Val Cys Gly Ser Leu Pro Ile
145                 150                 155                 160

Ala Leu Ala Leu Arg Gly His Arg Val Met Val Met Pro Arg Tyr
                165                 170                 175

Met Asn Gly Ala Leu Asn Lys Asn Phe Ala Asn Ala Phe Tyr Thr Glu
            180                 185                 190

Lys His Ile Lys Ile Pro Cys Phe Gly Gly Glu His Glu Val Thr Phe
        195                 200                 205

Phe His Glu Tyr Arg Asp Ser Val Asp Trp Val Phe Val Asp His Pro
    210                 215                 220

Ser Tyr His Arg Pro Gly Asn Leu Tyr Gly Asp Asn Phe Gly Ala Phe
225                 230                 235                 240

Gly Asp Asn Gln Phe Arg Tyr Thr Leu Leu Cys Tyr Ala Ala Cys Glu
                245                 250                 255

Ala Pro Leu Ile Leu Glu Leu Gly Gly Tyr Ile Tyr Gly Gln Lys Cys
            260                 265                 270

Met Phe Val Val Asn Asp Trp His Ala Ser Leu Val Pro Val Leu Leu
        275                 280                 285

Ala Ala Lys Tyr Arg Pro Tyr Gly Val Tyr Arg Asp Ala Arg Ser Val
    290                 295                 300
```

-continued

```
Leu Val Ile His Asn Leu Ala His Gln Gly Val Glu Pro Ala Ser Thr
305                 310                 315                 320

Tyr Pro Asp Leu Gly Leu Pro Pro Glu Trp Tyr Gly Ala Leu Glu Trp
            325                 330                 335

Val Phe Pro Glu Trp Ala Arg Arg His Ala Leu Asp Lys Gly Glu Ala
        340                 345                 350

Val Asn Phe Leu Lys Gly Ala Val Thr Ala Asp Arg Ile Val Thr
    355                 360                 365

Val Ser Gln Gly Tyr Ser Trp Glu Val Thr Thr Ala Glu Gly Gly Gln
370                 375                 380

Gly Leu Asn Glu Leu Leu Ser Ser Arg Lys Ser Val Leu Asn Gly Ile
385                 390                 395                 400

Val Asn Gly Ile Asp Ile Asn Asp Trp Asn Pro Ser Thr Asp Lys Phe
                405                 410                 415

Leu Pro Tyr His Tyr Ser Val Asp Asp Leu Ser Gly Lys Ala Lys Cys
            420                 425                 430

Lys Ala Glu Leu Gln Lys Glu Leu Gly Leu Pro Ile Arg Pro Asp Val
        435                 440                 445

Pro Leu Ile Gly Phe Ile Gly Arg Leu Asp Tyr Gln Lys Gly Ile Asp
    450                 455                 460

Leu Ile Lys Leu Ala Ile Pro Asp Leu Met Arg Asp Asn Ile Gln Phe
465                 470                 475                 480

Val Met Leu Gly Ser Gly Asp Pro Gly Phe Glu Gly Trp Met Arg Ser
                485                 490                 495

Thr Glu Ser Gly Tyr Arg Asp Lys Phe Arg Gly Trp Val Gly Phe Ser
            500                 505                 510

Val Pro Val Ser His Arg Ile Thr Ala Gly Cys Asp Ile Leu Leu Met
        515                 520                 525

Pro Ser Arg Phe Glu Pro Cys Gly Leu Asn Gln Leu Tyr Ala Met Gln
    530                 535                 540

Tyr Gly Thr Val Pro Val Val His Gly Thr Gly Gly Leu Arg Asp Thr
545                 550                 555                 560

Val Glu Asn Phe Asn Pro Phe Ala Glu Lys Gly Glu Gln Gly Thr Gly
                565                 570                 575

Trp Ala Phe Ser Pro Leu Thr Ile Glu Lys Asn Ala Val Gly Ile Ala
            580                 585                 590

Asp Gly Asn Phe Asp Ile Gln Gly Thr Gln Val Leu Leu Gly Gly Ser
        595                 600                 605

Asn Glu Ala Arg His Val Lys Arg Leu Tyr Met Gly Pro Cys Arg Leu
    610                 615                 620

Thr Val
625

<210> SEQ ID NO 11
<211> LENGTH: 4887
<212> TYPE: DNA
<213> ORGANISM: Triticum aestivum
<220> FEATURE:
<221> NAME/KEY: CDS
<222> LOCATION: (1)..(4884)
<223> OTHER INFORMATION: coding for SSS3

<400> SEQUENCE: 11 atg gag atg tct ctc tgg cca cgg agc ccc ctg tgc cct cgg agc agg    48
Met Glu Met Ser Leu Trp Pro Arg Ser Pro Leu Cys Pro Arg Ser Arg
1               5                   10                  15
```

-continued

| | | |
|---|---|---|
| cag ccg ctc gtc gtc gtc cgg ccg gcc ggc cgc ggc ggc ctc acg cag<br>Gln Pro Leu Val Val Val Arg Pro Ala Gly Arg Gly Gly Leu Thr Gln<br>        20                          25                        30 | 96 |
| cct ttt ttg atg aat ggc aga ttt act cga agc agg acc ctt cga tgc<br>Pro Phe Leu Met Asn Gly Arg Phe Thr Arg Ser Arg Thr Leu Arg Cys<br>        35                          40                        45 | 144 |
| atg gta gca agt tca gat cct cct aat agg aaa tca aga agg atg gta<br>Met Val Ala Ser Ser Asp Pro Pro Asn Arg Lys Ser Arg Arg Met Val<br>50                          55                        60 | 192 |
| cca cct cag gtt aaa gtc att tct tct aga gga tat acg aca aga ctc<br>Pro Pro Gln Val Lys Val Ile Ser Ser Arg Gly Tyr Thr Thr Arg Leu<br>65                     70                      75                    80 | 240 |
| att gtt gaa cca agc aac gag aat aca gaa cac aat aat cgg gat gaa<br>Ile Val Glu Pro Ser Asn Glu Asn Thr Glu His Asn Asn Arg Asp Glu<br>                      85                      90                    95 | 288 |
| gaa act ctt gat aca tac aat gcg cta tta agt acc gag aca gca gaa<br>Glu Thr Leu Asp Thr Tyr Asn Ala Leu Leu Ser Thr Glu Thr Ala Glu<br>                    100                   105               110 | 336 |
| tgg aca gat aat aga gaa gcc gag act gct aaa gcg gac tcg tcg caa<br>Trp Thr Asp Asn Arg Glu Ala Glu Thr Ala Lys Ala Asp Ser Ser Gln<br>                115                   120               125 | 384 |
| aat gct tta agc agt tct ata att ggg gaa gtg gat gtg gcg gat gaa<br>Asn Ala Leu Ser Ser Ser Ile Ile Gly Glu Val Asp Val Ala Asp Glu<br>130                      135                   140 | 432 |
| gat ata ctt gcg gct gat ctg aca gtg tat tca ttg agc agt gta atg<br>Asp Ile Leu Ala Ala Asp Leu Thr Val Tyr Ser Leu Ser Ser Val Met<br>145                      150                   155               160 | 480 |
| aag aag gaa gtg gat gca gcg gac aaa gct aga gtt aaa gaa gac gca<br>Lys Lys Glu Val Asp Ala Ala Asp Lys Ala Arg Val Lys Glu Asp Ala<br>                    165                   170               175 | 528 |
| ttt gag ctg gat ttg cca gca act aca ttg aga agt gtg ata gta gat<br>Phe Glu Leu Asp Leu Pro Ala Thr Thr Leu Arg Ser Val Ile Val Asp<br>                180                   185               190 | 576 |
| gtg atg gat cat aat ggg act gta caa gag aca ttg aga agt gtg ata<br>Val Met Asp His Asn Gly Thr Val Gln Glu Thr Leu Arg Ser Val Ile<br>                195                   200               205 | 624 |
| gta gat gtg atg gat cat aat ggg act gta caa gag aca ttg aga agt<br>Val Asp Val Met Asp His Asn Gly Thr Val Gln Glu Thr Leu Arg Ser<br>210                      215                   220 | 672 |
| gtg ata gta gat gtg atg gat gat gcg gcg gac aaa gct aga gtt gaa<br>Val Ile Val Asp Val Met Asp Asp Ala Ala Asp Lys Ala Arg Val Glu<br>225                      230                   235               240 | 720 |
| gaa gac gta ttt gag ctg gat ttg tca gga aat att tca agc agt gcg<br>Glu Asp Val Phe Glu Leu Asp Leu Ser Gly Asn Ile Ser Ser Ser Ala<br>                    245                   250               255 | 768 |
| acg acc gtg gaa cta gat gcg gtt gac gaa gtc ggg cct gtt caa gac<br>Thr Thr Val Glu Leu Asp Ala Val Asp Glu Val Gly Pro Val Gln Asp<br>                260                   265               270 | 816 |
| aaa ttt gag gcg acc tca tca gga aat gtt tca aac agt gca acg gta<br>Lys Phe Glu Ala Thr Ser Ser Gly Asn Val Ser Asn Ser Ala Thr Val<br>                275                   280               285 | 864 |
| cgg gaa gtg gat gca agt gat gaa gct ggg aat gat caa ggc ata ttt<br>Arg Glu Val Asp Ala Ser Asp Glu Ala Gly Asn Asp Gln Gly Ile Phe<br>290                      295                   300 | 912 |
| aga gca gat ttg tca gga aat gtt ttt tca agc agt aca aca gtg gaa<br>Arg Ala Asp Leu Ser Gly Asn Val Phe Ser Ser Ser Thr Thr Val Glu<br>305                      310                   315               320 | 960 |
| gtg ggt gca gtg gat gaa gct ggg tct ata aag gac agg ttt gag acg<br>Val Gly Ala Val Asp Glu Ala Gly Ser Ile Lys Asp Arg Phe Glu Thr<br>                325                   330               335 | 1008 |

| | | |
|---|---|---|
| gat tcg tca gga aat gtt tca aca agt gcg ccg atg tgg gat gca att<br>Asp Ser Ser Gly Asn Val Ser Thr Ser Ala Pro Met Trp Asp Ala Ile<br>340 345 350 | | 1056 |
| gat gaa acc gtg gct gat caa gac aca ttt gag gcg gat ttg tcg gga<br>Asp Glu Thr Val Ala Asp Gln Asp Thr Phe Glu Ala Asp Leu Ser Gly<br>355 360 365 | | 1104 |
| aat gct tca agc tgc gca aca tac aga gaa gtg gat gat gtg gtg gat<br>Asn Ala Ser Ser Cys Ala Thr Tyr Arg Glu Val Asp Asp Val Val Asp<br>370 375 380 | | 1152 |
| gaa act aga tca gaa gag gaa aca ttt gca atg gat ttg ttt gca agt<br>Glu Thr Arg Ser Glu Glu Glu Thr Phe Ala Met Asp Leu Phe Ala Ser<br>385 390 395 400 | | 1200 |
| gaa tca ggc cat gag aaa cat atg gca gtg gat tat gtg ggt gaa gct<br>Glu Ser Gly His Glu Lys His Met Ala Val Asp Tyr Val Gly Glu Ala<br>405 410 415 | | 1248 |
| acc gat gaa gaa gag act tac caa cag caa tat cca gta ccg tct tca<br>Thr Asp Glu Glu Glu Thr Tyr Gln Gln Gln Tyr Pro Val Pro Ser Ser<br>420 425 430 | | 1296 |
| ttc tct atg tgg gac aag gct att gct aaa aca ggt gta agt ttg aat<br>Phe Ser Met Trp Asp Lys Ala Ile Ala Lys Thr Gly Val Ser Leu Asn<br>435 440 445 | | 1344 |
| cct gag ctg cga ctt gtc agg gtt gaa gaa caa ggc aaa gta aat ttt<br>Pro Glu Leu Arg Leu Val Arg Val Glu Glu Gln Gly Lys Val Asn Phe<br>450 455 460 | | 1392 |
| agt gat aaa aaa gac ctg tca att gat gat tta cca gga caa aac caa<br>Ser Asp Lys Lys Asp Leu Ser Ile Asp Asp Leu Pro Gly Gln Asn Gln<br>465 470 475 480 | | 1440 |
| tcg atc att ggt tcc tat aaa caa gat aaa tca att gct gat gtt gcg<br>Ser Ile Ile Gly Ser Tyr Lys Gln Asp Lys Ser Ile Ala Asp Val Ala<br>485 490 495 | | 1488 |
| gga ccg acc caa tca att ttt ggt tct agt aaa caa cac cgg tca att<br>Gly Pro Thr Gln Ser Ile Phe Gly Ser Ser Lys Gln His Arg Ser Ile<br>500 505 510 | | 1536 |
| gtt gct ttc ccc aaa caa aac cag tca att gtt agt gtc act gag caa<br>Val Ala Phe Pro Lys Gln Asn Gln Ser Ile Val Ser Val Thr Glu Gln<br>515 520 525 | | 1584 |
| aag cag tcc ata gtt gga ttc cgt agt caa gat ctt tcg gct gtt agt<br>Lys Gln Ser Ile Val Gly Phe Arg Ser Gln Asp Leu Ser Ala Val Ser<br>530 535 540 | | 1632 |
| ctc cct aaa caa aac gta cca att gtt ggt acg tcg aga gag ggt caa<br>Leu Pro Lys Gln Asn Val Pro Ile Val Gly Thr Ser Arg Glu Gly Gln<br>545 550 555 560 | | 1680 |
| aca aag caa gtt cct gtt gtt gat aga cag gat gca ttg tat gtg aat<br>Thr Lys Gln Val Pro Val Val Asp Arg Gln Asp Ala Leu Tyr Val Asn<br>565 570 575 | | 1728 |
| gga ctg gaa gct aag gag gga gat cac aca tcc gag aaa act gat gag<br>Gly Leu Glu Ala Lys Glu Gly Asp His Thr Ser Glu Lys Thr Asp Glu<br>580 585 590 | | 1776 |
| gat gcg ctt cat gta aag ttt aat gtt gac aat gtg ttg cgg aag cat<br>Asp Ala Leu His Val Lys Phe Asn Val Asp Asn Val Leu Arg Lys His<br>595 600 605 | | 1824 |
| cag gca gat aga acc caa gca gtg gaa aag aaa act tgg aag aaa gtt<br>Gln Ala Asp Arg Thr Gln Ala Val Glu Lys Lys Thr Trp Lys Lys Val<br>610 615 620 | | 1872 |
| gat gag gaa cat ctt tac atg act gaa cat cag aaa cgt gct gcc gaa<br>Asp Glu Glu His Leu Tyr Met Thr Glu His Gln Lys Arg Ala Ala Glu<br>625 630 635 640 | | 1920 |
| gga cag atg gta gtt aac gag gat gag ctt tct ata act gaa att gga<br>Gly Gln Met Val Val Asn Glu Asp Glu Leu Ser Ile Thr Glu Ile Gly | | 1968 |

-continued

```
              645                 650                 655
atg ggg aga ggt gat aaa att cag cat gtg ctt tct gag gaa gag ctt         2016
Met Gly Arg Gly Asp Lys Ile Gln His Val Leu Ser Glu Glu Glu Leu
            660                 665                 670 tca tgg tct gaa gat gaa gtg cag tta att gag gat gat gga caa tat         2064
Ser Trp Ser Glu Asp Glu Val Gln Leu Ile Glu Asp Asp Gly Gln Tyr
        675                 680                 685 gaa gtt gac gag acc tct gtg tcc gtt aac gtt gaa caa gat atc cag         2112
Glu Val Asp Glu Thr Ser Val Ser Val Asn Val Glu Gln Asp Ile Gln
    690                 695                 700 ggg tca cca cag gat gtt gtg gat ccg caa gca cta aag gtg atg ctg         2160
Gly Ser Pro Gln Asp Val Val Asp Pro Gln Ala Leu Lys Val Met Leu
705                 710                 715                 720 caa gaa ctc gct gag aaa aat tat tcg atg agg aac aag ctg ttt gtt         2208
Gln Glu Leu Ala Glu Lys Asn Tyr Ser Met Arg Asn Lys Leu Phe Val
                725                 730                 735 ttt cca gag gta gtg aaa gct gat tca gtt att gat ctt tat tta aat         2256
Phe Pro Glu Val Val Lys Ala Asp Ser Val Ile Asp Leu Tyr Leu Asn
            740                 745                 750 cgt gac cta aca gct ttg gcg aat gaa ccc gat gtc gtc atc aaa gga         2304
Arg Asp Leu Thr Ala Leu Ala Asn Glu Pro Asp Val Val Ile Lys Gly
        755                 760                 765 gca ttc aat ggt tgg aaa tgg agg ctt ttc act gaa aga ttg cac aag         2352
Ala Phe Asn Gly Trp Lys Trp Arg Leu Phe Thr Glu Arg Leu His Lys
    770                 775                 780 agt gac ctt gga ggg gtt tgg tgg tct tgc aaa ctg tac ata ccc aag         2400
Ser Asp Leu Gly Gly Val Trp Trp Ser Cys Lys Leu Tyr Ile Pro Lys
785                 790                 795                 800 gag gcc tac aga tta gac ttt gtg ttc ttc aac ggt cgc acg gtc tat         2448
Glu Ala Tyr Arg Leu Asp Phe Val Phe Phe Asn Gly Arg Thr Val Tyr
                805                 810                 815 gag aac aat ggc aac aat gat ttc tgt ata gga ata gaa ggc act atg         2496
Glu Asn Asn Gly Asn Asn Asp Phe Cys Ile Gly Ile Glu Gly Thr Met
            820                 825                 830 aat gaa gat ctg ttt gag gat ttc ttg gtt aaa gaa aag caa agg gag         2544
Asn Glu Asp Leu Phe Glu Asp Phe Leu Val Lys Glu Lys Gln Arg Glu
        835                 840                 845 ctt gag aaa ctt gcc atg gaa gaa gct gaa agg agg aca cag act gaa         2592
Leu Glu Lys Leu Ala Met Glu Glu Ala Glu Arg Arg Thr Gln Thr Glu
    850                 855                 860 gaa cag cgg cga aga aag gaa gca agg gct gca gat gaa gct gtc agg         2640
Glu Gln Arg Arg Arg Lys Glu Ala Arg Ala Ala Asp Glu Ala Val Arg
865                 870                 875                 880 gca caa gcg aag gcc gag ata gag atc aag aag aaa aaa ttg caa agt         2688
Ala Gln Ala Lys Ala Glu Ile Glu Ile Lys Lys Lys Lys Leu Gln Ser
                885                 890                 895 atg ttg agt ttg gcc aga aca tgt gtt gat aat ttg tgg tac ata gag         2736
Met Leu Ser Leu Ala Arg Thr Cys Val Asp Asn Leu Trp Tyr Ile Glu
            900                 905                 910 gct agc aca gat aca aga gga gat act atc agg tta tat tac aac aga         2784
Ala Ser Thr Asp Thr Arg Gly Asp Thr Ile Arg Leu Tyr Tyr Asn Arg
        915                 920                 925 aac tcg agg cca ctt gcg cat agt act gag att tgg atg cat ggt ggt         2832
Asn Ser Arg Pro Leu Ala His Ser Thr Glu Ile Trp Met His Gly Gly
    930                 935                 940 tac aac aat tgg aca gat gga ctc tct att gtt gaa agc ttt gtc aag         2880
Tyr Asn Asn Trp Thr Asp Gly Leu Ser Ile Val Glu Ser Phe Val Lys
945                 950                 955                 960 tgc aat gac aaa gac ggc gat tgg tgg tat gca gat gtt att cca cct         2928
```

-continued

```
                Cys Asn Asp Lys Asp Gly Asp Trp Trp Tyr Ala Asp Val Ile Pro Pro
                            965                 970                 975 gaa aag gca ctt gtg ttg gac tgg gtt ttt gct gat ggg cca gct ggg        2976
Glu Lys Ala Leu Val Leu Asp Trp Val Phe Ala Asp Gly Pro Ala Gly
            980                 985                 990 aat gca agg aac tat gac aac aat gct cga caa gat ttc cat gct att        3024
Asn Ala Arg Asn Tyr Asp Asn Asn Ala Arg Gln Asp Phe His Ala Ile
        995                 1000                1005 ctt ccg aac aac aat gta acc gag gaa ggc ttc tgg gcg caa gag gag        3072
Leu Pro Asn Asn Asn Val Thr Glu Glu Gly Phe Trp Ala Gln Glu Glu
    1010                1015                1020 caa aac atc tat aca agg ctt ctg caa gaa agg aga gaa aag gaa gaa        3120
Gln Asn Ile Tyr Thr Arg Leu Leu Gln Glu Arg Arg Glu Lys Glu Glu
1025                1030                1035                1040 acc atg aaa aga aag gct gag aga agt gca aat atc aaa gct gag atg        3168
Thr Met Lys Arg Lys Ala Glu Arg Ser Ala Asn Ile Lys Ala Glu Met
                1045                1050                1055 aag gca aaa act atg cga agg ttt ctg ctt tcc cag aaa cac att gtt        3216
Lys Ala Lys Thr Met Arg Arg Phe Leu Leu Ser Gln Lys His Ile Val
            1060                1065                1070 tat acc gaa ccg ctt gaa ata cgt gcc gga acc aca gtg gat gtg cta        3264
Tyr Thr Glu Pro Leu Glu Ile Arg Ala Gly Thr Thr Val Asp Val Leu
        1075                1080                1085 tac aat ccc tct aac aca gtg cta aat gga aag tcg gag ggt tgg ttt        3312
Tyr Asn Pro Ser Asn Thr Val Leu Asn Gly Lys Ser Glu Gly Trp Phe
    1090                1095                1100 aga tgc tcc ttt aac ctt tgg atg cat tca agt ggg gca ttg cca ccc        3360
Arg Cys Ser Phe Asn Leu Trp Met His Ser Ser Gly Ala Leu Pro Pro
1105                1110                1115                1120 cag aag atg gtg aaa tca ggg gat ggg ccg ctc tta aaa gca aca gtt        3408
Gln Lys Met Val Lys Ser Gly Asp Gly Pro Leu Leu Lys Ala Thr Val
                1125                1130                1135 gat gtt cca ccg gat gcc tat atg atg gac ttt gtt ttc tcc gag tgg        3456
Asp Val Pro Pro Asp Ala Tyr Met Met Asp Phe Val Phe Ser Glu Trp
            1140                1145                1150 gaa gaa gat ggg atc tat gac aac agg aat ggg atg gac tat cat att        3504
Glu Glu Asp Gly Ile Tyr Asp Asn Arg Asn Gly Met Asp Tyr His Ile
        1155                1160                1165 cct gtt tct gat tca att gaa aca gag aat tac atg cgt att atc cac        3552
Pro Val Ser Asp Ser Ile Glu Thr Glu Asn Tyr Met Arg Ile Ile His
    1170                1175                1180 att gcc gtt gag atg gcc ccc gtt gca aag gtt gga ggt ctt ggg gat        3600
Ile Ala Val Glu Met Ala Pro Val Ala Lys Val Gly Gly Leu Gly Asp
1185                1190                1195                1200 gtt gtt aca agt ctt tca cgt gcc att caa gat cta gga cat act gtc        3648
Val Val Thr Ser Leu Ser Arg Ala Ile Gln Asp Leu Gly His Thr Val
                1205                1210                1215 gag gtt att ctc ccg aag tac gac tgt ttg aac caa agc agt gtc aag        3696
Glu Val Ile Leu Pro Lys Tyr Asp Cys Leu Asn Gln Ser Ser Val Lys
            1220                1225                1230 gat tta cat tta tat caa agt ttt tct tgg ggt ggt aca gaa ata aaa        3744
Asp Leu His Leu Tyr Gln Ser Phe Ser Trp Gly Gly Thr Glu Ile Lys
        1235                1240                1245 gta tgg gtt gga cga gtc gaa gac ctg acc gtt tac ttc ctg gaa cct        3792
Val Trp Val Gly Arg Val Glu Asp Leu Thr Val Tyr Phe Leu Glu Pro
    1250                1255                1260 caa aat ggg atg ttt ggc gtt gga tgt gta tat gga agg aat gat gac        3840
Gln Asn Gly Met Phe Gly Val Gly Cys Val Tyr Gly Arg Asn Asp Asp
1265                1270                1275                1280
```

-continued

| | |
|---|---|
| cgc aga ttt ggg ttc ttc tgt cat tct gct cta gag ttt atc ctc cag<br>Arg Arg Phe Gly Phe Phe Cys His Ser Ala Leu Glu Phe Ile Leu Gln<br>            1285                1290                1295 | 3888 |
| aat gaa ttt tct cca cat ata ata cat tgc cat gat tgg tca agt gct<br>Asn Glu Phe Ser Pro His Ile Ile His Cys His Asp Trp Ser Ser Ala<br>        1300                1305                1310 | 3936 |
| ccg gtc gcc tgg cta tat aag gaa cac tat tcc caa tcc aga atg gca<br>Pro Val Ala Trp Leu Tyr Lys Glu His Tyr Ser Gln Ser Arg Met Ala<br>    1315                1320                1325 | 3984 |
| agc act cgg gtt gta ttt acc atc cac aat ctt gaa ttt gga gca cat<br>Ser Thr Arg Val Val Phe Thr Ile His Asn Leu Glu Phe Gly Ala His<br>1330                1335                1340 | 4032 |
| tat att ggt aaa gca atg aca tac tgt gat aaa gcc aca act gtt tct<br>Tyr Ile Gly Lys Ala Met Thr Tyr Cys Asp Lys Ala Thr Thr Val Ser<br>1345                1350                1355                1360 | 4080 |
| cct aca tat tca agg gac gtg gca ggc cat ggc gcc att gct cct cat<br>Pro Thr Tyr Ser Arg Asp Val Ala Gly His Gly Ala Ile Ala Pro His<br>            1365                1370                1375 | 4128 |
| cgt gag aaa ttc tac ggc att ctc aat gga att gat cca gat atc tgg<br>Arg Glu Lys Phe Tyr Gly Ile Leu Asn Gly Ile Asp Pro Asp Ile Trp<br>        1380                1385                1390 | 4176 |
| gat ccg tac act gac aat ttt atc ccg gtc cct tat act tgt gag aat<br>Asp Pro Tyr Thr Asp Asn Phe Ile Pro Val Pro Tyr Thr Cys Glu Asn<br>    1395                1400                1405 | 4224 |
| gtt gtc gaa ggc aag aga gct gca aaa agg gcc ttg cag cag aag ttt<br>Val Val Glu Gly Lys Arg Ala Ala Lys Arg Ala Leu Gln Gln Lys Phe<br>1410                1415                1420 | 4272 |
| gga tta cag caa act gat gtc cct att gtc gga atc atc acc cgt ctg<br>Gly Leu Gln Gln Thr Asp Val Pro Ile Val Gly Ile Ile Thr Arg Leu<br>1425                1430                1435                1440 | 4320 |
| aca gcc cag aag gga atc cac ctc atc aag cac gca att cac cga act<br>Thr Ala Gln Lys Gly Ile His Leu Ile Lys His Ala Ile His Arg Thr<br>            1445                1450                1455 | 4368 |
| ctc gaa agc aac gga cat gtg gtt ttg ctt ggt tca gct cca gat cat<br>Leu Glu Ser Asn Gly His Val Val Leu Leu Gly Ser Ala Pro Asp His<br>        1460                1465                1470 | 4416 |
| cga ata caa ggc gat ttt tgc aga ttg gcc gat gct ctt cat ggt gtt<br>Arg Ile Gln Gly Asp Phe Cys Arg Leu Ala Asp Ala Leu His Gly Val<br>    1475                1480                1485 | 4464 |
| tac cat ggt agg gtg aag ctt gtt cta acc tat gat gag cct ctt tct<br>Tyr His Gly Arg Val Lys Leu Val Leu Thr Tyr Asp Glu Pro Leu Ser<br>1490                1495                1500 | 4512 |
| cac ctg ata tac gct ggc tcg gac ttc ata att gtt cct tca atc ttc<br>His Leu Ile Tyr Ala Gly Ser Asp Phe Ile Ile Val Pro Ser Ile Phe<br>1505                1510                1515                1520 | 4560 |
| gaa ccc tgt ggc tta aca caa ctt gtt gcc atg cgt tat gga tcg atc<br>Glu Pro Cys Gly Leu Thr Gln Leu Val Ala Met Arg Tyr Gly Ser Ile<br>            1525                1530                1535 | 4608 |
| cct ata gtt cgg aaa act gga gga ctt cac gac aca gtc ttc gac gta<br>Pro Ile Val Arg Lys Thr Gly Gly Leu His Asp Thr Val Phe Asp Val<br>        1540                1545                1550 | 4656 |
| gac aat gat aag gac cgg gct cgg tct ctt ggt ctt gaa cca aat ggg<br>Asp Asn Asp Lys Asp Arg Ala Arg Ser Leu Gly Leu Glu Pro Asn Gly<br>    1555                1560                1565 | 4704 |
| ttc agt ttc gac gga gcc gac agc aat ggc gtg gat tat gcc ctc aac<br>Phe Ser Phe Asp Gly Ala Asp Ser Asn Gly Val Asp Tyr Ala Leu Asn<br>1570                1575                1580 | 4752 |
| aga gca atc ggc gct tgg ttc gat gcc cgt gat tgg ttc cac tcc ctg<br>Arg Ala Ile Gly Ala Trp Phe Asp Ala Arg Asp Trp Phe His Ser Leu<br>1585                1590                1595                1600 | 4800 |

```
tgt aag agg gtc atg gag caa gac tgg tcg tgg aac cgg ccc gca ctg      4848
Cys Lys Arg Val Met Glu Gln Asp Trp Ser Trp Asn Arg Pro Ala Leu
            1605                1610                1615 gac tac att gaa ttg tac cat gcc gct cga aaa ttc tga                  4887
Asp Tyr Ile Glu Leu Tyr His Ala Ala Arg Lys Phe
        1620                1625
```

<210> SEQ ID NO 12
<211> LENGTH: 1628
<212> TYPE: PRT
<213> ORGANISM: Triticum aestivum

<400> SEQUENCE: 12

```
Met Glu Met Ser Leu Trp Pro Arg Ser Pro Leu Cys Pro Arg Ser Arg
 1               5                  10                  15

Gln Pro Leu Val Val Arg Pro Ala Gly Arg Gly Gly Leu Thr Gln
                20                  25                  30

Pro Phe Leu Met Asn Gly Arg Phe Thr Arg Ser Arg Thr Leu Arg Cys
            35                  40                  45

Met Val Ala Ser Ser Asp Pro Pro Asn Arg Lys Ser Arg Arg Met Val
 50                  55                  60

Pro Pro Gln Val Lys Val Ile Ser Ser Arg Gly Tyr Thr Thr Arg Leu
 65                  70                  75                  80

Ile Val Glu Pro Ser Asn Glu Asn Thr Glu His Asn Asn Arg Asp Glu
                85                  90                  95

Glu Thr Leu Asp Thr Tyr Asn Ala Leu Leu Ser Thr Glu Thr Ala Glu
            100                 105                 110

Trp Thr Asp Asn Arg Glu Ala Glu Thr Ala Lys Ala Asp Ser Ser Gln
        115                 120                 125

Asn Ala Leu Ser Ser Ser Ile Ile Gly Glu Val Asp Val Ala Asp Glu
130                 135                 140

Asp Ile Leu Ala Ala Asp Leu Thr Val Tyr Ser Leu Ser Ser Val Met
145                 150                 155                 160

Lys Lys Glu Val Asp Ala Ala Asp Lys Ala Arg Val Lys Glu Asp Ala
                165                 170                 175

Phe Glu Leu Asp Leu Pro Ala Thr Thr Leu Arg Ser Val Ile Val Asp
            180                 185                 190

Val Met Asp His Asn Gly Thr Val Gln Glu Thr Leu Arg Ser Val Ile
        195                 200                 205

Val Asp Val Met Asp His Asn Gly Thr Val Gln Glu Thr Leu Arg Ser
    210                 215                 220

Val Ile Val Asp Val Met Asp Ala Ala Asp Lys Ala Arg Val Glu
225                 230                 235                 240

Glu Asp Val Phe Glu Leu Asp Leu Ser Gly Asn Ile Ser Ser Ala
                245                 250                 255

Thr Thr Val Glu Leu Asp Ala Val Asp Glu Val Gly Pro Val Gln Asp
            260                 265                 270

Lys Phe Glu Ala Thr Ser Ser Gly Asn Val Ser Asn Ser Ala Thr Val
        275                 280                 285

Arg Glu Val Asp Ala Ser Asp Glu Ala Gly Asn Asp Gln Gly Ile Phe
    290                 295                 300

Arg Ala Asp Leu Ser Gly Asn Val Phe Ser Ser Thr Thr Val Glu
305                 310                 315                 320

Val Gly Ala Val Asp Glu Ala Gly Ser Ile Lys Asp Arg Phe Glu Thr
                325                 330                 335
```

```
Asp Ser Ser Gly Asn Val Ser Thr Ser Ala Pro Met Trp Asp Ala Ile
            340                 345                 350

Asp Glu Thr Val Ala Asp Gln Asp Thr Phe Glu Ala Asp Leu Ser Gly
            355                 360                 365

Asn Ala Ser Ser Cys Ala Thr Tyr Arg Glu Val Asp Asp Val Val Asp
            370                 375                 380

Glu Thr Arg Ser Glu Glu Thr Phe Ala Met Asp Leu Phe Ala Ser
385                 390                 395                 400

Glu Ser Gly His Glu Lys His Met Ala Val Asp Tyr Val Gly Glu Ala
            405                 410                 415

Thr Asp Glu Glu Glu Thr Tyr Gln Gln Gln Tyr Pro Val Pro Ser Ser
            420                 425                 430

Phe Ser Met Trp Asp Lys Ala Ile Ala Lys Thr Gly Val Ser Leu Asn
            435                 440                 445

Pro Glu Leu Arg Leu Val Arg Val Glu Gln Gly Lys Val Asn Phe
            450                 455                 460

Ser Asp Lys Lys Asp Leu Ser Ile Asp Asp Leu Pro Gly Gln Asn Gln
465                 470                 475                 480

Ser Ile Ile Gly Ser Tyr Lys Gln Asp Lys Ser Ile Ala Asp Val Ala
            485                 490                 495

Gly Pro Thr Gln Ser Ile Phe Gly Ser Ser Lys Gln His Arg Ser Ile
            500                 505                 510

Val Ala Phe Pro Lys Gln Asn Gln Ser Ile Val Ser Val Thr Glu Gln
            515                 520                 525

Lys Gln Ser Ile Val Gly Phe Arg Ser Gln Asp Leu Ser Ala Val Ser
            530                 535                 540

Leu Pro Lys Gln Asn Val Pro Ile Val Gly Thr Ser Arg Glu Gly Gln
545                 550                 555                 560

Thr Lys Gln Val Pro Val Val Asp Arg Gln Asp Ala Leu Tyr Val Asn
            565                 570                 575

Gly Leu Glu Ala Lys Glu Gly Asp His Thr Ser Glu Lys Thr Asp Glu
            580                 585                 590

Asp Ala Leu His Val Lys Phe Asn Val Asp Asn Val Leu Arg Lys His
            595                 600                 605

Gln Ala Asp Arg Thr Gln Ala Val Glu Lys Lys Thr Trp Lys Lys Val
            610                 615                 620

Asp Glu Glu His Leu Tyr Met Thr Glu His Gln Lys Arg Ala Ala Glu
625                 630                 635                 640

Gly Gln Met Val Val Asn Glu Asp Glu Leu Ser Ile Thr Glu Ile Gly
            645                 650                 655

Met Gly Arg Gly Asp Lys Ile Gln His Val Leu Ser Glu Glu Leu
            660                 665                 670

Ser Trp Ser Glu Asp Glu Val Gln Leu Ile Glu Asp Gly Gln Tyr
            675                 680                 685

Glu Val Asp Glu Thr Ser Val Ser Val Asn Val Glu Gln Asp Ile Gln
            690                 695                 700

Gly Ser Pro Gln Asp Val Val Asp Pro Gln Ala Leu Lys Val Met Leu
705                 710                 715                 720

Gln Glu Leu Ala Glu Lys Asn Tyr Ser Met Arg Asn Lys Leu Phe Val
            725                 730                 735

Phe Pro Glu Val Val Lys Ala Asp Ser Val Ile Asp Leu Tyr Leu Asn
            740                 745                 750
```

-continued

```
Arg Asp Leu Thr Ala Leu Ala Asn Glu Pro Asp Val Val Ile Lys Gly
    755                 760                 765

Ala Phe Asn Gly Trp Lys Trp Arg Leu Phe Thr Glu Arg Leu His Lys
    770                 775                 780

Ser Asp Leu Gly Gly Val Trp Trp Ser Cys Lys Leu Tyr Ile Pro Lys
785                 790                 795                 800

Glu Ala Tyr Arg Leu Asp Phe Val Phe Phe Asn Gly Arg Thr Val Tyr
                    805                 810                 815

Glu Asn Asn Gly Asn Asn Asp Phe Cys Ile Gly Ile Glu Gly Thr Met
                820                 825                 830

Asn Glu Asp Leu Phe Glu Asp Phe Leu Val Lys Glu Lys Gln Arg Glu
            835                 840                 845

Leu Glu Lys Leu Ala Met Glu Glu Ala Glu Arg Thr Gln Thr Glu
    850                 855                 860

Glu Gln Arg Arg Arg Lys Glu Ala Arg Ala Ala Asp Glu Ala Val Arg
865                 870                 875                 880

Ala Gln Ala Lys Ala Glu Ile Glu Ile Lys Lys Lys Leu Gln Ser
                    885                 890                 895

Met Leu Ser Leu Ala Arg Thr Cys Val Asp Asn Leu Trp Tyr Ile Glu
                900                 905                 910

Ala Ser Thr Asp Thr Arg Gly Asp Thr Ile Arg Leu Tyr Tyr Asn Arg
            915                 920                 925

Asn Ser Arg Pro Leu Ala His Ser Thr Glu Ile Trp Met His Gly Gly
        930                 935                 940

Tyr Asn Asn Trp Thr Asp Gly Leu Ser Ile Val Glu Ser Phe Val Lys
945                 950                 955                 960

Cys Asn Asp Lys Asp Gly Asp Trp Trp Tyr Ala Asp Val Ile Pro Pro
                    965                 970                 975

Glu Lys Ala Leu Val Leu Asp Trp Val Phe Ala Asp Gly Pro Ala Gly
                980                 985                 990

Asn Ala Arg Asn Tyr Asp Asn Asn Ala Arg Gln Asp Phe His Ala Ile
            995                 1000                1005

Leu Pro Asn Asn Asn Val Thr Glu Glu Gly Phe Trp Ala Gln Glu Glu
    1010                1015                1020

Gln Asn Ile Tyr Thr Arg Leu Leu Gln Glu Arg Arg Glu Lys Glu Glu
1025                1030                1035                1040

Thr Met Lys Arg Lys Ala Glu Arg Ser Ala Asn Ile Lys Ala Glu Met
                    1045                1050                1055

Lys Ala Lys Thr Met Arg Arg Phe Leu Leu Ser Gln Lys His Ile Val
                1060                1065                1070

Tyr Thr Glu Pro Leu Glu Ile Arg Ala Gly Thr Thr Val Asp Val Leu
            1075                1080                1085

Tyr Asn Pro Ser Asn Thr Val Leu Asn Gly Lys Ser Glu Gly Trp Phe
        1090                1095                1100

Arg Cys Ser Phe Asn Leu Trp Met His Ser Ser Gly Ala Leu Pro Pro
1105                1110                1115                1120

Gln Lys Met Val Lys Ser Gly Asp Gly Pro Leu Leu Lys Ala Thr Val
                    1125                1130                1135

Asp Val Pro Pro Asp Ala Tyr Met Met Asp Phe Val Phe Ser Glu Trp
                1140                1145                1150

Glu Glu Asp Gly Ile Tyr Asp Asn Arg Asn Gly Met Asp Tyr His Ile
            1155                1160                1165

Pro Val Ser Asp Ser Ile Glu Thr Glu Asn Tyr Met Arg Ile Ile His
```

-continued

```
                1170                1175                1180
Ile Ala Val Glu Met Ala Pro Val Ala Lys Val Gly Gly Leu Gly Asp
1185                1190                1195                1200

Val Val Thr Ser Leu Ser Arg Ala Ile Gln Asp Leu Gly His Thr Val
                1205                1210                1215

Glu Val Ile Leu Pro Lys Tyr Asp Cys Leu Asn Gln Ser Ser Val Lys
                1220                1225                1230

Asp Leu His Leu Tyr Gln Ser Phe Ser Trp Gly Gly Thr Glu Ile Lys
            1235                1240                1245

Val Trp Val Gly Arg Val Glu Asp Leu Thr Val Tyr Phe Leu Glu Pro
1250                1255                1260

Gln Asn Gly Met Phe Gly Val Gly Cys Val Tyr Gly Arg Asn Asp Asp
1265                1270                1275                1280

Arg Arg Phe Gly Phe Phe Cys His Ser Ala Leu Glu Phe Ile Leu Gln
            1285                1290                1295

Asn Glu Phe Ser Pro His Ile Ile His Cys His Asp Trp Ser Ser Ala
                1300                1305                1310

Pro Val Ala Trp Leu Tyr Lys Glu His Tyr Ser Gln Ser Arg Met Ala
            1315                1320                1325

Ser Thr Arg Val Val Phe Thr Ile His Asn Leu Glu Phe Gly Ala His
            1330                1335                1340

Tyr Ile Gly Lys Ala Met Thr Tyr Cys Asp Lys Ala Thr Thr Val Ser
1345                1350                1355                1360

Pro Thr Tyr Ser Arg Asp Val Ala Gly His Gly Ala Ile Ala Pro His
            1365                1370                1375

Arg Glu Lys Phe Tyr Gly Ile Leu Asn Gly Ile Asp Pro Asp Ile Trp
            1380                1385                1390

Asp Pro Tyr Thr Asp Asn Phe Ile Pro Val Pro Tyr Thr Cys Glu Asn
            1395                1400                1405

Val Val Glu Gly Lys Arg Ala Ala Lys Arg Ala Leu Gln Gln Lys Phe
            1410                1415                1420

Gly Leu Gln Gln Thr Asp Val Pro Ile Val Gly Ile Ile Thr Arg Leu
1425                1430                1435                1440

Thr Ala Gln Lys Gly Ile His Leu Ile Lys His Ala Ile His Arg Thr
            1445                1450                1455

Leu Glu Ser Asn Gly His Val Val Leu Leu Gly Ser Ala Pro Asp His
            1460                1465                1470

Arg Ile Gln Gly Asp Phe Cys Arg Leu Ala Asp Ala Leu His Gly Val
            1475                1480                1485

Tyr His Gly Arg Val Lys Leu Val Leu Thr Tyr Asp Glu Pro Leu Ser
            1490                1495                1500

His Leu Ile Tyr Ala Gly Ser Asp Phe Ile Ile Val Pro Ser Ile Phe
1505                1510                1515                1520

Glu Pro Cys Gly Leu Thr Gln Leu Val Ala Met Arg Tyr Gly Ser Ile
                1525                1530                1535

Pro Ile Val Arg Lys Thr Gly Gly Leu His Asp Thr Val Phe Asp Val
            1540                1545                1550

Asp Asn Asp Lys Asp Arg Ala Arg Ser Leu Gly Leu Glu Pro Asn Gly
            1555                1560                1565

Phe Ser Phe Asp Gly Ala Asp Ser Asn Gly Val Asp Tyr Ala Leu Asn
            1570                1575                1580

Arg Ala Ile Gly Ala Trp Phe Asp Ala Arg Asp Trp Phe His Ser Leu
1585                1590                1595                1600
```

```
Cys Lys Arg Val Met Glu Gln Asp Trp Ser Trp Asn Arg Pro Ala Leu
            1605                1610                1615

Asp Tyr Ile Glu Leu Tyr His Ala Ala Arg Lys Phe
        1620                1625

<210> SEQ ID NO 13
<211> LENGTH: 4836
<212> TYPE: DNA
<213> ORGANISM: Aegilops tauschii
<220> FEATURE:
<221> NAME/KEY: CDS
<222> LOCATION: (1)..(4833)
<223> OTHER INFORMATION: coding for SSS3 from Aegilops tauschii

<400> SEQUENCE: 13 atg gag atg gct ctc cgg cca cgg agc cct ctg tgc cct cgg agc agt        48
Met Glu Met Ala Leu Arg Pro Arg Ser Pro Leu Cys Pro Arg Ser Ser
 1               5                  10                  15 cag ccg ctc gtc gtc gtc cgg ccg gcc ggc cgc ggc ggc ggc ctc gcg        96
Gln Pro Leu Val Val Val Arg Pro Ala Gly Arg Gly Gly Gly Leu Ala
            20                  25                  30 cag cct ttt ttg atg aat ggc aga ttt act cga agc agg acc ctt cga       144
Gln Pro Phe Leu Met Asn Gly Arg Phe Thr Arg Ser Arg Thr Leu Arg
        35                  40                  45 tgc atg gta gca agt tca gat cct cct aat agg aaa tca aga aag atg       192
Cys Met Val Ala Ser Ser Asp Pro Pro Asn Arg Lys Ser Arg Lys Met
 50                  55                  60 gta tca cct cag gtt aaa gtc att tct tct aga gga tat acg aca aga       240
Val Ser Pro Gln Val Lys Val Ile Ser Ser Arg Gly Tyr Thr Thr Arg
 65                  70                  75                  80 ctc att gtt gaa cca agc acc gag aat ata gaa cac aat aat cgg gat       288
Leu Ile Val Glu Pro Ser Thr Glu Asn Ile Glu His Asn Asn Arg Asp
                85                  90                  95 gaa gaa act ctt gat aca tac aat gcg cta tta agt acc gag aca gca       336
Glu Glu Thr Leu Asp Thr Tyr Asn Ala Leu Leu Ser Thr Glu Thr Ala
            100                 105                 110 gaa tgg aca gat act aga gaa gcc gag act gct aaa gcg gac tcg tcg       384
Glu Trp Thr Asp Thr Arg Glu Ala Glu Thr Ala Lys Ala Asp Ser Ser
        115                 120                 125 caa aat gct tta agc agt tct ata atc ggg gga gtg gat gtg gcg gat       432
Gln Asn Ala Leu Ser Ser Ser Ile Ile Gly Gly Val Asp Val Ala Asp
    130                 135                 140 gaa gat ata ctt gcg gct gat ctg aca gtg aat tca tta agc agt ata       480
Glu Asp Ile Leu Ala Ala Asp Leu Thr Val Asn Ser Leu Ser Ser Ile
145                 150                 155                 160 acg aag aag gaa gtg gat gca gtg gac aaa gct aga gtt aaa gaa gac       528
Thr Lys Lys Glu Val Asp Ala Val Asp Lys Ala Arg Val Lys Glu Asp
                165                 170                 175 gta ttt gag ctg gat ttg cca gca act aca ttg aga agt gta ata gtg       576
Val Phe Glu Leu Asp Leu Pro Ala Thr Thr Leu Arg Ser Val Ile Val
            180                 185                 190 gat gtg atg gat cat aat ggg act gta caa gag aca ttg aga agt gtg       624
Asp Val Met Asp His Asn Gly Thr Val Gln Glu Thr Leu Arg Ser Val
        195                 200                 205 ata gta gat gtg atg gat gat gcg gcg gac aaa gct aga gtt gaa gaa       672
Ile Val Asp Val Met Asp Asp Ala Ala Asp Lys Ala Arg Val Glu Glu
    210                 215                 220 gac gta ttt gag ctg gat ttg tca gga aat att tca agc agt gcg acg       720
Asp Val Phe Glu Leu Asp Leu Ser Gly Asn Ile Ser Ser Ser Ala Thr
225                 230                 235                 240
```

```
acc gtg gaa cta gat gcg gtt gac gaa gtc ggg cct gtt caa gac aca        768
Thr Val Glu Leu Asp Ala Val Asp Glu Val Gly Pro Val Gln Asp Thr
            245                 250                 255 ttt gag gcg aac tcg tca gga aat gtt tca aac agt gca acg gta cgg        816
Phe Glu Ala Asn Ser Ser Gly Asn Val Ser Asn Ser Ala Thr Val Arg
        260                 265                 270 gaa gtg gat acg agt gct gaa gct ggg aat gat caa ggc ata ttt aga        864
Glu Val Asp Thr Ser Ala Glu Ala Gly Asn Asp Gln Gly Ile Phe Arg
    275                 280                 285 gca gat ttg tca gga aat gtt ttt tca agc agt aca aca gtg gaa gtg        912
Ala Asp Leu Ser Gly Asn Val Phe Ser Ser Ser Thr Thr Val Glu Val
290                 295                 300 ggt gca gtg gat gaa gct ggg tct ata aaa gac agg ttt gag acg gat        960
Gly Ala Val Asp Glu Ala Gly Ser Ile Lys Asp Arg Phe Glu Thr Asp
305                 310                 315                 320 tcg tca gga aat gtt tca aca agt gcg acg atg tgg gat gca att gat       1008
Ser Ser Gly Asn Val Ser Thr Ser Ala Thr Met Trp Asp Ala Ile Asp
            325                 330                 335 gaa acc gtg gct gat caa gac gca gtt gag gcg gat ttg tcg gga aat       1056
Glu Thr Val Ala Asp Gln Asp Ala Val Glu Ala Asp Leu Ser Gly Asn
        340                 345                 350 gct tca agc tgc gcg aca tac aga gaa gtg gat gat gtg gtg gat gaa       1104
Ala Ser Ser Cys Ala Thr Tyr Arg Glu Val Asp Asp Val Val Asp Glu
    355                 360                 365 act aga tca gaa gag gaa aca ttt gcg atg gat ttg ttt gca agt gaa       1152
Thr Arg Ser Glu Glu Glu Thr Phe Ala Met Asp Leu Phe Ala Ser Glu
370                 375                 380 tca ggc cat gag aaa cat atg gca gtg gat cat gtg ggt gaa gct acc       1200
Ser Gly His Glu Lys His Met Ala Val Asp His Val Gly Glu Ala Thr
385                 390                 395                 400 gat gaa gaa gag act tac caa cag caa tat cca gta ccg tct tca ttc       1248
Asp Glu Glu Glu Thr Tyr Gln Gln Gln Tyr Pro Val Pro Ser Ser Phe
            405                 410                 415 tct atg tgg gac aag gct att gct aaa aca ggt gta agt ttg aat cct       1296
Ser Met Trp Asp Lys Ala Ile Ala Lys Thr Gly Val Ser Leu Asn Pro
        420                 425                 430 gag ctg cga ctt gtc agg gtt gaa gaa caa ggc aaa gta aat ttt agt       1344
Glu Leu Arg Leu Val Arg Val Glu Glu Gln Gly Lys Val Asn Phe Ser
    435                 440                 445 gat aaa aaa gac ctg tca att gat gat tta cca gga caa aac caa tcg       1392
Asp Lys Lys Asp Leu Ser Ile Asp Asp Leu Pro Gly Gln Asn Gln Ser
450                 455                 460 atc att ggt tcc tat aaa caa gat aaa tca att gct gat gtt gcg gga       1440
Ile Ile Gly Ser Tyr Lys Gln Asp Lys Ser Ile Ala Asp Val Ala Gly
465                 470                 475                 480 ccg acc caa tca att ttt ggt tct agt aaa caa cac cgg tca att gtt       1488
Pro Thr Gln Ser Ile Phe Gly Ser Ser Lys Gln His Arg Ser Ile Val
            485                 490                 495 gct ttc ccc aaa caa aac cag tca att gtt agt gtc act gag caa aag       1536
Ala Phe Pro Lys Gln Asn Gln Ser Ile Val Ser Val Thr Glu Gln Lys
        500                 505                 510 cag tcc ata gtt gga ttc cgt agt caa gat ctt tcg gct gtt agt ctc       1584
Gln Ser Ile Val Gly Phe Arg Ser Gln Asp Leu Ser Ala Val Ser Leu
    515                 520                 525 cct aaa caa aac gta cca att gtt ggt acg tcg aga gag ggt caa aca       1632
Pro Lys Gln Asn Val Pro Ile Val Gly Thr Ser Arg Glu Gly Gln Thr
530                 535                 540 aag caa gtt cct gtt gtt gat aga cag gat gcg ttg tat gtg aat gga       1680
Lys Gln Val Pro Val Val Asp Arg Gln Asp Ala Leu Tyr Val Asn Gly
545                 550                 555                 560
```

-continued

```
ctg gaa gct aag gag gga gat cac aca tcc gag aaa acc gat gag gat    1728
Leu Glu Ala Lys Glu Gly Asp His Thr Ser Glu Lys Thr Asp Glu Asp
                565                 570                 575 gtg ctt cat gta aaa ttt aat gtt gac aat gtg ttg cgg aag cat cag    1776
Val Leu His Val Lys Phe Asn Val Asp Asn Val Leu Arg Lys His Gln
            580                 585                 590 gca gat aga acc caa gca gtg gaa acg ata act tgg aag aaa gtt gat    1824
Ala Asp Arg Thr Gln Ala Val Glu Thr Ile Thr Trp Lys Lys Val Asp
        595                 600                 605 gag gaa cat ctt tac atg act gaa cat cag ata ggt gct gcc gaa gga    1872
Glu Glu His Leu Tyr Met Thr Glu His Gln Ile Gly Ala Ala Glu Gly
    610                 615                 620 cag atg gta gtt aac gag gat gag ctt tct ata act gaa att gga atg    1920
Gln Met Val Val Asn Glu Asp Glu Leu Ser Ile Thr Glu Ile Gly Met
625                 630                 635                 640 ggg aga ggt gat aaa att cag cat gtg ctt tct gag gaa gag ctt tca    1968
Gly Arg Gly Asp Lys Ile Gln His Val Leu Ser Glu Glu Glu Leu Ser
                645                 650                 655 tgg tct gaa gat gaa gtg cag tta att gag gat gat gga caa tat gaa    2016
Trp Ser Glu Asp Glu Val Gln Leu Ile Glu Asp Asp Gly Gln Tyr Glu
            660                 665                 670 gtt gat gag acc tct gtg tcc gtt aac gtt gaa caa gat atc cag ggg    2064
Val Asp Glu Thr Ser Val Ser Val Asn Val Glu Gln Asp Ile Gln Gly
        675                 680                 685 tca cca cag gat gtt gtg gat ccg caa gca cta aag gtg atg ctg caa    2112
Ser Pro Gln Asp Val Val Asp Pro Gln Ala Leu Lys Val Met Leu Gln
    690                 695                 700 gaa ctc gct gag aaa aat tat tcg atg agg aac aag ctg ttt gtt ttt    2160
Glu Leu Ala Glu Lys Asn Tyr Ser Met Arg Asn Lys Leu Phe Val Phe
705                 710                 715                 720 cca gag gta gtg aaa gct gat tca gtt att gat ctt tat ttc aat cgt    2208
Pro Glu Val Val Lys Ala Asp Ser Val Ile Asp Leu Tyr Phe Asn Arg
                725                 730                 735 gac cta aca gct ttg gcg aat gaa ccc gat gtt gtc atc aaa gga gca    2256
Asp Leu Thr Ala Leu Ala Asn Glu Pro Asp Val Val Ile Lys Gly Ala
            740                 745                 750 ttc aat ggt tgg aaa tgg agg ctt ttc act gaa aga ttg cat aag agt    2304
Phe Asn Gly Trp Lys Trp Arg Leu Phe Thr Glu Arg Leu His Lys Ser
        755                 760                 765 gac ctt gga ggg gtt tgg tgg tct tgc aaa ctg tac ata ccc aag gag    2352
Asp Leu Gly Gly Val Trp Trp Ser Cys Lys Leu Tyr Ile Pro Lys Glu
    770                 775                 780 gcc tac aga tta gac ttt gtg ttc ttc aac ggt cgc acg gtc tat gag    2400
Ala Tyr Arg Leu Asp Phe Val Phe Phe Asn Gly Arg Thr Val Tyr Glu
785                 790                 795                 800 aac aat ggc aac aat gat ttc tgt ata gga ata gaa ggc act atg aat    2448
Asn Asn Gly Asn Asn Asp Phe Cys Ile Gly Ile Glu Gly Thr Met Asn
                805                 810                 815 gaa gat ctg ttt gag gat ttc ttg gtt aaa gaa aag caa agg gag ctt    2496
Glu Asp Leu Phe Glu Asp Phe Leu Val Lys Glu Lys Gln Arg Glu Leu
            820                 825                 830 gag aaa ctt gcc atg gaa gaa gct gaa agg agg aca cag act gaa gaa    2544
Glu Lys Leu Ala Met Glu Glu Ala Glu Arg Arg Thr Gln Thr Glu Glu
        835                 840                 845 cag cgg cga agt aag gaa gca agg gct gca gat gaa gct gtc agg gca    2592
Gln Arg Arg Ser Lys Glu Ala Arg Ala Ala Asp Glu Ala Val Arg Ala
    850                 855                 860 caa gcg aag gcc gag ata gag atc aag aac aaa aaa ttg cag agt atg    2640
Gln Ala Lys Ala Glu Ile Glu Ile Lys Asn Lys Lys Leu Gln Ser Met
```

-continued

```
            865                 870                 875                 880
ttg agt ttg gcc aga aca tgt gtt gat aat ttg tgg tac ata gag gct        2688
Leu Ser Leu Ala Arg Thr Cys Val Asp Asn Leu Trp Tyr Ile Glu Ala
                        885                 890                 895 agc aca gat aca agc gga gat act atc agg tta tac tat aac aga aac        2736
Ser Thr Asp Thr Ser Gly Asp Thr Ile Arg Leu Tyr Tyr Asn Arg Asn
                900                 905                 910 tcg agg cca ctt gcg cat agt act gag att tgg atg cat ggt ggt tac        2784
Ser Arg Pro Leu Ala His Ser Thr Glu Ile Trp Met His Gly Gly Tyr
            915                 920                 925 aac aat tgg tca gat gga ctc tct att gtt gaa agc ttt gtc aag tgc        2832
Asn Asn Trp Ser Asp Gly Leu Ser Ile Val Glu Ser Phe Val Lys Cys
        930                 935                 940 aat gac aga gac ggc gat tgg tgg tat gca gat gtt att cca cct gaa        2880
Asn Asp Arg Asp Gly Asp Trp Trp Tyr Ala Asp Val Ile Pro Pro Glu
945                 950                 955                 960 aaa gca ctt gtg ttg gac tgg gtt ttt gct gat ggg cca gct ggg aat        2928
Lys Ala Leu Val Leu Asp Trp Val Phe Ala Asp Gly Pro Ala Gly Asn
                965                 970                 975 gca agg aac tat gac aac aat gct cga caa gat ttc cat gct att ctt        2976
Ala Arg Asn Tyr Asp Asn Asn Ala Arg Gln Asp Phe His Ala Ile Leu
            980                 985                 990 cca aac aac aat gta acc gag gaa ggc ttc tgg gtg caa gag gag caa        3024
Pro Asn Asn Asn Val Thr Glu Glu Gly Phe Trp Val Gln Glu Glu Gln
        995                 1000                1005 aac atc tat aca agg ctt ctg caa gaa agg aga gaa aag gaa gaa acc        3072
Asn Ile Tyr Thr Arg Leu Leu Gln Glu Arg Arg Glu Lys Glu Glu Thr
    1010                1015                1020 atg aaa aga aag gct gag aga agt gca aat atc aaa gct gag atg aag        3120
Met Lys Arg Lys Ala Glu Arg Ser Ala Asn Ile Lys Ala Glu Met Lys
1025                1030                1035                1040 gca aaa act atg cga agg ttt ctg ctt tcc cag aaa cac att gtt tat        3168
Ala Lys Thr Met Arg Arg Phe Leu Leu Ser Gln Lys His Ile Val Tyr
                1045                1050                1055 acc gaa ccg ctt gaa ata cgt gcc gga acc aca gtg gat gtg cta tac        3216
Thr Glu Pro Leu Glu Ile Arg Ala Gly Thr Thr Val Asp Val Leu Tyr
            1060                1065                1070 aat ccc tct aac aca gtg cta aat gga aag ccg gag gtt tgg ttt aga        3264
Asn Pro Ser Asn Thr Val Leu Asn Gly Lys Pro Glu Val Trp Phe Arg
        1075                1080                1085 tgc tct ttt aac ctt tgg atg cat cca agt gga gca ttg cca ccc cag        3312
Cys Ser Phe Asn Leu Trp Met His Pro Ser Gly Ala Leu Pro Pro Gln
    1090                1095                1100 aag atg gtg aaa tca ggg gat ggg ccg ctc tta aaa gcc aca gtt aat        3360
Lys Met Val Lys Ser Gly Asp Gly Pro Leu Leu Lys Ala Thr Val Asn
1105                1110                1115                1120 gtt cca ccg gat gcc tat atg atg gac ttt gtt ttc tcc gag tgg gaa        3408
Val Pro Pro Asp Ala Tyr Met Met Asp Phe Val Phe Ser Glu Trp Glu
                1125                1130                1135 gaa gat ggg atc tat gac aac agg aat ggg atg gac tat cat att cct        3456
Glu Asp Gly Ile Tyr Asp Asn Arg Asn Gly Met Asp Tyr His Ile Pro
            1140                1145                1150 gtt tct gat tca att gaa aca gag aat tac atg cgt att atc cac att        3504
Val Ser Asp Ser Ile Glu Thr Glu Asn Tyr Met Arg Ile Ile His Ile
        1155                1160                1165 gcc gtt gag atg gcc ccc gtt gca aag gtt gga ggt ctc ggg gat gtt        3552
Ala Val Glu Met Ala Pro Val Ala Lys Val Gly Gly Leu Gly Asp Val
    1170                1175                1180 gtt aca agt ctt tca cgt gcc gtt caa gat cta ggg cat act gtc gag        3600
Val Thr Ser Leu Ser Arg Ala Val Gln Asp Leu Gly His Thr Val Glu
```

```
Val Thr Ser Leu Ser Arg Ala Val Gln Asp Leu Gly His Thr Val Glu
1185                1190                1195                1200 gtt att ctc ccg aag tac gac tgt ttg aac caa agc agt gtc aag gat        3648
Val Ile Leu Pro Lys Tyr Asp Cys Leu Asn Gln Ser Ser Val Lys Asp
            1205                1210                1215 tta cat tta tat caa agt ttt tct tgg ggt ggt aca gaa ata aaa gta        3696
Leu His Leu Tyr Gln Ser Phe Ser Trp Gly Gly Thr Glu Ile Lys Val
        1220                1225                1230 tgg gtt gga cga gtc gaa gac ctg acc gtt tac ttc ctg gaa cct caa        3744
Trp Val Gly Arg Val Glu Asp Leu Thr Val Tyr Phe Leu Glu Pro Gln
    1235                1240                1245 aat ggg atg ttt ggc gtc gga tgt gta tat gga agg aat gat gac cgc        3792
Asn Gly Met Phe Gly Val Gly Cys Val Tyr Gly Arg Asn Asp Asp Arg
1250                1255                1260 aga ttt ggg ttc ttc tgt cat tct gct ctt gag ttt atc ctc cag aat        3840
Arg Phe Gly Phe Phe Cys His Ser Ala Leu Glu Phe Ile Leu Gln Asn
1265                1270                1275                1280 gaa ttt tct cca cat ata ata cat tgc cat gat tgg tca agt gct ccg        3888
Glu Phe Ser Pro His Ile Ile His Cys His Asp Trp Ser Ser Ala Pro
            1285                1290                1295 gtc gcc tgg cta tat aag gaa cac tat tcc caa tcc aga atg gca agc        3936
Val Ala Trp Leu Tyr Lys Glu His Tyr Ser Gln Ser Arg Met Ala Ser
        1300                1305                1310 act cgg gtt gta ttt acc atc cac aat ctt gaa ttt gga gca cat tat        3984
Thr Arg Val Val Phe Thr Ile His Asn Leu Glu Phe Gly Ala His Tyr
    1315                1320                1325 att ggt aaa gca atg aca tac tgt gat aaa gcc aca act gtt tct cct        4032
Ile Gly Lys Ala Met Thr Tyr Cys Asp Lys Ala Thr Thr Val Ser Pro
1330                1335                1340 aca tat tca agg gac gtg gca ggc cat ggt gcc att gct cct cat cgt        4080
Thr Tyr Ser Arg Asp Val Ala Gly His Gly Ala Ile Ala Pro His Arg
1345                1350                1355                1360 gag aaa ttc tac ggc att ctc aat gga att gat cca gat atc tgg gat        4128
Glu Lys Phe Tyr Gly Ile Leu Asn Gly Ile Asp Pro Asp Ile Trp Asp
            1365                1370                1375 cca tac act gac aat ttt atc ccg gtc cct tat act tgt gag aat gtt        4176
Pro Tyr Thr Asp Asn Phe Ile Pro Val Pro Tyr Thr Cys Glu Asn Val
        1380                1385                1390 gtc gaa ggc aag aga gct gca aaa agg gcc ttg cag cag aag ttt gga        4224
Val Glu Gly Lys Arg Ala Ala Lys Arg Ala Leu Gln Gln Lys Phe Gly
    1395                1400                1405 tta cag caa act gat gtc cct att gtc gga atc atc acc cgt ctg aca        4272
Leu Gln Gln Thr Asp Val Pro Ile Val Gly Ile Ile Thr Arg Leu Thr
1410                1415                1420 gcc cag aag gga atc cac ctc atc aag cac gca att cac cga acc ctc        4320
Ala Gln Lys Gly Ile His Leu Ile Lys His Ala Ile His Arg Thr Leu
1425                1430                1435                1440 gaa agc aac gga cag gtg gtt ttg ctt ggt tca gct cca gat cat cga        4368
Glu Ser Asn Gly Gln Val Val Leu Leu Gly Ser Ala Pro Asp His Arg
            1445                1450                1455 ata caa ggc gat ttt tgc aga ttg gcc gat gct ctt cac ggt gtt tac        4416
Ile Gln Gly Asp Phe Cys Arg Leu Ala Asp Ala Leu His Gly Val Tyr
        1460                1465                1470 cac ggt agg gtg aag ctt gtt cta acc tac gat gag cct ctt tct cac        4464
His Gly Arg Val Lys Leu Val Leu Thr Tyr Asp Glu Pro Leu Ser His
    1475                1480                1485 ctg ata tac gct ggc tcc gac ttc att att gtc cct tca atc ttc gaa        4512
Leu Ile Tyr Ala Gly Ser Asp Phe Ile Ile Val Pro Ser Ile Phe Glu
1490                1495                1500
```

```
ccc tgt ggc tta aca caa ctt gtt gcc atg cgt tat gga tcg atc cct    4560
Pro Cys Gly Leu Thr Gln Leu Val Ala Met Arg Tyr Gly Ser Ile Pro
1505                1510                1515                1520 ata gtt cgg aaa acc gga gga ctt tac gac act gtc ttc gac gta gac    4608
Ile Val Arg Lys Thr Gly Gly Leu Tyr Asp Thr Val Phe Asp Val Asp
                1525                1530                1535 aat gat aag gac cgg gct cgg tct ctt ggt ctt gaa cca aat ggg ttc    4656
Asn Asp Lys Asp Arg Ala Arg Ser Leu Gly Leu Glu Pro Asn Gly Phe
            1540                1545                1550 agt ttc gac gga gcc gac agc aac ggc gtg gat tat gcc ctc aac aga    4704
Ser Phe Asp Gly Ala Asp Ser Asn Gly Val Asp Tyr Ala Leu Asn Arg
        1555                1560                1565 gca atc ggc gct tgg ttc gat gcc cgt gat tgg ttc cac tcc ctg tgt    4752
Ala Ile Gly Ala Trp Phe Asp Ala Arg Asp Trp Phe His Ser Leu Cys
    1570                1575                1580 aag agg gtc atg gaa caa gac tgg tca tgg aac cgg ccc gca ctg gac    4800
Lys Arg Val Met Glu Gln Asp Trp Ser Trp Asn Arg Pro Ala Leu Asp
1585                1590                1595                1600 tac att gaa ttg tac cat gcc gct cga aaa ttc tga                    4836
Tyr Ile Glu Leu Tyr His Ala Ala Arg Lys Phe
                1605                1610

<210> SEQ ID NO 14
<211> LENGTH: 1611
<212> TYPE: PRT
<213> ORGANISM: Aegilops tauschii

<400> SEQUENCE: 14

Met Glu Met Ala Leu Arg Pro Arg Ser Pro Leu Cys Pro Arg Ser Ser
 1               5                  10                  15

Gln Pro Leu Val Val Arg Pro Ala Gly Arg Gly Gly Gly Leu Ala
            20                  25                  30

Gln Pro Phe Leu Met Asn Gly Arg Phe Thr Arg Ser Arg Thr Leu Arg
        35                  40                  45

Cys Met Val Ala Ser Ser Asp Pro Pro Asn Arg Lys Ser Arg Lys Met
    50                  55                  60

Val Ser Pro Gln Val Lys Val Ile Ser Ser Arg Gly Tyr Thr Thr Arg
65                  70                  75                  80

Leu Ile Val Glu Pro Ser Thr Glu Asn Ile Glu His Asn Asn Arg Asp
                85                  90                  95

Glu Glu Thr Leu Asp Thr Tyr Asn Ala Leu Leu Ser Thr Glu Thr Ala
            100                 105                 110

Glu Trp Thr Asp Thr Arg Glu Ala Glu Thr Ala Lys Ala Asp Ser Ser
        115                 120                 125

Gln Asn Ala Leu Ser Ser Ile Ile Gly Gly Val Asp Val Ala Asp
    130                 135                 140

Glu Asp Ile Leu Ala Ala Asp Leu Thr Val Asn Ser Leu Ser Ser Ile
145                 150                 155                 160

Thr Lys Lys Glu Val Asp Ala Val Asp Lys Ala Arg Val Lys Glu Asp
                165                 170                 175

Val Phe Glu Leu Asp Leu Pro Ala Thr Thr Leu Arg Ser Val Ile Val
            180                 185                 190

Asp Val Met Asp His Asn Gly Thr Val Gln Glu Thr Leu Arg Ser Val
        195                 200                 205

Ile Val Asp Val Met Asp Ala Ala Asp Lys Ala Arg Val Glu Glu
    210                 215                 220

Asp Val Phe Glu Leu Asp Leu Ser Gly Asn Ile Ser Ser Ser Ala Thr
```

```
            225                 230                 235                 240
Thr Val Glu Leu Asp Ala Val Asp Glu Val Gly Pro Val Gln Asp Thr
                245                 250                 255
Phe Glu Ala Asn Ser Ser Gly Asn Val Ser Asn Ser Ala Thr Val Arg
            260                 265                 270
Glu Val Asp Thr Ser Ala Glu Ala Gly Asn Asp Gln Gly Ile Phe Arg
        275                 280                 285
Ala Asp Leu Ser Gly Asn Val Phe Ser Ser Thr Thr Val Glu Val
    290                 295                 300
Gly Ala Val Asp Glu Ala Gly Ser Ile Lys Asp Arg Phe Glu Thr Asp
305                 310                 315                 320
Ser Ser Gly Asn Val Ser Thr Ser Ala Thr Met Trp Asp Ala Ile Asp
                325                 330                 335
Glu Thr Val Ala Asp Gln Asp Ala Val Glu Ala Asp Leu Ser Gly Asn
            340                 345                 350
Ala Ser Ser Cys Ala Thr Tyr Arg Glu Val Asp Val Val Asp Glu
        355                 360                 365
Thr Arg Ser Glu Glu Glu Thr Phe Ala Met Asp Leu Phe Ala Ser Glu
    370                 375                 380
Ser Gly His Glu Lys His Met Ala Val Asp His Val Gly Glu Ala Thr
385                 390                 395                 400
Asp Glu Glu Glu Thr Tyr Gln Gln Gln Tyr Pro Val Pro Ser Ser Phe
                405                 410                 415
Ser Met Trp Asp Lys Ala Ile Ala Lys Thr Gly Val Ser Leu Asn Pro
            420                 425                 430
Glu Leu Arg Leu Val Arg Val Glu Glu Gln Gly Lys Val Asn Phe Ser
        435                 440                 445
Asp Lys Lys Asp Leu Ser Ile Asp Asp Leu Pro Gly Gln Asn Gln Ser
    450                 455                 460
Ile Ile Gly Ser Tyr Lys Gln Asp Lys Ser Ile Ala Asp Val Ala Gly
465                 470                 475                 480
Pro Thr Gln Ser Ile Phe Gly Ser Ser Lys Gln His Arg Ser Ile Val
                485                 490                 495
Ala Phe Pro Lys Gln Asn Gln Ser Ile Val Ser Val Thr Glu Gln Lys
            500                 505                 510
Gln Ser Ile Val Gly Phe Arg Ser Gln Asp Leu Ser Ala Val Ser Leu
        515                 520                 525
Pro Lys Gln Asn Val Pro Ile Val Gly Thr Ser Arg Glu Gly Gln Thr
    530                 535                 540
Lys Gln Val Pro Val Val Asp Arg Gln Asp Ala Leu Tyr Val Asn Gly
545                 550                 555                 560
Leu Glu Ala Lys Glu Gly Asp His Thr Ser Glu Lys Thr Asp Glu Asp
                565                 570                 575
Val Leu His Val Lys Phe Asn Val Asp Asn Val Leu Arg Lys His Gln
            580                 585                 590
Ala Asp Arg Thr Gln Ala Val Glu Thr Ile Thr Trp Lys Lys Val Asp
        595                 600                 605
Glu Glu His Leu Tyr Met Thr Glu His Gln Ile Gly Ala Ala Glu Gly
    610                 615                 620
Gln Met Val Val Asn Glu Asp Glu Leu Ser Ile Thr Glu Ile Gly Met
625                 630                 635                 640
Gly Arg Gly Asp Lys Ile Gln His Val Leu Ser Glu Glu Glu Leu Ser
                645                 650                 655
```

```
Trp Ser Glu Asp Glu Val Gln Leu Ile Glu Asp Asp Gly Gln Tyr Glu
            660                 665                 670

Val Asp Glu Thr Ser Val Ser Val Asn Val Glu Gln Asp Ile Gln Gly
            675                 680                 685

Ser Pro Gln Asp Val Val Asp Pro Gln Ala Leu Lys Val Met Leu Gln
            690                 695                 700

Glu Leu Ala Glu Lys Asn Tyr Ser Met Arg Asn Lys Leu Phe Val Phe
705                 710                 715                 720

Pro Glu Val Val Lys Ala Asp Ser Val Ile Asp Leu Tyr Phe Asn Arg
                725                 730                 735

Asp Leu Thr Ala Leu Ala Asn Glu Pro Asp Val Val Ile Lys Gly Ala
            740                 745                 750

Phe Asn Gly Trp Lys Trp Arg Leu Phe Thr Glu Arg Leu His Lys Ser
            755                 760                 765

Asp Leu Gly Gly Val Trp Trp Ser Cys Lys Leu Tyr Ile Pro Lys Glu
            770                 775                 780

Ala Tyr Arg Leu Asp Phe Val Phe Phe Asn Gly Arg Thr Val Tyr Glu
785                 790                 795                 800

Asn Asn Gly Asn Asn Asp Phe Cys Ile Gly Ile Glu Gly Thr Met Asn
                805                 810                 815

Glu Asp Leu Phe Glu Asp Phe Leu Val Lys Glu Lys Gln Arg Glu Leu
            820                 825                 830

Glu Lys Leu Ala Met Glu Glu Ala Glu Arg Arg Thr Gln Thr Glu Glu
            835                 840                 845

Gln Arg Arg Ser Lys Glu Ala Arg Ala Ala Asp Glu Ala Val Arg Ala
            850                 855                 860

Gln Ala Lys Ala Glu Ile Glu Ile Lys Asn Lys Lys Leu Gln Ser Met
865                 870                 875                 880

Leu Ser Leu Ala Arg Thr Cys Val Asp Asn Leu Trp Tyr Ile Glu Ala
                885                 890                 895

Ser Thr Asp Thr Ser Gly Asp Thr Ile Arg Leu Tyr Tyr Asn Arg Asn
            900                 905                 910

Ser Arg Pro Leu Ala His Ser Thr Glu Ile Trp Met His Gly Gly Tyr
            915                 920                 925

Asn Asn Trp Ser Asp Gly Leu Ser Ile Val Glu Ser Phe Val Lys Cys
            930                 935                 940

Asn Asp Arg Asp Gly Asp Trp Trp Tyr Ala Asp Val Ile Pro Pro Glu
945                 950                 955                 960

Lys Ala Leu Val Leu Asp Trp Val Phe Ala Asp Gly Pro Ala Gly Asn
                965                 970                 975

Ala Arg Asn Tyr Asp Asn Asn Ala Arg Gln Asp Phe His Ala Ile Leu
            980                 985                 990

Pro Asn Asn Asn Val Thr Glu Glu Gly Phe Trp Val Gln Glu Glu Gln
            995                 1000                1005

Asn Ile Tyr Thr Arg Leu Leu Gln Glu Arg Arg Glu Lys Glu Glu Thr
    1010                1015                1020

Met Lys Arg Lys Ala Glu Arg Ser Ala Asn Ile Lys Ala Glu Met Lys
1025                1030                1035                1040

Ala Lys Thr Met Arg Arg Phe Leu Leu Ser Gln Lys His Ile Val Tyr
                1045                1050                1055

Thr Glu Pro Leu Glu Ile Arg Ala Gly Thr Thr Val Asp Val Leu Tyr
            1060                1065                1070
```

```
Asn Pro Ser Asn Thr Val Leu Asn Gly Lys Pro Glu Val Trp Phe Arg
        1075                1080                1085

Cys Ser Phe Asn Leu Trp Met His Pro Ser Gly Ala Leu Pro Pro Gln
1090                1095                1100

Lys Met Val Lys Ser Gly Asp Gly Pro Leu Leu Lys Ala Thr Val Asn
1105                1110                1115                1120

Val Pro Pro Asp Ala Tyr Met Met Asp Phe Val Phe Ser Glu Trp Glu
                1125                1130                1135

Glu Asp Gly Ile Tyr Asp Asn Arg Asn Gly Met Asp Tyr His Ile Pro
            1140                1145                1150

Val Ser Asp Ser Ile Glu Thr Glu Asn Tyr Met Arg Ile Ile His Ile
        1155                1160                1165

Ala Val Glu Met Ala Pro Val Ala Lys Val Gly Gly Leu Gly Asp Val
    1170                1175                1180

Val Thr Ser Leu Ser Arg Ala Val Gln Asp Leu Gly His Thr Val Glu
1185                1190                1195                1200

Val Ile Leu Pro Lys Tyr Asp Cys Leu Asn Gln Ser Ser Val Lys Asp
                1205                1210                1215

Leu His Leu Tyr Gln Ser Phe Ser Trp Gly Gly Thr Glu Ile Lys Val
            1220                1225                1230

Trp Val Gly Arg Val Glu Asp Leu Thr Val Tyr Phe Leu Glu Pro Gln
        1235                1240                1245

Asn Gly Met Phe Gly Val Gly Cys Val Tyr Gly Arg Asn Asp Asp Arg
    1250                1255                1260

Arg Phe Gly Phe Phe Cys His Ser Ala Leu Glu Phe Ile Leu Gln Asn
1265                1270                1275                1280

Glu Phe Ser Pro His Ile Ile His Cys His Asp Trp Ser Ser Ala Pro
                1285                1290                1295

Val Ala Trp Leu Tyr Lys Glu His Tyr Ser Gln Ser Arg Met Ala Ser
            1300                1305                1310

Thr Arg Val Val Phe Thr Ile His Asn Leu Glu Phe Gly Ala His Tyr
        1315                1320                1325

Ile Gly Lys Ala Met Thr Tyr Cys Asp Lys Ala Thr Thr Val Ser Pro
    1330                1335                1340

Thr Tyr Ser Arg Asp Val Ala Gly His Gly Ala Ile Ala Pro His Arg
1345                1350                1355                1360

Glu Lys Phe Tyr Gly Ile Leu Asn Gly Ile Asp Pro Asp Ile Trp Asp
                1365                1370                1375

Pro Tyr Thr Asp Asn Phe Ile Pro Val Pro Tyr Thr Cys Glu Asn Val
            1380                1385                1390

Val Glu Gly Lys Arg Ala Ala Lys Arg Ala Leu Gln Gln Lys Phe Gly
        1395                1400                1405

Leu Gln Gln Thr Asp Val Pro Ile Val Gly Ile Ile Thr Arg Leu Thr
    1410                1415                1420

Ala Gln Lys Gly Ile His Leu Ile Lys His Ala Ile His Arg Thr Leu
1425                1430                1435                1440

Glu Ser Asn Gly Gln Val Val Leu Leu Gly Ser Ala Pro Asp His Arg
                1445                1450                1455

Ile Gln Gly Asp Phe Cys Arg Leu Ala Asp Ala Leu His Gly Val Tyr
            1460                1465                1470

His Gly Arg Val Lys Leu Val Leu Thr Tyr Asp Glu Pro Leu Ser His
        1475                1480                1485

Leu Ile Tyr Ala Gly Ser Asp Phe Ile Ile Val Pro Ser Ile Phe Glu
```

```
                1490                1495               1500
Pro Cys Gly Leu Thr Gln Leu Val Ala Met Arg Tyr Gly Ser Ile Pro
1505                1510               1515               1520

Ile Val Arg Lys Thr Gly Gly Leu Tyr Asp Thr Val Phe Asp Val Asp
                1525               1530               1535

Asn Asp Lys Asp Arg Ala Arg Ser Leu Gly Leu Glu Pro Asn Gly Phe
           1540               1545               1550

Ser Phe Asp Gly Ala Asp Ser Asn Gly Val Asp Tyr Ala Leu Asn Arg
       1555               1560               1565

Ala Ile Gly Ala Trp Phe Asp Ala Arg Asp Trp Phe His Ser Leu Cys
   1570               1575               1580

Lys Arg Val Met Glu Gln Asp Trp Ser Trp Asn Arg Pro Ala Leu Asp
1585                1590               1595               1600

Tyr Ile Glu Leu Tyr His Ala Ala Arg Lys Phe
                1605               1610

<210> SEQ ID NO 15
<211> LENGTH: 3444
<212> TYPE: DNA
<213> ORGANISM: Vigna unguiculata
<220> FEATURE:
<221> NAME/KEY: CDS
<222> LOCATION: (1)..(3441)
<223> OTHER INFORMATION: coding for sss3

<400> SEQUENCE: 15 atg gag atg tcg ttg cag cta aac tac aaa acg ccg ttt tgt ttc aag      48
Met Glu Met Ser Leu Gln Leu Asn Tyr Lys Thr Pro Phe Cys Phe Lys
  1               5                  10                  15 ctc act cca ttt tct gtt tta aca cct tct tca tgg cac aaa gca agt      96
Leu Thr Pro Phe Ser Val Leu Thr Pro Ser Ser Trp His Lys Ala Ser
             20                  25                  30 att cga gtt tct tgc gtt aat gct agt gca gat ttt tct agg aag aga     144
Ile Arg Val Ser Cys Val Asn Ala Ser Ala Asp Phe Ser Arg Lys Arg
         35                  40                  45 caa cag aag aag agt tca att gcg aag cca aag ggt tct aat cca aag     192
Gln Gln Lys Lys Ser Ser Ile Ala Lys Pro Lys Gly Ser Asn Pro Lys
     50                  55                  60 ggt ttt gtt cca aaa tca tct att gga tca agc agt aag aaa aat cct     240
Gly Phe Val Pro Lys Ser Ser Ile Gly Ser Ser Ser Lys Lys Asn Pro
 65                  70                  75                  80 aga gtc agt aag aag gga gat tct tta gct cca gtt gtt agt gag gtt     288
Arg Val Ser Lys Lys Gly Asp Ser Leu Ala Pro Val Val Ser Glu Val
                 85                  90                  95 ttg gag gat gat aat aaa caa aca ctt gat gtt att att gat gat gat     336
Leu Glu Asp Asp Asn Lys Gln Thr Leu Asp Val Ile Ile Asp Asp Asp
            100                 105                 110 gaa gat gaa ttt tcg gtg gag gaa aat tgt ggt gtg gat gat aaa att     384
Glu Asp Glu Phe Ser Val Glu Glu Asn Cys Gly Val Asp Asp Lys Ile
        115                 120                 125 aat aaa att gct cga gag ttc ggg gaa tcg tcc ttg ata gat gag aca     432
Asn Lys Ile Ala Arg Glu Phe Gly Glu Ser Ser Leu Ile Asp Glu Thr
    130                 135                 140 ttc gat gtt gaa aac att cct ata att gat gat gtt caa tta tat gag     480
Phe Asp Val Glu Asn Ile Pro Ile Ile Asp Asp Val Gln Leu Tyr Glu
145                 150                 155                 160 gag gga aat tct tac gtt gga gat gat ggg aat gtt aaa gat tca gag     528
Glu Gly Asn Ser Tyr Val Gly Asp Asp Gly Asn Val Lys Asp Ser Glu
                165                 170                 175
```

-continued

| | | | | | | | | | | | | | | | | |
|---|---|---|---|---|---|---|---|---|---|---|---|---|---|---|---|---|
| gga | agg | aga | tta | tac | tat | gct | gaa | att | gat | gga | aat | ctt | aga | ggt | aca | 576 |
| Gly | Arg | Arg | Leu | Tyr | Tyr | Ala | Glu | Ile | Asp | Gly | Asn | Leu | Arg | Gly | Thr | |
| | | 180 | | | | | 185 | | | | 190 | | | | | |

| tat | act | gat | act | aat | ggg | gaa | ata | gct | ggg | aat | atc | gtt | gag | gaa | aca | 624 |
| Tyr | Thr | Asp | Thr | Asn | Gly | Glu | Ile | Ala | Gly | Asn | Ile | Val | Glu | Glu | Thr | |
| | | | 195 | | | | 200 | | | | 205 | | | | | |

| agt | gct | gct | atc | gat | gat | gtt | aaa | att | aac | gag | gaa | gct | tct | cgg | atg | 672 |
| Ser | Ala | Ala | Ile | Asp | Asp | Val | Lys | Ile | Asn | Glu | Glu | Ala | Ser | Arg | Met | |
| | 210 | | | | 215 | | | | 220 | | | | | | | |

| ttg | aag | ttg | aag | ttg | gaa | gaa | aat | ttg | cga | aaa | cag | gaa | ata | gag | agg | 720 |
| Leu | Lys | Leu | Lys | Leu | Glu | Glu | Asn | Leu | Arg | Lys | Gln | Glu | Ile | Glu | Arg | |
| 225 | | | | 230 | | | | 235 | | | | 240 | | | | |

| att | gcg | gag | gaa | aat | ttt | tta | cga | ggg | gca | aag | ttg | ttt | gta | tat | cct | 768 |
| Ile | Ala | Glu | Glu | Asn | Phe | Leu | Arg | Gly | Ala | Lys | Leu | Phe | Val | Tyr | Pro | |
| | | | | 245 | | | | 250 | | | | 255 | | | | |

| cct | gtg | gtt | aaa | cct | gat | gaa | gat | ata | gag | gtg | ttt | ctt | aac | aag | aac | 816 |
| Pro | Val | Val | Lys | Pro | Asp | Glu | Asp | Ile | Glu | Val | Phe | Leu | Asn | Lys | Asn | |
| | | | 260 | | | | 265 | | | | 270 | | | | | |

| ctt | tcg | aca | cta | agt | gat | gaa | cct | gat | att | ttg | att | ttg | ggg | gcg | ttt | 864 |
| Leu | Ser | Thr | Leu | Ser | Asp | Glu | Pro | Asp | Ile | Leu | Ile | Leu | Gly | Ala | Phe | |
| | 275 | | | | 280 | | | | 285 | | | | | | | |

| aat | gat | tgg | gag | tgg | aaa | tct | ttt | acc | att | aga | ttg | aat | aaa | aca | cat | 912 |
| Asn | Asp | Trp | Glu | Trp | Lys | Ser | Phe | Thr | Ile | Arg | Leu | Asn | Lys | Thr | His | |
| | 290 | | | | 295 | | | | 300 | | | | | | | |

| ctt | aaa | gat | gat | tgg | tgg | agt | tgc | caa | ttg | tat | gtg | cca | aga | gaa | gcc | 960 |
| Leu | Lys | Asp | Asp | Trp | Trp | Ser | Cys | Gln | Leu | Tyr | Val | Pro | Arg | Glu | Ala | |
| 305 | | | | 310 | | | | 315 | | | | 320 | | | | |

| tat | aaa | ata | gac | ttt | gtg | ttc | ttt | aat | gga | caa | agt | gtt | tat | gac | aat | 1008 |
| Tyr | Lys | Ile | Asp | Phe | Val | Phe | Phe | Asn | Gly | Gln | Ser | Val | Tyr | Asp | Asn | |
| | | | 325 | | | | 330 | | | | 335 | | | | | |

| aat | gac | caa | aaa | gac | ttt | tgt | ata | cca | gtt | gtt | ggt | gga | atg | gat | gca | 1056 |
| Asn | Asp | Gln | Lys | Asp | Phe | Cys | Ile | Pro | Val | Val | Gly | Gly | Met | Asp | Ala | |
| | | 340 | | | | 345 | | | | 350 | | | | | | |

| ttg | gtg | ttc | gaa | gat | ttt | ttg | ctc | gag | gag | aag | cgt | aaa | gaa | tta | gaa | 1104 |
| Leu | Val | Phe | Glu | Asp | Phe | Leu | Leu | Glu | Glu | Lys | Arg | Lys | Glu | Leu | Glu | |
| | | 355 | | | | 360 | | | | 365 | | | | | | |

| aaa | ctt | gct | aag | gag | cag | gct | gaa | agg | gaa | aga | cag | gct | gaa | gag | caa | 1152 |
| Lys | Leu | Ala | Lys | Glu | Gln | Ala | Glu | Arg | Glu | Arg | Gln | Ala | Glu | Glu | Gln | |
| | 370 | | | | 375 | | | | 380 | | | | | | | |

| agg | cga | ata | gat | gca | gac | aaa | gct | gta | aag | gga | gag | gac | agg | ttg | cag | 1200 |
| Arg | Arg | Ile | Asp | Ala | Asp | Lys | Ala | Val | Lys | Gly | Glu | Asp | Arg | Leu | Gln | |
| 385 | | | | 390 | | | | 395 | | | | 400 | | | | |

| gca | agg | atg | gag | gtt | gaa | aaa | atg | caa | gat | acg | ttg | ctg | cag | ttg | atg | 1248 |
| Ala | Arg | Met | Glu | Val | Glu | Lys | Met | Gln | Asp | Thr | Leu | Leu | Gln | Leu | Met | |
| | | | | 405 | | | | 410 | | | | 415 | | | | |

| aaa | aat | gct | gta | acc | tct | att | gat | aat | gtt | tgg | tat | att | gag | cct | agt | 1296 |
| Lys | Asn | Ala | Val | Thr | Ser | Ile | Asp | Asn | Val | Trp | Tyr | Ile | Glu | Pro | Ser | |
| | | | 420 | | | | 425 | | | | 430 | | | | | |

| gag | ttt | aac | agc | aat | gac | tca | gtc | aga | tta | tat | tat | aat | gga | aac | tcg | 1344 |
| Glu | Phe | Asn | Ser | Asn | Asp | Ser | Val | Arg | Leu | Tyr | Tyr | Asn | Gly | Asn | Ser | |
| | | 435 | | | | 440 | | | | 445 | | | | | | |

| ggt | cct | ctt | caa | cat | gct | aag | gaa | gta | tgg | gtt | cat | ggc | ggt | cac | aac | 1392 |
| Gly | Pro | Leu | Gln | His | Ala | Lys | Glu | Val | Trp | Val | His | Gly | Gly | His | Asn | |
| | | 450 | | | | 455 | | | | 460 | | | | | | |

| aat | tgg | aag | gat | gga | tta | aca | att | gtt | gaa | agg | ctt | gtc | aaa | tca | ggt | 1440 |
| Asn | Trp | Lys | Asp | Gly | Leu | Thr | Ile | Val | Glu | Arg | Leu | Val | Lys | Ser | Gly | |
| 465 | | | | 470 | | | | 475 | | | | 480 | | | | |

| ttg | aaa | ggt | ggt | gct | tgg | tgg | tat | gct | gat | gtt | gtt | gta | cct | gac | caa | 1488 |
| Leu | Lys | Gly | Gly | Ala | Trp | Trp | Tyr | Ala | Asp | Val | Val | Val | Pro | Asp | Gln | |
| | | | | 485 | | | | 490 | | | | 495 | | | | |

```
gct ctt gtc ctg gat tgg gtc ttt gct gat ggt cca cct caa aat gca      1536
Ala Leu Val Leu Asp Trp Val Phe Ala Asp Gly Pro Pro Gln Asn Ala
        500                 505                 510 gtt gtg tat gat aac aac cgt atg caa gat ttc cat gct att gtc cct      1584
Val Val Tyr Asp Asn Asn Arg Met Gln Asp Phe His Ala Ile Val Pro
            515                 520                 525 atg gct aca ccc gac gca cag tat tgg gtt gag gaa gag cag cta ata      1632
Met Ala Thr Pro Asp Ala Gln Tyr Trp Val Glu Glu Glu Gln Leu Ile
        530                 535                 540 tac aga aaa ctt cag gag gag agg aag ttg aaa gag gaa gtt ata cgg      1680
Tyr Arg Lys Leu Gln Glu Glu Arg Lys Leu Lys Glu Glu Val Ile Arg
545                 550                 555                 560 gcg aag gct gaa aaa aca gca caa atg aaa gcc gaa aca aag gaa aaa      1728
Ala Lys Ala Glu Lys Thr Ala Gln Met Lys Ala Glu Thr Lys Glu Lys
                565                 570                 575 act ttg aaa aag ttt tta cta tct caa aag cat atc gtc tac act gag      1776
Thr Leu Lys Lys Phe Leu Leu Ser Gln Lys His Ile Val Tyr Thr Glu
            580                 585                 590 ccg ctt gat att caa gca ggg agt aca gtg acg gtg ttt tat aac ccc      1824
Pro Leu Asp Ile Gln Ala Gly Ser Thr Val Thr Val Phe Tyr Asn Pro
        595                 600                 605 tca aac aca aat ctg aat gga aga cct gag gtt tgg ttt aga ggc tca      1872
Ser Asn Thr Asn Leu Asn Gly Arg Pro Glu Val Trp Phe Arg Gly Ser
    610                 615                 620 ttt aat cgt tgg tct cat cgt aat ggt cca ttg cca cct cag aga atg      1920
Phe Asn Arg Trp Ser His Arg Asn Gly Pro Leu Pro Pro Gln Arg Met
625                 630                 635                 640 ttg cct gct gag agt ggc aca cat gtc aaa gcc tct gtt aaa gtt cca      1968
Leu Pro Ala Glu Ser Gly Thr His Val Lys Ala Ser Val Lys Val Pro
                645                 650                 655 ttg gat gca tac atg atg gac ttt gta ttc tct gag agt gaa aat ggt      2016
Leu Asp Ala Tyr Met Met Asp Phe Val Phe Ser Glu Ser Glu Asn Gly
            660                 665                 670 gga gtt ttt gat aac aaa ttt gga atg gat tac cac ata cct gtt ttt      2064
Gly Val Phe Asp Asn Lys Phe Gly Met Asp Tyr His Ile Pro Val Phe
        675                 680                 685 gga ggt att gtg aag gaa cct cct atg cat att gtt cat att gct gtt      2112
Gly Gly Ile Val Lys Glu Pro Pro Met His Ile Val His Ile Ala Val
    690                 695                 700 gag atg gcc cca att gca aag gtt gga ggc ctt ggt gat gtt gtt act      2160
Glu Met Ala Pro Ile Ala Lys Val Gly Gly Leu Gly Asp Val Val Thr
705                 710                 715                 720 agt ctt tcc cga gct gtt caa gat tta aat cat aat gtg gat atc att      2208
Ser Leu Ser Arg Ala Val Gln Asp Leu Asn His Asn Val Asp Ile Ile
                725                 730                 735 ctt cca aaa tat gac tgc ttg aac ctt agc aat gta aag gac ttg caa      2256
Leu Pro Lys Tyr Asp Cys Leu Asn Leu Ser Asn Val Lys Asp Leu Gln
            740                 745                 750 ttt cac aaa agc tat ttc tgg agt ggg act gaa ata aaa gta tgg cac      2304
Phe His Lys Ser Tyr Phe Trp Ser Gly Thr Glu Ile Lys Val Trp His
        755                 760                 765 gga aag gtc gag ggc ctc tcg gtc tac ttt ttg gag cct cag aat gga      2352
Gly Lys Val Glu Gly Leu Ser Val Tyr Phe Leu Glu Pro Gln Asn Gly
    770                 775                 780 tta ttt tgg gtg ggc tgt gta tat ggt cgt gca aat gat gca gag aga      2400
Leu Phe Trp Val Gly Cys Val Tyr Gly Arg Ala Asn Asp Ala Glu Arg
785                 790                 795                 800 ttt ggt ttt ttt tgc cat gcc gct ctt gaa ttt cta ctc caa aat gga      2448
Phe Gly Phe Phe Cys His Ala Ala Leu Glu Phe Leu Leu Gln Asn Gly
```

-continued

```
              805                 810                 815
agt cat cct gat atc atc cac tgc cat gac tgg tcg agt gct cca gtt      2496
Ser His Pro Asp Ile Ile His Cys His Asp Trp Ser Ser Ala Pro Val
        820                 825                 830 gca tgg cta ttt aaa gaa cag tat aca cat tat ggt ctt agt aag gct      2544
Ala Trp Leu Phe Lys Glu Gln Tyr Thr His Tyr Gly Leu Ser Lys Ala
            835                 840                 845 cga gtt gtc ttc aca att cat aac ctt gaa ttt ggt gcc aat ctc att      2592
Arg Val Val Phe Thr Ile His Asn Leu Glu Phe Gly Ala Asn Leu Ile
        850                 855                 860 gga aaa gct atg gca tac gct gac aag gct aca act gtc tcc ccc act      2640
Gly Lys Ala Met Ala Tyr Ala Asp Lys Ala Thr Thr Val Ser Pro Thr
865                 870                 875                 880 tat tca agg gag att gct ggg aat cat gca gtt gct act cat ctt cac      2688
Tyr Ser Arg Glu Ile Ala Gly Asn His Ala Val Ala Thr His Leu His
                885                 890                 895 aag ttt cat ggt ata ata aat gga atc gac cca gat ata tgg gac cca      2736
Lys Phe His Gly Ile Ile Asn Gly Ile Asp Pro Asp Ile Trp Asp Pro
            900                 905                 910 ttt aat gat aac tcc att cct gta cca tac aca gca gaa aat gtt gtt      2784
Phe Asn Asp Asn Ser Ile Pro Val Pro Tyr Thr Ala Glu Asn Val Val
        915                 920                 925 gaa gga aaa aga gcg tcc aag gaa gcc tta caa caa aag ctt ggt ttg      2832
Glu Gly Lys Arg Ala Ser Lys Glu Ala Leu Gln Gln Lys Leu Gly Leu
    930                 935                 940 aaa aaa gct gat ctt cct ttg gtg gga gtt att act cga ttg act cat      2880
Lys Lys Ala Asp Leu Pro Leu Val Gly Val Ile Thr Arg Leu Thr His
945                 950                 955                 960 caa aaa ggg atc cat ctc atc aaa cat gcc ata tgg cgt acc cta gaa      2928
Gln Lys Gly Ile His Leu Ile Lys His Ala Ile Trp Arg Thr Leu Glu
                965                 970                 975 cgc ggt gga cag gtc gta tta ctt ggt tcg gct cct gat cac cgt ata      2976
Arg Gly Gly Gln Val Val Leu Leu Gly Ser Ala Pro Asp His Arg Ile
            980                 985                 990 caa aat gat ttt gtg aat ttg gcc aat caa ttg cat tcc agt cat aat      3024
Gln Asn Asp Phe Val Asn Leu Ala Asn Gln Leu His Ser Ser His Asn
        995                 1000                1005 gat cgg gca aga ctt tgc ctt gca tat gat gaa cct ctt tcc cac atg      3072
Asp Arg Ala Arg Leu Cys Leu Ala Tyr Asp Glu Pro Leu Ser His Met
    1010                1015                1020 ata tat gct ggt gct gat ttc att ctt gtt cct tca atc ttt gag cca      3120
Ile Tyr Ala Gly Ala Asp Phe Ile Leu Val Pro Ser Ile Phe Glu Pro
1025                1030                1035                1040 tgt gga ctc act caa ctc aca gca atg aga tac ggt tca ata cca att      3168
Cys Gly Leu Thr Gln Leu Thr Ala Met Arg Tyr Gly Ser Ile Pro Ile
                1045                1050                1055 gtt cga aaa act ggg gga ctt tat gat acg gtg ttt gac gtt gat aat      3216
Val Arg Lys Thr Gly Gly Leu Tyr Asp Thr Val Phe Asp Val Asp Asn
            1060                1065                1070 gat aag gat aga gca caa gtg caa ggt ctt gag cca aat gga ttc agt      3264
Asp Lys Asp Arg Ala Gln Val Gln Gly Leu Glu Pro Asn Gly Phe Ser
        1075                1080                1085 ttt gat ggg gct gat gcg gga ggt gtt gat tat gct ctt aat agg gca      3312
Phe Asp Gly Ala Asp Ala Gly Gly Val Asp Tyr Ala Leu Asn Arg Ala
    1090                1095                1100 ata tct gct tgg tat gat ggc cgt gag tgg ttt aac aca tta tgc aag      3360
Ile Ser Ala Trp Tyr Asp Gly Arg Glu Trp Phe Asn Thr Leu Cys Lys
1105                1110                1115                1120 aca gta atg gag caa gat tgg tct tgg aac cgc cct gct ctc gac tat      3408
```

```
Thr Val Met Glu Gln Asp Trp Ser Trp Asn Arg Pro Ala Leu Asp Tyr
            1125                1130               1135 ttg gag ctt tac cat gca gca tgc aag ttg gaa tga                    3444
Leu Glu Leu Tyr His Ala Ala Cys Lys Leu Glu
        1140                1145
```

<210> SEQ ID NO 16
<211> LENGTH: 1147
<212> TYPE: PRT
<213> ORGANISM: Vigna unguiculata

<400> SEQUENCE: 16

```
Met Glu Met Ser Leu Gln Leu Asn Tyr Lys Thr Pro Phe Cys Phe Lys
 1               5                  10                  15

Leu Thr Pro Phe Ser Val Leu Thr Pro Ser Ser Trp His Lys Ala Ser
            20                  25                  30

Ile Arg Val Ser Cys Val Asn Ala Ser Ala Asp Phe Ser Arg Lys Arg
        35                  40                  45

Gln Gln Lys Lys Ser Ser Ile Ala Lys Pro Lys Gly Ser Asn Pro Lys
    50                  55                  60

Gly Phe Val Pro Lys Ser Ser Ile Gly Ser Ser Ser Lys Asn Pro
65                  70                  75                  80

Arg Val Ser Lys Lys Gly Asp Ser Leu Ala Pro Val Val Ser Glu Val
                85                  90                  95

Leu Glu Asp Asp Asn Lys Gln Thr Leu Asp Val Ile Asp Asp
            100                 105                 110

Glu Asp Glu Phe Ser Val Glu Glu Asn Cys Gly Val Asp Asp Lys Ile
        115                 120                 125

Asn Lys Ile Ala Arg Glu Phe Gly Glu Ser Ser Leu Ile Asp Glu Thr
    130                 135                 140

Phe Asp Val Glu Asn Ile Pro Ile Ile Asp Asp Val Gln Leu Tyr Glu
145                 150                 155                 160

Glu Gly Asn Ser Tyr Val Gly Asp Asp Gly Asn Val Lys Asp Ser Glu
                165                 170                 175

Gly Arg Arg Leu Tyr Tyr Ala Glu Ile Asp Gly Asn Leu Arg Gly Thr
            180                 185                 190

Tyr Thr Asp Thr Asn Gly Glu Ile Ala Gly Asn Ile Val Glu Glu Thr
        195                 200                 205

Ser Ala Ala Ile Asp Asp Val Lys Ile Asn Glu Glu Ala Ser Arg Met
    210                 215                 220

Leu Lys Leu Lys Leu Glu Glu Asn Leu Arg Lys Gln Glu Ile Glu Arg
225                 230                 235                 240

Ile Ala Glu Glu Asn Phe Leu Arg Gly Ala Lys Leu Phe Val Tyr Pro
                245                 250                 255

Pro Val Val Lys Pro Asp Glu Asp Ile Glu Val Phe Leu Asn Lys Asn
            260                 265                 270

Leu Ser Thr Leu Ser Asp Glu Pro Asp Ile Leu Ile Leu Gly Ala Phe
        275                 280                 285

Asn Asp Trp Glu Trp Lys Ser Phe Thr Ile Arg Leu Asn Lys Thr His
    290                 295                 300

Leu Lys Asp Asp Trp Trp Ser Cys Gln Leu Tyr Val Pro Arg Glu Ala
305                 310                 315                 320

Tyr Lys Ile Asp Phe Val Phe Phe Asn Gly Gln Ser Val Tyr Asp Asn
                325                 330                 335

Asn Asp Gln Lys Asp Phe Cys Ile Pro Val Val Gly Gly Met Asp Ala
```

-continued

```
              340                 345                 350
Leu Val Phe Glu Asp Phe Leu Leu Glu Glu Lys Arg Lys Glu Leu Glu
            355                 360                 365
Lys Leu Ala Lys Glu Gln Ala Glu Arg Glu Arg Gln Ala Glu Glu Gln
            370                 375                 380
Arg Arg Ile Asp Ala Asp Lys Ala Val Lys Gly Glu Asp Arg Leu Gln
385                 390                 395                 400
Ala Arg Met Glu Val Glu Lys Met Gln Asp Thr Leu Leu Gln Leu Met
                405                 410                 415
Lys Asn Ala Val Thr Ser Ile Asp Asn Val Trp Tyr Ile Glu Pro Ser
            420                 425                 430
Glu Phe Asn Ser Asn Asp Ser Val Arg Leu Tyr Tyr Asn Gly Asn Ser
            435                 440                 445
Gly Pro Leu Gln His Ala Lys Glu Val Trp Val His Gly His Asn
            450                 455                 460
Asn Trp Lys Asp Gly Leu Thr Ile Val Glu Arg Leu Val Lys Ser Gly
465                 470                 475                 480
Leu Lys Gly Gly Ala Trp Trp Tyr Ala Asp Val Val Pro Asp Gln
                485                 490                 495
Ala Leu Val Leu Asp Trp Val Phe Ala Asp Gly Pro Pro Gln Asn Ala
            500                 505                 510
Val Val Tyr Asp Asn Asn Arg Met Gln Asp Phe His Ala Ile Val Pro
            515                 520                 525
Met Ala Thr Pro Asp Ala Gln Tyr Trp Val Glu Glu Gln Leu Ile
            530                 535                 540
Tyr Arg Lys Leu Gln Glu Glu Arg Lys Leu Lys Glu Glu Val Ile Arg
545                 550                 555                 560
Ala Lys Ala Glu Lys Thr Ala Gln Met Lys Ala Glu Thr Lys Glu Lys
                565                 570                 575
Thr Leu Lys Lys Phe Leu Leu Ser Gln Lys His Ile Val Tyr Thr Glu
            580                 585                 590
Pro Leu Asp Ile Gln Ala Gly Ser Thr Val Thr Val Phe Tyr Asn Pro
            595                 600                 605
Ser Asn Thr Asn Leu Asn Gly Arg Pro Glu Val Trp Phe Arg Gly Ser
            610                 615                 620
Phe Asn Arg Trp Ser His Arg Asn Gly Pro Leu Pro Pro Gln Arg Met
625                 630                 635                 640
Leu Pro Ala Glu Ser Gly Thr His Val Lys Ala Ser Val Lys Val Pro
                645                 650                 655
Leu Asp Ala Tyr Met Met Asp Phe Val Phe Ser Glu Ser Glu Asn Gly
            660                 665                 670
Gly Val Phe Asp Asn Lys Phe Gly Met Asp Tyr His Ile Pro Val Phe
            675                 680                 685
Gly Gly Ile Val Lys Glu Pro Pro Met His Ile Val His Ile Ala Val
            690                 695                 700
Glu Met Ala Pro Ile Ala Lys Val Gly Gly Leu Gly Asp Val Val Thr
705                 710                 715                 720
Ser Leu Ser Arg Ala Val Gln Asp Leu Asn His Asn Val Asp Ile Ile
                725                 730                 735
Leu Pro Lys Tyr Asp Cys Leu Asn Leu Ser Asn Val Lys Asp Leu Gln
            740                 745                 750
Phe His Lys Ser Tyr Phe Trp Ser Gly Thr Glu Ile Lys Val Trp His
            755                 760                 765
```

```
Gly Lys Val Glu Gly Leu Ser Val Tyr Phe Leu Glu Pro Gln Asn Gly
        770                 775                 780

Leu Phe Trp Val Gly Cys Val Tyr Gly Arg Ala Asn Asp Ala Glu Arg
785                 790                 795                 800

Phe Gly Phe Phe Cys His Ala Ala Leu Glu Phe Leu Gln Asn Gly
            805                 810                 815

Ser His Pro Asp Ile Ile His Cys His Asp Trp Ser Ser Ala Pro Val
        820                 825                 830

Ala Trp Leu Phe Lys Glu Gln Tyr Thr His Tyr Gly Leu Ser Lys Ala
        835                 840                 845

Arg Val Val Phe Thr Ile His Asn Leu Glu Phe Gly Ala Asn Leu Ile
        850                 855                 860

Gly Lys Ala Met Ala Tyr Ala Asp Lys Ala Thr Thr Val Ser Pro Thr
865                 870                 875                 880

Tyr Ser Arg Glu Ile Ala Gly Asn His Ala Val Ala Thr His Leu His
            885                 890                 895

Lys Phe His Gly Ile Ile Asn Gly Ile Asp Pro Asp Ile Trp Asp Pro
            900                 905                 910

Phe Asn Asp Asn Ser Ile Pro Val Pro Tyr Thr Ala Glu Asn Val Val
        915                 920                 925

Glu Gly Lys Arg Ala Ser Lys Glu Ala Leu Gln Gln Lys Leu Gly Leu
    930                 935                 940

Lys Lys Ala Asp Leu Pro Leu Val Gly Val Ile Thr Arg Leu Thr His
945                 950                 955                 960

Gln Lys Gly Ile His Leu Ile Lys His Ala Ile Trp Arg Thr Leu Glu
            965                 970                 975

Arg Gly Gly Gln Val Val Leu Leu Gly Ser Ala Pro Asp His Arg Ile
            980                 985                 990

Gln Asn Asp Phe Val Asn Leu Ala Asn Gln Leu His Ser Ser His Asn
        995                 1000                1005

Asp Arg Ala Arg Leu Cys Leu Ala Tyr Asp Glu Pro Leu Ser His Met
    1010                1015                1020

Ile Tyr Ala Gly Ala Asp Phe Ile Leu Val Pro Ser Ile Phe Glu Pro
1025                1030                1035                1040

Cys Gly Leu Thr Gln Leu Thr Ala Met Arg Tyr Gly Ser Ile Pro Ile
            1045                1050                1055

Val Arg Lys Thr Gly Gly Leu Tyr Asp Thr Val Phe Asp Val Asp Asn
            1060                1065                1070

Asp Lys Asp Arg Ala Gln Val Gln Gly Leu Glu Pro Asn Gly Phe Ser
        1075                1080                1085

Phe Asp Gly Ala Asp Ala Gly Gly Val Asp Tyr Ala Leu Asn Arg Ala
    1090                1095                1100

Ile Ser Ala Trp Tyr Asp Gly Arg Glu Trp Phe Asn Thr Leu Cys Lys
1105                1110                1115                1120

Thr Val Met Glu Gln Asp Trp Ser Trp Asn Arg Pro Ala Leu Asp Tyr
            1125                1130                1135

Leu Glu Leu Tyr His Ala Ala Cys Lys Leu Glu
            1140                1145

<210> SEQ ID NO 17
<211> LENGTH: 5025
<212> TYPE: DNA
<213> ORGANISM: Zea mays
<220> FEATURE:
```

-continued

```
<221> NAME/KEY: CDS
<222> LOCATION: (1)..(5022)
<223> OTHER INFORMATION: coding for sss3

<400> SEQUENCE: 17 atg gag atg gtc cta cgg tcg cag agc cct ctc tgc ctt cgg agt ggg      48
Met Glu Met Val Leu Arg Ser Gln Ser Pro Leu Cys Leu Arg Ser Gly
 1               5                  10                  15 ccg gtg ctc att ttt cga cca acc gtc gcg ggc gga ggg ggc act          96
Pro Val Leu Ile Phe Arg Pro Thr Val Ala Gly Gly Gly Gly Thr
             20                  25                  30 cag tct ttg ttg agg act acc aga ttt gcg aga aga agg gtc att cga     144
Gln Ser Leu Leu Arg Thr Thr Arg Phe Ala Arg Arg Arg Val Ile Arg
         35                  40                  45 tgc gtt gta gca agt cca ggt tgt cct aat agg aaa tct agg aca gcg     192
Cys Val Val Ala Ser Pro Gly Cys Pro Asn Arg Lys Ser Arg Thr Ala
 50                  55                  60 tct ccc aac gta aaa gta gct gct tat agc aac tat gcg cca aga ctc     240
Ser Pro Asn Val Lys Val Ala Ala Tyr Ser Asn Tyr Ala Pro Arg Leu
 65                  70                  75                  80 ctc gtt gag tca agc tcc aag aag agc gaa cac cat gat agc agc aga     288
Leu Val Glu Ser Ser Ser Lys Lys Ser Glu His His Asp Ser Ser Arg
                 85                  90                  95 cac cgt gaa gaa act att gat aca tac aat ggg ctg tca ggt tct gat     336
His Arg Glu Glu Thr Ile Asp Thr Tyr Asn Gly Leu Ser Gly Ser Asp
            100                 105                 110 gca gca gaa ttg aca agt aat aga gat gta gaa att gaa gtg gat ttg     384
Ala Ala Glu Leu Thr Ser Asn Arg Asp Val Glu Ile Glu Val Asp Leu
        115                 120                 125 cag cac att tct gag gag gaa ttg cca gga aaa gta tcg att aat gca     432
Gln His Ile Ser Glu Glu Glu Leu Pro Gly Lys Val Ser Ile Asn Ala
    130                 135                 140 tca tta gga gaa atg gaa aca gtg gat gaa gct gag gtc gag gag gat     480
Ser Leu Gly Glu Met Glu Thr Val Asp Glu Ala Glu Val Glu Glu Asp
145                 150                 155                 160 aag ttt gag gta gat acc tca gga att gta ttg cgc aat gtt gca gtt     528
Lys Phe Glu Val Asp Thr Ser Gly Ile Val Leu Arg Asn Val Ala Val
                165                 170                 175 cgg gaa gtg gat cca aag gat gaa cat aat gct aaa gat gta ttt gtg     576
Arg Glu Val Asp Pro Lys Asp Glu His Asn Ala Lys Asp Val Phe Val
            180                 185                 190 gta gat tcg tca gga act gca cca gat aat gct gca gtg gag gaa gtg     624
Val Asp Ser Ser Gly Thr Ala Pro Asp Asn Ala Ala Val Glu Glu Val
        195                 200                 205 gta gat gaa gct gag gtt gaa gag gat atg gtt gat gtg gat atc ttg     672
Val Asp Glu Ala Glu Val Glu Glu Asp Met Val Asp Val Asp Ile Leu
    210                 215                 220 gga ctt gac ttg aat aat gca acg atc gag gaa att gat ttg atg gaa     720
Gly Leu Asp Leu Asn Asn Ala Thr Ile Glu Glu Ile Asp Leu Met Glu
225                 230                 235                 240 gag gct tta ctg gag aac ttc gac gtg gat tca cca ggc aat gct tct     768
Glu Ala Leu Leu Glu Asn Phe Asp Val Asp Ser Pro Gly Asn Ala Ser
                245                 250                 255 agt ggt cga acc tat ggg ggt gtg gat gag ttg ggt gag ctg cct tca     816
Ser Gly Arg Thr Tyr Gly Gly Val Asp Glu Leu Gly Glu Leu Pro Ser
            260                 265                 270 aca tcc gtg gat tgc atc gcc att aac gga aaa cgt aga agt ttg aag     864
Thr Ser Val Asp Cys Ile Ala Ile Asn Gly Lys Arg Arg Ser Leu Lys
        275                 280                 285 cct aag ccc ttg cca att gtc agg ttc cag gaa caa gaa cag ata gtt     912
```

```
            Pro Lys Pro Leu Pro Ile Val Arg Phe Gln Glu Gln Glu Gln Ile Val
                290                 295                 300 tta agc att gtt gac gaa gaa ggg ttg att gct agt tca tgt gaa gaa        960
Leu Ser Ile Val Asp Glu Glu Gly Leu Ile Ala Ser Ser Cys Glu Glu
305                 310                 315                 320 ggc caa ccg gtg gta gat tac gat aag caa gag gaa aac tct acc gct       1008
Gly Gln Pro Val Val Asp Tyr Asp Lys Gln Glu Glu Asn Ser Thr Ala
                325                 330                 335 ttc gat gaa cag aag caa tta act gat gat ttc cct gaa gaa ggc ata       1056
Phe Asp Glu Gln Lys Gln Leu Thr Asp Asp Phe Pro Glu Glu Gly Ile
                340                 345                 350 tct ata gtt cac ttc cct gag cca aac aat gat att gtt gga tcc tca       1104
Ser Ile Val His Phe Pro Glu Pro Asn Asn Asp Ile Val Gly Ser Ser
                355                 360                 365 aaa ttc ttg gag caa aaa caa gaa ttg gat ggt tct tat aaa caa gat       1152
Lys Phe Leu Glu Gln Lys Gln Glu Leu Asp Gly Ser Tyr Lys Gln Asp
                370                 375                 380 cga tca acc act gga ttg cat gaa caa gat cag tct gtt gtt agt tca       1200
Arg Ser Thr Thr Gly Leu His Glu Gln Asp Gln Ser Val Val Ser Ser
385                 390                 395                 400 cac gga caa gat aaa tca att gtt ggt gtg cct cag caa atc cag tac       1248
His Gly Gln Asp Lys Ser Ile Val Gly Val Pro Gln Gln Ile Gln Tyr
                405                 410                 415 aat gat caa tct att gct ggt tct cat aga caa gat caa tca att gcc       1296
Asn Asp Gln Ser Ile Ala Gly Ser His Arg Gln Asp Gln Ser Ile Ala
                420                 425                 430 ggt gca cct gag caa atc caa tcc gtt gct ggc tat ata aaa cca aat       1344
Gly Ala Pro Glu Gln Ile Gln Ser Val Ala Gly Tyr Ile Lys Pro Asn
                435                 440                 445 caa tct att gtt ggt tct tgt aaa caa cat gaa ttg att att cct gag       1392
Gln Ser Ile Val Gly Ser Cys Lys Gln His Glu Leu Ile Ile Pro Glu
                450                 455                 460 cct aag aaa atc gaa tcc atc atc agt tac aat gaa ata gat caa tct       1440
Pro Lys Lys Ile Glu Ser Ile Ile Ser Tyr Asn Glu Ile Asp Gln Ser
465                 470                 475                 480 att gtt ggt tct cac aaa caa gac aaa tct gtt gtt agt gtg cct gag       1488
Ile Val Gly Ser His Lys Gln Asp Lys Ser Val Val Ser Val Pro Glu
                485                 490                 495 caa atc caa tcc att gtt agt cac agc aaa cca aat caa tct act gtt       1536
Gln Ile Gln Ser Ile Val Ser His Ser Lys Pro Asn Gln Ser Thr Val
                500                 505                 510 gat tct tat aga caa gct gaa tca att att ggt gtg cct gag aaa gtc       1584
Asp Ser Tyr Arg Gln Ala Glu Ser Ile Ile Gly Val Pro Glu Lys Val
                515                 520                 525 caa tcc atc acc agt tac gat aaa cta gac cag tcc att gtt ggt tct       1632
Gln Ser Ile Thr Ser Tyr Asp Lys Leu Asp Gln Ser Ile Val Gly Ser
                530                 535                 540 ctt aaa caa gat gag cct att att agc gtg cct gag aaa atc caa tcc       1680
Leu Lys Gln Asp Glu Pro Ile Ile Ser Val Pro Glu Lys Ile Gln Ser
545                 550                 555                 560 att gtc cat tac act aaa cca aat cag tct att gtt ggc ttg ccc aaa       1728
Ile Val His Tyr Thr Lys Pro Asn Gln Ser Ile Val Gly Leu Pro Lys
                565                 570                 575 caa caa caa tca att gtt cat atc gtt gaa cca aaa cag tcc ata gat       1776
Gln Gln Gln Ser Ile Val His Ile Val Glu Pro Lys Gln Ser Ile Asp
                580                 585                 590 ggt ttc cct aaa caa gat cta tca atc gtt ggt atc tcc aat gag ttt       1824
Gly Phe Pro Lys Gln Asp Leu Ser Ile Val Gly Ile Ser Asn Glu Phe
                595                 600                 605
```

-continued

| | |
|---|---|
| caa aca aag caa ctg gct act gtt ggg act cat gat gga ttg ctt atg<br>Gln Thr Lys Gln Leu Ala Thr Val Gly Thr His Asp Gly Leu Leu Met<br>610                              615                        620 | 1872 |
| aag ggt gtg gaa gct aag gag aca tct caa aag act gaa ggg gat aca<br>Lys Gly Val Glu Ala Lys Glu Thr Ser Gln Lys Thr Glu Gly Asp Thr<br>625                              630                        635                        640 | 1920 |
| ctt cag gca acg ttc aat gtc gac aac ttg tca cag aaa cag gaa ggc<br>Leu Gln Ala Thr Phe Asn Val Asp Asn Leu Ser Gln Lys Gln Glu Gly<br>                        645                        650                        655 | 1968 |
| tta act aaa gaa gca gac gag ata aca att att gag aaa atc aat gat<br>Leu Thr Lys Glu Ala Asp Glu Ile Thr Ile Ile Glu Lys Ile Asn Asp<br>660                              665                        670 | 2016 |
| gaa gac ctt gtg atg att gaa gaa cag aaa agc ata gcc atg aat gaa<br>Glu Asp Leu Val Met Ile Glu Glu Gln Lys Ser Ile Ala Met Asn Glu<br>                        675                        680                        685 | 2064 |
| gaa cag acg att gtt acc gaa gaa gac att cca atg gct aag gtt gag<br>Glu Gln Thr Ile Val Thr Glu Glu Asp Ile Pro Met Ala Lys Val Glu<br>690                              695                        700 | 2112 |
| ata gga att gac aag gcc aaa ttt tta cat ctg ctt tct gaa gaa gag<br>Ile Gly Ile Asp Lys Ala Lys Phe Leu His Leu Leu Ser Glu Glu Glu<br>705                              710                        715                        720 | 2160 |
| agt tca tgg gat gaa aat gaa gtg gga ata att gag gct gat gaa cag<br>Ser Ser Trp Asp Glu Asn Glu Val Gly Ile Ile Glu Ala Asp Glu Gln<br>                        725                        730                        735 | 2208 |
| tat gaa gtc gat gag aca tct atg tcc act gaa caa gat atc cag gaa<br>Tyr Glu Val Asp Glu Thr Ser Met Ser Thr Glu Gln Asp Ile Gln Glu<br>                        740                        745                        750 | 2256 |
| tca cct aat gat gat ttg gat cca caa gca cta tgg agt atg ctt caa<br>Ser Pro Asn Asp Asp Leu Asp Pro Gln Ala Leu Trp Ser Met Leu Gln<br>                 755                        760                        765 | 2304 |
| gag ctt gct gaa aaa aat tat tcg ctg gga aac aag ttg ttt act tat<br>Glu Leu Ala Glu Lys Asn Tyr Ser Leu Gly Asn Lys Leu Phe Thr Tyr<br>770                              775                        780 | 2352 |
| cca gat gta ttg aaa gct gat tca aca att gat ctc tat ttc aat cgt<br>Pro Asp Val Leu Lys Ala Asp Ser Thr Ile Asp Leu Tyr Phe Asn Arg<br>785                              790                        795                        800 | 2400 |
| gat cta tca gct gtg gcc aat gag cct gat gta ctt atc aaa gga gca<br>Asp Leu Ser Ala Val Ala Asn Glu Pro Asp Val Leu Ile Lys Gly Ala<br>                 805                        810                        815 | 2448 |
| ttc aat ggg tgg aag tgg aga ttt ttc act gaa aaa ttg cac aag agc<br>Phe Asn Gly Trp Lys Trp Arg Phe Phe Thr Glu Lys Leu His Lys Ser<br>                        820                        825                        830 | 2496 |
| gag ctg gca ggg gac tgg tgg tgc tgc aaa cta tac att cct aag cag<br>Glu Leu Ala Gly Asp Trp Trp Cys Cys Lys Leu Tyr Ile Pro Lys Gln<br>                 835                        840                        845 | 2544 |
| gca tac aga atg gac ttt gtg ttt ttt aac gga cac acg gta tat gaa<br>Ala Tyr Arg Met Asp Phe Val Phe Phe Asn Gly His Thr Val Tyr Glu<br>850                              855                        860 | 2592 |
| aat aat aac aat aat gat ttc gtg ata caa ata gaa agc acc atg gat<br>Asn Asn Asn Asn Asn Asp Phe Val Ile Gln Ile Glu Ser Thr Met Asp<br>865                              870                        875                        880 | 2640 |
| gaa aat tta ttt gag gat ttc ttg gct gaa gaa aag caa cga gaa ctt<br>Glu Asn Leu Phe Glu Asp Phe Leu Ala Glu Glu Lys Gln Arg Glu Leu<br>                        885                        890                        895 | 2688 |
| gag aac ctt gca aat gag gaa gct gaa agg agg aga caa act gat gag<br>Glu Asn Leu Ala Asn Glu Glu Ala Glu Arg Arg Arg Gln Thr Asp Glu<br>                 900                        905                        910 | 2736 |
| cag cgg cga atg gag gaa gaa agg gcc gca gat aaa gct gac agg gta<br>Gln Arg Arg Met Glu Glu Glu Arg Ala Ala Asp Lys Ala Asp Arg Val<br>                 915                        920                        925 | 2784 |

```
caa gcc aag gtt gag gta gag acg aag aag aat aaa ttg tgc aat gta       2832
Gln Ala Lys Val Glu Val Glu Thr Lys Lys Asn Lys Leu Cys Asn Val
        930                 935                 940 ttg ggt tta gcc aga gct cct gtt gat aat tta tgg tac att gag ccc       2880
Leu Gly Leu Ala Arg Ala Pro Val Asp Asn Leu Trp Tyr Ile Glu Pro
945                 950                 955                 960 atc acg act gga caa gag gct act gtc aga ttg tat tat aac ata aac       2928
Ile Thr Thr Gly Gln Glu Ala Thr Val Arg Leu Tyr Tyr Asn Ile Asn
                965                 970                 975 tca aga cct cta gtt cac agt act gag ata tgg atg cat ggt ggc tat       2976
Ser Arg Pro Leu Val His Ser Thr Glu Ile Trp Met His Gly Gly Tyr
            980                 985                 990 aac aat tgg att gat gga ctc tct ttt gct gaa agg ctt gtt cat cat       3024
Asn Asn Trp Ile Asp Gly Leu Ser Phe Ala Glu Arg Leu Val His His
        995                 1000                1005 cat gac aaa gat tgt gat tgg tgg ttt gca gat gtt gtc gtg cct gaa       3072
His Asp Lys Asp Cys Asp Trp Trp Phe Ala Asp Val Val Val Pro Glu
    1010                1015                1020 aga aca tat gta ttg gac tgg gtt ttt gct gac ggc cca cca ggg agt       3120
Arg Thr Tyr Val Leu Asp Trp Val Phe Ala Asp Gly Pro Pro Gly Ser
1025                1030                1035                1040 gca agg aat tat gac aac aat gga gga cat gat ttt cat gct acc ctt       3168
Ala Arg Asn Tyr Asp Asn Asn Gly Gly His Asp Phe His Ala Thr Leu
                1045                1050                1055 cca aat aac atg act gag gaa gag tat tgg atg gaa gaa gaa caa agg       3216
Pro Asn Asn Met Thr Glu Glu Glu Tyr Trp Met Glu Glu Glu Gln Arg
            1060                1065                1070 atc tat aca agg ctt caa caa gag agg agg gaa agg gag gag gct att       3264
Ile Tyr Thr Arg Leu Gln Gln Glu Arg Arg Glu Arg Glu Glu Ala Ile
        1075                1080                1085 aaa agg aag gct gag aga aat gca aaa atg aaa gct gag atg aag gaa       3312
Lys Arg Lys Ala Glu Arg Asn Ala Lys Met Lys Ala Glu Met Lys Glu
    1090                1095                1100 aag act atg aga atg ttc ctg gtt tct cag aaa cac att gtt tac acc       3360
Lys Thr Met Arg Met Phe Leu Val Ser Gln Lys His Ile Val Tyr Thr
1105                1110                1115                1120 gaa cca ctt gaa ata cat gct gga act act att gat gtg ctt tat aat       3408
Glu Pro Leu Glu Ile His Ala Gly Thr Thr Ile Asp Val Leu Tyr Asn
                1125                1130                1135 cct tct aat aca gtt cta act gga aag cca gag gtt tgg ttt cga tgt       3456
Pro Ser Asn Thr Val Leu Thr Gly Lys Pro Glu Val Trp Phe Arg Cys
            1140                1145                1150 tcc ttt aat cgt tgg atg tat cca ggt ggg gtg ttg cca cct cag aag       3504
Ser Phe Asn Arg Trp Met Tyr Pro Gly Gly Val Leu Pro Pro Gln Lys
        1155                1160                1165 atg gta caa gca gaa aat ggt tca cac cta aaa gca aca gtt tac gtt       3552
Met Val Gln Ala Glu Asn Gly Ser His Leu Lys Ala Thr Val Tyr Val
    1170                1175                1180 cca cga gat gcc tat atg atg gac ttc gtt ttc tcg gag tca gaa gaa       3600
Pro Arg Asp Ala Tyr Met Met Asp Phe Val Phe Ser Glu Ser Glu Glu
1185                1190                1195                1200 ggt gga att tat gat aac aga aat ggg tta gac tat cat att cct gtt       3648
Gly Gly Ile Tyr Asp Asn Arg Asn Gly Leu Asp Tyr His Ile Pro Val
                1205                1210                1215 ttt ggg tca att gca aag gaa cca cct atg cac att gtc cac att gct       3696
Phe Gly Ser Ile Ala Lys Glu Pro Pro Met His Ile Val His Ile Ala
            1220                1225                1230 gtt gag atg gca cca atc gca aag gtt gga ggt ctt ggt gat gtt gtc       3744
Val Glu Met Ala Pro Ile Ala Lys Val Gly Gly Leu Gly Asp Val Val
```

-continued

```
              1235                1240                1245
act agt ctt tca cgt gct gtg caa gat tta gga cac aat gtg gag gtt      3792
Thr Ser Leu Ser Arg Ala Val Gln Asp Leu Gly His Asn Val Glu Val
    1250                1255                1260 att ctt cca aag tac ggt tgc ttg aat cta agc aat gtc aag aat cta      3840
Ile Leu Pro Lys Tyr Gly Cys Leu Asn Leu Ser Asn Val Lys Asn Leu
1265                1270                1275                1280 caa atc cat cag agt ttt tct tgg ggt ggt tct gaa ata aat gtg tgg      3888
Gln Ile His Gln Ser Phe Ser Trp Gly Gly Ser Glu Ile Asn Val Trp
        1285                1290                1295 cgt gga cta gtc gaa ggc ctt tgt gtt tac ttc ctg gaa cct caa aat      3936
Arg Gly Leu Val Glu Gly Leu Cys Val Tyr Phe Leu Glu Pro Gln Asn
    1300                1305                1310 ggg atg ttt gga gtc gga tat gta tat ggc agg gac gat gac cgc cga      3984
Gly Met Phe Gly Val Gly Tyr Val Tyr Gly Arg Asp Asp Asp Arg Arg
        1315                1320                1325 ttt ggc ttc ttc tgt cgt tct gct cta gag ttt ctc ctc caa agt gga      4032
Phe Gly Phe Phe Cys Arg Ser Ala Leu Glu Phe Leu Leu Gln Ser Gly
    1330                1335                1340 tct tct ccg aac ata ata cat tgc cat gat tgg tca agt gct cct gtt      4080
Ser Ser Pro Asn Ile Ile His Cys His Asp Trp Ser Ser Ala Pro Val
1345                1350                1355                1360 gcc tgg cta cac aag gaa aac tac gcg aag tct agc ttg gca aac gca      4128
Ala Trp Leu His Lys Glu Asn Tyr Ala Lys Ser Ser Leu Ala Asn Ala
        1365                1370                1375 cgg gtg gta ttc acc atc cac aat ctt gaa ttt gga gcg cat cat att      4176
Arg Val Val Phe Thr Ile His Asn Leu Glu Phe Gly Ala His His Ile
    1380                1385                1390 ggc aaa gca atg aga tat tgt gat aaa gca aca act gtc tct aat aca      4224
Gly Lys Ala Met Arg Tyr Cys Asp Lys Ala Thr Thr Val Ser Asn Thr
        1395                1400                1405 tat tca aag gaa gtg tca ggt cat ggt gcc ata gtt cct cat ctt ggg      4272
Tyr Ser Lys Glu Val Ser Gly His Gly Ala Ile Val Pro His Leu Gly
    1410                1415                1420 aaa ttc tat ggc att ctc aat gga att gat ccg gat ata tgg gat ccg      4320
Lys Phe Tyr Gly Ile Leu Asn Gly Ile Asp Pro Asp Ile Trp Asp Pro
1425                1430                1435                1440 tac aat gac aac ttt atc ccg gtc cac tac act tgt gag aat gtg gtt      4368
Tyr Asn Asp Asn Phe Ile Pro Val His Tyr Thr Cys Glu Asn Val Val
        1445                1450                1455 gaa ggc aag agg gct gct aag agg gca ctg cag cag aag ttt ggg tta      4416
Glu Gly Lys Arg Ala Ala Lys Arg Ala Leu Gln Gln Lys Phe Gly Leu
    1460                1465                1470 cag caa atc gat gtc ccc gtc gta gga atc gtc act cgc ctg aca gcc      4464
Gln Gln Ile Asp Val Pro Val Val Gly Ile Val Thr Arg Leu Thr Ala
        1475                1480                1485 caa aag ggg atc cac ctg atc aag cat gcg att cac cgt aca ctc gaa      4512
Gln Lys Gly Ile His Leu Ile Lys His Ala Ile His Arg Thr Leu Glu
    1490                1495                1500 cgg aac gga cag gtg gtt ttg ctt ggt tca gcg ccg gac tct cga atc      4560
Arg Asn Gly Gln Val Val Leu Leu Gly Ser Ala Pro Asp Ser Arg Ile
1505                1510                1515                1520 caa gct gat ttt gtc aac ctg gcg aat acg ctc cac ggc gta aac cat      4608
Gln Ala Asp Phe Val Asn Leu Ala Asn Thr Leu His Gly Val Asn His
        1525                1530                1535 ggg caa gtg agg ctt tcc ttg acc tac gac gag cct ctc tcg cat ctg      4656
Gly Gln Val Arg Leu Ser Leu Thr Tyr Asp Glu Pro Leu Ser His Leu
    1540                1545                1550 ata tac gct ggc tct gac ttc att ctg gtc cca tct ata ttt gag cct      4704
```

Ile Tyr Ala Gly Ser Asp Phe Ile Leu Val Pro Ser Ile Phe Glu Pro
        1555                1560                1565 tgc ggc cta act cag ctc gtc gcc atg cgg tat gga acc atc ccg att    4752
Cys Gly Leu Thr Gln Leu Val Ala Met Arg Tyr Gly Thr Ile Pro Ile
    1570                1575                1580 gtc cgc aag act gga ggg ctc ttc gac act gtc ttc gat gtg gac aat    4800
Val Arg Lys Thr Gly Gly Leu Phe Asp Thr Val Phe Asp Val Asp Asn
1585                1590                1595                1600 gac aag gaa cga gcc cga gat cga ggc ctt gag ccc aac ggg ttt agc    4848
Asp Lys Glu Arg Ala Arg Asp Arg Gly Leu Glu Pro Asn Gly Phe Ser
                1605                1610                1615 ttt gac gga gct gat agc aac ggt gtt gac tac gcg ctg aac agg gcg    4896
Phe Asp Gly Ala Asp Ser Asn Gly Val Asp Tyr Ala Leu Asn Arg Ala
            1620                1625                1630 atc tca gct tgg ttc gat gcc cgg agc tgg ttc cac tcc ctt tgc aag    4944
Ile Ser Ala Trp Phe Asp Ala Arg Ser Trp Phe His Ser Leu Cys Lys
        1635                1640                1645 aga gtc atg gag cag gac tgg tcg tgg aac cga cct gcc ctc gac tac    4992
Arg Val Met Glu Gln Asp Trp Ser Trp Asn Arg Pro Ala Leu Asp Tyr
    1650                1655                1660 atc gag ctc tac cgt tca gcg tcc aaa ttg taa                        5025
Ile Glu Leu Tyr Arg Ser Ala Ser Lys Leu
1665                1670

<210> SEQ ID NO 18
<211> LENGTH: 1674
<212> TYPE: PRT
<213> ORGANISM: Zea mays

<400> SEQUENCE: 18

Met Glu Met Val Leu Arg Ser Gln Ser Pro Leu Cys Leu Arg Ser Gly
1               5                   10                  15

Pro Val Leu Ile Phe Arg Pro Thr Val Ala Gly Gly Gly Gly Gly Thr
            20                  25                  30

Gln Ser Leu Leu Arg Thr Thr Arg Phe Ala Arg Arg Arg Val Ile Arg
        35                  40                  45

Cys Val Val Ala Ser Pro Gly Cys Pro Asn Arg Lys Ser Arg Thr Ala
    50                  55                  60

Ser Pro Asn Val Lys Val Ala Ala Tyr Ser Asn Tyr Ala Pro Arg Leu
65                  70                  75                  80

Leu Val Glu Ser Ser Ser Lys Lys Ser Glu His His Asp Ser Arg
                85                  90                  95

His Arg Glu Glu Thr Ile Asp Thr Tyr Asn Gly Leu Ser Gly Ser Asp
            100                 105                 110

Ala Ala Glu Leu Thr Ser Asn Arg Asp Val Glu Ile Glu Val Asp Leu
        115                 120                 125

Gln His Ile Ser Glu Glu Glu Leu Pro Gly Lys Val Ser Ile Asn Ala
    130                 135                 140

Ser Leu Gly Glu Met Glu Thr Val Asp Glu Ala Glu Val Glu Glu Asp
145                 150                 155                 160

Lys Phe Glu Val Asp Thr Ser Gly Ile Val Leu Arg Asn Val Ala Val
                165                 170                 175

Arg Glu Val Asp Pro Lys Asp Glu His Asn Ala Lys Asp Val Phe Val
            180                 185                 190

Val Asp Ser Ser Gly Thr Ala Pro Asp Asn Ala Ala Val Glu Glu Val
        195                 200                 205

Val Asp Glu Ala Glu Val Glu Glu Asp Met Val Asp Val Asp Ile Leu

```
              210                 215                 220
Gly Leu Asp Leu Asn Ala Thr Ile Glu Ile Asp Leu Met Glu
225                 230                 235                 240

Glu Ala Leu Leu Glu Asn Phe Asp Val Asp Ser Pro Gly Asn Ala Ser
                245                 250                 255

Ser Gly Arg Thr Tyr Gly Val Asp Glu Leu Gly Glu Leu Pro Ser
            260                 265                 270

Thr Ser Val Asp Cys Ile Ala Ile Asn Gly Lys Arg Arg Ser Leu Lys
            275                 280                 285

Pro Lys Pro Leu Pro Ile Val Arg Phe Gln Glu Gln Glu Gln Ile Val
290                 295                 300

Leu Ser Ile Val Asp Glu Glu Gly Leu Ile Ala Ser Ser Cys Glu Glu
305                 310                 315                 320

Gly Gln Pro Val Val Asp Tyr Asp Lys Gln Glu Asn Ser Thr Ala
                325                 330                 335

Phe Asp Glu Gln Lys Gln Leu Thr Asp Asp Phe Pro Glu Glu Gly Ile
                340                 345                 350

Ser Ile Val His Phe Pro Glu Pro Asn Asn Asp Ile Val Gly Ser Ser
            355                 360                 365

Lys Phe Leu Glu Gln Lys Gln Glu Leu Asp Gly Ser Tyr Lys Gln Asp
370                 375                 380

Arg Ser Thr Thr Gly Leu His Glu Gln Asp Gln Ser Val Val Ser Ser
385                 390                 395                 400

His Gly Gln Asp Lys Ser Ile Val Gly Val Pro Gln Gln Ile Gln Tyr
                405                 410                 415

Asn Asp Gln Ser Ile Ala Gly Ser His Arg Gln Asp Gln Ser Ile Ala
                420                 425                 430

Gly Ala Pro Glu Gln Ile Gln Ser Val Ala Gly Tyr Ile Lys Pro Asn
                435                 440                 445

Gln Ser Ile Val Gly Ser Cys Lys Gln His Glu Leu Ile Ile Pro Glu
            450                 455                 460

Pro Lys Lys Ile Glu Ser Ile Ile Ser Tyr Asn Glu Ile Asp Gln Ser
465                 470                 475                 480

Ile Val Gly Ser His Lys Gln Asp Lys Ser Val Val Ser Val Pro Glu
                485                 490                 495

Gln Ile Gln Ser Ile Val Ser His Ser Lys Pro Asn Gln Ser Thr Val
            500                 505                 510

Asp Ser Tyr Arg Gln Ala Glu Ser Ile Ile Gly Val Pro Glu Lys Val
            515                 520                 525

Gln Ser Ile Thr Ser Tyr Asp Lys Leu Asp Gln Ser Ile Val Gly Ser
            530                 535                 540

Leu Lys Gln Asp Glu Pro Ile Ile Ser Val Pro Glu Lys Ile Gln Ser
545                 550                 555                 560

Ile Val His Tyr Thr Lys Pro Asn Gln Ser Ile Val Gly Leu Pro Lys
                565                 570                 575

Gln Gln Gln Ser Ile Val His Ile Val Glu Pro Lys Gln Ser Ile Asp
                580                 585                 590

Gly Phe Pro Lys Gln Asp Leu Ser Ile Val Gly Ile Ser Asn Glu Phe
            595                 600                 605

Gln Thr Lys Gln Leu Ala Thr Val Gly Thr His Asp Gly Leu Leu Met
            610                 615                 620

Lys Gly Val Glu Ala Lys Glu Ser Gln Lys Thr Glu Gly Asp Thr
625                 630                 635                 640
```

-continued

```
Leu Gln Ala Thr Phe Asn Val Asp Asn Leu Ser Gln Lys Gln Glu Gly
            645                 650                 655
Leu Thr Lys Glu Ala Asp Glu Ile Thr Ile Ile Glu Lys Ile Asn Asp
            660                 665                 670
Glu Asp Leu Val Met Ile Glu Gln Lys Ser Ile Ala Met Asn Glu
        675                 680                 685
Glu Gln Thr Ile Val Thr Glu Glu Asp Ile Pro Met Ala Lys Val Glu
        690                 695                 700
Ile Gly Ile Asp Lys Ala Lys Phe Leu His Leu Leu Ser Glu Glu Glu
705                 710                 715                 720
Ser Ser Trp Asp Glu Asn Glu Val Gly Ile Ile Glu Ala Asp Glu Gln
                725                 730                 735
Tyr Glu Val Asp Glu Thr Ser Met Ser Thr Glu Gln Asp Ile Gln Glu
            740                 745                 750
Ser Pro Asn Asp Asp Leu Asp Pro Gln Ala Leu Trp Ser Met Leu Gln
        755                 760                 765
Glu Leu Ala Glu Lys Asn Tyr Ser Leu Gly Asn Lys Leu Phe Thr Tyr
    770                 775                 780
Pro Asp Val Leu Lys Ala Asp Ser Thr Ile Asp Leu Tyr Phe Asn Arg
785                 790                 795                 800
Asp Leu Ser Ala Val Ala Asn Glu Pro Asp Val Leu Ile Lys Gly Ala
                805                 810                 815
Phe Asn Gly Trp Lys Trp Arg Phe Phe Thr Glu Lys Leu His Lys Ser
            820                 825                 830
Glu Leu Ala Gly Asp Trp Trp Cys Cys Lys Leu Tyr Ile Pro Lys Gln
        835                 840                 845
Ala Tyr Arg Met Asp Phe Val Phe Phe Asn Gly His Thr Val Tyr Glu
    850                 855                 860
Asn Asn Asn Asn Asn Asp Phe Val Ile Gln Ile Glu Ser Thr Met Asp
865                 870                 875                 880
Glu Asn Leu Phe Glu Asp Phe Leu Ala Glu Glu Lys Gln Arg Glu Leu
                885                 890                 895
Glu Asn Leu Ala Asn Glu Glu Ala Glu Arg Arg Arg Gln Thr Asp Glu
            900                 905                 910
Gln Arg Arg Met Glu Glu Arg Ala Ala Asp Lys Ala Asp Arg Val
        915                 920                 925
Gln Ala Lys Val Glu Val Glu Thr Lys Lys Asn Lys Leu Cys Asn Val
    930                 935                 940
Leu Gly Leu Ala Arg Ala Pro Val Asp Asn Leu Trp Tyr Ile Glu Pro
945                 950                 955                 960
Ile Thr Thr Gly Gln Glu Ala Thr Val Arg Leu Tyr Tyr Asn Ile Asn
                965                 970                 975
Ser Arg Pro Leu Val His Ser Thr Glu Ile Trp Met His Gly Gly Tyr
            980                 985                 990
Asn Asn Trp Ile Asp Gly Leu Ser Phe Ala Glu Arg Leu Val His His
        995                 1000                1005
His Asp Lys Asp Cys Asp Trp Trp Phe Ala Asp Val Val Pro Glu
    1010                1015                1020
Arg Thr Tyr Val Leu Asp Trp Val Phe Ala Asp Gly Pro Pro Gly Ser
1025                1030                1035                1040
Ala Arg Asn Tyr Asp Asn Asn Gly Gly His Asp Phe His Ala Thr Leu
                1045                1050                1055
```

-continued

```
Pro Asn Asn Met Thr Glu Glu Glu Tyr Trp Met Glu Glu Gln Arg
        1060                1065                1070
Ile Tyr Thr Arg Leu Gln Gln Glu Arg Arg Glu Arg Glu Glu Ala Ile
    1075                1080                1085
Lys Arg Lys Ala Glu Arg Asn Ala Lys Met Lys Ala Glu Met Lys Glu
1090                1095                1100
Lys Thr Met Arg Met Phe Leu Val Ser Gln Lys His Ile Val Tyr Thr
1105                1110                1115                1120
Glu Pro Leu Glu Ile His Ala Gly Thr Thr Ile Asp Val Leu Tyr Asn
        1125                1130                1135
Pro Ser Asn Thr Val Leu Thr Gly Lys Pro Glu Val Trp Phe Arg Cys
        1140                1145                1150
Ser Phe Asn Arg Trp Met Tyr Pro Gly Gly Val Leu Pro Pro Gln Lys
        1155                1160                1165
Met Val Gln Ala Glu Asn Gly Ser His Leu Lys Ala Thr Val Tyr Val
    1170                1175                1180
Pro Arg Asp Ala Tyr Met Met Asp Phe Val Phe Ser Glu Ser Glu Glu
1185                1190                1195                1200
Gly Gly Ile Tyr Asp Asn Arg Asn Gly Leu Asp Tyr His Ile Pro Val
        1205                1210                1215
Phe Gly Ser Ile Ala Lys Glu Pro Pro Met His Ile Val His Ile Ala
        1220                1225                1230
Val Glu Met Ala Pro Ile Ala Lys Val Gly Gly Leu Gly Asp Val Val
    1235                1240                1245
Thr Ser Leu Ser Arg Ala Val Gln Asp Leu Gly His Asn Val Glu Val
    1250                1255                1260
Ile Leu Pro Lys Tyr Gly Cys Leu Asn Leu Ser Asn Val Lys Asn Leu
1265                1270                1275                1280
Gln Ile His Gln Ser Phe Ser Trp Gly Gly Ser Glu Ile Asn Val Trp
        1285                1290                1295
Arg Gly Leu Val Glu Gly Leu Cys Val Tyr Phe Leu Glu Pro Gln Asn
        1300                1305                1310
Gly Met Phe Gly Val Gly Tyr Val Tyr Gly Arg Asp Asp Asp Arg Arg
    1315                1320                1325
Phe Gly Phe Phe Cys Arg Ser Ala Leu Glu Phe Leu Leu Gln Ser Gly
    1330                1335                1340
Ser Ser Pro Asn Ile Ile His Cys His Asp Trp Ser Ser Ala Pro Val
1345                1350                1355                1360
Ala Trp Leu His Lys Glu Asn Tyr Ala Lys Ser Ser Leu Ala Asn Ala
        1365                1370                1375
Arg Val Val Phe Thr Ile His Asn Leu Glu Phe Gly Ala His His Ile
        1380                1385                1390
Gly Lys Ala Met Arg Tyr Cys Asp Lys Ala Thr Thr Val Ser Asn Thr
    1395                1400                1405
Tyr Ser Lys Glu Val Ser Gly His Gly Ala Ile Val Pro His Leu Gly
    1410                1415                1420
Lys Phe Tyr Gly Ile Leu Asn Gly Ile Asp Pro Asp Ile Trp Asp Pro
1425                1430                1435                1440
Tyr Asn Asp Asn Phe Ile Pro Val His Tyr Thr Cys Glu Asn Val Val
        1445                1450                1455
Glu Gly Lys Arg Ala Ala Lys Arg Ala Leu Gln Gln Lys Phe Gly Leu
        1460                1465                1470
Gln Gln Ile Asp Val Pro Val Val Gly Ile Val Thr Arg Leu Thr Ala
```

-continued

```
              1475                1480                1485

Gln Lys Gly Ile His Leu Ile Lys His Ala Ile His Arg Thr Leu Glu
        1490                1495                1500

Arg Asn Gly Gln Val Val Leu Leu Gly Ser Ala Pro Asp Ser Arg Ile
1505                1510                1515                1520

Gln Ala Asp Phe Val Asn Leu Ala Asn Thr Leu His Gly Val Asn His
            1525                1530                1535

Gly Gln Val Arg Leu Ser Leu Thr Tyr Asp Glu Pro Leu Ser His Leu
        1540                1545                1550

Ile Tyr Ala Gly Ser Asp Phe Ile Leu Val Pro Ser Ile Phe Glu Pro
        1555                1560                1565

Cys Gly Leu Thr Gln Leu Val Ala Met Arg Tyr Gly Thr Ile Pro Ile
    1570                1575                1580

Val Arg Lys Thr Gly Gly Leu Phe Asp Thr Val Phe Asp Val Asp Asn
1585                1590                1595                1600

Asp Lys Glu Arg Ala Arg Asp Arg Gly Leu Glu Pro Asn Gly Phe Ser
            1605                1610                1615

Phe Asp Gly Ala Asp Ser Asn Gly Val Asp Tyr Ala Leu Asn Arg Ala
        1620                1625                1630

Ile Ser Ala Trp Phe Asp Ala Arg Ser Trp Phe His Ser Leu Cys Lys
        1635                1640                1645

Arg Val Met Glu Gln Asp Trp Ser Trp Asn Arg Pro Ala Leu Asp Tyr
    1650                1655                1660

Ile Glu Leu Tyr Arg Ser Ala Ser Lys Leu
1665                1670

<210> SEQ ID NO 19
<211> LENGTH: 12
<212> TYPE: PRT
<213> ORGANISM: Artificial sequence
<220> FEATURE:
<223> OTHER INFORMATION: Description of the artificial sequence:
      sequence motif for SSS3 proteins
<220> FEATURE:
<221> NAME/KEY: VARIANT
<222> LOCATION: (3)
<223> OTHER INFORMATION: P/S Variation
<220> FEATURE:
<221> NAME/KEY: misc_feature
<222> LOCATION: (6)..(6)
<223> OTHER INFORMATION: Xaa is unknown or other
<220> FEATURE:
<221> NAME/KEY: VARIANT
<222> LOCATION: (8)
<223> OTHER INFORMATION: M/K Variation

<400> SEQUENCE: 19

Asn Glu Pro Asp Val Xaa Ile Lys Gly Ala Phe Asn
  1               5                  10

<210> SEQ ID NO 20
<211> LENGTH: 14
<212> TYPE: PRT
<213> ORGANISM: Artificial sequence
<220> FEATURE:
<223> OTHER INFORMATION: Description of the artificial sequence:
      sequence motif for SSS3 proteins
<220> FEATURE:
<221> NAME/KEY: VARIANT
<222> LOCATION: (3)
<223> OTHER INFORMATION: E/Q Variation
<220> FEATURE:
<221> NAME/KEY: VARIANT
<222> LOCATION: (6)
```

```
<223> OTHER INFORMATION: R/K Variation
<220> FEATURE:
<221> NAME/KEY: misc_feature
<222> LOCATION: (7)..(7)
<223> OTHER INFORMATION: Xaa is unknown or other

<400> SEQUENCE: 20

Pro Lys Glu Ala Tyr Arg Xaa Asp Phe Val Phe Phe Asn Gly
 1               5                  10

<210> SEQ ID NO 21
<211> LENGTH: 8
<212> TYPE: PRT
<213> ORGANISM: Artificial sequence
<220> FEATURE:
<223> OTHER INFORMATION: Description of the artificial sequence:
      sequence motif for SSS3 proteins

<400> SEQUENCE: 21

Asp Trp Val Phe Ala Asp Gly Pro
 1               5

<210> SEQ ID NO 22
<211> LENGTH: 14
<212> TYPE: PRT
<213> ORGANISM: Artificial sequence
<220> FEATURE:
<223> OTHER INFORMATION: Description of the artificial sequence:
      sequence motif for SSS3 proteins
<220> FEATURE:
<221> NAME/KEY: VARIANT
<222> LOCATION: (3)
<223> OTHER INFORMATION: V/L Variation
<220> FEATURE:
<221> NAME/KEY: VARIANT
<222> LOCATION: (7)
<223> OTHER INFORMATION: H/D Variation
<220> FEATURE:
<221> NAME/KEY: VARIANT
<222> LOCATION: (8)
<223> OTHER INFORMATION: V/I Variation

<400> SEQUENCE: 22

Phe Leu Val Ser Gln Lys His Val Val Tyr Thr Glu Pro Leu
 1               5                  10

<210> SEQ ID NO 23
<211> LENGTH: 21
<212> TYPE: PRT
<213> ORGANISM: Artificial sequence
<220> FEATURE:
<223> OTHER INFORMATION: Description of the artificial sequence:
      sequence motif for SSS3 proteins
<220> FEATURE:
<221> NAME/KEY: VARIANT
<222> LOCATION: (4)
<223> OTHER INFORMATION: A/S Variation
<220> FEATURE:
<221> NAME/KEY: VARIANT
<222> LOCATION: (14)
<223> OTHER INFORMATION: V/I Variation
<220> FEATURE:
<221> NAME/KEY: VARIANT
<222> LOCATION: (7)
<223> OTHER INFORMATION: V/N Variation
<220> FEATURE:
<221> NAME/KEY: VARIANT
<222> LOCATION: (9)
<223> OTHER INFORMATION: N/T Variation
<220> FEATURE:
<221> NAME/KEY: misc_feature
<222> LOCATION: (18)..(18)
<223> OTHER INFORMATION: Xaa is unknown or other
```

-continued

```
<400> SEQUENCE: 23

Tyr Asn Pro Ala Asn Thr Val Leu Asn Gly Lys Pro Glu Val Trp Phe
1               5                   10                  15

Arg Xaa Ser Phe Asn
            20

<210> SEQ ID NO 24
<211> LENGTH: 11
<212> TYPE: PRT
<213> ORGANISM: Artificial sequence
<220> FEATURE:
<223> OTHER INFORMATION: Description of the artificial sequence:
      sequence motif for SSS3 proteins

<400> SEQUENCE: 24

Asp Ala Tyr Met Met Asp Phe Val Phe Ser Glu
1               5                   10

<210> SEQ ID NO 25
<211> LENGTH: 11
<212> TYPE: PRT
<213> ORGANISM: Artificial sequence
<220> FEATURE:
<223> OTHER INFORMATION: Description of the artificial sequence:
      sequence motif for SSS3 proteins
<220> FEATURE:
<221> NAME/KEY: VARIANT
<222> LOCATION: (6)
<223> OTHER INFORMATION: G/A Variation

<400> SEQUENCE: 25

Lys Val Gly Gly Leu Gly Asp Val Val Thr Ser
1               5                   10

<210> SEQ ID NO 26
<211> LENGTH: 16
<212> TYPE: PRT
<213> ORGANISM: Artificial sequence
<220> FEATURE:
<223> OTHER INFORMATION: Description of the artificial sequence:
      sequence motif for SSS3 proteins
<220> FEATURE:
<221> NAME/KEY: VARIANT
<222> LOCATION: (7)
<223> OTHER INFORMATION: G/A Variation

<400> SEQUENCE: 26

Ala Lys Val Gly Gly Leu Gly Asp Val Val Thr Ser Leu Ser Arg Ala
1               5                   10                  15

<210> SEQ ID NO 27
<211> LENGTH: 13
<212> TYPE: PRT
<213> ORGANISM: Artificial sequence
<220> FEATURE:
<223> OTHER INFORMATION: Description of the artificial sequence:
      sequence motif for SSS3 proteins
<220> FEATURE:
<221> NAME/KEY: VARIANT
<222> LOCATION: (13)
<223> OTHER INFORMATION: A/S Variation

<400> SEQUENCE: 27

His Cys His Asp Trp Ser Ser Ala Pro Val Ala Trp Leu
1               5                   10

<210> SEQ ID NO 28
```

```
<211> LENGTH: 10
<212> TYPE: PRT
<213> ORGANISM: Artificial sequence
<220> FEATURE:
<223> OTHER INFORMATION: Description of the artificial sequence:
      sequence motif for SSS3 proteins

<400> SEQUENCE: 28

Phe Thr Ile His Asn Leu Glu Phe Gly Ala
 1               5                  10

<210> SEQ ID NO 29
<211> LENGTH: 10
<212> TYPE: PRT
<213> ORGANISM: Artificial sequence
<220> FEATURE:
<223> OTHER INFORMATION: Description of the artificial sequence:
      sequence motif for SSS3 proteins

<400> SEQUENCE: 29

Asn Gly Ile Asp Pro Asp Ile Trp Asp Pro
 1               5                  10

<210> SEQ ID NO 30
<211> LENGTH: 20
<212> TYPE: PRT
<213> ORGANISM: Artificial sequence
<220> FEATURE:
<223> OTHER INFORMATION: Description of the artificial sequence:
      sequence motif for SSS3 proteins
<220> FEATURE:
<221> NAME/KEY: VARIANT
<222> LOCATION: (3)
<223> OTHER INFORMATION: L/V/I Variation
<220> FEATURE:
<221> NAME/KEY: VARIANT
<222> LOCATION: (14)
<223> OTHER INFORMATION: Y/L Variation
<220> FEATURE:
<221> NAME/KEY: VARIANT
<222> LOCATION: (15)
<223> OTHER INFORMATION: T/N Variation
<220> FEATURE:
<221> NAME/KEY: VARIANT
<222> LOCATION: (17)
<223> OTHER INFORMATION: N/K Variation

<400> SEQUENCE: 30

Gly Ile Leu Asn Gly Ile Asp Pro Asp Ile Trp Asp Pro Tyr Thr Asp
 1               5                  10                  15

Asn Phe Ile Pro
            20

<210> SEQ ID NO 31
<211> LENGTH: 12
<212> TYPE: PRT
<213> ORGANISM: Artificial sequence
<220> FEATURE:
<223> OTHER INFORMATION: Description of the artificial sequence:
      sequence motif for SSS3 proteins
<220> FEATURE:
<221> NAME/KEY: VARIANT
<222> LOCATION: (3)
<223> OTHER INFORMATION: V/I Variation
<220> FEATURE:
<221> NAME/KEY: VARIANT
<222> LOCATION: (9)
<223> OTHER INFORMATION: A/H Variation

<400> SEQUENCE: 31

Val Gly Ile Ile Thr Arg Leu Thr Ala Gln Lys Gly
```

-continued

```
<210> SEQ ID NO 32
<211> LENGTH: 19
<212> TYPE: PRT
<213> ORGANISM: Artificial sequence
<220> FEATURE:
<223> OTHER INFORMATION: Description of the artificial sequence:
      sequence motif for SSS3 proteins
<220> FEATURE:
<221> NAME/KEY: VARIANT
<222> LOCATION: (3)
<223> OTHER INFORMATION: I/V Variation
<220> FEATURE:
<221> NAME/KEY: VARIANT
<222> LOCATION: (9)
<223> OTHER INFORMATION: A/H Variation

<400> SEQUENCE: 32

Val Gly Ile Ile Thr Arg Leu Thr Ala Gln Lys Gly Ile His Leu Ile
  1               5                  10                  15

Lys His Ala

<210> SEQ ID NO 33
<211> LENGTH: 10
<212> TYPE: PRT
<213> ORGANISM: Artificial sequence
<220> FEATURE:
<223> OTHER INFORMATION: Description of the artificial sequence:
      sequence motif for SSS3 proteins

<400> SEQUENCE: 33

Asn Gly Gln Val Val Leu Leu Gly Ser Ala
  1               5                  10

<210> SEQ ID NO 34
<211> LENGTH: 16
<212> TYPE: PRT
<213> ORGANISM: Artificial sequence
<220> FEATURE:
<223> OTHER INFORMATION: Description of the artificial sequence:
      sequence motif for SSS3 proteins

<400> SEQUENCE: 34

Thr Leu Glu Arg Asn Gly Gln Val Val Leu Leu Gly Ser Ala Pro Asp
  1               5                  10                  15

<210> SEQ ID NO 35
<211> LENGTH: 12
<212> TYPE: PRT
<213> ORGANISM: Artificial sequence
<220> FEATURE:
<223> OTHER INFORMATION: Description of the artificial sequence:
      sequence motif for SS3 protein

<400> SEQUENCE: 35

Leu Thr Tyr Asp Glu Pro Leu Ser His Leu Ile Tyr
  1               5                  10

<210> SEQ ID NO 36
<211> LENGTH: 17
<212> TYPE: PRT
<213> ORGANISM: Artificial sequence
<220> FEATURE:
<223> OTHER INFORMATION: Description of the artificial sequence:
      sequence motif for SSS3 proteins
<220> FEATURE:
<221> NAME/KEY: VARIANT
<222> LOCATION: (4)
```

```
<223> OTHER INFORMATION: L/I Variation

<400> SEQUENCE: 36

Asp Phe Ile Leu Val Pro Ser Ile Phe Glu Pro Cys Gly Leu Thr Gln
 1               5                  10                  15

Leu

<210> SEQ ID NO 37
<211> LENGTH: 26
<212> TYPE: PRT
<213> ORGANISM: Artificial sequence
<220> FEATURE:
<223> OTHER INFORMATION: Description of the artificial sequence:
      sequence motif for SSS3 proteins
<220> FEATURE:
<221> NAME/KEY: VARIANT
<222> LOCATION: (3)
<223> OTHER INFORMATION: S/A Variation
<220> FEATURE:
<221> NAME/KEY: VARIANT
<222> LOCATION: (7)
<223> OTHER INFORMATION: L/I Variation
<220> FEATURE:
<221> NAME/KEY: VARIANT
<222> LOCATION: (21)
<223> OTHER INFORMATION: V/I Variation

<400> SEQUENCE: 37

Ala Gly Ser Asp Phe Ile Leu Val Pro Ser Ile Phe Glu Pro Cys Gly
 1               5                  10                  15

Leu Thr Gln Leu Val Ala Met Arg Tyr Gly
            20                  25

<210> SEQ ID NO 38
<211> LENGTH: 10
<212> TYPE: PRT
<213> ORGANISM: Artificial sequence
<220> FEATURE:
<223> OTHER INFORMATION: Description of the artificial sequence:
      sequence motif for SSS3 proteins
<220> FEATURE:
<221> NAME/KEY: VARIANT
<222> LOCATION: (8)
<223> OTHER INFORMATION: H/N Variation

<400> SEQUENCE: 38

Asp Thr Val Phe Asp Val Asp His Asp Lys
 1               5                  10

<210> SEQ ID NO 39
<211> LENGTH: 11
<212> TYPE: PRT
<213> ORGANISM: Artificial sequence
<220> FEATURE:
<223> OTHER INFORMATION: Description of the artificial sequence:
      sequence motif for SSS3 proteins

<400> SEQUENCE: 39

Val Met Glu Gln Asp Trp Ser Trp Asn Arg Pro
 1               5                  10

<210> SEQ ID NO 40
<211> LENGTH: 27
<212> TYPE: DNA
<213> ORGANISM: Artificial sequence
<220> FEATURE:
<223> OTHER INFORMATION: Description of the artificial sequence:
      oligonucleotide primer
```

```
<400> SEQUENCE: 40
tgcattggag acacttgtgc aactcaa                                         27

<210> SEQ ID NO 41
<211> LENGTH: 27
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 41
tgtggttcca tgagagacaa acccaag                                         27

<210> SEQ ID NO 42
<211> LENGTH: 44
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 42
gtcgactcta gaggaagaaa tcttctctgt ctaaaaaatt gacg                      44

<210> SEQ ID NO 43
<211> LENGTH: 38
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 43
cccgggatcc tctctccctc tctgtatctg tgctgcaa                             38

<210> SEQ ID NO 44
<211> LENGTH: 1008
<212> TYPE: DNA
<213> ORGANISM: Solanum tuberosum
<220> FEATURE:
<221> NAME/KEY: promoter
<222> LOCATION: (1)..(1008)
<223> OTHER INFORMATION: promoter region of the SSS3 gene

<400> SEQUENCE: 44
ggaagaaatc ttctctgtct aaaaaattga cggttgatgt tataagagtt ttttttttt      60 ttttcctttt acaaattgaa gtgacaaaag actgaatcac agtggatcgt gataacaagg    120
aatgttctga gagtattgct attgtgaatt ttattttata tgacgtaaat ggtcaaattt    180
gcttaatttt gtgaaataga acaaatttat cctctagttg gagacaaata tactcttgaa    240
ctatacaaaa tagaataatt ttttgttat ttttaaattt atcgcctaat gatattaaag     300 atagttttt tttttttaa atgaattgaa actttcgcat agttcaattt tttttcttg       360 cacaatatat aggaaaattt aatccttctt tctagttttg aattttagaa atcttttctt    420
cctcctttct ctctctacca cccattaccc ctttttttct ccttcttcct tgaacaacgc    480
catacaattt tttatttctt ttttcccctc atttttttt taattccaat caaattgtat     540
aatccaagta tagttaattt tgataacata taaattataa agtaatgtgt aaataatagt    600
actatagtat aataagttaa ataaatccaa ctcaaataaa tttagaccgc tgctgtcact    660
ctctagactc tccataccca aatttgtcg caacctttt ttgctcattt ccaagaaaaa     720
```

-continued

```
agagcctact gtaattaaaa aattccacgt gtcaatatct aaattaccac cgtcatatcg      780
aaccaaacaa tttcaaccgt cagatttact ggtccaacgt aagcaaaata gagagcatta      840
cacagaaaca acacacttca ggctgaaaat tgtaggactc ctccaatttg ttatcgcagt      900
tcgtagaatc tgaagaaaga gtattattct tgatttttta atagattttt aaaaccccat      960
taaagcaaat acgtatataa ttgcagcaca gatacagaga gggagaga                 1008
```

<210> SEQ ID NO 45
<211> LENGTH: 23
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 45
atggcagacg gtgaggatat tca                                               23

<210> SEQ ID NO 46
<211> LENGTH: 23
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 46
gcctttgcaa tccacatctg ttg                                               23

<210> SEQ ID NO 47
<211> LENGTH: 24
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 47
gcagcacaga tacagagagg gaga                                              24

<210> SEQ ID NO 48
<211> LENGTH: 22
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 48
tggctgtgac gcacagttca ta                                                22